US008604040B2

(12) United States Patent
Cristau et al.

(10) Patent No.: US 8,604,040 B2
(45) Date of Patent: Dec. 10, 2013

(54) PYRIDINYLCARBOXYLIC ACID DERIVATIVES AS FUNGICIDES

(75) Inventors: Pierre Cristau, Lyons (FR); Sebastian Hoffmann, Neuss (DE); Joachim Kluth, Langenfeld (DE); Nicola Rahn, Düsseldorf (DE); Tomoki Tsuchiya, Düsseldorf (DE); Pierre Wasnaire, Düsseldorf (DE); Jürgen Benting, Leichlingen (DE); Ulrike Wachendorff-Neumann, Neuwied (DE)

(73) Assignee: Bayer CropScience AG, Monheim (DE)

( * ) Notice: Subject to any disclaimer, the term of this patent is extended or adjusted under 35 U.S.C. 154(b) by 128 days.

(21) Appl. No.: 13/117,041

(22) Filed: May 26, 2011

(65) Prior Publication Data

US 2012/0065197 A1 Mar. 15, 2012

Related U.S. Application Data

(60) Provisional application No. 61/348,981, filed on May 27, 2010.

(30) Foreign Application Priority Data

May 27, 2010 (EP) .................................... 10164099

(51) Int. Cl.
A01N 43/60 (2006.01)
C07D 401/12 (2006.01)
C07D 401/14 (2006.01)
C07D 409/14 (2006.01)
A01N 43/40 (2006.01)
A01N 43/42 (2006.01)

(52) U.S. Cl.
USPC ............ 514/253.05; 514/253.06; 514/253.07; 514/253.09; 514/314; 514/318; 544/363; 544/364; 544/105; 544/121; 544/238; 544/353; 544/354; 546/171; 546/193; 546/194

(58) Field of Classification Search
None
See application file for complete search history.

(56) References Cited

U.S. PATENT DOCUMENTS

| | | | |
|---|---|---|---|
| 4,245,432 | A | 1/1981 | Dannelly |
| 4,272,417 | A | 6/1981 | Barke et al. |
| 4,808,430 | A | 2/1989 | Kouno |
| 5,876,739 | A | 3/1999 | Turnblad et al. |
| 8,367,844 | B2 * | 2/2013 | Sulzer-Mosse et al. ...... 548/235 |
| 2003/0176428 | A1 | 9/2003 | Schneidersmann et al. |
| 2007/0244088 | A1 * | 10/2007 | Brickmann et al. ...... 514/210.2 |
| 2009/0197859 | A1 | 8/2009 | Collantes et al. |
| 2010/0056569 | A1 | 3/2010 | Nan et al. |
| 2010/0137245 | A1 | 6/2010 | Cristau et al. |
| 2010/0190828 | A1 | 7/2010 | Cristau et al. |
| 2011/0046178 | A1 | 2/2011 | Cristau et al. |
| 2011/0105429 | A1 | 5/2011 | Cristau et al. |

FOREIGN PATENT DOCUMENTS

| | | |
|---|---|---|
| WO | WO 96/33270 A1 | 10/1996 |
| WO | WO 02/28186 A2 | 4/2002 |
| WO | WO 02/080675 A1 | 10/2002 |
| WO | WO 2007/014290 A2 | 2/2007 |
| WO | WO 2007/024782 A2 | 3/2007 |
| WO | WO 2007/027777 A2 | 3/2007 |
| WO | WO 2008/013622 A2 | 1/2008 |
| WO | WO 2008/013925 A2 | 1/2008 |
| WO | WO 2008/091580 A2 | 7/2008 |
| WO | WO 2008/091594 A2 | 7/2008 |
| WO | WO 2009/055514 A2 | 4/2009 |
| WO | WO 2009/094407 A2 | 7/2009 |
| WO | WO 2009/094445 A2 | 7/2009 |
| WO | WO 2009/098576 A1 | 8/2009 |
| WO | WO 2010/008739 A2 | 1/2010 |
| WO | WO 2010/065579 A2 | 6/2010 |
| WO | WO 2011/018401 A1 | 2/2011 |
| WO | WO 2011/018415 A2 | 2/2011 |

OTHER PUBLICATIONS

Barany, G., et al., "A General Strategy for Elaboration of the Dithiocarbonyl Functionality, -(C=O)SS-: Application to the Synthesis of Bis(chlorocarbonyl)disulfane and Related Derivatives of Thiocarbonic Acids," *J. Org. Chem.* 48(24): 4750-4761, American Chemical Society, United States (1983).

Chen, W., et al., "The Design and Synthesis of Bis(thiourea) Ligands and Their Application in Pd-Catalyzed Heck and Suzuki Reactions Under Aerobic Conditions," *Eur. J. Org. Chem.* 2006(5):1177-1184, Wiley-VCH Verlag GmbH & Co. KGaA, Germany (2006).

Grzyb, J.A. and Batey, R.A. "Achieving functional group diversity in parallel synthesis: solution-phase synthesis of a library of ureas, carbamates, thiocarbamates, and amides using carbamoylimidazolium salts," *Tetrahedron Letters* 49:5279-5282, Elsevier Ltd., England (2008).

(Continued)

*Primary Examiner* — Emily Bernhardt
(74) *Attorney, Agent, or Firm* — Sterne, Kessler, Goldstein & Fox P.L.L.C.

(57) ABSTRACT

Pyridinylcarboxylic acid derivatives of the formula (I)

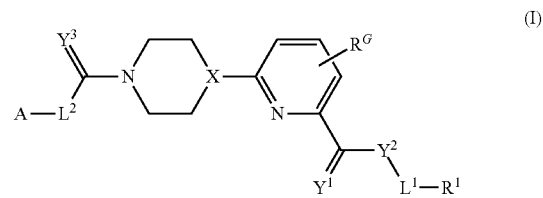

in which the symbols A, X, $Y^1$, $Y^2$, $Y^3$, $L^1$, $L^2$, $R^G$, and $R^1$ are each as defined in the description, and also salts, metal complexes and N-oxides of the compounds of the formula (I), and the use thereof for controlling phytopathogenic harmful fungi and processes for preparing compounds of the formula (I).

13 Claims, No Drawings

(56) References Cited

OTHER PUBLICATIONS

Grzyb, J.A., et al., "Carbamoylimidazolium and thiocarbamoylimidazolium salts: novel reagents for the synthesis of ureas, thioureas, carbamates, thiocarbamates and amides," *Tetrahedron* 61:7153-7175, Elsevier Ltd., England (2005).

Jensen, O.E. and Senning, A., "Studies on Amino Acids and Peptides XII Synthesis of Thiated Analogues of Boc-S-Ala-Aib-S-Ala-OMe and Ac-S-Ala-Aib-S-Ala-OMe," *Tetrahedron* 42(23):6555-6564, Pergamon Journals Ltd., England (1986).

Montalbetti, C.A.G.N. and Falque,V., "Amide bond formation and peptide coupling," *Tetrahedron* 61:10827-10852, Elsevier Ltd., England (2005).

Qiao, J.X., et al., "Highly efficacious factor Xa inhibitors containing α-substituted phenylcycloalkyl P4 moieties," *Bioorganic & Medicinal Chemistry Letters* 19(2): 462-468, Elsevier Ltd., England (2009).

Rodik, R., et al., "Calix[4]arenesulfonylamidines. Synthesis, structure and influence on $Mg^{2+}$, ATP-dependent calcium pumps," *Tetrahedron Letters* 46:7459-7462, Elsevier Ltd., England (2005).

Rouden, J., et al., "Studies toward Labeling Cytisine with [$^{11}$C]Phosgene: Rapid Synthesis of a δ-Lactam Involving a New Chemoselective Lithiation-Annulation Method," *J. Org. Chem.* 69(11): 3787-3793, American Chemical Society, United States (2004).

Schweifer, A. and Hammerschmidt, F.,"Formal and improved synthesis of enantiopure chiral methanol," *Tetrahedron* 64:7605-7610, Elsevier Ltd., United States (2008).

Wardell, J.L., "Preparation of thiols," in *The chemistry of the thiol group*, Part 1, p. 163-269, Patai, S., ed., John Wiley & Sons, Ltd., United States (1974).

English language translation of Draber, W., "Chemie der Pflanzenschutz-und Schadlingsbekampfungsmittel [Chemistry of Plant Protection and Pest Control Agents]," *R. Wegler ed.* 2:1-15, Springer-Verlag, Berlin, Germany (1970).

\* cited by examiner

PYRIDINYLCARBOXYLIC ACID DERIVATIVES AS FUNGICIDES

CROSS REFERENCE TO RELATED APPLICATIONS

This application claims priority to U.S. Provisional Application No. 61/348,981, filed on May 27, 2010, and to European Application No. 10164099.3, filed on May 27, 2010. The contents of both applications are incorporated by reference herein in their entireties.

The invention relates to pyridinylcarboxylic acid derivatives, and to the salts, metal complexes and N-oxides thereof, to the use thereof and to methods and compositions for controlling phytopathogenic harmful fungi in and/or on plants or in and/or on seed of plants, to processes for producing such compositions and treated seed, and to the use thereof for controlling phytopathogenic harmful fungi in agriculture, horticulture and forestry, in animal health, in the protection of materials and in the domestic and hygiene sector. The present invention further relates to a process for preparing pyridinylcarboxylic acid derivatives.

WO-A-2010/008739 describes particular heterocyclically substituted piperidines for the treatment of diabetic diseases.

US-A-2009/0197859 discloses particular piperidinyl derivatives for treatment of diseases of the nervous system.

In addition, it is already known that particular heterocyclically substituted thiazoles can be used as fungicidal crop protection compositions (see WO-A-07/014,290, WO-A-08/013,925, WO-A-08/013,622, WO-A-08/091,594, WO-A-08/091,580, WO-A-09/055,514, WO-A-09/094,407, WO-A-09/094,445, WO-A-09/132,785, WO-A-10/037,479, WO 2010/065579, WO 2010/149275, WO 2010/066353, WO 2011/018401, WO 2011/018415). However, particularly at relatively low application rates, the fungicidal activity of these compounds is not always sufficient.

Since the ecological and economic demands made on modern crop protection compositions are increasing constantly, for example with respect to activity spectrum, toxicity, selectivity, application rate, formation of residues and favourable manufacture, and there can also be problems, for example, with resistances, it is a constant objective to develop novel crop protection compositions, especially fungicides, which have advantages over the known compositions at least in some areas.

It has now been found that, surprisingly, the present pyridinylcarboxylic acid derivatives achieve at least some aspects of the objects mentioned and are suitable for use as crop protection compositions, especially as fungicides.

The invention provides compounds of the formula (I)

$$\text{(I)}$$

in which the radicals are each defined as follows:

A is phenyl which may contain up to three substituents, where the substituents are each independently selected from $Z^{A-1}$, or A is an optionally benzofused, unsubstituted or substituted 5- or 6-membered heteroaryl, where the substituents on the carbon are each independently selected from $Z^{A-2}$ and the substituents on the nitrogen are each independently selected from $Z^{A-3}$, $L^1$ is $(C(R^{L1})_2)_p$, p is 0, 1, 2 or 3, with the proviso that $R^1$ must not be a radical bonded to nitrogen when p is 0, $R^{L1}$ are the same or different and are each independently hydrogen, halogen, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl, $C_1$-$C_4$-haloalkyl or phenyl, with the proviso that $L^1$ may contain not more than two $R^{L1}$ other than hydrogen, $L^2$ is $NR^{L21}$ or $C(R^{L22})_2$, $R^{L21}$ is hydrogen, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_2$-$C_4$-alkoxyalkyl, $C_2$-$C_4$-alkylthioalkyl, $C_2$-$C_4$-alkylsulphonylalkyl, $C_2$-$C_4$-alkylcarbonyl, $C_2$-$C_4$-haloalkylcarbonyl, $C_2$-$C_5$-alkoxycarbonyl, $C_3$-$C_5$-alkoxycarbonylalkyl, $C_2$-$C_5$-alkylaminocarbonyl, $C_3$-$C_5$-dialkylaminocarbonyl, $C_1$-$C_4$-alkylsulphonyl or $C_1$-$C_4$-haloalkylsulphonyl, $R^{L22}$ are the same or different and are each independently hydrogen, $C_1$-$C_4$-alkyl, $C_1$-$C_4$-haloalkyl, cyclopropyl, halogen, or the two $R^{L22}$ radicals, together with the carbon atom to which they are bonded, form a cyclopropyl ring, $Y^1$ and $Y^3$ are the same or different and are each independently sulphur or oxygen, $Y^2$ is —$(NR^{Y2})$—, sulphur or oxygen, $R^{Y2}$ is hydrogen, $C_1$-$C_6$-alkyl, $C_2$-$C_6$-alkenyl, $C_2$-$C_6$-alkynyl, $C_1$-$C_6$-haloalkyl, $C_3$-$C_6$-cycloalkyl, $C_3$-$C_6$-halocycloalkyl, benzyl, phenyl, $NR^3R^4$, $C_1$-$C_4$-alkoxy, $C_1$-$C_4$-haloalkoxy, phenoxy or benzyloxy, or the $R^{Y2}$, $L^1$ and $R^1$ radicals form, together with the nitrogen atom of $Y^2$, a 5- to 15-membered, unsubstituted or substituted, saturated or partly saturated or unsaturated mono-, bi- or tricyclic ring system which may contain up to two further heteroatoms selected from N, O and S, where no two oxygen atoms are adjacent and where possible substituents on the carbon are each independently selected from $Z^{Y-1}$ and where the substituents on the nitrogen are each independently selected from $Z^{Y-2}$, $R^3$ and $R^4$ are the same or different and are each independently hydrogen, $C_1$-$C_4$-alkyl, $C_3$-$C_6$-alkenyl, $C_3$-$C_6$-alkynyl, $C_1$-$C_3$-haloalkyl, $C_3$-$C_6$-cycloalkyl, benzyl or phenyl, X is —$CR^{X1}$— or nitrogen, $R^{X1}$ is hydrogen, halogen, cyano, hydroxyl, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy, $C_2$-$C_4$-carbonylalkoxy, OC(=O)H, C(=O)H, C(=O)OH, $C_2$-$C_4$-alkoxycarbonyl or $C_1$-$C_3$-alkylcarbonyl, $R^G$ is hydrogen, halogen or $C_1$-$C_3$-alkyl, $R^1$ is hydrogen, $C_1$-$C_6$-alkyl, $C_1$-$C_6$-haloalkyl, $C_2$-$C_6$-alkenyl, $C_2$-$C_6$-alkynyl, $C_2$-$C_8$-alkoxyalkyl or $C_5$-$C_9$-cycloalkoxyalkyl, or $R^1$ is unsubstituted or substituted $C_3$-$C_{10}$-cycloalkyl, where the substituents are each independently selected from Q or from $Z^1$, or R$^1$ is unsubstituted or substituted C$_5$-C$_{10}$-cycloalkenyl,
where the substituents are each independently selected from Z$^2$, or R$^1$ is unsubstituted or substituted phenyl,
where the substituents are each independently selected from L$^3$-Q or from Z$^3$, or R$^1$ is unsubstituted or substituted naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 2,3-dihydro-1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl,
where the substituents are each independently selected from Z$^4$, or R$^1$ is an unsubstituted or substituted 5- or 6-membered heteroaryl radical, where the substituents on the carbon are each independently selected from L$^3$-Q or from Z$^5$ and the substituents on the nitrogen are each independently selected from Z$^6$, or R$^1$ is benzofused unsubstituted or substituted 5- or 6-membered heteroaryl, where the substituents on the carbon are each independently selected from Z$^7$ and the substituents on the nitrogen are each independently selected from Z$^8$, or R$^1$ is unsubstituted or substituted C$_5$-C$_{15}$-heterocyclyl, where the substituents on the carbon are each independently selected from Z$^9$ and the substituents on the nitrogen are each independently selected from Z$^{10}$, L$^3$ is a direct bond, —O—, —C(=O)—, —S(O)$_m$—, —CHR$^{L31}$— or —NR$^{L32}$—, m is 0, 1 or 2, R$^{L31}$ is hydrogen, C$_1$-C$_4$-alkyl or C$_1$-C$_4$-haloalkyl, R$^{L32}$ is hydrogen, C$_1$-C$_6$-alkyl, C$_1$-C$_6$-haloalkyl, C$_3$-C$_8$-cycloalkyl, C$_2$-C$_6$-alkylcarbonyl, C$_2$-C$_6$-haloalkylcarbonyl, C$_2$-C$_6$-alkoxycarbonyl or C$_2$-C$_6$-haloalkoxycarbonyl, Q is a phenyl which may contain up to two substituents, where the substituents are the same or different and are each independently selected from the following list:
halogen, cyano, hydroxyl, SH, amino, nitro, NR$^3$R$^4$, C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_2$-C$_6$-haloalkynyl, C$_3$-C$_6$-cycloalkyl, C$_3$-C$_6$-halocycloalkyl, C$_4$-C$_{10}$-alkylcycloalkyl, C$_4$-C$_{10}$-cycloalkylalkyl, C$_6$-C$_{14}$-cycloalkylcycloalkyl, C$_5$-C$_{10}$-alkylcycloalkylalkyl, C$_2$-C$_4$-alkoxyalkyl, C$_2$-C$_4$-alkylcarbonyl, C$_2$-C$_6$-alkoxycarbonyl, C$_2$-C$_6$-alkylaminocarbonyl, C$_3$-C$_8$-dialkylaminocarbonyl, C$_1$-C$_4$-hydroxyalkyl, C$_1$-C$_4$-alkoxy, C$_1$-C$_4$-haloalkoxy, C$_2$-C$_6$-alkylcarbonyloxy, C$_2$-C$_6$-alkylcarbonylthio, C$_1$-C$_4$-alkylthio, C$_1$-C$_4$-haloalkylthio, C$_1$-C$_4$-alkylsulphinyl, C$_1$-C$_4$-haloalkylsulphinyl, C$_1$-C$_4$-alkylsulphonyl, C$_1$-C$_4$-haloalkylsulphonyl or phenyl, or Q is a 5- or 6-membered heteroaryl radical which may contain up to two substituents, where the substituents are the same or different and are each independently selected from the following list:
substituents on carbon: halogen, cyano, hydroxyl, SH, amino, nitro, NR$^3$R$^4$, C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_2$-C$_6$-haloalkynyl, C$_3$-C$_6$-cycloalkyl, C$_3$-C$_6$-halocycloalkyl, C$_4$-C$_{10}$-alkylcycloalkyl, C$_4$-C$_{10}$-cycloalkylalkyl, C$_6$-C$_{14}$-cycloalkylcycloalkyl, C$_5$-C$_{10}$-alkylcycloalkylalkyl, C$_2$-C$_4$-alkoxyalkyl, C$_2$-C$_4$-alkylcarbonyl, C$_2$-C$_6$-alkoxycarbonyl, C$_2$-C$_6$-alkylaminocarbonyl, C$_3$-C$_8$-dialkylaminocarbonyl, C$_1$-C$_4$-hydroxyalkyl, C$_1$-C$_4$-alkoxy, C$_1$-C$_4$-haloalkoxy, C$_2$-C$_6$-alkylcarbonyloxy, C$_2$-C$_6$-alkylcarbonylthio, C$_1$-C$_4$-alkylthio, C$_1$-C$_4$-haloalkylthio, C$_1$-C$_4$-alkylsulphinyl, C$_1$-C$_4$-haloalkylsulphinyl, C$_1$-C$_4$-alkylsulphonyl, C$_1$-C$_4$-haloalkylsulphonyl or phenyl, substituents on nitrogen: C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_2$-C$_6$-haloalkynyl, C$_3$-C$_6$-cycloalkyl, C$_3$-C$_6$-halo-cycloalkyl, C$_4$-C$_{10}$-alkylcycloalkyl, C$_4$-C$_{10}$-cycloalkylalkyl, C$_1$-C$_4$-alkylsulphonyl, C(=O)H, C(=O)Me, C(=O)OMe or phenyl, Z$^{A-1}$ and Z$^3$ are the same or different and are each independently halogen, cyano, hydroxyl, SH, amino, nitro, C(=O)H, C(=O)OH, CONR$^3$R$^4$, NR$^3$R$^4$, C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_2$-C$_6$-haloalkynyl, C$_3$-C$_8$-cycloalkyl, C$_3$-C$_8$-halocycloalkyl, C$_4$-C$_{10}$-alkylcycloalkyl, C$_4$-C$_{10}$-cycloalkylalkyl, C$_6$-C$_{14}$-cycloalkylcycloalkyl, C$_4$-C$_{10}$-halocycloalkylalkyl, C$_5$-C$_{10}$-alkylcycloalkylalkyl, C$_3$-C$_8$-cycloalkenyl, C$_3$-C$_8$-halocycloalkenyl, C$_2$-C$_6$-alkoxyalkyl, C$_4$-C$_{10}$-cycloalkoxyalkyl, C$_3$-C$_8$-alkoxyalkoxyalkyl, C$_2$-C$_6$-alkylthioalkyl, C$_2$-C$_6$-alkylsulphinylalkyl, C$_2$-C$_6$-alkylsulphonylalkyl, C$_2$-C$_6$-alkylaminoalkyl, C$_3$-C$_8$-dialkylaminoalkyl, C$_2$-C$_6$-haloalkylaminoalkyl, C$_4$-C$_{10}$-cycloalkylaminoalkyl, C$_2$-C$_6$-alkylcarbonyl, C$_2$-C$_6$-haloalkylcarbonyl, C$_4$-C$_8$-cycloalkylcarbonyl, C$_2$-C$_6$-alkoxycarbonyl, C$_4$-C$_8$-cycloalkoxycarbonyl, C$_5$-C$_{10}$-cycloalkylalkoxycarbonyl, C$_2$-C$_6$-alkylaminocarbonyl, C$_3$-C$_8$-dialkylaminocarbonyl, C$_4$-C$_8$-cycloalkylaminocarbonyl, C$_2$-C$_6$-haloalkoxyalkyl, C$_1$-C$_6$-hydroxyalkyl, C$_1$-C$_6$-alkoxy, C$_1$-C$_6$-haloalkoxy, C$_3$-C$_8$-cycloalkoxy, C$_3$-C$_8$-halocycloalkoxy, C$_4$-C$_{10}$-cycloalkylalkoxy, C$_3$-C$_6$-alkenyloxy, C$_3$-C$_6$-haloalkenyloxy, C$_3$-C$_6$-alkynyloxy, C$_3$-C$_6$-haloalkynyloxy, C$_2$-C$_6$-alkoxyalkoxy, C$_2$-C$_6$-alkylcarbonyloxy, C$_2$-C$_6$-haloalkylcarbonyloxy, C$_4$-C$_8$-cycloalkylcarbonyloxy, C$_3$-C$_6$-alkylcarbonylalkoxy, C$_1$-C$_6$-alkylthio, C$_1$-C$_6$-haloalkylthio, C$_3$-C$_6$-cycloalkylthio, C$_1$-C$_6$-alkylsulphinyl, C$_1$-C$_6$-haloalkylsulphinyl, C$_1$-C$_6$-alkylsulphonyl, C$_1$-C$_6$-haloalkylsulphonyl, C$_3$-C$_8$-cycloalkylsulphonyl, tri(C$_1$-C$_4$-alkyl)silyl, C$_1$-C$_6$-alkylsulphonylamino, C$_1$-C$_6$-haloalkylsulphonylamino or SF$_5$, Z$^1$ and Z$^2$ are the same or different and are each independently cyano, halogen, C$_1$-C$_6$-alkyl, C$_1$-C$_6$-haloalkyl, C$_3$-C$_6$-cycloalkyl, C$_2$-C$_6$-alkenyl, C$_2$-C$_6$-haloalkenyl, C$_2$-C$_6$-alkynyl, C$_2$-C$_6$-haloalkynyl, hydroxyl, oxo, C$_1$-C$_6$-alkoxy, C$_1$-C$_6$-haloalkoxy, C$_2$-C$_6$-alkenyloxy, C$_2$-C$_6$-alkynyloxy, C$_1$-C$_6$-alkylthio or C$_1$-C$_6$-haloalkylthio, C$_2$-C$_4$-alkylcarbonyl, or C$_2$-C$_6$-alkylcarbonyloxy, Z$^4$ and Z$^7$ are the same or different and are each independently halogen, cyano, hydroxyl, SH, amino, nitro, NR$^3$R$^4$, C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_2$-C$_6$-haloalkynyl, C$_3$-C$_6$-cycloalkyl, C$_3$-C$_6$-halo-cycloalkyl, C$_2$-C$_4$-alkoxyalkyl, C$_2$-C$_4$-alkylcarbonyl, C$_2$-C$_6$-alkoxycarbonyl, C$_2$-C$_6$-alkylaminocarbonyl, C$_3$-C$_8$-dialkylaminocarbonyl, C$_1$-C$_4$-hydroxyalkyl, C$_1$-C$_4$-alkoxy, C$_1$-C$_4$-haloalkoxy, C$_2$-C$_6$-alkylcarbonyloxy, C$_2$-C$_6$-alkylcarbonylthio, C$_1$-C$_4$-alkylthio, C$_1$-C$_4$-haloalkylthio, C$_1$-C$_4$-alkylsulphinyl, C$_1$-C$_4$-haloalkylsulphinyl, C$_1$-C$_4$-alkylsulphonyl or C$_1$-C$_4$-haloalkylsulphonyl, $Z^{4-2}$ and $Z^5$ are the same or different and are each independently halogen, cyano, hydroxyl, SH, amino, nitro, $NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_8$-haloalkynyl, $C_3$-$C_6$-cycloalkyl, $C_3$-$C_6$-halo-cycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_3$-$C_6$-alkenyloxy, $C_3$-$C_6$-alkynyloxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl or $C_1$-$C_4$-haloalkylsulphonyl, $Z^{4-3}$, $Z^{Y-2}$, $Z^6$, $Z^8$, and $Z^{10}$ are the same or different and are each independently $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, phenyl, benzyl, $C_1$-$C_4$-alkylsulphonyl, $C(=O)H$, $C_2$-$C_4$-alkylcarbonylalkoxy or $C_1$-$C_3$-alkylcarbonyl, $Z^{Y-1}$ and $Z^9$ are the same or different and are each independently hydroxyl, cyano, halogen, SH, amino, nitro, oxo, $NR^3R^4$, $C_1$-$C_6$-alkyl, $C_1$-$C_6$-haloalkyl, $C_3$-$C_6$-Cycloalkyl, $C_2$-$C_6$-alkenyl, $C_2$-$C_6$-haloalkenyl, $C_2$-$C_8$-alkynyl, $C_2$-$C_6$-haloalkynyl, phenyl, $C_1$-$C_6$-alkoxy, $C_1$-$C_6$-haloalkoxy, $C_2$-$C_6$-alkenyloxy, $C_2$-$C_6$-alkynyloxy, $C_1$-$C_8$-alkylthio or $C_1$-$C_6$-haloalkylthio, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_2$-$C_6$-alkylcarbonyloxy, $C_2$-$C_6$-alkylcarbonylthio, $C_1$-$C_4$-alkylsulphinyl, $C_1$-$C_4$-haloalkylsulphinyl, $C_1$-$C_4$-alkylsulphonyl or $C_1$-$C_4$-haloalkylsulphonyl, and salts, metal complexes and N-oxides of the compounds of the formula (I).

The invention further provides for the use of the compounds of the formula (I) as fungicides.

Inventive pyridinylcarboxylic acid derivatives of the formula (I) and the salts, metal complexes and N-oxides thereof are very suitable for controlling phytopathogenic harmful fungi. The aforementioned inventive compounds exhibit, in particular, potent fungicidal efficacy and can be used in crop protection, in the domestic and hygiene sector and in the protection of materials.

The compounds of the formula (I) may be present either in pure form or as mixtures of various possible isomeric forms, especially of stereoisomers, such as E and Z, threo and erythro, and also optical isomers, such as R and S isomers or atropisomers, and, if appropriate, also of tautomers. Both the E and the Z isomers are claimed, as are the threo and erythro isomers, and also the optical isomers, all mixtures of these isomers, and also the possible tautomeric forms.

The radical definitions of the inventive compounds of the formula (I) have preferred, more preferred and most preferred definitions:

A is preferably phenyl which may contain up to two substituents, where the substituents are each independently selected from $Z^{A-1}$, or A is preferably a heteroaromatic radical selected from the following group: furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,3-triazol-1-yl, 1,2,4-triazol-1-yl, pyridin-2-yl, pyridin-3-yl, pyridin-4-yl, pyridazin-3-yl, pyridazin-4-yl, pyrazin-2-yl, pyrazin-3-yl, pyrimidin-2-yl, pyrimidin-4-yl or pyrimidin-5-yl, which may contain up to two substituents, where the substituents on the carbon are each independently selected from $Z^{A-2}$, and the substituents on the nitrogen are each independently selected from $Z^{A-3}$, A is more preferably phenyl which may contain up to two substituents, where the substituents are each independently selected from the following list:
fluorine, bromine, iodine, chlorine, cyano, nitro, methyl, ethyl, propyl, 1-methylethyl, 1,1-dimethylethyl, chlorofluoromethyl, dichloromethyl, dichlorofluoromethyl, difluoromethyl, trichloromethyl, trifluoromethyl, cyclopropyl, ethoxy, 1-methylethoxy, propoxy, methoxy, trifluoromethoxy, difluoromethoxy, 1-methylethylthio, methylthio, ethylthio, propylthio, difluoromethylthio or trifluoromethylthio, or A is more preferably a heteroaromatic radical selected from the following group: furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,3-triazol-1-yl, 1,2,4-triazol-1-yl, pyridin-2-yl, pyridin-3-yl, pyridin-4-yl, pyridazin-3-yl, pyridazin-4-yl, pyrimidin-2-yl, pyrimidin-4-yl or pyrimidin-5-yl, which may contain up to two substituents, where the substituents are the same or different and are each independently selected from the following list:
substituents on carbon:
fluorine, chlorine, bromine, iodine, cyano, nitro, methyl, ethyl, propyl, 1-methylethyl, 1,1-dimethylethyl, chlorofluoromethyl, dichloromethyl, dichlorofluoromethyl, difluoromethyl, trichloromethyl, trifluoromethyl, cyclopropyl, ethoxy, 1-methylethoxy, propoxy, methoxy, trifluoromethoxy, difluoromethoxy, 1-methylethylthio, methylthio, ethylthio, propylthio, difluoromethylthio, trifluoromethylthio or phenyl,
substituents on nitrogen:
methyl, ethyl, propyl, 1-methylethyl, 2,2-trifluoroethyl, 2,2-difluoroethyl, 2,2-dichloro-2-fluoroethyl, 2-chloro-2-difluoroethyl or 2-chloro-2-fluoroethyl, A is most preferably pyrazol-1-yl which may contain up to two substituents, where the substituents are each independently selected from the following list:
methyl, difluoromethyl or trifluoromethyl, or A is most preferably phenyl which may contain up to two substituents, where the substituents are each independently selected from the following list:
methyl, ethyl, iodine, chlorine, bromine, fluorine, methoxy, ethoxy, difluoromethyl or trifluoromethyl, $L^1$ is preferably a direct bond, $-CH_2-$, $-CHCH_3-$, $CH_2CH_2CH_2-$ or $-CH_2C\equiv C-$, $L^2$ is preferably $CHR^{L22}$, $NR^{L21}$ and more preferably $CH_2$, $R^{L21}$ is preferably hydrogen, methyl, ethyl or cyclopropyl and more preferably hydrogen or methyl, $R^{L22}$ is preferably hydrogen or methyl and more preferably hydrogen, $Y^1$ is preferably oxygen or sulphur and more preferably oxygen, $R^{Y2}$ is preferably hydrogen, $C_1$-$C_6$-alkyl, $C_2$-$C_6$-alkenyl, $C_2$-$C_6$-alkynyl, $C_1$-$C_6$-haloalkyl, $C_3$-$C_6$-cycloalkyl, $C_3$-$C_6$-halocycloalkyl, benzyl or phenyl, Or the $R^{Y2}$, $L^1$ and $R^1$ radicals form, together with the nitrogen atom of $Y^2$, a 5- to 15-membered, unsubstituted saturated or partly saturated or unsaturated mono-, bi- or tricyclic ring system which may contain up to two further heteroatoms selected from N, O and S, where no two oxygen atoms are adjacent and where possible substituents on the carbon are each independently selected from $Z^{Y-1}$ and where the substituents on the nitrogen are each independently selected from $Z^{Y-2}$, $R^{Y2}$ is more preferably hydrogen, methyl, ethyl, propyl, 1-methylethyl, prop-2-enyl, 1-methylprop-2-enyl, ethynyl, prop-2-ynyl, 2,2,2-trifluoroethyl, cyclopropyl, 1-chlorocyclopropyl, benzyl or phenyl, or the $R^{Y2}$, $L^1$ and $R^1$ radicals, more preferably together with the nitrogen atom of $Y^2$, form piperidine, morpholine, thiomorpholine, 2,3-dihydro-4H-1,4-oxazine, 2,3-dihydro-4H-1,4-benzoxazine, or 1,2,3,4-tetrahydroquinoline, $R^{Y2}$ is most preferably hydrogen, methyl or cyclopropyl, or the $R^{Y2}$, $L^1$ and $R^1$ radicals, most preferably together with the nitrogen atom of $Y^2$, form 2,3-dihydro-4H-1,4-benzoxazin-4-yl, $R^3$, $R^4$ are preferably the same or different and are each independently hydrogen, methyl, ethyl, propyl, isopropyl, butyl, isobutyl or tert-butyl, X is preferably —$CR^{X1}$— or nitrogen and more preferably —CH—, —CF— or nitrogen and most preferably —CH— or nitrogen, $R^{X1}$ is preferably hydrogen, halogen, cyano, hydroxyl, $C_1$-$C_4$-alkoxy, $C_1$-$C_4$-haloalkoxy or $C_2$-$C_4$-carbonylalkoxy, $R^G$ is preferably hydrogen or halogen and more preferably hydrogen, $R^1$ is preferably hydrogen, $C_1$-$C_6$-alkyl, $C_1$-$C_6$-haloalkyl, $C_2$-$C_6$-alkenyl or $C_2$-$C_6$-alkynyl and more preferably hydrogen, 1,1-dimethylethyl, 3,3-dimethylbutyl, 2,2-dimethylpropyl, 1,2,2-trimethylpropyl, n-pentyl, 1-ethylpropyl, n-butyl, 2-methylpropyl, 1-methylethyl, ethyl, n-propyl, 4-methylpentyl, n-hexyl, trifluoromethyl, methoxymethyl, ethoxymethyl, ethenyl, prop-2-en-1-yl or but-3-en-1-yl, or $R^1$ is preferably unsubstituted or substituted $C_3$-$C_{10}$-cycloalkyl, where the substituents are each independently selected from -Q or from $Z^1$, and more preferably cyclopentyl, cyclohexyl, cycloheptyl or cyclooctyl, each of which may contain up to two substituents, where the substituents are each independently selected from the following list:
cyano, chlorine, fluorine, bromine, iodine, methyl, ethyl, propyl, 1-methylethyl, 1,1-dimethylethyl, ethenyl, 2-propenyl, 2-propynyloxy, phenyl, methoxy, ethoxy, propyloxy, trifluoromethoxy, ethynyl, 2-propynyloxy, methylthio, ethylthio or trifluoromethylthio, $R^1$ is most preferably cyclopentyl, cyclohexyl, cycloheptyl or cyclooctyl, which may contain up to two substituents, where the substituents are each independently selected from the following list: methyl or fluoro, or $R^1$ is preferably unsubstituted or substituted $C_5$-$C_6$-cycloalkenyl, where the substituents are each independently selected from $Z^2$, and more preferably cyclopentenyl, cyclohexenyl or cycloheptenyl, each of which may contain up to two substituents, where the substituents are each independently selected from the following list: methyl, ethyl, methoxy, ethoxy, trifluoromethoxy, ethynyl, 2-propynyloxy, methylthio, ethylthio or trifluoromethylthio and most preferably cyclopent-2-en-1-yl, cyclopent-3-en-1-yl, cyclohex-1-en-1-yl, cyclohex-2-en-1-yl, cyclohex-3-en-1-yl, cyclohept-1-en-1-yl, cyclohept-2-en-1-yl, cyclohept-3-en-1-yl or cyclohept-4-en-1-yl, or $R^1$ is preferably unsubstituted or substituted phenyl, where the substituents are each independently selected from $L^3$-Q or from $Z^3$, and more preferably phenyl which may contain up to three substituents, where the substituents are each independently selected from the following list: fluorine, chlorine, bromine, iodine, cyano, nitro, methyl, ethyl, propyl, 1-methylethyl, butyl, 1,1-dimethylethyl, 1,2-dimethylethyl, ethenyl, ethynyl, trifluoromethyl, difluoromethyl, trichloromethyl, dichloromethyl, cyclopropyl, methoxy, ethoxy, propoxy, 1-methylethoxy, 1,1-dimethylethoxy, methylcarbonyl, ethylcarbonyl, trifluoromethylcarbonyl, methoxycarbonyl, ethoxycarbonyl, propoxycarbonyl, 1-methylethoxycarbonyl, 1,1-dimethylethoxycarbonyl, 2-propynyloxy, methylthio, ethylthio, methylsulphinyl or methylsulphonyl or -$L^3$Q, most preferably phenyl which may contain up to three substituents, where the substituents are each independently selected from the following list: fluorine, chlorine, bromine, iodine, cyano, nitro, methyl, ethyl, propyl, 1-methylethyl, butyl, 1,1-dimethylethyl, 1,2-dimethylethyl, ethenyl, ethynyl, trifluoromethyl, difluoromethyl, trichloromethyl, dichloromethyl, cyclopropyl, methoxy, ethoxy, propoxy, 1-methylethoxy, 1,1-dimethylethoxy, methylcarbonyl, ethylcarbonyl, trifluoromethylcarbonyl, methoxycarbonyl, ethoxycarbonyl, propoxycarbonyl, 1-methylethoxycarbonyl, 1,1-dimethylethoxycarbonyl, 2-propynyloxy, methylthio, ethylthio, methylsulphinyl or methylsulphonyl, or $R^1$ is preferably unsubstituted or substituted naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 2,3-dihydro-1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl,
where the substituents are each independently selected from $Z^4$ and are more preferably unsubstituted or substituted naphthalen-1-yl, naphthalen-2-yl, 5,6,7,8-tetrahydronaphthalen-1-yl or 5,6,7,8-tetrahydronaphthalen-2-yl, where the substituents are each independently selected from the following list: methyl, methoxy, cyano, fluorine, chlorine, bromine, iodine, where not more than three substituents are present in the particularly preferred variant and most preferably no substituents are present, or $R^1$ is preferably an unsubstituted or substituted 5- or 6-membered heteroaryl radical, where the substituents on the carbon are each independently selected from $L^3$-Q or from $Z^5$, and the substituents on the nitrogen are each independently selected from $Z^6$, and more preferably furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl or pyrazin-2-yl, each of which may contain up to two substituents, where the substituents are each independently selected from the following list:

substituents on carbon: chlorine, fluorine, bromine, iodine, cyano, nitro, methyl, ethyl, propyl, 1-methylethyl, butyl, 1,1-dimethylethyl, ethenyl, ethynyl, trifluoromethyl, difluoromethyl, cyclopropyl, cyclopentyl, cyclohexyl, methylcarbonyl, ethylcarbonyl, methoxycarbonyl, ethoxycarbonyl, methoxy, ethoxy, propoxy, 1-methylethoxy, 2-propynyloxy, trifluoromethoxy, methylcarbonyloxy, methylcarbonylthio, methylthio, ethylthio, trifluoromethylthio, methylsulphinyl, ethylsulphinyl, trifluoromethylsulphinyl, methylsulphonyl, ethylsulphonyl or trifluoromethylsulphonyl, substituents on nitrogen: methyl, ethyl, propyl, cyclopropyl, cyclohexyl, phenyl or 2-propynyl, and most preferably no substituents are present on the heteroaryl radicals, or $R^1$ is preferably benzofused unsubstituted or substituted 5- or 6-membered heteroaryl, where the substituents on the carbon are each independently selected from $Z^7$ and the substituents on the nitrogen are each independently selected from $Z^8$, and more preferably indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl, each of which may contain up to two substituents, where the substituents are each independently selected from the following list:

substituents on carbon: fluorine, chlorine, bromine, iodine, methyl, methoxy, 2-propynyloxy, 2-propenyloxy, substituents on nitrogen: methyl, ethyl, propyl, cyclopropyl, cyclohexyl, phenyl or 2-propynyl, and most preferably no substituents are present on the benzofused heteroaryl radicals, or $R^1$ is preferably unsubstituted or substituted $C_5$-$C_{15}$-heterocyclyl, where the substituents on the carbon are each independently selected from $Z^9$ and the substituents on the nitrogen are each independently selected from $Z^{10}$, and more preferably piperidin-1-yl, piperidin-2-yl, piperidin-3-yl, piperidin-4-yl, piperazin-1-yl, piperazin-2-yl, piperazin-3-yl, morpholin-1-yl, morpholin-2-yl, morpholin-3-yl, tetrahydropyran-2-yl, tetrahydropyran-3-yl, tetrahydropyran-4-yl, 1,2,3,4-tetrahydroquinolin-1-yl, 1,2,3,4-tetrahydroisoquinolin-2-yl, 1,2,3,4-tetrahydroquinoxalin-1-yl, indolin-1-yl, isoindolin-2-yl, decahydroquinolin-1-yl or decahydroisoquinolin-2-yl, each of which may contain up to two substituents, where the substituents are each independently selected from the following list:

substituents on carbon: fluorine, chlorine, bromine, iodine, methyl, methoxy, 2-propynyloxy, 2-propenyloxy, substituents on nitrogen: methyl, ethyl, propyl, cyclopropyl, cyclohexyl, phenyl or 2-propynyl, and most preferably no substituents are present on the heterocyclyl radicals, Q is preferably phenyl which may contain up to two substituents, where the substituents are the same or different and are each independently selected from the following list:

fluorine, chlorine, bromine, iodine, cyano, hydroxyl, SH, nitro, $C_1$-$C_6$-alkyl, $C_1$-$C_6$-haloalkyl, $C_3$-$C_6$-cycloalkyl, $C_1$-$C_4$-alkoxy, $C_1$-$C_4$-haloalkoxy, $C_1$-$C_4$-alkylthio or $C_1$-$C_4$-haloalkylthio, and Q is more preferably unsubstituted phenyl, and Q is most preferably only unsubstituted phenyl, or Q is preferably furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, tetrazol-5-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, tetrazol-5-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl or 1,2,4-triazin-3-yl which may contain up to two substituents, where the substituents are each independently selected from the following list:

substituents on carbon:

fluorine, chlorine, bromine, iodine, cyano, hydroxyl, SH, nitro, $C_1$-$C_6$-alkyl, $C_1$-$C_6$-haloalkyl, $C_3$-$C_6$-cycloalkyl, $C_1$-$C_4$-alkoxy, $C_1$-$C_4$-haloalkoxy, $C_1$-$C_4$-alkylthio or $C_1$-$C_4$-haloalkylthio, substituents on nitrogen: $C_1$-$C_6$-alkyl, $C_2$-$C_6$-alkenyl, $C_2$-$C_6$-alkynyl, $C_3$-$C_6$-cycloalkyl or phenyl, $Z^{A-1}$ is preferably halogen, cyano, hydroxyl, amino, nitro, $C_1$-$C_6$-alkyl, $C_2$-$C_6$-alkenyl, $C_2$-$C_6$-alkynyl, $C_3$-$C_8$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-alkylsulphonyl, $C_1$-$C_4$-haloalkylthio, $C_1$-$C_4$-haloalkylsulphonyl, $C_2$-$C_4$-alkoxyalkyl, $C_1$-$C_4$-hydroxyalkyl, $C_2$-$C_5$-alkylcarbonyl, $C_2$-$C_6$-alkoxycarbonyl, $C_2$-$C_6$-alkylcarbonyloxy or C(=O)H, $Z^{A-2}$ is preferably halogen, cyano, hydroxyl, amino, nitro, $C_1$-$C_8$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-alkylsulphonyl, $C_1$-$C_4$-haloalkylthio, $C_1$-$C_4$-haloalkylsulphonyl, $C_2$-$C_4$-alkoxyalkyl, $C_1$-$C_4$-hydroxyalkyl, $C_2$-$C_4$-alkylcarbonyl, $C_2$-$C_6$-alkoxycarbonyl or $C_2$-$C_6$-alkylcarbonyloxy, $Z^{A-3}$, $Z^{Y-2}$, $Z^6$, $Z^8$ and $Z^{19}$ are the same or different and are preferably each independently $C_1$-$C_6$-alkyl, $C_2$-$C_8$-alkenyl, $C_2$-$C_6$-alkynyl, $C_1$-$C_6$-haloalkyl, $C_2$-$C_6$-haloalkenyl, $C_2$-$C_6$-haloalkynyl, $C_4$-$C_{10}$-cycloalkylalkyl, phenyl, benzyl, $C_1$-$C_4$-alkylsulphonyl, C(=O)H, or $C_1$-$C_3$-alkylcarbonyl, $Z^{Y-1}$ and $Z^9$ are the same or different and are preferably each independently cyano, halogen, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, phenyl, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio, $NR^3R^4$, $C_2$-$C_4$-alkylcarbonyl, $C_2$-$C_6$-alkoxycarbonyl, $C_3$-$C_8$-dialkylaminocarbonyl, $C_2$-$C_6$-alkylcarbonyloxy or $C_1$-$C_6$-haloalkylthio, $Z^1$ and $Z^2$ are the same or different and are preferably each independently cyano, halogen, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, hydroxyl, oxo, $C_1$-$C_6$-alkoxy, $C_1$-$C_6$-haloalkoxy, $C_3$-$C_6$-alkenyloxy, $C_3$-$C_6$-alkynyloxy, $C_1$-$C_6$-alkylthio or $C_1$-$C_6$-haloalkylthio, $Z^3$ is preferably halogen, cyano, hydroxyl, nitro, $CONR^3R^4$, $NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_3$-$C_8$-cycloalkenyl, $C_3$-$C_8$-halocycloalkenyl, $C_2$-$C_6$-alkoxyalkyl, $C_2$-$C_6$-alkylcarbonyl, $C_2$-$C_6$-haloalkylcarbonyl, $C_4$-$C_8$-cycloalkylcarbonyl, $C_2$-$C_6$-alkoxycarbonyl, $C_4$-$C_8$-cycloalkoxycarbonyl, $C_2$-$C_6$-alkylaminocarbonyl, $C_3$-$C_8$-Dialkylaminocarbonyl, $C_4$-$C_8$-cycloalkylaminocarbonyl, $C_1$-$C_6$-alkoxy, $C_1$-$C_6$-haloalkoxy, $C_3$-$C_8$-cycloalkoxy, $C_3$-$C_8$-halocycloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_2$-$C_6$-alkoxyalkoxy, $C_2$-$C_6$-alkylcarbonyloxy, $C_2$-$C_6$-haloalkylcarbonyloxy, $C_4$-$C_8$-cycloalkylcarbonyloxy, $C_3$-$C_6$-alkylcarbonylalkoxy, $C_1$-$C_6$-alkylthio, $C_1$-$C_6$-haloalkylthio, $C_3$-$C_6$-cycloalkylthio, $C_1$-$C_6$-alkylsulphonyl, $C_1$-$C_6$-haloalkylsulphonyl, $C_3$-$C_8$-cycloalkylsulphonyl, $C_1$-$C_6$-alkylsulphonylamino, $C_1$-$C_6$-haloalkylsulphonylamino, $Z^4$ and $Z^7$ are the same or different and are preferably each independently halogen, cyano, nitro, $NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-haloalkylthio, $C_1$-$C_4$-alkylsulphonyl, $C_1$-$C_4$-haloalkylsulphonyl, $Z^5$ is preferably halogen, cyano, nitro, $NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_2$-$C_4$-alkoxyalkyl, $C_3$-$C_6$-alkenyloxy, $C_3$-$C_6$-alkynyloxy, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphonyl, $C_1$-$C_4$-haloalkylsulphonyl.

The pyridinylcarboxylic acid derivatives usable in accordance with the invention are defined in general terms by the formula (I). The radical definitions above and specified below of the formula (I) apply to the end products of the formula (I), and also equally to all intermediates (see also below under "Explanations of the processes and intermediates").

The radical definitions and elucidations listed above and below, in general terms or in areas of preference, can also be combined with one another as desired, i.e. including combinations between the particular areas and areas of preference. They apply to the end products and correspondingly to the precursors and intermediates. In addition, individual definitions may not apply.

Preference is given to compounds of the formula (I) in which all radicals each have the preferred definitions specified above.

Particular preference is given to those compounds of the formula (I) in which all radicals each have the more preferred definitions specified above.

Very particular preference is given to those compounds of the formula (I) in which all radicals each have the most preferred definitions specified above.

Preference is also given to compounds of the formula (I) in which A is 3,5-bis-(difluoromethyl)-1H-pyrazol-1-yl, Preference is also given to compounds of the formula (I) in which A is 5-methyl-3-(trifluoromethyl)-1H-pyrazol-1-yl, Preference is also given to compounds of the formula (I) in which $Y^1$ is oxygen.

Preference is also given to compounds of the formula (I) in which $Y^2$ is oxygen.

Preference is also given to compounds of the formula (I) in which $Y^2$ is sulphur.

Preference is also given to compounds of the formula (I) in which $Y^3$ is oxygen.

Preference is also given to compounds of the formula (I) in which X is CH.

Preference is also given to compounds of the formula (I) in which X is nitrogen.

Preference is also given to compounds of the formula (I) in which $R^G$ is hydrogen.

Preference is also given to compounds of the formula (I) in which $L^1$ is a direct bond.

Preference is also given to compounds of the formula (I) in which $L^1$ is —$CH_2$—.

Preference is also given to compounds of the formula (I) in which $L^2$ is —$CH_2$—.

Preference is also given to compounds of the formula (I) in which $R^1$ is cyclohexyl.

Preference is also given to compounds of the formula (I) in which $R^1$ is 1,2,3,4-tetrahydronaphthalen-1-yl, Preference is also given to compounds of the formula (I) in which $R^1$ is (1R)-1,2,3,4-tetrahydronaphthalen-1-yl, Preference is also given to compounds of the formula (I) in which $R^1$ is naphthalen-1-yl, Preference is also given to compounds of the formula (I) in which $R^1$ is naphthalen-2-yl, Preference is also given to compounds of the formula (I) in which $R^1$ is 2,3-dihydro-1H-inden-1-yl, Preference is also given to compounds of the formula (I) in which $R^1$ is 2-bromophenyl.

Preference is also given to compounds of the formula (I) in which $R^1$ is 2,6-difluorophenyl.

Preference is also given to compounds of the formula (I) in which $R^1$ is 2-(trifluoromethoxy)phenyl.

Preference is also given to compounds of the formula (I) in which $R^1$ is 2-(trifluoromethyl)phenyl.

Preference is also given to compounds of the formula (I) in which $R^1$ is 2-chlorophenyl.

Preference is also given to compounds of the formula (I) in which $R^1$ is 2,4-dichlorophenyl.

Preference is also given to compounds of the formula (I) in which $R^1$ is pyridin-2-yl, Preference is also given to compounds of the formula (I) in which $R^1$ is thiophen-2-yl, Preference is also given to compounds of the formula (I) in which $R^1$ is quinolin-8-yl, Preference is also given to compounds of the formula (I) in which $R^1$ is cyclohex-2-en-1-yl.

Preference is also given to compounds of the formula (I) in which $R^1$ is 2,4-difluorophenyl.

Preference is also given to compounds of the formula (I) in which $R^1$ is 2,4,6-trifluorophenyl.

Preference is also given to compounds of the formula (I) in which $R^1$ is 2-methylphenyl.

Preference is also given to compounds of the formula (I) in which $R^1$ is 2-(trifluoromethyl)phenyl.

Preference is also given to compounds of the formula (I) in which $R^1$ is 2-fluorophenyl.

Preference is also given to compounds of the formula (I) in which $R^1$ is 4-fluorophenyl.

Preference is also given to compounds of the formula (I) in which $R^1$ is phenyl.

Preference is also given to compounds of the formula (I) in which $R^1$ is 1,2,3,4-tetrahydronaphthalen-8-yl, Preference is also given to compounds of the formula (I) in which $R^1$ is 2-fluorocyclohexyl.

Preference is also given to compounds of the formula (I) in which $R^1$ is 3-methylpyridin-2-yl.

Preference is also given to compounds of the formula (I) in which $R^1$ is 4-methylthiophen-2-yl, Preference is also given to compounds of the formula (I) in which $R^1$ is 2-methylcyclohexyl.

Preference is also given to compounds of the formula (I) in which $Y^2L^1R^1$ is 2,3-dihydro-4H-1,4-benzoxazin-4-yl, Preference is also given to compounds of the formula (I) in which $R^1$ is $CF_3$ and $L^1$ is —$(CH_2)_3$—.

Preference is also given to compounds of the formula (I) in which $R^1$ is pentyl and L' is —$CH(CH_3)$—.

Preference is also given to compounds of the formula (I) in which $R^1$ is butyl and L' is —$(CH_2)_3$—

Preference is also given to compounds of the formula (I) in which $R^1$ is tert-butyl and $L^1$ is Preference is also given to compounds of the formula (I) in which $R^1$ is but-3-en-1-yl and $L^1$ is —$(CH_2)_2$—.

Preference is also given to compounds of the formula (I) in which $R^1$ is pentyl and $L^1$ is —$(CH_2)_2$—.

Preference is also given to compounds of the formula (I) in which $R^1$ is methoxymethyl and $L^1$ is —$CH_2$—.

Preference is also given to compounds of the formula (Ix):

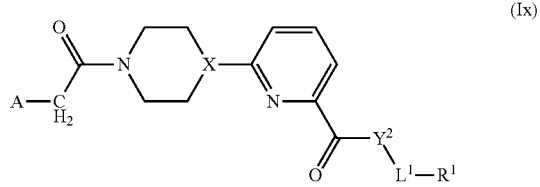

(Ix)

in which A, X, $Y^2$, $L^1$ and $R^1$ each independently have the general, preferred, more preferred or most preferred definitions specified above for the compound of the formula (I).

The radical definitions specified above can be combined with one another as desired. In addition, individual definitions may not apply.

According to the type of substituents defined above, the compounds of the formula (I) have acidic or basic properties and can form salts, possibly also internal salts or adducts, with inorganic or organic acids or with bases or with metal ions. If the compounds of the formula (I) bear amino, alkylamino or other groups which induce basic properties, these compounds can be reacted with acids to give salts, or they are obtained directly as salts by the synthesis. If the compounds of the formula (I) bear hydroxyl, carboxyl or other groups which induce acidic properties, these compounds can be reacted with bases to give salts. Suitable bases are, for example, hydroxides, carbonates, hydrogencarbonates of the alkali metals and alkaline earth metals, especially those of sodium, potassium, magnesium and calcium, and also ammonia, primary, secondary and tertiary amines having $C_1$-$C_4$-alkyl groups, mono-, di- and trialkanolamines of $C_1$-$C_4$-alkanols, choline and chlorocholine.

The salts obtainable in this way likewise have fungicidal properties.

Examples of inorganic acids are hydrohalic acids, such as hydrogen fluoride, hydrogen chloride, hydrogen bromide and hydrogen iodide, sulphuric acid, phosphoric acid and nitric acid, and acidic salts, such as $NaHSO_4$ and $KHSO_4$. Useful organic acids include, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated $C_6$-$C_{20}$ fatty acids, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

Useful metal ions are especially the ions of the elements of the second main group, especially calcium and magnesium, of the third and fourth main group, especially aluminium, tin and lead, and also of the first to eighth transition groups, especially chromium, manganese, iron, cobalt, nickel, copper, zinc and others. Particular preference is given to the metal ions of the elements of the fourth period. The metals may be present in the different valencies that they can assume.

Optionally substituted groups may be mono- or polysubstituted, and the substituents in the case of polysubstitutions may be identical or different.

The definitions of the symbols given in the above formulae used collective terms which are generally representative of the following substituents:

halogen: fluorine, chlorine, bromine and iodine;

alkyl: saturated, straight-chain or branched hydrocarbon radicals having 1 to 8 carbon atoms, for example (but not limited to) $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methyl-propyl;

alkenyl: unsaturated, straight-chain or branched hydrocarbon radicals having 2 to 8 carbon atoms and a double bond in any position, for example (but not limited to) $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1- dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups having 2 to 8 carbon atoms and a triple bond in any position, for example (but not limited to) $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

alkoxy: saturated, straight-chain or branched alkoxy radicals having 1 to 8 carbon atoms, for example (but not limited to) $C_1$-$C_6$-alkoxy, such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-di-methylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-tri-methylpropoxy, 1-ethyl-1-methylpropoxy and 1-ethyl-2-methylpropoxy;

alkylthio: saturated, straight-chain or branched alkylthio radicals having 1 to 8 carbon atoms, for example (but not limited to) $C_1$-$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methyl-butylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

alkoxycarbonyl: an alkoxy group which has 1 to 6 carbon atoms (as specified above) and is attached to the skeleton via a carbonyl group (—CO—);

alkylsulphinyl: saturated, straight-chain or branched alkylsulphinyl radicals having 1 to 8 carbon atoms, for example (but not limited to) $C_1$-$C_6$-alkylsulphinyl, such as methylsulphinyl, ethylsulphinyl, propylsulphinyl, 1-methylethylsulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropyl sulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentylsulphinyl, 3-methylpentylsulphinyl, 4-methylpentylsulphinyl, 1,1-dimethylbutylsulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutylsulphinyl, 2-ethylbutylsulphinyl, 1,1,2-trimethylpropylsulphinyl, 1,2,2-tri-methylpropylsulphinyl, 1-ethyl-1-methylpropylsulphinyl and 1-ethyl-2-methylpropylsulphinyl;

alkylsulphonyl: saturated, straight-chain or branched alkylsulphonyl radicals having 1 to 8 carbon atoms, for example (but not limited to) $C_1$-$C_6$-alkylsulphonyl, such as methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethyl sulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentyl sulphonyl, 2-methylpentylsulphonyl, 3-methylpentylsulphonyl, 4-methylpentyl sulphonyl, 1,1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethyl-butylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl;

cycloalkyl: monocyclic saturated hydrocarbon groups having 3 to 10 carbon ring members, for example (but not limited to) cyclopropyl, cyclopentyl and cyclohexyl;

haloalkyl: straight-chain or branched alkyl groups having 1 to 8 carbon atoms (as specified above), where some or all of the hydrogen atoms in these groups may be replaced by halogen atoms as specified above, for example (but not limited to) $C_1$-$C_3$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl;

haloalkoxy: straight-chain or branched alkoxy groups having 1 to 8 carbon atoms (as specified above), where some or all of the hydrogen atoms in these groups may be replaced by halogen atoms as specified above, for example (but not limited to) $C_1$-$C_3$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy;

haloalkylthio: straight-chain or branched alkylthio groups having 1 to 8 carbon atoms (as specified above), where some or all of the hydrogen atoms in these groups may be replaced by halogen atoms as specified above, for example (but not limited to) $C_1$-$C_3$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2-difluoroethylthio, 2,2-dichloro-2-fluoroethylthio, 2,2,2-trichloroethylthio, pentafluoroethylthio and 1,1,1-trifluoroprop-2-ylthio;

heteroaryl: 5 or 6-membered, fully unsaturated monocyclic ring system containing one to four heteroatoms from the group of oxygen, nitrogen and sulphur; if the ring contains a plurality of oxygen atoms, none are directly adjacent;

5-membered heteroaryl: containing one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example (but not limited to) 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

5-membered heteroaryl which contains one to four nitrogen atoms and is bonded via nitrogen, or benzofused 5-membered heteroaryl which contains one to three nitrogen atoms and is bonded via nitrogen: 5-membered heteroaryl groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms, where these rings are bonded to the skeleton via one of the nitrogen ring members, for example (but not limited to) 1-pyrrolyl, 1-pyrazolyl, 1,2,4-triazol-1-yl, 1-imidazolyl, 1,2,3-triazol-1-yl, 1,3,4-triazol-1-yl;

6-membered heteroaryl containing one to four nitrogen atoms: 6-membered heteroaryl groups which, in addition to carbon atoms, may contain one to three or one to four nitrogen atoms as ring members, for example (but not limited to) 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzofused 5-membered heteroaryl containing one to three nitrogen atoms or one nitrogen atom and one oxygen or sulphur atom: for example (but not limited to) indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl, benzofused 6-membered heteroaryl containing one to three nitrogen atoms: for example (but not limited to) quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl;

heterocyclyl: a three- to fifteen-membered saturated or partially unsaturated heterocycle containing one to four heteroatoms from the group of oxygen, nitrogen and sulphur: mono-, bi- or tricyclic heterocycles which contain, in addition to carbon ring members, one to three nitrogen atoms and/or one oxygen or sulphur atom or one or two oxygen and/or sulphur atoms; if the ring contains a plurality of oxygen atoms, none are directly adjacent; for example (but not limited to) oxiranyl, aziridinyl, 2-tetrahydrofuranyl, 3-tetrahydro-furanyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

Leaving group: $S_N1$ or $S_N2$ leaving group, for example chlorine, bromine, iodine, alkylsulphonates (—$OSO_2$-alkyl, e.g. —$OSO_2CH_3$, —$OSO_2CF_3$) or arylsulphonates (—$OSO_2$-aryl, e.g. —$OSO_2Ph$, —$OSO_2PhMe$);

In the naming of combinations of a plurality of radicals, for example Cx-Cy-alkylcarbonyl or Cx-Cy-alkoxyalkyl, the expression Cx-Cy in each case denotes the sum of all carbon atoms present in each overall fragment. X and Y are each an integer, where the number Y is greater than that of X.

Not included are combinations which contravene the laws of nature and which the person skilled in the art would therefore have ruled out on the basis of his/her expert knowledge. Ring structures having three or more adjacent oxygen atoms, for example, are ruled out.

Illustration of the Preparation Processes and Intermediates

The pyridinylcarboxylic acid derivatives of the formula (I) can be prepared in different ways. First of all, the possible processes are shown schematically below. Unless indicated otherwise, the radicals specified are each as defined above.

The processes according to the invention for preparing compounds of the formula (I) are, if appropriate, carried out using one or more reaction auxiliaries.

Useful reaction auxiliaries are, as appropriate, inorganic or organic bases or acid acceptors. These preferably include alkali metal or alkaline earth metal acetates, amides, carbonates, hydrogencarbonates, hydrides, hydroxides or alkoxides, for example sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; and also basic organic nitrogen compounds, for example trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

If appropriate, the processes according to the invention are carried out using one or more diluents. Useful diluents are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters, such as methyl acetate and ethyl acetate, nitriles, for example acetonitrile and propionitrile, amides, for example dimethylformamide, dimethylacetamide and N-methylpyrrolidone, and also dimethyl sulphoxide, tetramethylenesulphone and hexamethylphosphoramide and DMPU.

In the processes according to the invention, the reaction temperatures can be varied within a relatively wide range. In general, the working temperatures are between 0° C. and 250° C., preferably temperatures between 10° C. and 185° C.

The reaction time varies according to the scale of the reaction and the reaction temperature, but is generally between a few minutes and 48 hours.

The processes according to the invention are generally carried out under standard pressure. However, it is also possible to work under elevated or reduced pressure.

For performance of the processes according to the invention, the starting materials required in each case are generally used in approximately equimolar amounts. However, it is also possible to use one of the components used in each case in a relatively large excess.

Process A

Scheme 1: Process A

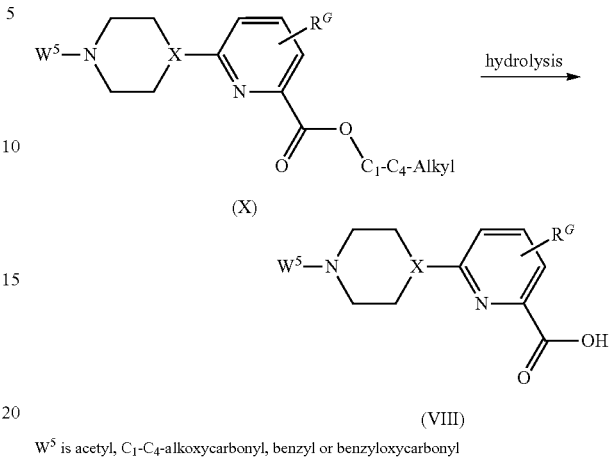

$W^5$ is acetyl, $C_1$-$C_4$-alkoxycarbonyl, benzyl or benzyloxycarbonyl

One means of preparing the intermediate (VIII) from corresponding compounds (X) is shown in Scheme 1.

The compounds of the formula (X) can be prepared from commercially available precursors by methods described in the literature (see, for example, US-A-2009/0197859, WO-A-2010/008739).

The carboxylic acid of the formula (VIII) can be prepared by hydrolysing the corresponding $C_1$-$C_4$-alkyl ester of the formula (X). For example, the method which is described in WO-A-2007/014290, can be used.

Suitable alkali metal hydroxides are, for example, LiOH, NaOH or KOH, usually in the presence of water together with a cosolvent, preferably THF and/or methanol, to facilitate dissolution of the ester. The carboxylate salt formed is converted to the free acid by treatment with a slight excess of mineral acids, for example hydrochloric acid or sulphuric acid.

The reaction is normally carried out at temperatures of 0° C.-60° C., but it can also be carried out at reflux temperature of the reaction mixture. The reaction time varies according to the scale of the reaction and the reaction temperature, but is generally between a few minutes and 48 hours.

After the reaction has ended, the compounds (VIII) are separated from the reaction mixture by one of the customary separation techniques. If necessary, the compounds are purified by recrystallization, or can optionally also be used in the next step without prior purification.

Process B

Scheme 2: Process B

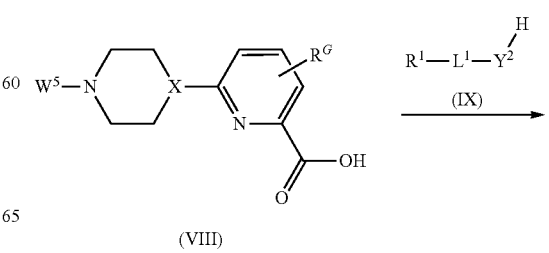

-continued

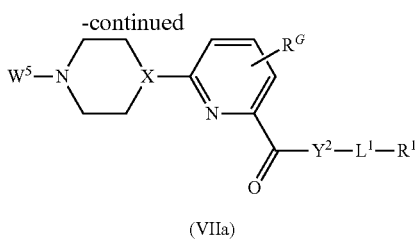

(VIIa)

$W^5$ is acetyl, $C_1$-$C_4$-alkoxycarbonyl, benzyl or benzyloxycarbonyl

One means of preparing compounds of the formula (VIIa) from corresponding compounds (VIII) is shown in Scheme 2.

A compound of the formula (VIIa) can be synthesized from the corresponding compound of the formula (VIII) with a substrate of the formula (IX) in the presence of a coupling reagent, analogously to methods described in the literature (e.g. *Tetrahedron* 2005, 61, 10827-10852, and references cited therein).

Suitable coupling reagents are, for example, peptide coupling reagents (for instance N-(3-dimethylaminopropyl)-N'-ethylcarbodiimide mixed with 4-dimethylaminopyridine, N-(3-dimethylaminopropyl)-N'-ethylcarbodiimide mixed with 1-hydroxybenzotriazole, bromotripyrrolidinophosphonium hexafluorophosphate, O-(7-azabenzotriazol-1-yl)-N,N,N',N'-tetramethyluronium hexafluorophosphate, etc.).

If appropriate, a base, for example triethylamine or Hünig's base, can be used in the reaction.

The preferred solvents are N,N-dimethylformamide and dichloromethane.

Alternatively, a compound of the formula (VIIa) can also be synthesized proceeding from the compound of the formula (VIII) by a two-stage transformation, using processes known from the literature (e.g. *Tetrahedron* 2005, 61, 10827-10852, and literature cited therein), optionally in the presence of an acid scavenger/base. Typically, a compound of the formula (VIII) is first converted to the corresponding acid halide or sulphonate, followed by a coupling reaction with a substrate of the formula (IX).

Substrates with the general formula (IX) are commercially available or preparable by processes described in the literature (see, for example, "The Chemistry of Functional groups"; "The Chemistry of the Thiol Group"; John Wiley & Sons, 1974, 163-269, and references cited therein; "The Chemistry of Functional groups"; "Supplement F2: The Chemistry of amino, nitroso, nitro and related groups"; John Wiley & Sons, and the references cited therein; "Science of Synthesis"; "Alcohols", Volume 36, Thieme, 2008 and the references cited therein; "Science of Synthesis"; "Amines and Ammonium Salts", Volume 40a, Thieme, 2008, and the references cited therein).

At least one equivalent of an acid scavenger/a base (for example Hünig's base, triethylamine or commercially available polymeric acid scavengers) is used, in relation to the starting material of the general formula (IX). If the starting material is a salt, at least two equivalents of the acid scavenger are required.

After the reaction has ended, the compounds (VIIa) are separated from the reaction mixture by one of the customary separation techniques. If necessary, the compounds are purified by recrystallization or chromatography, or can optionally also be used in the next step without prior purification.

Process C

Scheme 3: Process C

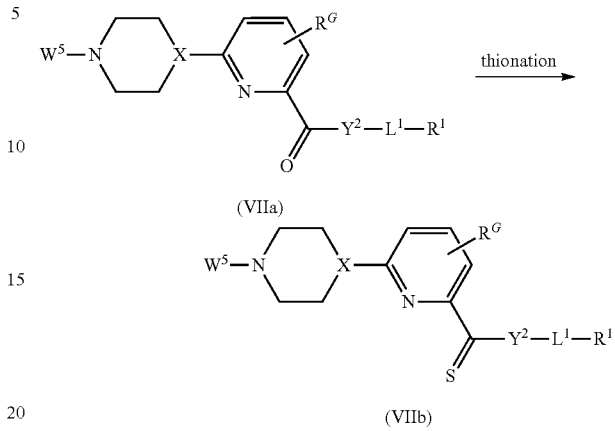

$W^5$ is acetyl, $C_1$-$C_4$-alkoxycarbonyl, benzyl or benzyloxycarbonyl

One means of preparing compounds of the formula (VIIb) from corresponding compounds (VIIa) is shown in Scheme 3.

Process C according to the invention is preferably carried out using one or more diluents. The preferred solvents are toluenes, tetrahydrofuran and 1,2-dimethoxyethane.

Suitable thionating agents are, for example, Lawesson's reagent (see *Tetrahedron* 1986, 42, 6555-6564, *Tetrahedron Lett.* 1993, 46, 7459-7462) and phosphorus pentasulphide.

After the reaction has ended, the compounds (VIIb) are separated from the reaction mixture by one of the customary separation techniques. If necessary, the compounds are purified by recrystallization or chromatography, or can optionally also be used in the next step without prior purification.

Process D

Scheme 4: Process D

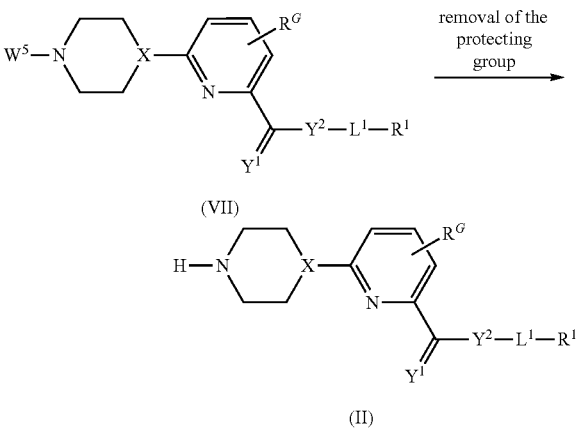

$W^5$ is acetyl, $C_1$-$C_4$-alkoxycarbonyl, benzyl or benzyloxycarbonyl

One means of preparing compounds of the formula (II) from corresponding compounds (VII) is shown in Scheme 4.

A compound of the formula (VII) is converted to a compound of the formula (II) by suitable methods for removing protecting groups described in the literature ("*Protective Groups in Organic Synthesis*"; Third Edition; 494-653, and the literature cited therein).

tert-Butoxycarbonyl and benzyloxycarbonyl protecting groups can be removed in an acidic medium (for example using hydrochloric acid or trifluoroacetic acid). Acetyl protecting groups can be removed under basic conditions (for example with potassium carbonate or caesium carbonate). Benzylic protecting groups can be removed by hydrogenolysis with hydrogen in the presence of a catalyst (for example palladium on activated carbon).

Acids which can be used for this reaction, the deprotection of tert-butoxycarbonyl and benzyloxycarbonyl groups, are, for example, trifluoroacetic acid, hydrochloric acid or other acids, as described in the literature (for example "*Protective Groups in Organic Synthesis*"; Third Edition; pp. 494-653).

After the reaction has ended, the compounds (II) are removed from the reaction mixture by one of the customary separation techniques. If necessary, the compounds are purified by recrystallization or chromatography, or can, if desired, also be used in the next step without prior purification. It is also possible to isolate the compound of the general formula (II) as a salt, for example as a salt of hydrochloric acid or of trifluoroacetic acid.

Process E

Scheme 5: Process E

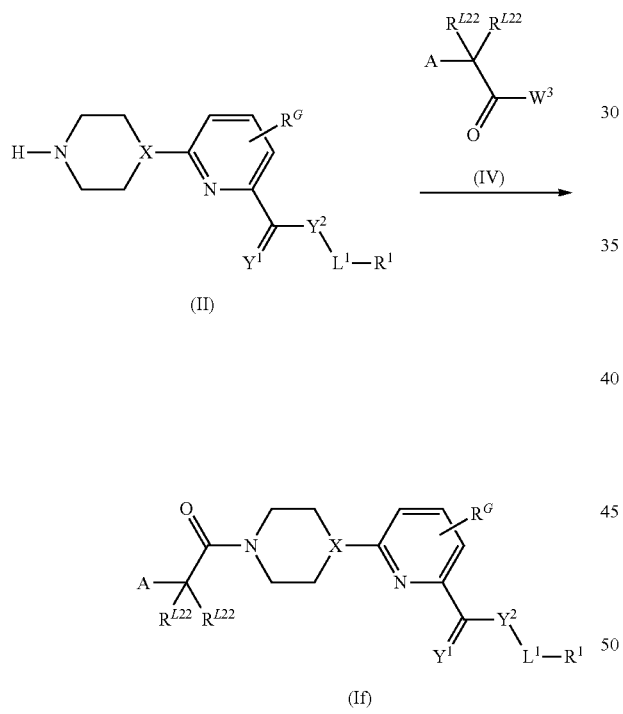

$W^3$ = OH or Cl

One means of preparing compounds of the formula (If) from corresponding compounds (II) with the compounds (IV) is shown in Scheme 5.

Compounds (IV) are preparable by processes described in the literature (see, for example, WO-A-2008/013622 and WO-A-2008/013925).

A compound with the general formula (If) can be synthesized analogously to methods described in the literature (see, for example WO-A-2007/147336), by a coupling reaction of a compound with the corresponding general formula (II) with a substrate of the general formula (IV), where $W^3$ is chlorine, optionally in the presence of an acid scavenger/base.

At least one equivalent of an acid scavenger/a base (for example Hünig's base, triethylamine or commercially available polymeric acid scavengers) is used, in relation to the starting material of the general formula (II). If the starting material is a salt, at least two equivalents of the acid scavenger are required.

Alternatively, a compound of the formula (If) can also be synthesized from the corresponding compound of the formula (II) with a substrate of the formula (IV) where $W^3$ is hydroxyl in the presence of a coupling reagent analogously to procedures described in the literature (for example Tetrahedron 2005, 61, 10827-10852, and references cited therein).

Suitable coupling reagents are, for example, peptide coupling reagents (for example N-(3-dimethylaminopropyl)-N'-ethylcarbodiimide mixed with 4-dimethylaminopyridine, N-(3-dimethylaminopropyl)-N'-ethylcarbodiimide mixed with 1-hydroxybenzotriazole, bromotripyrrolidinophosphonium hexafluorophosphate, O-(7-azabenzotriazol-1-yl)-N,N,N',N'-tetramethyluronium hexafluorophosphate, etc.).

After the reaction has ended, the compounds (II) are separated from the reaction mixture by one of the customary separation techniques. If necessary, the compounds are purified by recrystallization or chromatography.

Process F

Scheme 6: Process F

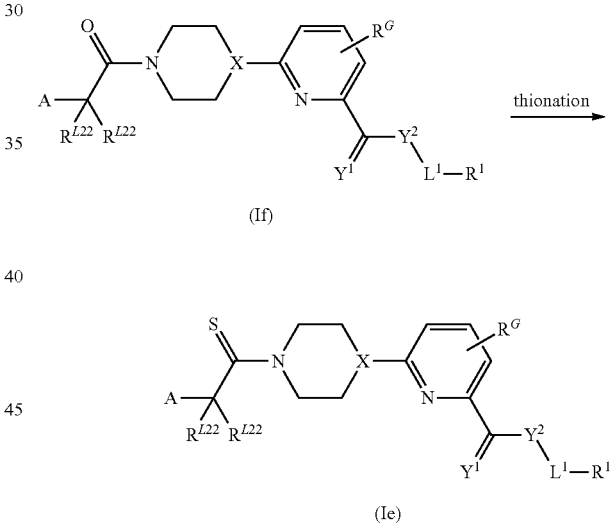

The amides (Ie) obtained in the performance of process F according to the invention (Scheme 6) can be converted by means of methods described in the literature to the corresponding thioamides (e.g. Bioorganic & Medicinal Chemistry Letters (2009), 19(2), 462-468). This involves reacting the compounds of the formula (Ie) typically with phosphorus pentasulphide or 2,4-bis(4-methoxyphenyl)-1,3-dithia-2,4-diphosphetane 2,4-disulphide (Lawesson's reagent).

Process C according to the invention is preferably carried out using one or more diluents. The preferred solvents are toluene, tetrahydrofuran and 1,2-dimethoxyethane.

After the reaction has ended, the compounds (Ie) are separated from the reaction mixture by one of the customary separation techniques. If necessary, the compounds are purified by recrystallization or chromatography.

Process G

Scheme 7: Process G

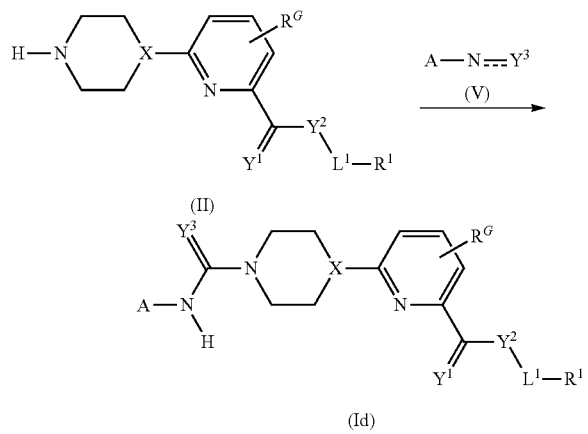

One means of preparing compounds of the formula (Id) from corresponding compounds (II) with the compounds (V) is shown in Scheme 7.

A compound with the general formula (Id) can be synthesized analogously to methods described in the literature (see, for example WO-A-2009/055514), by a coupling reaction of a compound with the corresponding general formula (II) with a substrate of the general formula (V), optionally in the presence of an acid scavenger/base, for example triethylamine, 1,8-diazabicyclo[5.4.0]undec-7-ene or Hünig's base.

After the reaction has ended, the compounds (Id) are separated from the reaction mixture by one of the customary separation techniques. If necessary, the compounds are purified by recrystallization or chromatography.

Process H

Scheme 8: Process H

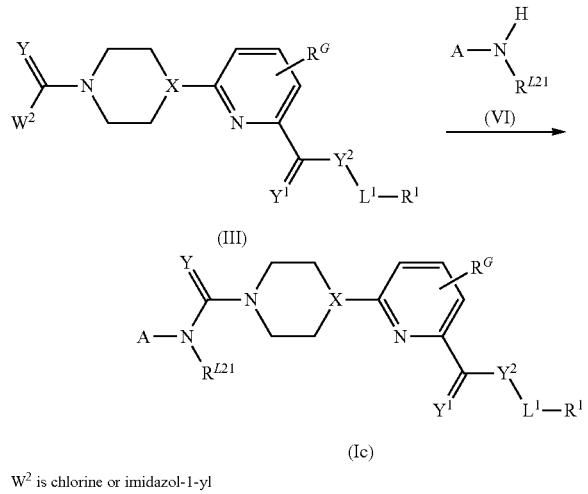

$W^2$ is chlorine or imidazol-1-yl

The carbamoyl and thiocarbamoyl chlorides of the formula (IIIa, $W^2$=chlorine) required as starting materials in the performance of process H according to the invention (Scheme 8) can be prepared by means of methods described in the literature (see, for example, *Tetrahedron*, 2008, 7605; *Journal of Organic Chemistry*, 2004, 3787; *Journal of Organic Chemistry*, 1983, 4750; *European Journal of Organic Chemistry*, 2006, 1177). Typically, the compounds of the formula (IIIa, $W^2$=chlorine) are prepared proceeding from amines of the formula (II) and phosgene, thiophosgene or the equivalents thereof.

The carbamoyl- and thiocarbamoylimidazoles of the formula (Mb, $W^2$=imidazol-1-yl) required as starting materials in the performance of the process according to the invention can be prepared by means of methods described in the literature (see, for example, *Tetrahedron Letters*, 2008, 5279; *Tetrahedron*, 2005, 7153). Typically, the compounds of the formula (Mb, $W^2$=imidazol-1-yl) are prepared proceeding from amines of the formula (II) and 1,1'-carbonyldiimidazoles or 1,1'-thiocarbonyldimidazoles.

Scheme 8 describes the preparation of compounds of the structure (Ic) by reaction of compounds of the structure (III) and amines (VI).

If appropriate, process H is carried out in the presence of a suitable acid acceptor.

The compounds (Ic) obtained in the performance of the process H according to the invention can alternatively in some cases also be obtained without using an acid acceptor, as the corresponding acid chlorides [(Ic)-HCl]. If required, the compounds (Ic) are released by customary methods.

After the reaction has ended, the compounds (Ic) are separated from the reaction mixture by one of the customary separation techniques. If necessary, the compounds are purified by recrystallization or chromatography.

Process I

Scheme 9: Process I

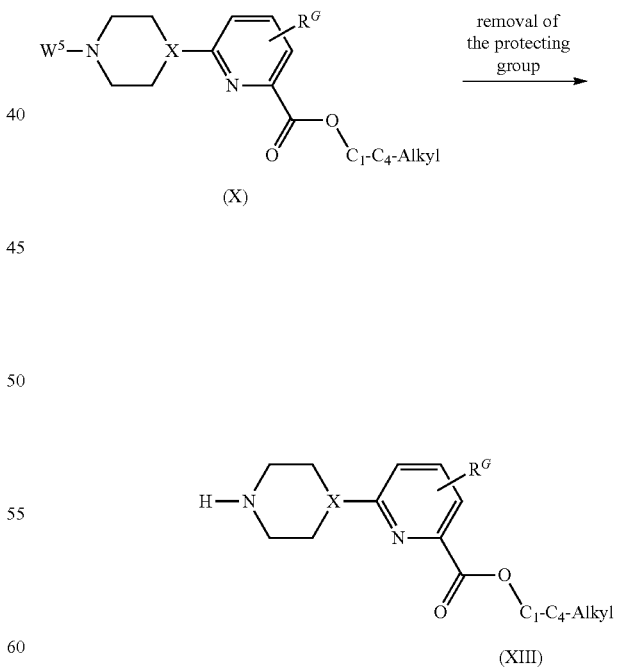

$W^5$ is acetyl, $C_1$-$C_4$-alkoxycarbonyl, benzyl or benzyloxycarbonyl

One means of preparing compounds of the formula (XIII) from corresponding compounds (X) is shown in Scheme 9.

Process I is performed analogously to process D.

Process J

Scheme 10: Process J

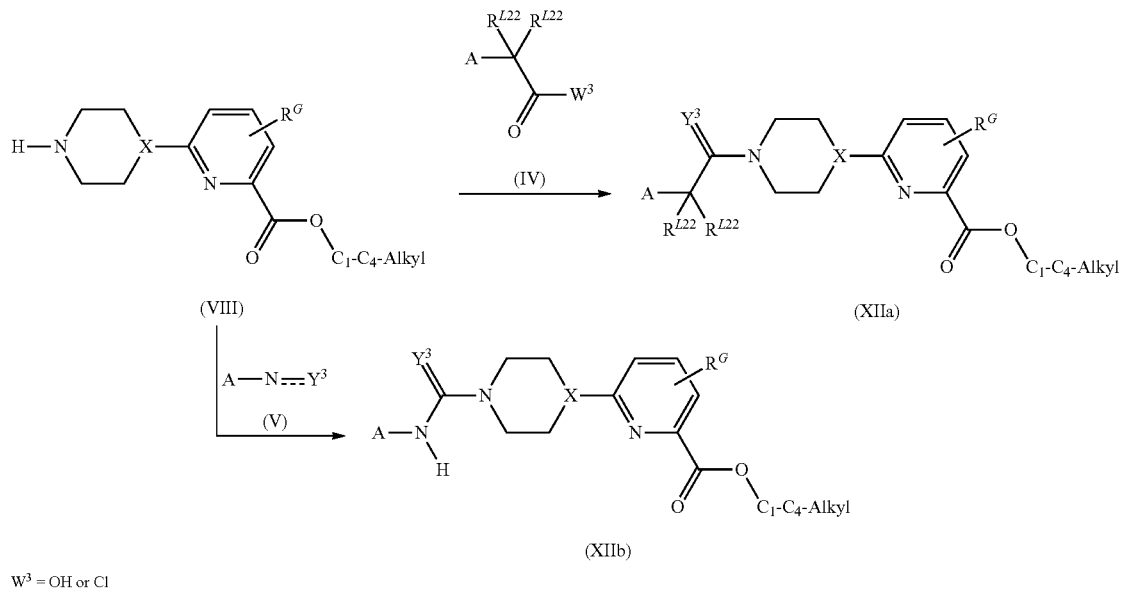

W³ = OH or Cl

One means of preparing compounds of the formula (XIIa) and (XIIb) from corresponding compounds (VIII) is shown in Scheme 10.

Process J is performed analogously to process E and process G.

Process K

Scheme 11: Process K

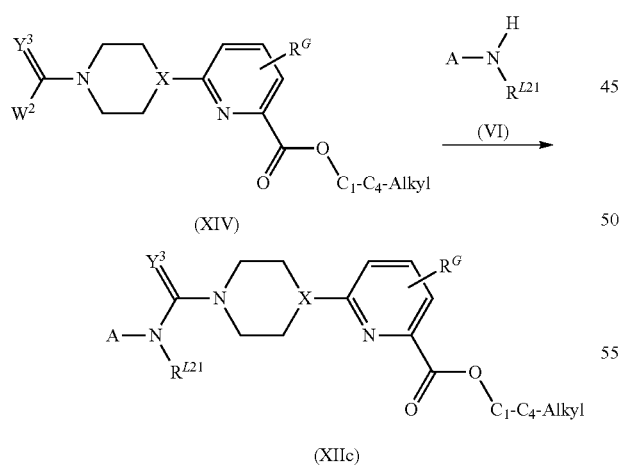

W² is chlorine or imidazol-1-yl

One means of preparing compounds of the formula (XIIc) from corresponding compounds (XIV) is shown in Scheme 11.

Process K is performed analogously to process H.

Process L

Scheme 12: Process L

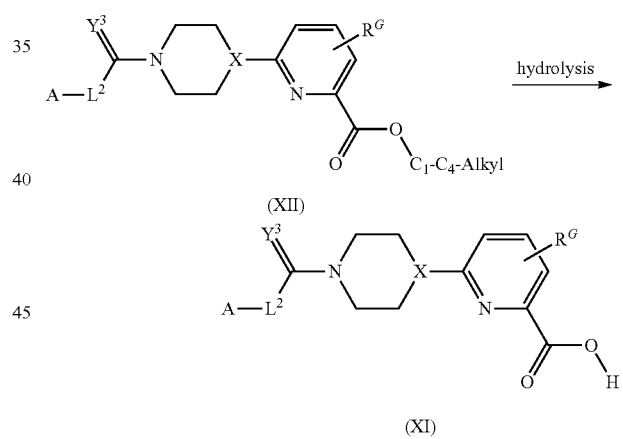

One means of preparing compounds of the formula (XI) from corresponding compounds (XII) is shown in Scheme 12.

Process L is performed analogously to process A.

Process M

Scheme 13: Process M

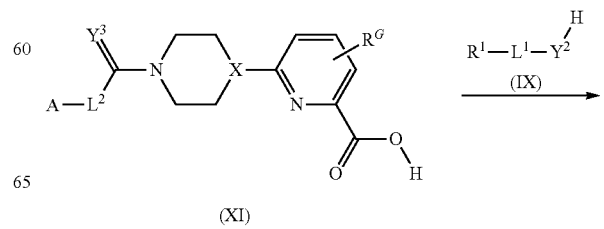

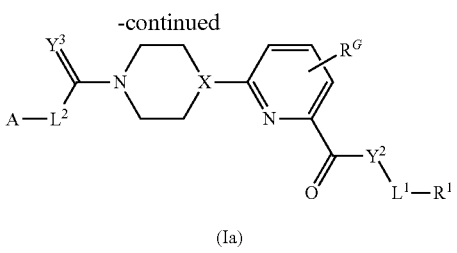

(Ia)

One means of preparing compounds of the formula (Ia) from corresponding compounds (XI) is shown in Scheme 13.

Process M is performed analogously to process B.

Process N

Scheme 14: Process N

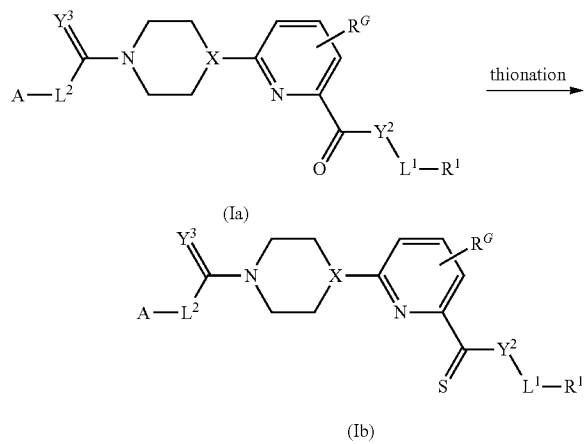

One means of preparing compounds of the formula (Ib) from corresponding compounds (Ia) is shown in Scheme 14.

Process N is performed analogously to process C.

The invention further provides for the non-medical use of the inventive pyridinylcarboxylic acid derivatives of the formula (I) for control of unwanted microorganisms.

The invention further provides a composition for controlling unwanted microorganisms, comprising at least one pyridinylcarboxylic acid derivative according to the present invention.

The invention also relates to a method for controlling unwanted microorganisms, characterized in that the inventive pyridinylcarboxylic acid derivatives are applied to the microorganisms and/or in their habitat.

The invention further relates to seed which has been treated with at least one inventive pyridinylcarboxylic acid derivative.

The invention finally provides a method for protecting seed against unwanted microorganisms by using seed treated with at least one pyridinylcarboxylic acid derivative according to the present invention.

The inventive substances have potent microbicidal activity and can be used for control of unwanted microorganisms, such as fungi and bacteria, in crop protection and in the protection of materials.

The inventive pyridinylcarboxylic acid derivatives of the formula (I) have very good fungicidal properties and can be used in crop protection, for example for control of Plasmodiophoromycetes, Oomycetes, Chytridiomycetes, Zygomycetes, Ascomycetes, Basidiomycetes and Deuteromycetes.

Bactericides can be used in crop protection, for example, for control of Pseudomonadaceae, Rhizobiaceae, Enterobacteriaceae, Corynebacteriaceae and Streptomycetaceae.

The inventive fungicidal compositions can be used for curative or protective control of phytopathogenic fungi. Accordingly, the invention also relates to curative and protective methods for control of phytopathogenic fungi by the use of the inventive active ingredients or compositions, which are applied to the seed, the plant or plant parts, the fruit or the soil in which the plants grow.

The inventive compositions for controlling phytopathogenic fungi in crop protection comprise an effective but non-phytotoxic amount of the inventive active ingredients. An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant varieties protectable and non-protectable by plant breeders' rights. Plant parts shall be understood to mean all parts and organs of plants above and below the ground, such as shoot, leaf, flower and root, examples of which include leaves, needles, stalks, stems, flowers, fruit bodies, fruits, seeds, roots, tubers and rhizomes. Parts of plants also include harvested plants and vegetative and generative propagation material, for example seedlings, tubers, rhizomes, cuttings and seeds.

Plants which can be treated in accordance with the invention include the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for example banana plants and banana plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leeks, onions), *Papilionaceae* sp. (for example peas); major crop plants such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, radishes, and also oilseed rape, mustard, horseradish and cress), *Fabacae* sp. (for example beans, peanuts), *Papilionaceae* sp. (for example soybean), *Solanaceae* sp. (for example potatoes), *Chenopodiaceae* sp. (for example sugar beet, fodder beet, Swiss chard, beetroot); useful plants and ornamental plants in gardens and forests; and genetically modified types of each of these plants.

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*; diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* or *Phakopsora meibomiae*; *Puccinia* species, for example *Puccinia recondita*, *Puccinia graminis* or *Puccinia striiformis*; *Uromyces* species, for example *Uromyces appendiculatus*;

diseases caused by pathogens from the group of the Oomycetes, for example *Albugo* species, for example *Albugo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladosporium* species, for example *Cladosporium cucumerinum*; *Cochliobolus* species, for example *Cochliobolus sativus* (conidial form: *Drechslera*, syn: *Helminthosporium*) or *Cochliobolus miyabeanus*; *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans*; *Magnaporthe* species, for example *Magnaporthe grisea*; *Microdochium* species, for example *Microdochium nivale*; *Mycosphaerella* species, for example *Mycosphaerella graminicola*, *Mycosphaerella arachidicola* or *Mycosphaerella fijiensis*; *Phaeosphaeria* species, for example *Phaeosphaeria nodorum*; *Pyrenophora* species, for example *Pyrenophora teres* or *Pyrenophora tritici repentis*; *Ramularia* species, for example *Ramularia collo-cygni* or *Ramularia areola*; *Rhynchosporium* species, for example *Rhynchosporium secalis*; *Septoria* species, for example *Septoria apii* or *Septoria lycopersici*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Plasmodiophora* species, for example *Plasmodiophora brassicae*; *Rhizoctonia* species, such as, for example *Rhizoctonia solani*; *Sarocladium* species, for example *Sarocladium oryzae*; *Sclerotium* species, for example *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Stagonospora* species, for example *Stagonospora nodorum*;

diseases caused by smut fungi, for example *Sphacelotheca* species, for example *Sphacelotheca reiliana*; *Tilletia* species, for example *Tilletia caries* or *Tilletia controversa*; *Urocystis* species, for example *Urocystis occulta*; *Ustilago* species, for example *Ustilago nuda*;

fruit rot caused, for example, by *Aspergillus* species, for example *Aspergillus flavus*; *Botrytis* species, for example *Botrytis cinerea*; *Penicillium* species, for example *Penicillium expansum* or *Penicillium purpurogenum*; *Rhizopus* species, for example *Rhizopus stolonifer*; *Sclerotinia* species, for example *Sclerotinia sclerotiorum*; *Verticilium* species, for example *Verticilium alboatrum*;

Seed- and soil-borne rot and wilt diseases, and also diseases of seedlings, caused, for example, by *Alternaria* species, for example *Alternaria* brassicicola; *Aphanomyces* species, for example *Aphanomyces euteiches*; *Ascochyta* species, for example *Ascochyta lentis*; *Aspergillus* species, for example *Aspergillus flavus*; *Cladosporium* species, for example *Cladosporium herbarum*; *Cochliobolus* species, for example *Cochliobolus sativus* (conidia form: *Drechslera*, *Bipolaris* Syn: *Helminthosporium*); *Colletotrichum* species, for example *Colletotrichum coccodes*; *Fusarium* species, for example *Fusarium culmorum*; *Gibberella* species, for example *Gibberella zeae*; *Macrophomina* species, for example *Macrophomina phaseolina*; *Microdochium* species, for example *Microdochium nivale*; *Monographella* species, for example *Monographella nivalis*; *Penicillium* species, for example *Penicillium expansum*; *Phoma* species, for example *Phoma lingam*; *Phomopsis* species, for example *Phomopsis sojae*; *Phytophthora* species, for example *Phytophthora cactorum*; *Pyrenophora* species, for example *Pyrenophora graminea*; *Pyricularia* species, for example *Pyricularia oryzae*; *Pythium* species, for example *Pythium ultimum*; *Rhizoctonia* species, for example *Rhizoctonia solani*; *Rhizopus* species, for example *Rhizopus oryzae*; *Sclerotium* species, for example *Sclerotium*; *Septoria* species, for example *Septoria nodorum*; *Typhula* species, for example *Typhula incarnata*; *Verticillium* species, for example *Verticillium dahliae*;

cancers, galls and witches' broom caused, for example, by *Nectria* species, for example *Nectria galligena*;

wilt diseases caused, for example, by *Monilinia* species, for example *Monilinia laxa*;

deformations of leaves, flowers and fruits caused, for example, by *Exobasidium* species, for example *Exobasidium vexans*; *Taphrina* species, for example *Taphrina deformans*;

degenerative diseases in woody plants, caused, for example, by Esca species, for example *Phaeomoniella chlamydospora*, *Phaeoacremonium aleophilum* or *Fomitiporia mediterranea*; *Ganoderma* species, for example *Ganoderma boninense*;

diseases of flowers and seeds caused, for example, by *Botrytis* species, for example *Botrytis cinerea*;

diseases of plant tubers caused, for example, by *Rhizoctonia* species, for example *Rhizoctonia solani*; *Helminthosporium* species, for example *Helminthosporium solani*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

Preference is given to controlling the following diseases of soya beans:

Fungal diseases on leaves, stems, pods and seeds caused, for example, by *alternaria* leaf spot (*Alternaria* spec. atrans tenuissima), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The inventive active ingredients also have very good fortifying action in plants. They can therefore be used to mobilize the plant's own defences from attack by undesirable microorganisms.

Plant-fortifying (resistance-inducing) substances are understood to mean, in the present context, those substances which are capable of stimulating the defence system of plants in such a way that the treated plants, when subsequently inoculated with undesirable microorganisms, develop a high degree of resistance to these microorganisms.

In the present case, undesirable microorganisms are understood to mean phytopathogenic fungi and bacteria. The inventive substances can thus be used to protect plants for a certain period after the treatment from attack by the pathogens mentioned. The period within which protection is brought about generally extends for 1 to 10 days, preferably 1 to 7 days, after the treatment of the plants with the active ingredients.

The fact that the active ingredients are well tolerated by plants at the concentrations needed to control plant diseases allows the treatment of above-ground parts of plants, of propagation stock and seeds, and of the soil.

The inventive active ingredients can be used particularly successfully to control diseases in viticulture and potato, fruit and vegetable growing, for example especially against powdery mildew fungi, Oomycetes, for example *Phytophthora, Plasmopara, Pseudoperonospora* and *Pythium* species.

The inventive active ingredients are also suitable for enhancing the yield of crops. In addition, they have reduced toxicity and are well tolerated by plants.

If appropriate, the inventive compounds can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be used as insecticides. If appropriate, they can also be used as intermediates or precursors for the synthesis of other active ingredients.

The inventive active ingredients, when they are well tolerated by plants, have favourable homeotherm toxicity and are well tolerated by the environment, are suitable for protecting plants and plant organs, for enhancing harvest yields, for improving the quality of the harvested material in agriculture, in horticulture, in animal husbandry, in forests, in gardens and leisure facilities, in the protection of stored products and of materials, and in the hygiene sector. They can be preferably employed as crop protection compositions. They are active against normally sensitive and resistant species and also against all or some stages of development.

The inventive treatment of the plants and plant parts with the active ingredients or compositions is effected directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. It is also possible to deploy the active ingredients by the ultra-low volume method or to inject the active ingredient preparation or the active ingredient itself into the soil.

In addition, in the protection of materials, the inventive active ingredients or compositions can be employed for protecting industrial materials from attack and destruction by unwanted microorganisms, for example fungi.

Industrial materials in the present context are understood to mean inanimate materials which have been prepared for use in industry. For example, industrial materials which are to be protected by inventive active ingredients from microbial alteration or destruction may be adhesives, sizes, paper and board, textiles, leather, wood, paints and plastic articles, cooling lubricants and other materials which can be infected with or destroyed by microorganisms. The range of materials to be protected also includes parts of production plants, for example cooling water circuits, which may be impaired by the proliferation of microorganisms. Industrial materials within the context of the present invention preferably include adhesives, sizes, paper and board, leather, wood, paints, cooling lubricants and heat-transfer liquids, more preferably wood. The inventive active ingredients or compositions may prevent adverse effects, such as rotting, decay, discoloration, decolouration or formation of mould.

The inventive method for control of unwanted fungi can also be used for protection of storage goods. Storage goods are understood to mean natural substances of vegetable or animal origin or processed products thereof, which are of natural origin and for which long-term protection is desired. Storage goods of vegetable origin, for example plants or plant parts, such as stems, leaves, tubers, seeds, fruits, grains, can be protected in the freshly harvested state or after processing by (pre)drying, moistening, comminuting, grinding, pressing or roasting. Storage goods also include timber, whether unprocessed, such as construction timber, electricity poles and barriers, or in the form of finished products, such as furniture. Storage goods of animal origin are, for example, hides, leather, furs and hairs. The inventive active ingredients may prevent adverse effects, such as rotting, decay, discoloration, decolouration or formation of mould.

Microorganisms capable of degrading or altering the industrial materials include, for example, bacteria, fungi, yeasts, algae and slime organisms. The inventive active ingredients preferably act against fungi, especially moulds, wood-discolouring and wood-destroying fungi (Basidiomycetes), and against slime organisms and algae. Examples include microorganisms of the following genera: *Alternaria*, such as *Alternaria tennis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Escherichia*, such as *Escherichia coli*; *Pseudomonas*, such as *Pseudomonas aeruginosa*; *Staphylococcus*, such as *Staphylococcus aureus*.

The present invention further relates to a composition for controlling unwanted microorganisms, comprising at least one of the inventive pyridinylcarboxylic acid derivatives. The composition is preferably a fungicidal composition which comprises agriculturally suitable auxiliaries, solvents, carriers, surfactants or extenders.

According to the invention, a carrier is a natural or synthetic, organic or inorganic substance with which the active ingredients are mixed or bonded for better applicability, in particular for application to plants or plant parts or seed. The carrier, which may be solid or liquid, is generally inert and should be suitable for use in agriculture.

Useful solid carriers include: for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and also granules of organic material such as paper, sawdust, coconut shells, maize cobs and tobacco stalks; suitable emulsifiers and/or foam formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or —POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Further suitable oligomers or polymers are, for example those derived from vinylic monomers, from acrylic acid, from EO and/or PO alone or in combination with, for example, (poly)alcohols or (poly)amines. It is also possible to use lignin and its sulphonic acid derivatives, unmodified and modified celluloses, aromatic and/or aliphatic sulphonic acids and also their adducts with formaldehyde.

The active ingredients can be converted to the customary formulations, such as solutions, emulsions, wettable powders, water- and oil-based suspensions, powders, dusts, pastes, soluble powders, soluble granules, granules for broadcasting, suspoemulsion concentrates, natural substances impregnated with active ingredient, synthetic substances impregnated with active ingredient, fertilizers and also microencapsulations in polymeric substances.

The active ingredients can be applied as such, in the form of their formulations or the use forms prepared therefrom, such as ready-to-use solutions, emulsions, water- or oil-based suspensions, powders, wettable powders, pastes, soluble powders, dusts, soluble granules, granules for broadcasting, suspoemulsion concentrates, natural products impregnated with active ingredient, synthetic materials impregnated with active ingredient, fertilizers and also microencapsulations in polymeric substances. Application is accomplished in a customary manner, for example by watering, spraying, atomizing, broadcasting, dusting, foaming, spreading, etc. It is also possible to apply the active ingredients by the ultra-low volume method, or to inject the active ingredient preparation or the active ingredient itself into the soil. It is also possible to treat the seed of the plants.

The formulations mentioned can be prepared in a manner known per se, for example by mixing the active ingredients with at least one customary extender, solvent or diluent, emulsifier, dispersant and/or binder or fixing agent, wetting agent a water repellent, if appropriate siccatives and UV stabilizers and if appropriate dyes and pigments, antifoams, preservatives, secondary thickeners, stickers, gibberellins and also other processing auxiliaries.

The present invention includes not only formulations which are already ready for use and can be deployed with a suitable apparatus to the plant or the seed, but also commercial concentrates which have to be diluted with water prior to use.

The inventive active ingredients may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The auxiliaries used may be those substances which are suitable for imparting particular properties to the composition itself and/or to preparations derived therefrom (for example spray liquors, seed dressings), such as certain technical properties and/or also particular biological properties. Typical auxiliaries include: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted atnines, amides, lactams (such as N-alkylpyrrolidones) and lactones, the sulphones and sulphoxides (such as dimethyl sulphoxide).

Liquefied gaseous extenders or carriers are understood to mean liquids which are gaseous at standard temperature and under standard pressure, for example aerosol propellants such as halohydrocarbons, or else butane, propane, nitrogen and carbon dioxide.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water.

The inventive compositions may comprise additional further components, for example surfactants. Suitable surfactants are emulsifiers and/or foam formers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is required if one of the active ingredients and/or one of the inert carriers is insoluble in water and when the application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Other possible additives are perfumes, mineral or vegetable oils which are optionally modified, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability, may also be present.

If appropriate, other additional components may also be present, for example protective colloids, binders, adhesives, thickeners, thixotropic substances, penetrants, stabilizers, sequestering agents, complexing agents. In general, the active ingredients can be combined with any solid or liquid additive commonly used for formulation purposes.

The formulations generally contain between 0.05 and 99% by weight, 0.01 and 98% by weight, preferably between 0.1 and 95% by weight and more preferably between 0.5 and 90% active ingredient, most preferably between 10 and 70 percent by weight.

The formulations described above can be used in an inventive method for controlling unwanted microorganisms, in which the inventive pyridinylcarboxylic acid derivatives are applied to the microorganisms and/or to their habitat.

The inventive active ingredients can also be used, as such or in formulations thereof, in a mixture with known fungicides, bactericides, acaricides, nematicides or insecticides, in order thus to broaden, for example, the activity spectrum or to prevent development of resistance.

Useful mixing partners include, for example, known fungicides, insecticides, acaricides, nematicides or else bactericides (see also Pesticide Manual, 14th ed.).

A mixture with other known active ingredients, such as herbicides, or with fertilizers and growth regulators, safeners and/or semiochemicals is also possible.

The compounds are applied in a customary manner appropriate for the use forms.

The invention further comprises a method for treatment of seed.

A further aspect of the present invention relates in particular to seed treated with at least one of the inventive pyridinylcarboxylic acid derivatives. The inventive seeds are used in methods for protection of seed from phytopathogenic harmful fungi. In these methods, seed treated with at least one inventive active ingredient is employed.

The inventive active ingredients or compositions are also suitable for treating seed. A large part of the damage to crop plants caused by harmful organisms is triggered by the infection of the seed during storage or after sowing, and also during and after germination of the plant. This phase is particularly critical because the roots and shoots of the growing plant are particularly sensitive, and even minor damage may lead to the death of the plant. Accordingly, there is great interest in protecting the seed and the germinating plant by using appropriate compositions.

The control of phytopathogenic harmful fungi by treating the seed of plants has been known for a long time and is the subject of constant improvements. However, the treatment of seed entails a series of problems which cannot always be solved in a satisfactory manner. Thus, it is desirable to develop methods for protecting the seed and the germinating plant which dispense with, or at least reduce considerably, the additional deployment of crop protection compositions after sowing or after emergence of the plants. It is also desirable to optimize the amount of active ingredient used so as to provide the best possible protection for the seed and the germinating plant from attack by phytopathogenic fungi, without damaging the plant itself by the active ingredient used. In particular, methods for the treatment of seed should also take account of the intrinsic fungicidal properties of transgenic plants in order to achieve optimal protection of the seed and the germinating plant with minimum expenditure of crop protection compositions.

The present invention therefore also relates to a method for protecting seed and germinating plants from attack by animal pests and/or phytopathogenic harmful fungi by treating the seed with an inventive composition. The invention likewise relates to the use of the inventive compositions for treatment of seed to protect the seed and the germinating plant from phytopathogenic fungi. The invention further relates to seed which has been treated with an inventive composition for protection from phytopathogenic fungi.

The control of animal pests and/or phytopathogenic harmful fungi which damage plants post-emergence is effected primarily by treating the soil and the above-ground parts of plants with crop protection compositions. Owing to the concerns regarding possible influence of the crop protection compositions on the environment and the health of humans and animals, there are efforts to reduce the amount of active ingredients deployed.

One of the advantages of the present invention is that, because of the particular systemic properties of the inventive compositions, the treatment of the seed with these compositions not only protects the seed itself, but also the resulting plants after emergence, from animal pests and/or phytopathogenic harmful fungi. In this manner, the direct treatment of the crop at the time of sowing or shortly thereafter can be dispensed with.

It is also considered to be advantageous that the inventive active ingredients or compositions can especially also be used with transgenic seed, in which case the plant growing from this seed is capable of expressing a protein which acts against pests. By the treatment of such seed with the inventive active ingredients or compositions, even the expression of the protein, for example an insecticidal protein, can control certain pests. Surprisingly, a further synergistic effect can be observed here, which additionally increases the effectiveness of the protection from attack by pests.

The inventive compositions are suitable for protection of seed of any plant variety which is used in agriculture, in the greenhouse, in forests or in horticulture. In particular, this is the seed of cereals (such as wheat, barley, rye, millet and oats), maize, cotton, soybeans, rice, potatoes, sunflowers, beans, coffee, beets (for example sugarbeets and fodder beets), peanuts, vegetables (such as tomatoes, cucumbers, onions and lettuce), lawns and ornamental plants. The treatment of the seed of cereals (such as wheat, barley, rye and oats), maize and rice is of particular importance.

As also described below, the treatment of transgenic seed with the inventive active ingredients or compositions is of particular importance. This refers to the seed of plants containing at least one heterologous gene which allows the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. More preferably, the heterologous gene originates from *Bacillus thuringiensis*.

Within the context of the present invention, the inventive composition is applied to the seed alone or in a suitable formulation. Preferably, the seed is treated in a state in which it is sufficiently stable for no damage to occur in the course of treatment. In general, the seed may be treated at any time between harvest and sowing. It is customary to use seed which has been separated from the plant and freed from cobs, shells, stalks, coats, hairs or fruit flesh. For example, it is possible to use seed which has been harvested, cleaned and dried down to a moisture content of less than 15% by weight. Alternatively, it is also possible to use seed which has been dried and then treated, for example, with water and then dried again.

When treating the seed, care must generally be taken that the amount of the inventive composition and/or of further additives applied to the seed is selected such that the germination of the seed is not impaired, and that the resulting plant is not damaged. This must be borne in mind in particular in the case of active ingredients which can exhibit phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for treating seed are known to the person skilled in the art and are described, for example, in the following documents: U.S. Pat. No. 4,272, 417, U.S. Pat. No. 4,245,432, U.S. Pat. No. 4,808,430, U.S. Pat. No. 5,876,739, US-A-2003/0176428, WO-A-2002/ 080675, WO-A-2002/028186.

The active ingredients usable in accordance with the invention can be converted to the customary seed dressing formulations, such as solutions, emulsions, suspensions, powders, foams, slurries or other coating compositions for seed, and also ULV formulations.

These formulations are prepared in a known manner, by mixing the active ingredients or active ingredient combinations with customary additives, for example customary extenders and also solvents or diluents, dyes, wetting agents, dispersants, emulsifiers, antifoams, preservatives, secondary thickeners, adhesives, gibberellins and also water.

Dyes which may be present in the seed dressing formulations usable in accordance with the invention are all dyes which are customary for such purposes. In this context, it is possible to use either pigments, which are sparingly soluble in water, or dyes, which are soluble in water. Examples include the dyes known by the names Rhodamine B, C.I. Pigment Red 112 and C.I. Solvent Red 1.

Wetting agents which may be present in the seed dressing formulations usable in accordance with the invention are all substances which promote wetting and which are customary for the formulation of active agrochemical ingredients. Preference is given to using alkyl naphthalenesulphonates, such as diisopropyl or diisobutyl naphthalenesulphonates.

Suitable dispersants and/or emulsifiers which may be present in the seed dressing formulations usable in accordance with the invention are all nonionic, anionic and cationic dispersants customary for the formulation of active agrochemical ingredients. Preference is given to using nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ether, and their phosphated or sulphated derivatives. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances customary for the formulation of active agrochemical ingredients. Usable with preference are silicone antifoams and magnesium stearate.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention include all customary binders usable in seed dressing products. Preferred examples are polyvinylpyrrolidone, polyvinyl acetate, polyvinyl alcohol and tylose.

The gibberellins which may be present in the seed dressing formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz- and Schädlingsbekämpfungsmittel" [Chemistry of Crop Protection Compositions and Pesticides], vol. 2, Springer Verlag, 1970, p. 401-412).

The seed dressing formulations usable in accordance with the invention can be used for the treatment of a wide range of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, and beets, or else a of wide variety of different vegetable seed. The seed dressing formulations usable in accordance with the invention, or the dilute preparations thereof, can also be used to dress seed of transgenic plants. In this context, additional synergistic effects may also occur in interaction with the substances formed by expression.

For the treatment of seed with the seed dressing formulations usable in accordance with the invention or with the preparations prepared therefrom by addition of water, useful equipment is all mixing units usable customarily for seed dressing. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying process.

The application rate of the seed dressing formulations usable in accordance with the invention can be varied within a relatively wide range. It depends on the particular content of the active ingredients in the formulations and on the seed. The application rates of active ingredient combination are generally between 0.001 and 50 g per kilogram of seed, preferably between 0.01 and 15 g per kilogram of seed.

In addition, the inventive compounds of the formula (I) also have very good antimycotic effects. They have a very broad antimycotic activity spectrum, especially against dermatophytes and yeasts, moulds and diphasic fungi, (for example against Candida species such as Candida albicans, Candida glabrata), and Epidermophyton floccosum, Aspergillus species such as Aspergillus niger and Aspergillus fumigatus, Trichophyton species such as Trichophyton mentagrophytes, Microsporon species such as Microsporon canis and audouinii. The list of these fungi in no way constitutes a restriction of the mycotic spectrum which can be covered, but merely has illustrative character.

The inventive active ingredients of the formula (I) can therefore be used both in medical and in non-medical applications.

The active ingredients can be used as such, in the form of their formulations or the use forms prepared therefrom, such as ready-to-use solutions, suspensions, wettable powders, pastes, soluble powders, dusts and granules. Application is accomplished in a customary manner, for example by watering, spraying, atomizing, broadcasting, dusting, foaming, spreading, etc. It is also possible to apply the active ingredients by the ultra-low volume method, or to inject the active ingredient preparation or the active ingredient itself into the soil. It is also possible to treat the seed of the plants.

When using the inventive active ingredients as fungicides, the application rates can be varied within a relatively wide range, depending on the kind of application. The application rate of the inventive active ingredients is
- when treating plant parts, for example leaves: from 0.1 to 10 000 g/ha, preferably from 10 to 1000 g/ha, more preferably from 50 to 300 g/ha (when the application is carried out by watering or dripping, it is even possible to reduce the application rate, especially when inert substrates such as rockwool or perlite are used);
- when treating seed: from 2 to 200 g per 100 kg of seed, preferably from 3 to 150 g per 100 kg of seed, more preferably from 2.5 to 25 g per 100 kg of seed, most preferably from 2.5 to 12.5 g per 100 kg of seed;
- when treating the soil: from 0.1 to 10 000 g/ha, preferably from 1 to 5000 g/ha.

These application rates are mentioned merely by way of example and are not limiting in the sense of the invention.

The inventive active ingredients are used in the veterinary sector and in animal husbandry in a known manner by enteral administration in the form of for example, tablets, capsules, potions, drenches, granules, pastes, boluses, the feed-through process and suppositories, by parenteral administration, for example by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active ingredient, such as collars, ear marks, tail marks, limb bands, halters, marking devices and the like.

When used for livestock, poultry, domestic animals and the like, the active ingredients of the formula (I) can be used as formulations (for example powders, emulsions, flowables) comprising the active ingredients in an amount of from 1 to 80% by weight, either directly or after 100 to 10 000-fold dilution, or they may be used as a chemical bath.

The ready-to-use compositions can also comprise other insecticides if appropriate, and also one or more fungicides if appropriate.

With respect to possible additional partners for mixing, reference is made to the insecticides and fungicides mentioned above.

The inventive compounds can at the same time be employed for protection of objects which come into contact with saltwater or brackish water, especially hulls, screens, nets, buildings, moorings and signalling systems, from fouling.

In addition, the inventive compounds can be used as antifouling compositions, alone or in combinations with other active ingredients.

The inventive treatment method can be used for the treatment of genetically modified organisms (CMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene that is located in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. For example, the following effects which exceed the effects which were actually to be expected are possible: reduced application rates and/or a widening of the activity spectrum and/or an increase in the activity of the active ingredients and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products.

At certain application rates, the inventive active ingredient combinations may also have a fortifying effect on plants. Accordingly, they are suitable for mobilizing the defence system of the plant from attack by unwanted phytopathogenic fungi and/or microorganisms and/or viruses. This may be one of the reasons for the enhanced activity of the inventive combinations, for example against fungi. Plant-fortifying (resistance-inducing) substances shall be understood to mean, in the present context, also those substances or combinations of substances which are capable of stimulating the defence system of plants in such a way that, when subsequently inoculated with unwanted phytopathogenic fungi and/or microorganisms and/or viruses, the plants treated display a substantial degree of resistance to these unwanted phytopathogenic fungi and/or microorganisms and/or viruses. In the present case, unwanted phytopathogenic fungi and/or microorganisms and/or viruses are understood to mean phytopathogenic fungi, bacteria and viruses. The inventive substances can therefore be employed for protection of plants from attack by the pathogens mentioned within a certain period of time after the treatment. The period within which protection is achieved generally extends for from 1 to 10 days, preferably 1 to 7 days, after the treatment of the plants with the active ingredients.

Plants and plant varieties which are preferably treated in accordance with the invention include all plants which have genetic material which imparts particularly advantageous, useful traits to these plants (whether obtained by breeding and/or biotechnological means).

Plants and plant varieties which are also preferably treated in accordance with the invention are resistant against one or more biotic stress factors, i.e. said plants have a better defence against animal and microbial pests, such as against nematodes, insects, mites, phytopathogenic fungi, bacteria, viruses and/or viroids.

Plants and plant varieties which may also be treated in accordance with the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which may also be treated in accordance with the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated in accordance with the invention are hybrid plants that already express the characteristics of heterosis, or hybrid vigour, which results in generally higher yield, increased vigour, better health and better resistance towards biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in maize) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant varieties (obtained by plant biotechnology methods such as genetic engineering) which may be treated in accordance with the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyl transferase enzyme. Glyphosate-tolerant plants can also be obtained by selecting plants naturally-occurring mutations of the above-mentioned genes.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species for example). Plants expressing an exogenous phosphinothricin acetyltransferase have been described.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme. Tolerance to HPPD-inhibitors can also be obtained by transforming plants with genes encoding certain enzymes enabling the formation of homogentisate despite the inhibition of the native HPPD enzyme by the HPPD-inhibitor. Tolerance of plants to HPPD inhibitors can also be improved by transforming plants with a gene encoding an enzyme prephenate dehydrogenase in addition to a gene encoding an HPPD-tolerant enzyme.

Further herbicide-resistant plants are plants that have been made tolerant to acetolactate synthase (ALS) inhibitors. Known ALS inhibitors include, for example, sulphonylurea, imidazolinone, triazolopyrimidines, pyrimidinyl oxy(thio) benzoates, and/or sulphonylaminocarbonyltriazolinone herbicides. Different mutations in the ALS enzyme (also known as acetohydroxyacid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding.

Plants or plant varieties (obtained by plant biotechnology methods such as genetic engineering) which may also be treated in accordance with the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:
1) an insecticidal crystal protein from *Bacillus thuringiensis* or an insecticidal portion thereof, such as the insecticidal crystal proteins listed online at: http://www.lifesci.sussex-.ac.uk/Home/Neil_Crickmore/Bt/, or insecticidal portions thereof, for example proteins of the Cry protein classes Cry1Ab, Cry1Ac, Cry1F, Cry2Ab, Cry3Ae or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or
3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or
4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR 604;
5) an insecticidal secreted protein from *Bacillus thuringiensis* or *Bacillus cereus*, or an insecticidal portion thereof, such as the vegetative insecticidal proteins (VIP) listed at: http://www.lifescisussex.ac.uk/home/Neil_Crickmore/Bt/vip.html, for example proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins;
7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated in accordance with the invention are tolerant to abiotic stress factors. Such plants can be obtained by genetic transformation, or by selection of plants containing a mutation imparting such stress resistance. Particularly useful stress-tolerant plants include the following:
a. plants which contain a transgene capable of reducing the expression and/or the activity of the poly(ADP-ribose) polymerase (PARP) gene in the plant cells or plants;
b. plants which contain a stress tolerance-enhancing transgene capable of reducing the expression and/or the activity of the PARG-encoding genes of the plants or plant cells;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyl transferase, nicotinamide adenine dinucleotide synthetase or nicotinamide phosphoribosyltransferase.

Plants or plant varieties (obtained by plant biotechnology methods such as genetic engineering) which may also be treated in accordance with the invention show altered quantity, quality and/or storage stability of the harvested product and/or altered properties of specific ingredients of the harvested product such as, for example:
1) Transgenic plants which synthesize a modified starch which is altered with respect to its chemophysical traits, in particular the amylose content or the amylose/amylopectin ratio, the degree of branching, the average chain length, the distribution of the side chains, the viscosity behaviour, the gel resistance, the grain size and/or grain morphology of the starch in comparison to the synthesized starch in wild-type plant cells or plants, such that this modified starch is better suited for certain applications.
2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.

3) Transgenic plants which produce hyaluronan.

Plants or plant varieties (obtained by plant biotechnology methods such as genetic engineering) which may also be treated in accordance with the invention are plants, such as cotton plants, with altered fibre characteristics. Such plants can be obtained by genetic transformation, or by selection of plants containing a mutation imparting such altered fibre characteristics and include:

a) plants, such as cotton plants, which contain an altered form of cellulose synthase genes;
b) plants, such as cotton plants, which contain an altered form of rsw2 or rsw3 homologous nucleic acids;
c) plants, such as cotton plants, with an increased expression of sucrose phosphate synthase;
d) plants, such as cotton plants, with an increased expression of sucrose synthase;
e) plants, such as cotton plants, wherein the timing of the plasmodesmatal gating at the basis of the fibre cell is altered, for example through downregulation of fibre-selective β-1,3-glucanase;
f) plants, such as cotton plants, which have fibres with altered reactivity, for example through the expression of the N-acetylglucosaminetransferase gene including nodC and chitin synthase genes.

Plants or plant cultivars (obtained by plant biotechnology methods such as genetic engineering) which may also be treated in accordance with the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, which produce oil having a high oleic acid content;
b) plants, such as oilseed rape plants, which produce oil having a low linolenic acid content;
c) plants, such as oilseed rape plants, which produce oil having a low level of saturated fatty acids.

Particularly useful transgenic plants which may be treated in accordance with the invention are plants which comprise one or more genes which encode one or more toxins and are the transgenic plants available under the following trade names: YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are available under the following trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated in accordance with the invention are plants containing transformation events, or a combination of transformation events, and that are listed for example in the databases for various national or regional regulatory agencies (see for example http://gmoinfo.jrc.it/gmp_browse.aspx and http://www.agbios.com/dbase.php).

The plants listed can be treated in accordance with the invention in a particularly advantageous manner with the compounds of the general formula (I) and/or the active ingredient mixtures according to the invention. The preferred ranges stated above for the active ingredients or mixtures also apply to the treatment of these plants. Particular emphasis is given to the treatment of plants with the compounds or mixtures specifically mentioned in the present text.

The inventive active ingredients or compositions can thus be employed for protecting plants for a certain period of time after treatment from attack by the pathogens mentioned. The period for which protection is provided extends generally for 1 to 28 days, preferably for 1 to 14 days, more preferably for 1 to 10 days, most preferably for 1 to 7 days after the treatment of the plants with the active ingredients, or for up to 200 days after a seed treatment.

The preparation and the use of the inventive active ingredients of the formula (I) is illustrated by the examples below. However, the invention is not limited to these examples.

EXAMPLES

General note: Unless indicated otherwise, all chromatographic purification and separation steps are carried out on silica gel and using a solvent gradient from 0:100 ethyl acetate/cyclohexane to 100:0 ethyl acetate/cyclohexane.

Preparation of (I-12)

Step 1 tert-Butyl 4-(6-bromopyridin-2-yl)-4-hydroxypiperidine-1-carboxylate

To a solution of 2,6-dibromopyridine (34 g) in dichloromethane (740 ml) is added dropwise, at −78° C. under argon, n-butyllithium (1.6 M in tetrahydrofuran, 100 ml). The reaction mixture is stirred at −78° C. for 20 minutes and then tert-butyl 4-oxopiperidine-1-carboxylate is added. The mixture is stirred at room temperature for 20 minutes. The reaction mixture is subsequently admixed with saturated ammonium chloride solution at −30° C. and the aqueous phase is removed. After the aqueous phase has been extracted with dichloromethane, the combined organic phases are dried over sodium sulphate and concentrated under reduced pressure. The residue is purified by chromatography. This gives tert-butyl 4-(6-bromopyridin-2-yl)-4-hydroxypiperidine-1-carboxylate (60 g).

logP (pH2.7): 3.05

$^1$H NMR (DMSO-d$_6$, 400 MHz): δ$_{ppm}$: 1.43 (s, 9H), 1.95 (td, 2H), 2.35 (t, 2H), 3.15 (t, 2H), 3.84 (bd, 2H), 5.24 (bs, 1H), 7.46 (dd, 1H), 7.68 (dd, 1H), 7.73 (t, 1H)

MS (ESI): 301 and 303 ([M-COOC(CH$_3$)$_3$+2H]$^+$)

Step 2 tert-Butyl 6-bromo-3',6'-dihydro-2,4'-bipyridine-1'(2'H)-carboxylate

To a solution of tert-butyl 4-(6-bromopyridin-2-yl)-4-hydroxypiperidine-1-carboxylate (100 mg) in pyridine (2.5 ml) is added, at 0° C. under argon, POCl$_3$ (0.26 ml). The mixture is stirred at 0° C. and then slowly warmed to room temperature. The mixture is stirred at room temperature overnight.

The reaction mixture is subsequently admixed with saturated sodium hydrogencarbonate solution and the aqueous phase is removed. After the aqueous phase has been extracted with tert-butyl methyl ether, the combined organic phases are dried over sodium sulphate and concentrated under reduced pressure. The residue is purified by chromatography. This gives tert-butyl 6-bromo-3',6'-dihydro-2,4'-bipyridine-1'(2'H)-carboxylate (60 mg).

logP (pH2.7): 4.14

$^1$H NMR (DMSO-$d_6$, 400 MHz): $\delta_{ppm}$: 1.43 (s, 9H), 2.53-2.49 (m, 2H), 3.54 (t, 2H), 4.06 (td, 2H), 6.70 (m, 1H), 7.46 (d, 1H), 7.53 (d, 1H), 7.70 (t, 1H)

MS (ESI): 283 and 285 ([M-C(CH$_3$)$_3$+2H]$^+$)

Step 3

1'-tent-Butyl 6-ethyl-3',6'-dihydro-2,4'-bipyridine-1', 6(2'H)-dicarboxylate tert-Butyl 6-bromo-3',6'-dihydro-2,4'-bipyridine-1'(2'H)-carboxylate (500 mg) is dissolved in ethanol (10 ml) and stirred at 70° C. under 3 bar of CO for 20 hours in the presence of PdCl$_2$(PPh)$_2$ (52 mg) and triethylamine (1.44 ml). The catalyst is removed by filtration through Celite and concentrated under reduced pressure. Purification by chromatography gives 1'-tert-butyl 6-ethyl-3',6'-dihydro-2,4'-bipyridine-1',6(2'H)-dicarboxylate (380 mg).

logP (pH2.7): 3.48

$^1$H NMR (DMSO-$d_6$, 400 MHz): $\delta_{ppm}$: 1.34 (t, 3H), 1.44 (s, 9H), 2.63-2.57 (m, 2H), 3.56 (t, 2H), 4.07 (td, 2H), 4.36 (q, 2H), 6.74 (m, 1H), 7.75 (dd, 1H), 7.88 (dd, 1H), 7.94 (t, 1H)

MS (ESI): 333 ([M+H]$^+$)

Step 4

Ethyl 6-[1-(tert-butoxycarbonyl)piperidin-4-yl]pyridine-2-carboxylate

1'-tert-Butyl 6-ethyl-3',6'-dihydro-2,4'-bipyridine-1',6 (2'H)-dicarboxylate (31.5 g) is dissolved in ethanol (315 ml) and hydrogenated at room temperature under 1 bar of H$_2$ in the presence of Pd/C (10%, 4.5 g) for 12 hours. Filtration and removal of the solvent under reduced pressure gives ethyl 6-[1-(tert-butoxycarbonyl)piperidin-4-yl]pyridine-2-carboxylate (30.5 g).

logP (pH2.7): 3.29

$^1$H NMR (DMSO-$d_6$, 400 MHz): $\delta_{ppm}$: 1.33 (t, 3H), 1.42 (s, 9H), 1.62 (tdd, 2H), 1.86 (d, 2H), 2.87 (dd, 2H), 2.95 (m, 1H), 4.07 (bd, 2H), 4.35 (q, 2H), 7.51 (dd, 1H), 7.85 (dd, 1H), 7.89 (t, 1H)

MS (ESI): 335 ([M+H]$^+$)

Step 5

6-[1-(tert-Butoxycarbonyl)piperidin-4-yl]pyridine-2-carboxylic acid

To a solution of ethyl 6-[1-(tert-butoxycarbonyl)piperidin-4-yl]pyridine-2-carboxylate (500 mg) in tetrahydrofuran (5 ml) and water (1.3 ml) is added, at room temperature, lithium hydroxide monohydrate (125 mg). The mixture is stirred at room temperature for 2 h and then admixed with ice-cold 1N HCl solution. The aqueous phase is extracted with ethyl acetate and then the combined organic phases are dried over sodium sulphate. The solids are filtered off and the solvent is distilled off. This gives 6-[1-(tert-butoxycarbonyl)piperidin-4-yl]pyridine-2-carboxylic acid (310 mg).

logP (pH2.7): 1.78

$^1$H NMR (DMSO-$d_6$, 400 MHz): $\delta_{ppm}$ 1.42 (s, 9H), 1.64 (tdd, 2H), 1.86 (d, 2H), 2.87 (dd, 2H), 2.95 (m, 1H), 4.08 (bd, 2H), 7.50 (dd, 1H), 7.85 (dd, 1H), 7.89 (t, 1H)

MS (ESI): 251 ([M-C(CH$_3$)$_3$+2H]$^+$)

Step 6 tert-Butyl 4-{6-[methyl(1,2,3,4-tetrahydronaphthalen-1-yl)carbamoyl]pyridin-2-yl}-piperidine-1-carboxylate To a solution of 6-[1-(tert-butoxycarbonyl)piperidin-4-yl] pyridine-2-carboxylic acid (247 mg) in dichloromethane (5 ml) are added, at room temperature, N-methyl-1,2,3,4-tetrahydronaphthalen-1-amine (130 mg), 4-dimethylaminopyridine (10 mg) and 1-ethyl-3-(3'-dimethylaminopropyl)carbodiimide (162 mg). The mixture is stirred at room temperature overnight, and then water is added. The aqueous phase is removed and extracted with ethyl acetate. The combined organic phases are dried over sodium sulphate and concentrated under reduced pressure. The residue is purified by chromatography. This gives tert-butyl 4-{6-[methyl(1,2,3,4-tetrahydronaphthalen-1-yl)carbamoyl]pyridin-2-yl}piperidine-1-carboxylate (219 mg).

logP (pH2.7): 5.09

MS (ESI): 393 ([M-C(CH$_3$)$_3$+2H]$^+$)

Step 7

N-Methyl-6-(1-{[5-methyl-3-(trifluoromethyl)-1H-pyrazol-1-yl]acetyl}piperidin-4-yl)-N-(1,2,3,4-tetrahydronaphthalen-1-yl)pyridine-2-carboxamide To tert-butyl 4-{6-[methyl(1,2,3,4-tetrahydronaphthalen-1-yl)carbamoyl]pyridin-2-yl}-piperidine-1-carboxylate (302 mg) is added dropwise, at room temperature, a solution of trifluoroacetic acid (0.52 ml). The reaction mixture is stirred for 30 minutes, then the solvent and excess trifluoroacetic acid are removed. This gives 4-{6-[methyl(1,2,3,4-tetrahydronaphthalen-1-yl)carbamoyl]pyridin-2-yl}piperidinium trifluoroacetate.

To a solution of [5-methyl-3-(trifluoromethyl)-1H-pyrazol-1-yl]acetic acid (140 mg) in dichloromethane (5 ml) are added oxalyl chloride (256 mg) and one drop of N,N-dimethylformamide. Then the reaction mixture is stirred for 30 minutes. Then the excess of oxalyl chloride is removed under reduced pressure and the residue is dissolved again in dichloromethane (1 ml). The solution is then added to the former solution of 4-{6-[methyl(1,2,3,4-tetrahydronaphthalen-1-yl) carbamoyl]pyridin-2-yl}piperidinium trifluoroacetate in dichloromethane (5 ml) and diisopropylethylamine (869 mg). The reaction mixture is stirred for 2 hours. After addition of conc ammonium chloride solution, the aqueous phase is removed and extracted with ethyl acetate. The combined organic phases are dried over sodium sulphate and concentrated under reduced pressure. The residue is purified by chromatography. This gives N-methyl-6-(1-{[5-methyl-3-(trifluoromethyl)-1H-pyrazol-1-yl]acetyl}piperidin-4-yl)-N-(1,2,3,4-tetrahydronaphthalen-1-yl)pyridine-2-carboxamide (150 mg).

logP (pH2.7): 3.61

$^1$H NMR (DMSO-$d_6$, 400 MHz): $\delta_{ppm}$: 1.45-2.15 (m, 8H), 2.22 (s, 3H), 2.61 and 2.68 (s, 3H), 2.65-2.88 (m, 3H), 2.95-3.31 (m, 2H), 3.98 (bs, 1H), 4.38 (bs, 1H), 4.99 and 5.83 (m, 1H), 5.17 (bs, 2H), 6.45 (s, 1H), 7.05-7.25 (m, 4H), 7.38 (m, 1H), 7.50 (m, 1H), 7.86 (m, 1H)

MS (ESI): 410 ([M−1,2-dihydronaphthalene+H]$^+$)

Preparation of Compound (I-99)

Step 1

4-[6-(Ethoxycarbonyl)pyridin-2-yl]piperidinium chloride

To a solution of ethyl 6-[1-(tert-butoxycarbonyl)piperidin-4-yl]pyridine-2-carboxylate (2.0 g) was added dropwise, at 0° C., a 4 molar solution of hydrochloric acid in 1,4-dioxane (45 ml). The reaction mixture was stirred at 0° C. and then gradually warmed to room temperature. After stirring overnight, the solvent and excess hydrogen chloride were removed. This gave 4-[6-(ethoxycarbonyl)pyridin-2-yl]piperidinium chloride (1.75 g).

logP (pH2.7): 0.55

$^1$H NMR (DMSO-d$_6$, 400 MHz): δ$_{ppm}$: 1.34 (t, 3H), 2.10-1.95 (m, 4H), 3.07-2.96 (m, 2H), 3.12 (m, 1H), 3.48-3.33 (m, 2H), 4.21 (bs, 2H), 4.36 (q, 2H), 7.53 (dd, 1H), 7.89 (dd, 1H), 7.95 (t, 1H), 8.94 (bs, 1H), 9.32 (bs, 1H)

MS (ESI): 235 ([M−Cl]$^+$)

Step 2

Ethyl 6-(1-{[3,5-bis(difluoromethyl)-1H-pyrazol-1-yl]acetyl}piperidin-4-yl)pyridine-2-carboxylate To a solution of [1,5-bis(difluoromethyl)-1H-pyrazol-1-yl]acetic acid (11.4 g) in dichloromethane (50 ml) is slowly added dropwise oxalyl chloride (17.5 g), and one drop of N,N-dimethylformamide. Then the reaction mixture is stirred overnight. Then the excess of oxalyl chloride is removed under reduced pressure and the residue is dissolved again in dichloromethane (20 ml). The solution is then added to the solution of 4-[6-(ethoxycarbonyl)pyridin-2-yl]piperidinium chloride in dichloromethane (30 ml) and diisopropylethylamine (17.8 g). The reaction mixture is stirred overnight. After addition of conc. ammonium chloride solution, the aqueous phase is removed and extracted with ethyl acetate. The combined organic phases are dried over sodium sulphate and concentrated under reduced pressure. The residue is purified by chromatography. This gives ethyl 6-(1-{[3,5-bis(difluoromethyl)-1H-pyrazol-1-yl]acetyl}piperidin-4-yl)pyridine-2-carboxylate (15.8 g).

logP (pH2.7): 2.68

$^1$H NMR (DMSO-d$_6$, 400 MHz): δ$_{ppm}$: 1.34 (t, 3H), 1.65 (bs, 1H), 1.80 (bs, 1H), 1.99-1.90 (m, 2H), 2.83 (bs, 1H), 3.10 (m, 1H), 3.25 (bs, 1H), 4.03 (bs, 1H), 4.36 (q, 2H), 4.40 (bs, 1H), 5.38-4.33 (m, 2H), 6.86 (s, 1H), 6.98 (t, 1H), 7.15 (t, 1H), 7.54 (dd, 1H), 7.87 (dd, 1H), 7.92 (t, 1H)

MS (ESI): 443 ([M+H]$^+$)

Step 3

6-(1-{[3,5-Bis(difluoromethyl)-1H-pyrazol-1-yl]acetyl}piperidin-4-yl)pyridine-2-carboxylic acid To a solution of ethyl 6-(1-{[3,5-bis(difluoromethyl)-1H-pyrazol-1-yl]acetyl}piperidin-4-yl)pyridine-2-carboxylate (15.5 g) in tetrahydrofuran (160 ml) and water (40 ml) is added, at room temperature, lithium hydroxide monohydrate (1.99 g). The mixture is stirred at room temperature for 1 hour, and then ice-cold 1N HCl solution is added. The aqueous phase is extracted with ethyl acetate. The combined organic phases are dried over sodium sulphate and concentrated under reduced pressure. This gives 6-(1-{[3,5-bis(difluoromethyl)-1H-pyrazol-1-yl]acetyl}piperidin-4-yl)pyridine-2-carboxylic acid (11.5 g).

logP (pH2.7): 1.55

$^1$H NMR (DMSO-d$_6$, 400 MHz): δ$_{ppm}$: 1.70 (bs, 1H), 1.82 (bs, 1H), 1.99-1.90 (m, 2H), 2.82 (bs, 1H), 3.08 (m, 1H), 3.25 (bs, 1H), 4.02 (bs, 1H), 4.43 (bs, 1H), 5.36 (bs, 2H), 6.86 (s, 1H), 6.98 (t, 1H), 7.16 (t, 1H), 7.52 (dd, 1H), 7.93-7.86 (m, 2H)

MS (ESI): 415 ([M+H]$^+$)

Step 4

Cyclohexyl 6-(1-{[3,5-bis(difluoromethyl)-1H-pyrazol-1-yl]acetyl}piperidin-4-yl)-pyridine-2-carboxylate To a solution of 6-(1-{[3,5-bis(difluoromethyl)-1H-pyrazol-1-yl]acetyl}piperidin-4-yl)-pyridine-2-carboxylic acid (157 mg) in dichloromethane (5 ml) are added, at room temperature, cyclohexanol (42 mg), 4-dimethylaminopyridine (4.6 mg) and 1-ethyl-3-(3'-dimethylaminopropyl)carbodiimide (80 mg). The mixture is stirred at room temperature overnight, and then water is added. The aqueous phase is removed and extracted with ethyl acetate. The combined organic phases are dried over sodium sulphate and concentrated under reduced pressure. The residue is purified by chromatography. This gives cyclohexyl 6-(1-{[3,5-bis(difluoromethyl)-1H-pyrazol-1-yl]acetyl}piperidin-4-yl)pyridine-2-carboxylate (87 mg).

logP (pH2.7): 3.83

$^1$H NMR (DMSO-d$_6$, 400 MHz): δ$_{ppm}$: 1.27-1.98 (m, 14H), 2.76-2.84 (m, 1H), 3.02-3.11 (m, 1H), 3.25 (m, 1H), 3.98-4.03 (m, 1H), 4.38-4.43 (m, 1H), 4.91-4.98 (m, 1H), 5.34 (d, 1H), 5.44 (d, 1H), 6.90 (s, 1H), 7.03 (t, 1H), 7.18 (t, 1H), 7.56 (dd, 1H), 7.87-7.95 (m, 2H)

MS (ESI): 497 ([M+H]$^+$)

Preparation of Compound (I-117)

Step 1 tert-Butyl 4-(6-bromopyridin-2-yl)piperazine-1-carboxylate 2,6-Dibromopyridine (1.0 g) and tert-butyl piperazine-1-carboxylate (870 mg) are dissolved in N,N-dimethylformamide (10 ml) and stirred at 80° C. in the presence of potassium carbonate (1.17 g) for 5 hours. To the reaction mixture is added tert-butyl piperazine-1-carboxylate (200 mg). The mixture is stirred at room temperature overnight, and then water is added. The aqueous phase is removed and extracted with dichloromethane. The combined organic phases are dried over sodium sulphate and concentrated under reduced pressure. The residue is purified by chromatography. This gives tert-butyl 4-(6-bromopyridin-2-yl)piperazine-1-carboxylate (900 mg).

logP (pH2.7): 4.08

$^1$H NMR (DMSO-d$_6$, 400 MHz): δ$_{ppm}$: 1.42 (s, 9H), 3.44-3.40 (m, 4H), 3.50-3.46 (m, 4H), 6.78 (dd, 2H), 7.43 (dd, 1H)

MS (ESI): 342 and 344 ([M+H]$^+$)

Step 2 tert-Butyl 4-[6-(ethoxycarbonyl)pyridin-2-yl]piperazine-1-carboxylate tert-Butyl 4-(6-bromopyridin-2-yl)piperazine-1-carboxylate (40 g) is dissolved in ethanol (300 ml) and stirred at 70° C. under 3 bar of CO for 48 hours in the presence of PdCl$_2$(PPh)$_2$ (4.10 g) and triethylamine (114 ml). The catalyst is removed by filtration through Celite and concentrated under reduced pressure. Purification by chromatography gives tert-butyl 4-[6-(ethoxycarbonyl)pyridin-2-yl]piperazine-1-carboxylate (43 g).

logP (pH2.7): 3.32

$^1$H NMR (DMSO-d$_6$, 400 MHz): δ$_{ppm}$: 1.30 (t, 3H), 1.42 (s, 9H), 3.44-3.41 (m, 4H), 3.56-3.52 (m, 4H), 4.29 (q, 2H), 7.08 (d, 1H), 7.32 (d, 1H), 7.70 (dd, 1H)

MS (ESI): 336 ([M+H]$^+$)

Step 3

Ethyl 6-(4-{[3,5-bis(difluoromethyl)-1H-pyrazol-1-yl]acetyl}piperazin-1-yl)pyridine-2-carboxylate To tert-butyl 4-[6-(ethoxycarbonyl)pyridin-2-yl]piperazine-1-carboxylate (2.36 g) is added, under argon and at 0° C., a solution of hydrogen chloride in dioxane (4 M, 10.5 ml). The mixture is stirred at 0° C. and then slowly warmed to room temperature. After stirring for 2 hours, the excess acid and the solvent are removed under reduced pressure. This gives 4-[6-(ethoxycarbonyl)pyridin-2-yl]piperazin-1-ium chloride.

To a solution of [3,5-bis(difluoromethyl)-1H-pyrazol-1-yl]acetic acid (1.67 g) in dichloromethane are added, at 0° C., oxalyl chloride (2.68 g) and one drop of N,N-dimethylformamide. The mixture is stirred at room temperature for 40 minutes. The solvent and the excess reagent are removed under reduced pressure. The solid residue is then dissolved again in dichloromethane and added dropwise at 0° C. to a solution of 4-[6-(ethoxycarbonyl)pyridin-2-yl]piperazin-1-ium chloride and triethylamine (9.8 ml) in dichloromethane (10 ml). Then concentrated sodium hydrogencarbonate solution is added to the reaction solution, and the aqueous phase is removed and extracted with ethyl acetate. The combined organic phases are dried over anhydrous sodium sulphate and concentrated. This gives ethyl 6-(4-{[3,5-bis(difluoromethyl)-1H-pyrazol-1-yl]acetyl}piperazin-1-yl)pyridine-2-carboxylate (1.3 g).

logP (pH2.7): 2.71

$^1$H NMR (DMSO-d$_6$, 400 MHz): δ$_{ppm}$: 1.31 (t, 3H), 3.59 (bs, 4H), 3.72-3.62 (m, 4H), 4.30 (q, 2H), 5.42 (bs, 2H), 6.91 (s, 1H), 7.03 (t, 1H), 7.13 (d, 1H), 7.18 (t, 1H), 7.35 (d, 1H), 7.73 (dd, 1H)

MS (ESI): 444 ([M+H]$^+$)

Step 4

6-(4-{[3,5-Bis(difluoromethyl)-1H-pyrazol-1-yl]acetyl}piperazin-1-yl)pyridine-2-carboxylic acid To a solution of ethyl 6-(4-{[3,5-bis(difluoromethyl)-1H-pyrazol-1-yl]acetyl}piperazin-1-yl)pyridine-2-carboxylate (1.3 g) in tetrahydrofuran (20 ml) and water (5 ml) is added, at room temperature, lithium hydroxide monohydrate (185 mg). The mixture is stirred at room temperature for 5 hours, and then ice-cold 1N HCl solution is added. The aqueous phase is extracted with ethyl acetate and then the combined organic phases are dried over sodium sulphate. The solids are filtered off and the solvent is distilled off. This gives 6-(4-{[3,5-bis(difluoromethyl)-1H-pyrazol-1-yl]acetyl}piperidin-1-yl)pyridine-2-carboxylic acid (700 mg).

logP (pH2.7): 0.68

$^1$H NMR (DMSO-d$_6$, 400 MHz): δ$_{ppm}$: 3.67-3.55 (m, 6H), 3.74-3.69 (m, 2H), 5.14 (bs, 1H), 5.42 (bs, 2H), 6.91 (s, 1H), 7.03 (t, 1H), 7.11 (d, 1H), 7.18 (t, 1H), 7.35 (d, 1H), 7.73 (dd, 1H)

MS (ESI): 416 ([M+H]$^+$)

Step 5

1,2,3,4-Tetrahydronaphthalen-1-yl 6-(4-{[3,5-bis(difluoromethyl)-1H-pyrazol-1-yl]-acetyl}piperazin-1-yl)pyridine-2-carboxylate To a solution of 6-(4-{[3,5-bis(difluoromethyl)-1H-pyrazol-1-yl]acetyl}piperazin-1-yl)-pyridine-2-carboxylic acid (150 mg) in dichloromethane (5 ml) are added, at room temperature, 1,2,3,4-tetrahydronaphthalen-1-ol (70 mg), 4-dimethylaminopyridine (4.4 mg) and 1-ethyl-3-(3'-dimethylaminopropyl)carbodiimide (104 mg). The mixture is stirred at room temperature overnight, and then water is added. The aqueous phase is removed and extracted with ethyl acetate, and then the combined organic phases are dried over sodium sulphate. The solids are filtered off and the solvent is distilled off. The residue is purified by chromatography. This gives 1,2,3,4-tetrahydronaphthalen-1-yl 6-(4-{[3,5-bis(difluoromethyl)-1H-pyrazol-1-yl]acetyl}piperazin-1-yl)pyridine-2-carboxylate (70 mg).

logP (pH2.7): 4.02

$^1$H NMR (DMSO-d$_6$, 400 MHz): δ$_{ppm}$: 1.86 (m, 1H), 2.11-1.90 (m, 3H), 2.81-2.73 (m, 1H), 2.92-2.84 (m, 1H), 3.57 (s, 4H), 3.65-3.60 (m, 2H), 3.70-3.66 (m, 2H), 5.41 (bs, 2H), 6.13 (t, 1H), 6.91 (s, 1H), 7.02 (t, 1H), 7.28-7.10 (m, 5H), 7.31 (d, 2H), 7.70 (dd, 1H)

MS (ESI): 546 ([M+H]$^+$)

Examples

Analogously to the methods specified above, it is also possible to obtain the compounds of the formula (I) listed in Table 1 below.

TABLE I

| Example E | | X | Y¹ | Y² | L¹ | R¹ | log P |
|---|---|---|---|---|---|---|---|
| 1 | [3,5-bis(difluoromethyl)-1H-pyrazol-1-yl]acetyl | CH | O | NCH₃ | CH₂ | 2-bromophenyl | 3.32[b]; 3.37[c] |
| 2 | [5-methyl-3-(trifluoromethyl)-1H-pyrazol-1-yl]acetyl | CH | O | NCH₃ | CH₂ | 2-bromophenyl | 3.47[b]; 3.49[c] |
| 3 | [5-methyl-3-(trifluoromethyl)-1H-pyrazol-1-yl]acetyl | N | O | NCH₃ | CH₂ | 2-bromophenyl | 3.44[b]; 3.46[c] |
| 4 | [3,5-bis(difluoromethyl)-1H-pyrazol-1-yl]acetyl | CH | O | NH | CH₂ | 2-bromophenyl | 3.44[b]; 3.47[c] |
| 5 | [5-methyl-3-(trifluoromethyl)-1H-pyrazol-1-yl]acetyl | CH | O | NH | CH₂ | 2-bromophenyl | 3.59[b]; 3.59[c] |
| 6 | [5-methyl-3-(trifluoromethyl)-1H-pyrazol-1-yl]acetyl | CH | O | O | CH₂CH₂CH₂ | CF₃ | 3.37[b] |
| 7 | [3,5-bis(difluoromethyl)-1H-pyrazol-1-yl]acetyl | CH | O | O | CH₂ | 2-(trifluoromethoxy)-phenyl | 3.98[b] |
| 8 | [5-methyl-3-(trifluoromethyl)-1H-pyrazol-1-yl]acetyl | CH | O | O | CH₂ | 2-(trifluoromethoxy)-phenyl | 4.06[b] |
| 9 | [3,5-bis(difluoromethyl)-1H-pyrazol-1-yl]acetyl | CH | O | O | CH₂ | 2-(trifluoromethoxy)-phenyl | 3.89[b] |
| 10 | [5-methyl-3-(trifluoromethyl)-1H-pyrazol-1-yl]acetyl | CH | O | NCH₃ | bond | 2-chlorophenyl | 3.18[b]; 3.2[c] |
| 11 | [5-methyl-3-(trifluoromethyl)-1H-pyrazol-1-yl]acetyl | CH | O | NCH₃ | bond | cyclohexyl | 3.15[b]; 3.18[c] |
| 12 | [5-methyl-3-(trifluoromethyl)-1H-pyrazol-1-yl]acetyl | CH | O | NCH₃ | bond | 1,2,3,4-tetrahydro-naphthalen-1-yl | 3.61[b] |
| 13 | [5-methyl-3-(trifluoromethyl)-1H-pyrazol-1-yl]acetyl | CH | O | NCH₃ | CH₂ | 2,4-dichlorophenyl | 3.85[b]; 3.85[c] |
| 14 | [5-methyl-3-(trifluoromethyl)-1H-pyrazol-1-yl]acetyl | CH | O | NCH₃ | CH₂ | pyridin-2-yl | 2.23[c] |
| 15 | [5-methyl-3-(trifluoromethyl)-1H-pyrazol-1-yl]acetyl | CH | O | Y²—L¹—R¹ = 2,3-dihydro-4H-1,4-benzoxazin-4-yl | | | 3.04[b]; 3.04[c] |
| 16 | [5-methyl-3-(trifluoromethyl)-1H-pyrazol-1-yl]acetyl | CH | O | NH | CH(CH₃) | 2-chlorophenyl | 3.82[b]; 3.75[c] |
| 17 | [5-methyl-3-(trifluoromethyl)-1H-pyrazol-1-yl]acetyl | CH | O | NH | CH(CH₃) | pentyl | 4.17[b]; 4.13[c] |
| 18 | [5-methyl-3-(trifluoromethyl)-1H-pyrazol-1-yl]acetyl | CH | O | NH | bond | cyclohexyl | 3.46[c] |
| 19 | [5-methyl-3-(trifluoromethyl)-1H-pyrazol-1-yl]acetyl | CH | O | NH | bond | 2,3-dihydro-1H-inden-1-yl | 3.56[b]; 3.56[c] |
| 20 | [5-methyl-3-(trifluoromethyl)-1H-pyrazol-1-yl]acetyl | CH | O | NH | CH₂CH₂CH₂ | butyl | 4.25[b]; 4.24[c] |
| 21 | [5-methyl-3-(trifluoromethyl)-1H-pyrazol-1-yl]acetyl | CH | O | NH | CH₂ | 2,4-dichlorophenyl | 4.1[b]; 4[c] |
| 22 | [5-methyl-3-(trifluoromethyl)-1H-pyrazol-1-yl]acetyl | CH | O | NH | CH₂ | 2,4-difluorophenyl | 3.36[b]; 3.36[c] |
| 23 | [5-methyl-3-(trifluoromethyl)-1H-pyrazol-1-yl]acetyl | CH | O | NH | CH₂ | 2-chlorophenyl | 3.49[b]; 3.52[c] |
| 24 | [5-methyl-3-(trifluoromethyl)-1H-pyrazol-1-yl]acetyl | CH | O | NH | CH₂ | 2,6-difluorophenyl | 3.33[b]; 3.26[c] |
| 25 | [5-methyl-3-(trifluoromethyl)-1H-pyrazol-1-yl]acetyl | CH | O | NH | CH₂ | pyridin-2-yl | 1.97[b]; 2.44[c] |
| 26 | [5-methyl-3-(trifluoromethyl)-1H-pyrazol-1-yl]acetyl | CH | O | NH | CH₂ | thiophen-2-yl | 3.15[b]; 3.1[c] |
| 27 | [5-methyl-3-(trifluoromethyl)-1H-pyrazol-1-yl]acetyl | CH | O | NH | CH₂ | 3-methylthiophen-2-yl | 3.29[b]; 3.34[c] |
| 28 | [5-methyl-3-(trifluoromethyl)-1H-pyrazol-1-yl]acetyl | CH | O | NH | bond | 2,6-difluorophenyl | 3.13[b]; 3.15[c] |
| 29 | [5-methyl-3-(trifluoromethyl)-1H-pyrazol-1-yl]acetyl | CH | O | NH | bond | naphthalen-1-yl | 3.94[b]; 3.91[c] |
| 30 | [5-methyl-3-(trifluoromethyl)-1H-pyrazol-1-yl]acetyl | CH | O | NH | bond | naphthalen-2-yl | 4.09[b]; 4.11[c] |
| 31 | [5-methyl-3-(trifluoromethyl)-1H-pyrazol-1-yl]acetyl | CH | O | NH | bond | quinolin-8-yl | 4.02[b]; 4.04[c] |
| 32 | [5-methyl-3-(trifluoromethyl)-1H-pyrazol-1-yl]acetyl | CH | O | O | CH(CH₃) | 2-chlorophenyl | 4.12[b] |
| 33 | [5-methyl-3-(trifluoromethyl)-1H-pyrazol-1-yl]acetyl | CH | O | O | bond | cyclohex-2-en-1-yl | 3.64[b] |
| 34 | [5-methyl-3-(trifluoromethyl)-1H-pyrazol-1-yl]acetyl | CH | O | O | bond | cyclohexyl | 3.9[b] |
| 35 | [5-methyl-3-(trifluoromethyl)-1H-pyrazol-1-yl]acetyl | CH | O | O | bond | 1,2,3,4-tetra-hydronaphthalen-1-yl | 4.15[b] |

TABLE I-continued

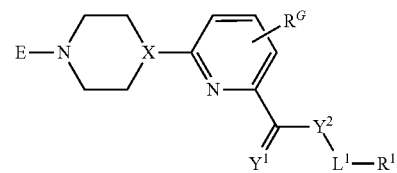

| Example E | | X | $Y^1$ | $Y^2$ | $L^1$ | $R^1$ | log P |
|---|---|---|---|---|---|---|---|
| 36 | [5-methyl-3-(trifluoromethyl)-1H-pyrazol-1-yl]acetyl | CH | O | O | CH$_2$C≡C | 2-chlorophenyl | 4.03[b] |
| 37 | [5-methyl-3-(trifluoromethyl)-1H-pyrazol-1-yl]acetyl | CH | O | O | CH$_2$ | tert-butyl | 3.86[b] |
| 38 | [5-methyl-3-(trifluoromethyl)-1H-pyrazol-1-yl]acetyl | CH | O | O | CH$_2$ | cyclohexyl | 4.38[b] |
| 39 | [5-methyl-3-(trifluoromethyl)-1H-pyrazol-1-yl]acetyl | CH | O | O | CH$_2$CH$_2$ | but-3-en-1-yl | 3.86[b] |
| 40 | [5-methyl-3-(trifluoromethyl)-1H-pyrazol-1-yl]acetyl | CH | O | O | CH$_2$CH$_2$ | pentyl | 4.73[b] |
| 41 | [5-methyl-3-(trifluoromethyl)-1H-pyrazol-1-yl]acetyl | CH | O | O | CH$_2$CH$_2$ | methoxy | 2.46[b] |
| 42 | [5-methyl-3-(trifluoromethyl)-1H-pyrazol-1-yl]acetyl | CH | O | O | CH$_2$ | 2,4-difluorophenyl | 3.6[b] |
| 43 | [5-methyl-3-(trifluoromethyl)-1H-pyrazol-1-yl]acetyl | CH | O | O | CH$_2$ | 2,4,6-trifluorophenyl | 3.69[b] |
| 44 | [5-methyl-3-(trifluoromethyl)-1H-pyrazol-1-yl]acetyl | CH | O | O | CH$_2$ | 2-methylphenyl | 3.8[b] |
| 45 | [5-methyl-3-(trifluoromethyl)-1H-pyrazol-1-yl]acetyl | CH | O | O | CH$_2$ | 2-(trifluoromethyl)-phenyl | 3.97[b] |
| 46 | [5-methyl-3-(trifluoromethyl)-1H-pyrazol-1-yl]acetyl | CH | O | O | CH$_2$ | 2-chlorophenyl | 3.84[b] |
| 47 | [5-methyl-3-(trifluoromethyl)-1H-pyrazol-1-yl]acetyl | CH | O | O | CH$_2$ | 2-fluorophenyl | 3.52[b] |
| 48 | [5-methyl-3-(trifluoromethyl)-1H-pyrazol-1-yl]acetyl | CH | O | O | CH$_2$ | 2,6-difluorophenyl | 3.51[b] |
| 49 | [5-methyl-3-(trifluoromethyl)-1H-pyrazol-1-yl]acetyl | CH | O | O | CH$_2$ | 3-methylpyridin-2-yl | 2.23[b] |
| 50 | [5-methyl-3-(trifluoromethyl)-1H-pyrazol-1-yl]acetyl | CH | O | O | CH$_2$ | 4-methylpyridin-2-yl | 3.67[b] |
| 51 | [5-methyl-3-(trifluoromethyl)-1H-pyrazol-1-yl]acetyl | CH | O | O | bond | naphthalen-1-yl | 3.97[b] |
| 52 | [5-methyl-3-(trifluoromethyl)-1H-pyrazol-1-yl]acetyl | CH | O | O | bond | naphthalen-2-yl | 3.9[b] |
| 53 | [5-methyl-3-(trifluoromethyl)-1H-pyrazol-1-yl]acetyl | CH | O | S | bond | cyclohexyl | 4.83[c] |
| 54 | [5-methyl-3-(trifluoromethyl)-1H-pyrazol-1-yl]acetyl | CH | O | S | CH$_2$CH$_2$CH$_2$ | butyl | |
| 55 | [5-methyl-3-(trifluoromethyl)-1H-pyrazol-1-yl]acetyl | CH | O | S | CH$_2$ | 2,4-dichlorophenyl | 5.17[b]; 5.21[c] |
| 56 | [5-methyl-3-(trifluoromethyl)-1H-pyrazol-1-yl]acetyl | CH | O | S | CH$_2$ | 2-methylphenyl | 4.57[b]; 4.58[c] |
| 57 | [5-methyl-3-(trifluoromethyl)-1H-pyrazol-1-yl]acetyl | CH | O | S | CH$_2$ | 2-chlorophenyl | 4.61[b]; 4.61[c] |
| 58 | [5-methyl-3-(trifluoromethyl)-1H-pyrazol-1-yl]acetyl | CH | O | S | CH$_2$ | 2,6-difluorophenyl | 4.27[b]; 4.29[c] |
| 59 | [5-methyl-3-(trifluoromethyl)-1H-pyrazol-1-yl]acetyl | CH | O | S | CH$_2$ | 4-fluorophenyl | 4.29[b]; 4.31[c] |
| 60 | [5-methyl-3-(trifluoromethyl)-1H-pyrazol-1-yl]acetyl | CH | O | S | bond | naphthalen-1-yl | 4.41[b]; 4.46[c] |
| 61 | [5-methyl-3-(trifluoromethyl)-1H-pyrazol-1-yl]acetyl | CH | O | S | bond | naphthalen-2-yl | 4.57[b]; 4.61[c] |
| 62 | [5-methyl-3-(trifluoromethyl)-1H-pyrazol-1-yl]acetyl | CH | O | S | bond | phenyl | 3.95[b]; 3.95[c] |
| 63 | [5-methyl-3-(trifluoromethyl)-1H-pyrazol-1-yl]acetyl | CH | O | S | bond | thiophen-2-yl | 3.85[b]; 3.88[c] |
| 64 | [5-methyl-3-(trifluoromethyl)-1H-pyrazol-1-yl]acetyl | N | O | NCH$_3$ | bond | cyclohexyl | 3.19[b]; 3.21[c] |
| 65 | [5-methyl-3-(trifluoromethyl)-1H-pyrazol-1-yl]acetyl | N | O | NH | CH$_2$ | 2-chlorophenyl | 3.34[b]; 3.36[c] |
| 66 | [5-methyl-3-(trifluoromethyl)-1H-pyrazol-1-yl]acetyl | N | O | NH | CH$_2$ | 2,6-difluorophenyl | 3.11[b]; 3.12[c] |
| 67 | [5-methyl-3-(trifluoromethyl)-1H-pyrazol-1-yl]acetyl | N | O | NH | CH$_2$ | thiophen-2-yl | 2.92[b]; 2.93[c] |
| 68 | [5-methyl-3-(trifluoromethyl)-1H-pyrazol-1-yl]acetyl | N | O | O | bond | cyclohex-2-en-1-yl | 3.67[b]; 3.7[c] |
| 69 | [5-methyl-3-(trifluoromethyl)-1H-pyrazol-1-yl]acetyl | N | O | O | bond | cyclohexyl | 3.96[b]; 3.98[c] |

TABLE I-continued

| Example E | | X | $Y^1$ | $Y^2$ | $L^1$ | $R^1$ | log P |
|---|---|---|---|---|---|---|---|
| 70 | [5-methyl-3-(trifluoromethyl)-1H-pyrazol-1-yl]acetyl | N | O | O | bond | 1,2,3,4-tetra-hydronaphthalen-1-yl | 4.19[b]; 4.2[c] |
| 71 | [5-methyl-3-(trifluoromethyl)-1H-pyrazol-1-yl]acetyl | N | O | O | CH$_2$CH$_2$ | but-3-en-1-yl | 3.92[b]; 3.95[c] |
| 72 | [5-methyl-3-(trifluoromethyl)-1H-pyrazol-1-yl]acetyl | N | O | O | CH$_2$ | 2-chlorophenyl | 3.89[b]; 3.9[c] |
| 73 | [5-methyl-3-(trifluoromethyl)-1H-pyrazol-1-yl]acetyl | N | O | O | CH$_2$ | 2-fluorophenyl | 3.58[b]; 3.6[c] |
| 74 | [5-methyl-3-(trifluoromethyl)-1H-pyrazol-1-yl]acetyl | N | O | O | CH$_2$ | 2,6-difluorophenyl | 3.54[b]; 3.55[c] |
| 75 | [5-methyl-3-(trifluoromethyl)-1H-pyrazol-1-yl]acetyl | N | O | O | bond | naphthalen-1-yl | 3.99[b]; 4[c] |
| 76 | [5-methyl-3-(trifluoromethyl)-1H-pyrazol-1-yl]acetyl | N | O | O | bond | naphthalen-2-yl | 4.01[b]; 4.02[c] |
| 77 | [3,5-bis(difluoromethyl)-1H-pyrazol-1-yl]acetyl | CH | O | NCH$_3$ | bond | 2-chlorophenyl | 3.01[b]; 3.01[c] |
| 78 | [3,5-bis(difluoromethyl)-1H-pyrazol-1-yl]acetyl | CH | O | NCH$_3$ | bond | cyclohexyl | 3.02[b]; 3.08[c] |
| 79 | [3,5-bis(difluoromethyl)-1H-pyrazol-1-yl]acetyl | CH | O | NCH$_3$ | CH$_2$ | 2,4-dichlorophenyl | 3.66[b]; 3.73[c] |
| 80 | [3,5-bis(difluoromethyl)-1H-pyrazol-1-yl]acetyl | CH | O | NCH$_3$ | CH$_2$ | pyridin-2-yl | 1.81[b]; 2.18[c] |
| 81 | [3,5-bis(difluoromethyl)-1H-pyrazol-1-yl]acetyl | CH | O | $Y^2$—$L^1$—$R^1$ = 2,3-dihydro-4H-1,4-benzoxazin-4-yl | | | 2.98[b]; 2.97[c] |
| 82 | [3,5-bis(difluoromethyl)-1H-pyrazol-1-yl]acetyl | CH | O | NH | CH(CH$_3$) | 2-chlorophenyl | 3.53[b]; 3.61[c] |
| 83 | [3,5-bis(difluoromethyl)-1H-pyrazol-1-yl]acetyl | CH | O | NH | CH(CH$_3$) | pentyl | 3.99[b]; 3.95[c] |
| 84 | [3,5-bis(difluoromethyl)-1H-pyrazol-1-yl]acetyl | CH | O | NH | bond | 2,3-dihydro-1H-iden-1-yl | 3.4[b]; 3.44[c] |
| 85 | [3,5-bis(difluoromethyl)-1H-pyrazol-1-yl]acetyl | CH | O | NH | CH$_2$CH$_2$CH$_2$ | butyl | 3.96[b]; 4.05[c] |
| 86 | [3,5-bis(difluoromethyl)-1H-pyrazol-1-yl]acetyl | CH | O | NH | CH$_2$ | 2,4-dichlorophenyl | 3.86[b]; 3.86[c] |
| 87 | [3,5-bis(difluoromethyl)-1H-pyrazol-1-yl]acetyl | CH | O | NH | CH$_2$ | 2,4-difluorophenyl | 3.22[b]; 3.24[c] |
| 88 | [3,5-bis(difluoromethyl)-1H-pyrazol-1-yl]acetyl | CH | O | NH | CH$_2$ | 2-chlorophenyl | 3.35[b]; 3.39[c] |
| 89 | [3,5-bis(difluoromethyl)-1H-pyrazol-1-yl]acetyl | CH | O | NH | CH$_2$ | 2,6-difluorophenyl | 3.11[b]; 3.14[c] |
| 90 | [3,5-bis(difluoromethyl)-1H-pyrazol-1-yl]acetyl | CH | O | NH | CH$_2$ | pyridin-2-yl | 1.83[b]; 2.37[c] |
| 91 | [3,5-bis(difluoromethyl)-1H-pyrazol-1-yl]acetyl | CH | O | NH | CH$_2$ | thiophen-2-yl | 2.98[b]; 2.97[c] |
| 92 | [3,5-bis(difluoromethyl)-1H-pyrazol-1-yl]acetyl | CH | O | NH | CH$_2$ | 3-methylthiophen-2-yl | 3.19[b]; 3.18[c] |
| 93 | [3,5-bis(difluoromethyl)-1H-pyrazol-1-yl]acetyl | CH | O | NH | bond | 2,6-difluorophenyl | 3.06[b]; 3.04[c] |
| 94 | [3,5-bis(difluoromethyl)-1H-pyrazol-1-yl]acetyl | CH | O | NH | bond | naphthalen-1-yl | 3.79[b]; 3.79[c] |
| 95 | [3,5-bis(difluoromethyl)-1H-pyrazol-1-yl]acetyl | CH | O | NH | bond | naphthalen-2-yl | 4.03[b]; 3.98[c] |
| 96 | [3,5-bis(difluoromethyl)-1H-pyrazol-1-yl]acetyl | CH | O | NH | bond | quinolin-8-yl | 3.91[b]; 3.92[c] |
| 97 | [3,5-bis(difluoromethyl)-1H-pyrazol-1-yl]acetyl | CH | O | O | bond | 2-methoxycyclohexyl | 4.17[b] |
| 98 | [3,5-bis(difluoromethyl)-1H-pyrazol-1-yl]acetyl | CH | O | O | bond | cyclohex-2-en-1-yl | 3.87[b] |
| 99 | [3,5-bis(difluoromethyl)-1H-pyrazol-1-yl]acetyl | CH | O | O | bond | cyclohexyl | 3.83[b] |
| 100 | [3,5-bis(difluoromethyl)-1H-pyrazol-1-yl]acetyl | CH | O | O | bond | (1R)-1,2,3,4-tetra-hydronaphthalen-1-yl | 4.07[b] |
| 101 | [3,5-bis(difluoromethyl)-1H-pyrazol-1-yl]acetyl | CH | O | O | CH$_2$CH$_2$ | but-3-en-1-yl | 3.8[b] |
| 102 | [3,5-bis(difluoromethyl)-1H-pyrazol-1-yl]acetyl | CH | O | O | CH$_2$CH$_2$ | pentyl | 4.59[b] |
| 103 | [3,5-bis(difluoromethyl)-1H-pyrazol-1-yl]acetyl | CH | O | O | CH$_2$ | 2,4-difluorophenyl | 3.54[b] |
| 104 | [3,5-bis(difluoromethyl)-1H-pyrazol-1-yl]acetyl | CH | O | O | CH$_2$ | 2,4,6-trifluorophenyl | 3.57[b] |
| 105 | [3,5-bis(difluoromethyl)-1H-pyrazol-1-yl]acetyl | CH | O | O | CH$_2$ | 2-chlorophenyl | 3.77[b] |
| 106 | [3,5-bis(difluoromethyl)-1H-pyrazol-1-yl]acetyl | CH | O | O | CH$_2$ | 2-fluorophenyl | 3.45[b] |
| 107 | [3,5-bis(difluoromethyl)-1H-pyrazol-1-yl]acetyl | CH | O | O | CH$_2$ | 2,6-difluorophenyl | 3.44[b] |
| 108 | [3,5-bis(difluoromethyl)-1H-pyrazol-1-yl]acetyl | CH | O | O | CH$_2$ | 3-methylpyridin-2-yl | 2.14[b] |
| 109 | [3,5-bis(difluoromethyl)-1H-pyrazol-1-yl]acetyl | CH | O | O | CH$_2$ | 4-methylthiophen-2-yl | 3.6[b] |
| 110 | [3,5-bis(difluoromethyl)-1H-pyrazol-1-yl]acetyl | CH | O | O | bond | naphthalen-1-yl | 3.82[b] |
| 111 | [3,5-bis(difluoromethyl)-1H-pyrazol-1-yl]acetyl | CH | O | O | bond | naphthalen-2-yl | 3.86[b] |
| 112 | [3,5-bis(difluoromethyl)-1H-pyrazol-1-yl]acetyl | CH | O | S | bond | cyclohexyl | 4.63[a]; 4.65[c] |
| 113 | [3,5-bis(difluoromethyl)-1H-pyrazol-1-yl]acetyl | CH | O | S | CH$_2$ | 2,6-difluorophenyl | 4.12[b]; 4.13[c] |
| 114 | [3,5-bis(difluoromethyl)-1H-pyrazol-1-yl]acetyl | CH | O | S | bond | naphthalen-1-yl | 4.4[a]; 4.42[c] |
| 115 | [3,5-bis(difluoromethyl)-1H-pyrazol-1-yl]acetyl | CH | O | O | bond | 2-fluorocyclohexyl | 3.37[b] |
| 116 | [5-methyl-3-(trifluoromethyl)-1H-pyrazol-1-yl]acetyl | CH | O | O | bond | 2-fluorocyclohexyl | 3.43[b] |
| 117 | [3,5-bis(difluoromethyl)-1H-pyrazol-1-yl]acetyl | N | O | O | bond | 1,2,3,4-tetra-hydronaphthalen-1-yl | 4.02[a]; 4.07[c] |
| 118 | [5-methyl-3-(trifluoromethyl)-1H-pyrazol-1-yl]acetyl | N | O | O | CH$_2$ | 2,4,6-trifluorophenyl | 3.68[b]; 3.71[c] |
| 119 | [3,5-bis(difluoromethyl)-1H-pyrazol-1-yl]acetyl | N | O | O | bond | cyclohexyl | 4.61[a]; 4.65[c] |
| 120 | [3,5-bis(difluoromethyl)-1H-pyrazol-1-yl]acetyl | N | O | S | bond | naphthalen-1-yl | 4.25[a]; 4.28[c] |
| 121 | [3,5-bis(difluoromethyl)-1H-pyrazol-1-yl]acetyl | CH | O | S | bond | phenyl | 3.8[a]; 3.85[c] |
| 122 | [3,5-bis(difluoromethyl)-1H-pyrazol-1-yl]acetyl | N | O | S | bond | phenyl | 3.79[a]; 3.81[c] |

TABLE I-continued

| Example E | | X | Y¹ | Y² | L¹ | R¹ | log P |
|---|---|---|---|---|---|---|---|
| 123 | [3,5-bis(difluoromethyl)-1H-pyrazol-1-yl]acetyl | CH | O | S | bond | thiophen-2-yl | 3.76[a]; 3.77[c] |
| 124 | [3,5-bis(difluoromethyl)-1H-pyrazol-1-yl]acetyl | N | O | S | bond | thiophen-2-yl | 3.73[a]; 3.75[c] |
| 125 | [3,5-bis(difluoromethyl)-1H-pyrazol-1-yl]acetyl | N | O | S | $CH_2$ | 2,6-difluorophenyl | 4.11[a]; 4.14[c] |
| 126 | [3,5-bis(difluoromethyl)-1H-pyrazol-1-yl]acetyl | CH | O | S | $CH_2$ | 2-chlorophenyl | 4.44[a]; 4.49[c] |
| 127 | [3,5-bis(difluoromethyl)-1H-pyrazol-1-yl]acetyl | N | O | S | $CH_2$ | 2-chlorophenyl | 4.42[a]; 4.44[c] |
| 128 | [3,5-bis(difluoromethyl)-1H-pyrazol-1-yl]acetyl | CH | O | S | $CH_2$ | 4-fluorophenyl | 4.1[a]; 4.15[c] |
| 129 | [3,5-bis(difluoromethyl)-1H-pyrazol-1-yl]acetyl | CH | O | S | $CH_2CH_2CH_2$ | butyl | 5.43[a]; 5.44[c] |
| 130 | [3,5-bis(difluoromethyl)-1H-pyrazol-1-yl]acetyl | N | O | S | $CH_2CH_2CH_2$ | butyl | 5.4[a]; 5.38[c] |
| 131 | [3,5-bis(difluoromethyl)-1H-pyrazol-1-yl]acetyl | CH | O | O | $CH_2$ | $CH_3$ | 2.68[b] |
| 132 | [5-methyl-3-(trifluoromethyl)-1H-pyrazol-1-yl]acetyl | CH | O | O | $CH_2$ | $CH_3$ | 2.73[b] |
| 133 | [3,5-bis(difluoromethyl)-1H-pyrazol-1-yl]acetyl | CH | O | S | $CH_2$ | 2-methylphenyl | 4.39[a]; 4.41[c] |
| 134 | [5-methyl-3-(trifluoromethyl)-1H-pyrazol-1-yl]acetyl | CH | O | O | $CH_2$ | $CH_3$ | 2.74[b] |
| 135 | [3,5-bis(difluoromethyl)-1H-pyrazol-1-yl]acetyl | CH | O | O | bond | H | 1.55[b] |
| 136 | [5-methyl-3-(trifluoromethyl)-1H-pyrazol-1-yl]acetyl | CH | O | O | bond | H | |
| 137 | [3,5-bis(difluoromethyl)-1H-pyrazol-1-yl]acetyl | N | O | O | $CH_2$ | 2-fluorophenyl | 3.47[a]; 3.49[c] |
| 138 | [3,5-bis(difluoromethyl)-1H-pyrazol-1-yl]acetyl | N | O | O | $CH_2$ | 2,6-difluorophenyl | 3.43[a]; 3.43[c] |
| 139 | [3,5-bis(difluoromethyl)-1H-pyrazol-1-yl]acetyl | N | O | O | bond | 5,6,7,8-tetrahydro-naphthalen-1-yl | 4.25[a]; 4.29[c] |
| 140 | [3,5-bis(difluoromethyl)-1H-pyrazol-1-yl]acetyl | N | O | O | bond | cyclohexyl | 3.83[a]; 3.86[c] |
| 141 | [3,5-bis(difluoromethyl)-1H-pyrazol-1-yl]acetyl | N | O | O | bond | naphthalen-1-yl | 3.88[c] |
| 142 | [3,5-bis(difluoromethyl)-1H-pyrazol-1-yl]acetyl | N | O | O | bond | cyclohex-2-en-1-yl | 3.56[a]; 3.6[c] |
| 143 | [3,5-bis(difluoromethyl)-1H-pyrazol-1-yl]acetyl | N | O | $NCH_3$ | bond | 1,2,3,4-tetrahydro-naphthalen-1-yl | 3.42[a]; 3.45[c] |
| 144 | [3,5-bis(difluoromethyl)-1H-pyrazol-1-yl]acetyl | N | O | NH | $CH_2$ | 2,4-dichlorophenyl | 3.68[a]; 3.7[c] |
| 145 | [5-methyl-3-(trifluoromethyl)-1H-pyrazol-1-yl]acetyl | N | O | S | $CH_2$ | 2-methylphenyl | 4.52[b]; 4.55[c] |
| 146 | [3,5-bis(difluoromethyl)-1H-pyrazol-1-yl]acetyl | N | O | NH | $CH_2$ | 2-chlorophenyl | 3.24[a]; 3.26[c] |
| 147 | [5-methyl-3-(trifluoromethyl)-1H-pyrazol-1-yl]acetyl | N | O | $NCH_3$ | bond | 1,2,3,4-tetrahydro-naphthalen-1-yl | 3.55[b]; 3.59[c] |
| 148 | [3,5-bis(difluoromethyl)-1H-pyrazol-1-yl]acetyl | N | O | $NCH_3$ | $CH_2$ | 2-chlorophenyl | 3.22[a]; 3.25[c] |
| 149 | [5-methyl-3-(trifluoromethyl)-1H-pyrazol-1-yl]acetyl | N | O | S | $CH_2$ | 2,6,-difluorophenyl | 4.11[b]; 4.29[c] |

$R^G$ = H

The examples are numbered and are abbreviated in the text to "I-and the appropriate example number", for example I-5 = Example 5 in Table I.
The log P values were measured in accordance with EEC Directive 79/831 Annex V.A8 by HPLC (High Performance Liquid Chromatography)

[a]The determination in the acidic range is carried out at pH 2.3 with 0.1% aqueous phosphoric acid and acetonitrile as eluents; linear gradient from 10% acetonitrile to 95% acetonitrile.
[b]The LC-MS determination in the acidic range is effected at pH 2.7 with 0.1% aqueous formic acid and acetonitrile (contains 0.1% formic acid) as eluents; linear gradient from 10% acetonitrile to 95% acetonitrile
[c]The LC-MS determination in the neutral range is effected at pH 7.8 using 0.001 molar aqueous ammonium hydrogencarbonate solution and acetonitrile as eluents; linear gradient from 10% acetonitrile to 95% acetonitrile NMR Data of Selected Examples The NMR data of selected examples are listed either in conventional form (δ values, number of hydrogen atoms, multiplet splitting) or as NMR peak lists.

If the ¹H NMR data of selected examples are noted in the form of ¹H NMR peak lists, for each signal peak, first the δ value in ppm and then the signal intensity are listed, separated by a space. The δ-signal intensity number pairs of different signal peaks are listed separated from one another by semicolons.

The peak list of one example therefore takes the form of:
$\delta_1$ intensity$_1$; $\delta_2$ intensity$_2$; ...; $\delta_i$ intensity$_i$; ...; $\delta_n$ intensity$_n$ The solvent in which the NMR spectrum was recorded is listed in square brackets before the NMR peak list.

| Ex. | NMR data |
|---|---|
| I-1 | ¹H NMR (DMSO-$d_6$, 400 MHz): $d_{ppm}$: [7.91 (t), 7.83 (t)] (1H), [7.68 (d,) 7.55 (d)] (1H), 7.55-7.20 (m, 5H), 7.18 (t, 1H). 7.05 (t, 1H), 6.92 (s. 1H), [5.40 (q), 5.31 (s)] (2H), [4.73 (s), 4.64 (s)] (2H), [4.42 (d), 4.24 (d)] (1H), [4.01 (d), 3.80 (d)] (1H), 3.40-2.50 (m, 3H) [3.04 (s), 2.98 (s)] (3H), 2.02-1.50 (m, 3H), 1.45-1.09 (m, 1H) |
| I-2 | [DMSO-$d_6$] 7.8768 0.54; 7.814 0.94; 7.7928 0.59; 7.6449 0.51; 7.5739 0.89; 7.5593 0.83; 7.5216 1.14; 7.5036 1.42; 7.4367 1.31; 7.434 1.35; 7.4177 3.71; 7.3997 3.61; 7.3969 3.43; 7.3754 2.97; 7.356 1.49; 7.3314 1; 7.3115 0.85; 7.2299 1.05; 7.2142 1.02; 6.4581 2.47; 5.6893 14.21; 5.2258 0.54; 5.2223 0.59; 5.2037 0.67; 5.1781 0.74; 5.1453 2.98; 5.1228 0.38; 4.7459 1.49; 4.7105 0.58; 4.6719 2.32; 4.2859 0.34; 4.272 0.39; 4.2447 0.42; 4.0643 1.25; 4.0465 3.59; 4.0287 3.64; 4.0109 1.29; 3.9991 0.33; 3.8689 0.39; 3.8301 0.4; 3.3028 0.36; 3.2952 |

-continued

| Ex. | NMR data |
|---|---|
| | 0.37; 3.2828 0.42; 3.2495 0.54; 3.2155 0.57; 3.2038 0.63; 3.1909 0.7; 3.1706 0.93; 3.146 1.69; 3.1092 476.359985; 3.0737 1.24; 3.0323 4.64; 2.974 2.25; 2.8156 0.93; 2.6894 0.33; 2.6658 0.76; 2.6614 1.15; 2.6566 1.5; 2.6521 1.12; 2.6237 0.51; 2.5909 0.57; 2.526 3.41; 2.5098 4.77; 2.4969 72.150002; 2.4923 141.779999; 2.4876 194.380005; 2.4829 135.910004; 2.4782 65.370003; 2.3192 0.79; 2.3146 1.14; 2.3097 0.8; 2.2303 9.63; 2.0404 0.73; 1.9738 16; 1.9475 0.68; 1.7693 0.34; 1.7444 0.39; 1.6796 0.8; 1.6656 0.91; 1.6501 0.70; 1.6343 0.8; 1.6288 0.74; 1.4304 0.33; 1.4038 1.24; 1.3939 0.39; 1.3617 0.32; 1.2955 0.55; 1.2447 0.69; 1.2259 0.39; 1.1949 4.56; 1.1771 8.73; 1.1593 4.22; −0.0001 11.98; −0.0084 0.49 |
| I-3 | [CD$_3$CN] 7.6943 0.63; 7.6738 0.9; 7.6499 0.95; 7.6309 2.08; 7.6101 1.87; 7.6005 1.84; 7.5914 1.61; 7.5806 1.92; 7.4377 3.38; 7.4266 4.38; 7.4119 0.96; 7.3917 1.19; 7.3842 1.13; 7.3705 0.37; 7.2515 0.8; 7.2414 1.47; 7.2296 1.41; 7.2213 1.47; 7.2094 0.77; 6.9848 2.26; 6.9666 2.15; 6.9224 1.15; 6.9045 1.09; 6.87 1.16; 6.8488 1.11; 6.7722 2.27; 6.7507 2.16; 6.395 3.46; 5.4456 2.62; 5.0907 4.28; 5.0018 8.43; 4.7535 3.94; 4.6509 7.47; 4.0861 1.07; 4.0683 3.2; 4.0505 3.25; 4.0327 1.13; 3.701 1.09; 3.6866 1.08; 3.6652 1.18; 3.6512 1.48; 3.6239 2.35; 3.3875 1.38; 3.3759 2.1; 3.3625 1.87; 3.3268 1.96; 3.3115 2.12; 3.2776 2.16; 3.2628 1.88; 3.1956 1.79; 3.1825 2.05; 3.1702 1.33; 3.0368 15; 2.989 7.58; 2.2349 7.05; 2.2144 13.29; 2.1442 140.580002; 2.1063 0.84; 2.0998 0.57; 1.9712 14.78; 1.951 19.549999; 1.9449 35.98; 1.9387 50.169998; 1.9325 34.59; 1.9264 17.74; 1.4369 0.58; 1.2756 0.42; 1.2707 0.42; 1.2581 0.47; 1.2399 0.31; 1.2214 3.74; 1.2036 7.32; 1.1858 3.6; −0.0001 29.389999; −0.0083 1.37 |
| I-4 | [DMSO-d$_6$] 9.2216 1.57; 9.2055 3.07; 9.1899 1.53; 7.9757 2.45; 7.9565 6.31; 7.9375 4.96; 7.9098 6.05; 7.893 3.12; 7.6413 4.15; 7.6214 4.47; 7.5636 4.45; 7.5448 4.14; 7.3777 1.56; 7.3583 4.03; 7.3401 3.3; 7.2967 7.14; 7.281 2.5; 7.2776 2.4; 7.2363 2.32; 7.2319 2.06; 7.2168 3.28; 7.1982 1.67; 7.1942 1.51; 7.163 6.04; 7.1459 3.04; 7.0293 3.02; 7.0098 6.38; 6.8924 6.27; 6.8737 3.18; 5.7387 2.86; 5.4292 0.85; 5.3873 5.11; 5.3607 5.05; 5.3176 0.84; 4.5779 7.41; 4.5622 7.43; 4.4713 1.43; 4.4359 1.45; 4.0579 1.4; 4.0402 4.49; 4.0224 3.82; 4.005 2.51; 3.2822 693.52002; 3.2583 57.169998; 3.2281 1.32; 3.2202 1.47; 3.1785 0.43; 3.1653 0.5; 3.1183 1.07; 3.1093 0.84; 3.097 1.39; 3.0895 2.15; 3.0684 0.96; 3.0605 1.17; 3.0512 0.71; 2.8177 0.97; 2.7896 1.75; 2.7597 1.02; 2.6714 0.88; 2.6675 1.12; 2.6631 0.94; 2.5846 0.31; 2.5376 1.88; 2.5029 128.520004; 2.4986 162.830002; 2.4944 114.690002; 2.4403 0.47; 2.4246 0.33; 2.3253 1.15; 2.0656 0.78; 2.0457 1.25; 2.0358 1.27; 1.985 15; 1.9579 1.74; 1.9064 0.96; 1.8932 0.67; 1.8632 1.28; 1.831 1.37; 1.7967 1.38; 1.7616 1.14; 1.7345 0.52; 1.2354 0.33; 1.193 3.69; 1.1752 7.12; 1.1575 3.58; −0.0001 17.690001 |
| I-5 | [DMSO-d$_6$] 9.0541 0.59; 9.0386 1.03; 9.0238 0.59; 7.9543 1.31; 7.9353 3.55; 7.9165 3.38; 7.9041 2.99; 7.9008 3.38; 7.8849 1.38; 7.8816 0.99; 7.6255 1.87; 7.6235 1.92; 7.6042 2.3; 7.5403 2.16; 7.5371 2.13; 7.5217 1.99; 7.5184 1.84; 7.3694 0.42; 7.3666 0.42; 7.35 1.9; 7.3473 1.97; 7.3374 2.69; 7.3343 3.72; 7.3317 5.09; 7.3182 0.59; 7.2262 1.01; 7.2193 1.09; 7.2104 0.9; 7.2063 1.21; 7.199 0.98; 7.1911 0.68; 7.1837 0.66; 6.444 3.59; 5.6895 7.12; 5.2091 2.74; 4.5975 4.59; 4.5816 4.53; 3.2581 0.33; 3.2457 0.34; 3.2387 0.32; 3.2175 0.32; 3.1086 181.279999; 3.0863 1.95; 3.0652 0.54; 3.0561 0.72; 3.0477 0.43; 2.6613 0.42; 2.6565 0.6; 2.6521 0.43; 2.526 1.31; 2.5098 1.84; 2.4969 31.620001; 2.4922 62.970001; 2.4875 87.209999; 2.4828 61.57; 2.4782 30.059999; 2.3191 0.41; 2.3144 0.49; 2.3097 0.35; 2.2182 15.94; 2.2172 16; 2.0405 0.51; 2.0173 0.9; 1.9864 1.07; 1.9737 0.86; 1.9624 0.39; 1.8618 0.38; 1.8102 0.63; −0.0001 5.58 |
| I-6 | [DMSO-d$_6$] 7.9697 0.78; 7.9504 3.14; 7.9388 3.69; 7.9339 6.46; 7.9196 0.84; 7.6005 1.96; 7.5946 1.86; 7.5842 1.69; 7.5783 1.68; 6.4972 3.86; 5.7469 1.64; 5.3391 0.71; 5.297 2.47; 5.2522 2.53; 5.2098 0.69; 4.4586 0.71; 4.4255 0.77; 4.3787 2.18; 4.3626 4.42; 4.3464 2.18; 4.0263 0.67; 3.9934 0.73; 3.3082 391.470001; 3.2499 1.08; 3.2209 0.57; 3.1182 0.5; 3.1089 0.37; 3.0978 0.6; 3.089 1.01; 3.0797 0.59; 3.0681 0.41; 3.0596 0.55; 2.8235 0.49; 2.7923 0.86; 2.7655 0.49; 2.6742 0.36; 2.6698 0.49; 2.6653 0.37; 2.5399 0.85; 2.523 2.25; 2.5096 29.34; 2.5053 54.080002; 2.5008 70.139999; 2.4964 47.639999; 2.492 22.690001; 2.4725 1.61; 2.4528 1.3; 2.4437 1.38; 2.4326 1.41; 2.424 1.21; 2.4179 0.81; 2.4037 1.22; 2.3952 0.48; 2.3893 0.31; 2.3748 0.44; 2.332 0.38; 2.3275 0.5; 2.3228 0.39; 2.2207 15; 2.2009 0.54; 1.9983 0.75; 1.9819 1.94; 1.962 2.31; 1.9425 2.39; 1.9263 1.82; 1.9083 0.78; 1.8928 0.78; 1.8474 0.32; 1.826 0.6; 1.8183 0.61; 1.7949 0.53; 1.7854 0.5; 1.6423 0.57; 1.633 0.61; 1.611 0.55; 1.6015 0.56; −0.0001 2.37 |
| I-7 | $^1$H NMR (DMSO-d$_6$, 400 MHz): d$_{ppm}$: 1.57-1.66 (m, 1H), 1.75-1.84 (m, 1H), 1.88-1.98 (m, 2H), 2.75-2.81 (m, 1H), 3.05-3.11 (m, 1H), 3.24 (m, 1H), 4.01-4.04 (m, 1H), 4.39-4.43 (m, 1H), 5.34 (d, 1H), 5.42 (d, 1H), 5.45 (s, 2H), 6.90 (s, 1H), 7.02 (t, 1H), 7.17 (t, 1H), 7.43-7.56 (m, 3H), 7.59 (dd, 1H), 7.68 (dd, 1H), 7.89-7.97 (m, 2H) |
| I-8 | [DMSO-d$_6$] 7.9714 1.2; 7.9522 3.38; 7.9333 3; 7.9253 0.43; 7.9175 3; 7.9144 3.31; 7.8983 1.46; 7.8952 1.14; 7.7023 1.43; 7.6987 1.59; 7.6839 1.67; 7.6797 1.84; 7.61 2.22; 7.607 2.24; 7.5911 2.12; 7.5882 1.92; 7.5628 0.66; 7.5583 0.68; 7.5435 1.62; 7.5389 1.59; 7.5239 1.59; 7.5193 1.39; 7.481 1.29; 7.478 1.75; 7.4593 3.19; 7.4532 1.71; 7.4436 1.07; 7.4404 1.2; 7.437 0.95; 7.4331 1.11; 6.4929 3.94; 5.7471 3.33; 5.4534 9.8; 5.3324 0.66; 5.2894 2.49; 5.2454 2.44; 5.2023 0.69; 4.4535 0.69; 4.4198 0.74; 4.0216 0.69; 3.988 0.72; 3.3141 331.75; 3.2905 7.82; 3.2714 1.07; 3.2414 1.05; 3.2099 0.63; 3.1145 0.52; 3.1054 0.41; 3.0941 0.66; 3.0854 1.04; 3.0762 0.64; 3.0651 0.46; 3.0556 0.59; 2.8107 0.48; 2.7841 0.87; 2.7795 0.88; 2.7524 0.5; 2.6708 0.3; 2.5408 0.65; 2.5238 1.01; 2.5105 17.379999; 2.5061 32.990002; 2.5017 43.34; 2.4973 30.110001; 2.493 14.65; 2.3284 0.34; 2.2243 0.98; 2.2099 15; 2.1985 1.2; 2.07 0.31; 1.9513 0.57; 1.9218 1.35; 1.8833 0.81; 1.8508 0.32; 1.842 0.34; 1.8203 0.61; 1.8121 0.64; 1.7906 0.57; 1.7814 0.54; 1.6695 0.3; 1.6607 0.32; 1.6394 0.62; 1.6285 0.65; 1.6078 0.6; 1.5991 0.6; −0.0001 5.87 |
| I-9 | |
| I-10 | [DMSO-d$_6$] 7.7674 1.63; 7.748 3.73; 7.7287 2.29; 7.6152 2.53; 7.5959 1.94; 7.4569 0.6; 7.4447 0.56; 7.4384 0.58; 7.4332 0.81; 7.4173 0.68; 7.4084 0.62; 7.4024 0.7; 7.3936 0.72; 7.3428 0.45; 7.333 0.6; 7.3266 0.56; 7.3189 0.89; 7.3069 0.64; 7.3004 0.51; 7.2943 0.67; 7.283 0.89; 7.2749 0.5; 7.2658 1.62; 7.2566 1.3; 7.2512 1.3; 7.242 1.34; 7.2304 1.4; 7.221 1.49; 7.2103 1.02; 7.198 2.48; 7.1802 2.26; 6.5293 3.34; 5.7465 2.4; 5.2513 1.81; 5.2407 4.86; 5.1886 0.81; 4.3117 0.46; 4.2956 0.6; 4.0569 0.87; 4.0391 2.58; 4.0213 2.62; 4.0035 0.89; 3.8652 0.6; 3.8468 |

-continued

| Ex. | NMR data |
|---|---|
|  | 0.45; 3.3068 563.47998; 3.2905 26.950001; 3.1015 0.61; 3.069 0.98; 3.0433 1.78; 2.8552 1.18; 2.7357 0.51; 2.7269 0.41; 2.7156 0.62; 2.7066 1.03; 2.6974 0.67; 2.6858 0.44; 2.6743 0.82; 2.6691 0.88; 2.6652 0.65; 2.6154 0.54; 2.5846 0.98; 2.5549 0.72; 2.5393 2.99; 2.5223 2.25; 2.509 33.91; 2.5047 63.220001; 2.5002 81.910004; 2.4958 55.900002; 2.4915 26.41; 2.3315 0.48; 2.3269 0.63; 2.3223 0.47; 2.2634 15; 2.2222 1.56; 2.1937 1.16; 1.9866 11.35; 1.5397 0.33; 1.5031 0.72; 1.4685 0.47; 1.4336 0.41; 1.3984 1.19; 1.352 0.58; 1.318 0.32; 1.3092 0.31; 1.2203 0.38; 1.2127 0.38; 1.1927 3.35; 1.1749 6.26; 1.1571 3.19; 1.1404 0.39; 1.1297 0.36; 1.1087 0.35; 1.0985 0.32; 1.0141 0.34; 1.0045 0.33; 0.9813 0.31; −0.0001 4.57 |
| I-11 | [DMSO-$d_6$] 7.843 1.53; 7.8236 3.28; 7.8042 1.84; 7.3602 1.29; 7.3351 2.82; 7.316 2.15; 6.4446 4.01; 5.6876 10.56; 5.1938 1.47; 4.4264 0.33; 4.0646 0.38; 4.0466 0.79; 4.0289 0.91; 4.0209 0.36; 4.0109 0.52; 4.0014 0.33; 3.4317 0.4; 3.2541 0.42; 3.2397 0.46; 3.2264 0.51; 3.1127 300.720001; 3.056 1.11; 3.0374 0.99; 3.0279 1.41; 3.0199 0.89; 3.0068 0.68; 2.9987 0.77; 2.9886 0.56; 2.871 2.57; 2.8217 0.64; 2.7651 0.98; 2.6618 0.53; 2.657 0.69; 2.6524 0.45; 2.5264 1.45; 2.5101 2.26; 2.4973 37.790001; 2.4927 74.620003; 2.488 102.900002; 2.4833 72.550003; 2.4786 35.509998; 2.3836 0.44; 2.3193 0.48; 2.3146 0.67; 2.3099 0.48; 2.26 0.33; 2.2215 16; 2.0399 0.37; 1.9737 2.87; 1.9398 1.13; 1.9073 1.45; 1.9007 1.54; 1.8269 0.5; 1.7895 0.72; 1.6927 2.34; 1.5537 1.32; 1.5316 1.32; 1.195 0.85; 1.1773 1.59; 1.1645 0.62; 1.1595 0.9; 1.0827 1.1; 1.0569 0.41; 0.9978 0.75; 0.9866 0.7; 0.9815 0.7; −0.0001 2.42 |
| I-12 | $^1$H NMR (DMSO-$d_6$, 400 MHz): $d_{ppm}$: 1.45-2.15 (m, 8H), 2.22 (s, 3H), 2.61 and 2.68 (s, 3H), 2.65-2.88 (m, 3H), 2.95-3.31 (m, 2H), 3.98 (bs, 1H), 4.38 (bs, 1H), 4.99 and 5.83 (m, 1H), 5.17 (bs, 2H), 6.45 (s, 1H), 7.05-7.25 (m, 4H), 7.38 (m, 1H), 7.50 (m, 1H), 7.86 (m, 1H) |
| I-13 | [DMSO-$d_6$] 7.8893 0.35; 7.8491 0.6; 7.8391 0.61; 7.8262 0.67; 7.6093 0.51; 7.5421 0.63; 7.4922 1.03; 7.4514 1.04; 7.4466 1.02; 7.4309 2.5; 7.4259 2.56; 7.3993 2.08; 7.35 0.66; 7.4469 3.3; 5.688 16; 5.1692 1.86; 4.7434 2.29; 4.7086 0.49; 4.0471 0.41; 4.029 0.43; 3.1091 291.630005; 3.0406 1.66; 3.01 3.54; 2.9826 2.9; 2.9156 0.66; 2.8868 0.55; 2.8213 0.7; 2.8151 0.65; 2.7267 0.32; 2.662 0.52; 2.657 0.7; 2.6523 0.47; 2.5263 1.69; 2.4972 30.93; 2.4925 68.470001; 2.4878 100.620003; 2.4832 75.510002; 2.4785 40.799999; 2.3946 0.91; 2.3835 0.94; 2.3477 0.6; 2.3247 0.69; 2.3198 0.83; 2.3147 1.03; 2.3099 0.9; 2.3051 0.7; 2.2787 0.44; 2.2264 10.98; 2.1814 0.68; 2.1259 0.46; 2.1082 0.42; 2.1007 0.41; 2.0813 0.39; 2.0667 0.37; 2.04 0.75; 2.0371 0.58; 2.0316 0.39; 1.9738 2.33; 1.9434 0.77; 1.9008 0.47; 1.8851 0.39; 1.8737 0.4; 1.8568 0.36; 1.827 0.37; 1.7916 0.46; 1.7081 0.81; 1.6931 0.78; 1.6293 0.56; 1.6007 0.46; 1.5662 0.4; 1.5481 0.44; 1.5071 0.42; 1.4868 0.43; 1.4597 0.39; 1.4545 0.4; 1.4419 0.37; 1.4341 0.35; 1.404 0.46; 1.3939 0.36; 1.3328 0.38; 1.3287 0.36; 1.3156 0.4; 1.296 0.52; 1.243 0.41; 1.195 0.66; 1.1772 1.08; 1.1596 0.64; −0.0001 6.57 |
| I-14 | [DMSO-$d_6$] 8.541 0.54; 8.4784 0.81; 7.9741 0.34; 7.8644 0.49; 7.8475 0.41; 7.8117 0.72; 7.7941 1.31; 7.7746 1.01; 7.7428 0.9; 7.7256 0.47; 7.4653 3.42; 7.4634 3.63; 7.446 3.18; 7.4441 3.18; 7.4025 0.53; 7.3678 0.7; 7.349 0.64; 7.3203 1.09; 7.2999 1.34; 7.2863 1.44; 7.2665 1.2; 7.2427 0.7; 7.2268 0.77; 6.4563 2.31; 5.6877 16; 5.1709 2.23; 4.7649 1.62; 4.7047 2.98; 4.0646 0.37; 4.0467 0.83; 4.0291 0.84; 4.0112 0.44; 3.207 0.38; 3.1977 0.47; 3.1123 348.380005; 3.0267 18.4; 2.8931 0.46; 2.8883 0.48; 2.865 0.69; 2.8273 0.39; 2.6878 0.34; 2.662 0.66; 2.6573 0.86; 2.6524 0.68; 2.6478 0.47; 2.5266 1.37; 2.5104 2.07; 2.4975 35.860001; 2.4928 71.870003; 2.4882 99.709999; 2.4835 70.410004; 2.4788 34.419998; 2.3197 0.43; 2.3151 0.66; 2.3103 0.44; 2.2304 9.15; 2.0398 1.19; 1.9738 3.5; 1.9471 0.66; 1.9011 1.42; 1.7367 0.85; 1.7251 0.87; 1.7176 0.84; 1.2959 0.34; 1.2438 0.41; 1.195 1.17; 1.1772 1.86; 1.1595 0.83; 0.008 0.74; −0.0001 16.370001; −0.0084 0.6 |
| I-15 | [DMSO-$d_6$] 7.9289 0.74; 7.9093 1.58; 7.8899 0.95; 7.581 1.54; 7.5621 1.44; 7.4464 1.06; 7.4269 1.04; 7.0322 0.39; 7.0143 0.81; 6.9969 0.57; 6.9155 1.72; 6.8984 1.25; 6.895 1.2; 6.4869 3.19; 5.7468 0.8; 5.2499 1.51; 5.2276 2.1; 5.1859 0.36; 4.3591 0.42; 4.3529 0.44; 4.3072 1.73; 4.0568 1.19; 4.039 3.38; 4.0212 3.44; 4.0033 1.2; 3.9446 0.48; 3.8851 1.31; 3.3029 483.839996; 3.2272 0.49; 3.1956 0.69; 3.1668 0.38; 3.0219 0.3; 3.0062 0.4; 2.997 0.48; 2.7829 0.41; 2.7504 0.7; 2.7207 0.43; 2.6734 0.46; 2.6687 0.62; 2.6641 0.47; 2.5389 3.54; 2.522 2.55; 2.5086 34.439999; 2.5042 63.5; 2.4998 81.970001; 2.4954 55.18; 2.491 25.66; 2.3312 0.39; 2.3264 0.54; 2.3218 0.4; 2.205 12.27; 2.1883 0.34; 2.1797 0.67; 1.9866 15; 1.8479 0.56; 1.7969 0.37; 1.4934 0.32; 1.4852 0.32; 1.3984 0.58; 1.1926 4.14; 1.1748 8.26; 1.157 4.03; 0.008 0.75; −0.0001 16.389999; −0.0085 0.55 |
| I-16 | [DMSO-$d_6$] 8.7649 1.1; 8.745 1.04; 7.9348 1.56; 7.9156 3.77; 7.8963 2.6; 7.844 2.68; 7.8417 2.8; 7.825 1.78; 7.8224 1.63; 7.556 1.68; 7.5518 1.75; 7.5365 4.04; 7.5335 3.79; 7.5169 2.14; 7.5147 2.03; 7.4315 1.64; 7.4279 1.59; 7.4119 2.14; 7.4084 2.13; 7.3451 0.82; 7.3297 1.92; 7.3263 1.69; 7.3108 1.27; 7.3072 1; 7.2878 1.49; 7.2832 1.48; 7.2686 1.62; 7.2643 1.61; 7.2495 0.68; 7.2456 0.54; 6.4562 3.69; 5.6897 0.49; 5.4873 1.13; 5.468 1.41; 5.4493 1.11; 5.236 1.29; 4.479 0.33; 4.4703 0.33; 4.0644 1.2; 4.0466 3.28; 4.0288 3.23; 4.0111 1.15; 3.3009 0.35; 3.2707 0.41; 3.2508 0.39; 3.2437 0.38; 3.1977 0.38; 3.1152 306.679993; 3.0824 1.11; 2.8262 0.35; 2.8194 0.33; 2.6623 0.38; 2.6575 0.58; 2.6523 0.36; 2.5266 2.89; 2.5104 2.13; 2.4975 33.73; 2.4928 66.910004; 2.4881 92.330002; 2.4835 64.959999; 2.4788 31.68; 2.3198 0.42; 2.3151 0.55; 2.3103 0.38; 2.2356 16; 2.0375 1.17; 2.0109 1.15; 1.9741 13.56; 1.9649 0.4; 1.8415 0.42; 1.8112 0.54; 1.7911 0.51; 1.7684 0.5; 1.7611 0.48; 1.7553 0.48; 1.7488 0.43; 1.7382 0.41; 1.5536 9.59; 1.5361 9.55; 1.195 3.77; 1.1772 7.43; 1.1594 3.65; −0.0001 9.71 |
| I-17 | [DMSO-$d_6$] 8.2111 1.33; 8.1965 1.35; 7.9421 1.74; 7.9293 4.29; 7.9165 2.93; 7.8769 3.26; 7.8754 3.39; 7.8642 2.29; 7.8626 2.16; 7.5319 2.53; 7.5308 2.52; 7.5191 2.47; 6.5157 4.73; 5.3461 0.77; 5.3382 0.73; 5.3174 1.54; 5.3097 1.52; 5.2655 3; 5.2371 1.35; 4.4895 0.83; 4.4676 0.86; 4.0458 0.82; 4.0377 0.83; 4.034 1.68; 4.0221 2.16; 4.0191 1.53; 4.0103 1.43; 3.9964 0.75; 3.9831 0.38; 3.3843 0.47; 3.3517 322.350006; 3.3171 0.36; 3.2648 0.59; 3.261 0.67; 3.2422 1.1; 3.2395 1.12; 3.2212 0.65; 3.2174 0.55; 3.0892 0.57; 3.0832 0.37; 3.075 0.68; 3.0692 1.17; 3.0634 0.67; 3.0554 0.4; 3.0493 0.61; 3.0436 0.32; 2.7931 0.55; 2.7719 1.1; 2.7502 0.57; 2.6187 0.54; 2.6157 0.74; 2.6127 0.53; 2.5432 2.42; 2.5247 1.59; 2.5216 2.07; 2.5185 2.35; 2.5096 43.450001; 2.5067 91.019997; 2.5037 122.970001; 2.5007 88.709999; 2.4978 40.5; 2.3905 0.55; 2.3876 0.74; 2.3845 0.53; 2.2214 16; 2.0781 0.37; 1.9906 4.65; 1.9729 0.85; 1.9523 0.64; 1.9307 0.71; 1.8491 0.33; 1.8348 0.45; 1.8282 0.77; 1.8213 |

| Ex. | NMR data |
|---|---|
| | 0.5; 1.8141 0.46; 1.8071 0.7; 1.8005 0.41; 1.7258 0.33; 1.7188 0.38; 1.7046 0.78; 1.6978 0.8; 1.6836 0.75; 1.677 0.71; 1.5803 0.65; 1.5745 0.65; 1.5676 0.56; 1.5172 0.7; 1.5069 0.89; 1.4941 0.74; 1.4834 0.51; 1.2673 4.7; 1.1881 5.3; 1.1862 6.04; 1.1772 5.47; 1.1745 7.18; 1.1626 1.27; 0.8453 4.25; 0.8388 4.07; 0.8279 1.37; 0.0053 0.48; 0 12.84; −0.0055 0.41 |
| I-18 | [DMSO-$d_6$] 8.0927 0.84; 8.0712 0.86; 7.9265 1.29; 7.9075 3.58; 7.8887 3.35; 7.8753 2.94; 7.8719 3.4; 7.8562 1.4; 7.8528 1.08; 7.5034 2.1; 7.5002 2.14; 7.4848 1.96; 7.4815 1.91; 6.4554 3.62; 5.6878 10.32; 5.2285 0.96; 5.2117 0.97; 4.0469 0.47; 4.0292 0.49; 3.8077 0.61; 3.7977 0.6; 3.7862 0.57; 3.7768 0.46; 3.1136 174.580002; 3.0917 4.82; 3.0728 1.68; 3.0634 0.95; 3.0526 0.61; 3.0433 0.8; 3.0336 0.48; 2.5268 0.62; 2.5107 0.92; 2.4978 16.9; 2.4931 34.049999; 2.4884 47.43; 2.4837 33.720001; 2.479 16.610001; 2.3153 0.34; 2.2369 15.99; 2.2358 16; 2.0401 0.62; 1.9969 0.94; 1.9739 2.19; 1.8649 1.24; 1.8523 1.3; 1.8405 1.94; 1.8059 0.47; 1.7345 1.67; 1.7246 1.83; 1.712 1.53; 1.7015 1.53; 1.6158 0.7; 1.5849 0.73; 1.4568 0.48; 1.4495 0.36; 1.4279 1.28; 1.4212 1.06; 1.399 2.84; 1.3748 2.77; 1.352 0.88; 1.3456 1.26; 1.3232 0.32; 1.3159 0.51; 1.266 0.39; 1.2579 0.34; 1.2447 0.58; 1.2366 0.64; 1.2148 0.48; 1.207 0.5; 1.1953 0.53; 1.1775 0.77; 1.1597 0.34; −0.0001 2.87 |
| I-19 | [DMSO-$d_6$] 8.5537 0.98; 8.5331 1.02; 7.9551 0.49; 7.9458 7.4; 7.9362 4.59; 7.9331 4.65; 7.914 0.4; 7.5287 0.35; 7.5184 1.94; 7.5064 2.14; 7.4962 1.76; 7.2911 1.11; 7.2724 1.75; 7.2439 0.88; 7.2406 0.91; 7.2277 1.91; 7.2231 2.19; 7.2088 3.19; 7.1969 1.89; 7.1937 1.92; 7.1808 1.14; 7.1595 0.43; 6.4223 3.61; 5.6892 11.06; 5.5779 0.51; 5.5579 1.4; 5.5372 1.38; 5.5165 0.49; 5.1883 1.29; 4.0465 0.68; 4.0287 0.74; 4.011 0.43; 3.2144 0.36; 3.1934 0.33; 3.11 181.839996; 3.0741 0.95; 3.0625 0.86; 3.054 1.28; 3.0442 1.44; 3.0376 1.07; 3.0213 1.16; 3.0146 1.46; 2.9987 0.93; 2.991 0.89; 2.9228 0.62; 2.9031 1.25; 2.8827 0.98; 2.863 0.75; 2.8425 0.49; 2.6611 0.34; 2.6568 0.49; 2.652 0.34; 2.5468 0.55; 2.5389 0.59; 2.5262 1.8; 2.5186 1.29; 2.5149 1.25; 2.5052 2.66; 2.4969 26.870001; 2.4923 52.77; 2.4876 73.559998; 2.4829 51.639999; 2.4782 25.469999; 2.319 0.35; 2.3145 0.46; 2.3097 0.34; 2.1883 15.89; 2.1875 16; 2.1101 0.51; 2.0881 1.16; 2.0788 0.51; 2.0675 1.13; 2.0566 1.07; 2.0455 0.5; 2.0403 0.65; 2.0359 1.04; 2.0137 0.45; 1.9738 3.3; 1.9395 1.12; 1.9005 0.37; 1.7963 0.33; 1.7399 0.41; 1.7292 0.43; 1.6888 0.4; 1.1949 0.69; 1.1771 1.39; 1.1593 0.69; −0.0001 4.81 |
| I-20 | [DMSO-$d_6$] 8.6172 0.59; 8.6019 1.17; 8.5865 0.63; 7.934 1.29; 7.9149 3.48; 7.8959 2.77; 7.8695 2.84; 7.8667 3.14; 7.8504 1.64; 7.8476 1.43; 7.513 2.08; 7.5104 2.15; 7.494 2.02; 7.4914 1.94; 6.501 3.86; 5.7475 2.56; 5.3235 0.46; 5.2812 2.93; 5.2586 2.87; 5.2163 0.67; 4.4969 0.67; 4.462 0.71; 4.0567 0.44; 4.0393 1.1; 4.0214 0.93; 4.0105 0.73; 4.0039 0.73; 3.3244 1.93; 3.3004 273.100006; 3.2766 9.11; 3.2402 1.14; 3.2101 0.66; 3.0832 0.52; 3.074 0.38; 3.0625 0.64; 3.054 1.05; 3.0441 0.76; 3.0332 0.43; 3.0242 0.59; 2.8008 0.49; 2.7742 0.88; 2.7428 0.51; 2.6737 0.39; 2.669 0.53; 2.6646 0.41; 2.5392 1.42; 2.5222 2.03; 2.5088 31.110001; 2.5044 57.610001; 2.5 74.370003; 2.4957 51.02; 2.4915 24.549999; 2.3313 0.42; 2.3267 0.56; 2.3222 0.44; 2.2236 15; 2.1996 0.76; 2.0697 0.68; 1.9869 2.74; 1.9556 1.23; 1.9176 0.84; 1.8898 0.31; 1.8791 0.35; 1.8572 0.62; 1.8477 0.64; 1.826 0.57; 1.8168 0.55; 1.7951 0.48; 1.7854 0.49; 1.7709 0.8; 1.7643 0.67; 1.7543 0.66; 1.733 0.57; 1.7229 0.54; 1.5555 1.2; 1.5377 1.73; 1.5209 1.22; 1.3983 0.87; 1.2978 5.18; 1.2918 5.03; 1.2698 3.56; 1.2628 4.82; 1.1928 0.71; 1.175 1.3; 1.1572 0.68; 0.8722 2.47; 0.8553 7.57; 0.8378 2.75; 0.008 0.33; −0.0001 7.26 |
| I-21 | [DMSO-$d_6$] 9.062 1.11; 9.0462 0.65; 7.9508 1.35; 7.9319 3.53; 7.913 3.15; 7.8963 2.86; 7.8931 3.2; 7.877 1.44; 7.874 1.08; 7.5698 2.78; 7.5651 2.93; 7.5384 2.11; 7.5354 2.13; 7.5196 1.93; 7.5166 1.82; 7.3982 1.03; 7.3934 0.86; 7.3773 3.33; 7.3724 3.47; 7.3614 4.21; 7.3403 1.05; 6.4472 3.76; 5.6898 7.15; 5.2106 2.72; 4.5987 4.47; 4.5832 4.4; 4.4557 0.34; 4.4403 0.32; 4.0642 0.68; 4.0466 1.54; 4.0288 1.53; 4.011 0.64; 3.288 0.4; 3.2496 0.48; 3.2366 0.47; 3.2237 0.48; 3.1165 372.149994; 3.0807 1.57; 3.0712 0.75; 3.0525 0.61; 2.6623 0.45; 2.6574 0.57; 2.6531 0.47; 2.5267 3.04; 2.4976 35.049999; 2.4929 69.699997; 2.4883 96.309998; 2.4836 68.110001; 2.4787 33.299999; 2.32 0.48; 2.315 0.56; 2.3104 0.37; 2.2196 16; 2.0373 0.6; 2.0033 0.91; 1.9742 6.44; 1.8366 0.52; 1.8282 0.68; 1.8076 0.68; 1.7974 0.64; 1.762 0.4; 1.4038 0.42; 1.195 1.58; 1.1772 3.16; 1.1595 1.51; 0.0081 0.46; −0.0001 10.38 |
| I-22 | [DMSO-$d_6$] 8.9842 0.59; 8.9705 0.99; 8.9558 0.59; 7.9392 1.27; 7.9201 3.55; 7.9016 3.57; 7.8911 3.12; 7.8875 3.49; 7.8718 1.36; 7.8684 0.98; 7.5202 2.23; 7.5169 2.14; 7.5017 1.97; 7.4985 1.87; 7.4425 0.72; 7.4254 0.87; 7.4206 1.4; 7.4042 1.44; 7.3826 0.69; 7.1679 0.87; 7.1616 0.87; 7.1444 1.04; 7.1418 1.08; 7.1384 1.16; 7.1354 1.1; 7.1183 0.81; 7.1119 0.86; 7.0415 0.69; 7.0392 0.7; 7.0351 0.65; 7.0201 1.24; 7.0175 1.25; 7.0136 1.16; 6.9985 0.6; 6.9957 0.62; 6.9922 0.53; 6.4469 3.71; 5.6879 10.34; 5.2085 2.38; 4.563 3.56; 4.5473 3.55; 4.0472 0.45; 4.0296 0.45; 4.0115 0.33; 3.2823 0.32; 3.2641 0.37; 3.2494 0.42; 3.2424 0.41; 3.2361 0.44; 3.2198 0.4; 3.1632 0.6; 3.1109 312.809998; 3.077 1.09; 3.0678 1.48; 3.0586 0.82; 3.0477 0.6; 3.0379 0.73; 3.0288 0.4; 2.6618 0.39; 2.6571 0.51; 2.6524 0.39; 2.5264 2.52; 2.5103 1.82; 2.4974 29.35; 2.4927 58.200001; 2.488 80.199997; 2.4833 56.470001; 2.4787 27.540001; 2.3197 0.39; 2.3148 0.49; 2.3104 0.35; 2.2218 16; 2.2208 16; 2.2029 0.46; 2.1917 0.34; 2.04 0.48; 2.0371 0.36; 1.9942 0.99; 1.9738 1.88; 1.7934 0.7; 1.1774 0.49; −0.0001 6.05 |
| I-23 | $^1$H NMR (DMSO-$d_6$, 400 MHz): d$_{ppm}$: 9.02 (t, 1H), 8.05-7.85 (m, 2H), 7.53 (dd, 1H), 7.44 (dd, 1H), 7.40-7.25 (m, 3H), 6.44 (s, 1H), 5.21 (bs, 2H), 4.62 (d, 2H), 4.55-4.35 (m, 1H), 4.10-3.95 m, 1H), 3.40-3.00 (m, 2H), 2.90-2.70 (m, 1H), 2.21 (s, 3H), 2.05-1.95 (m, 2H), 1.90-1.70 (m, 2H) |
| I-24 | $^1$H NMR (DMSO-$d_6$, 400 MHz): d$_{ppm}$: 8.72 (t, 1H), 7.91 (t, 1H), 7.87 (t, 1H), 7.50 (dd, 1H), 7.43-7.32 (m, 1H), 7.05 (t, 2H), 6.45 (s, 1H), 5.21 (bs, 2H), 4.64 (d, 2H), 4.52-4.45 (bs, 1H), 4.10-3.95 (bs, 1H), 3.35-3.00 (m, 2H), 2.90-2.70 (bs, 1H), 2.22 (t, 3H), 2.05-1.90 (m, 2H), 1.85-1.60 (m, 2H) |
| I-25 | [DMSO-$d_6$] 9.1657 0.62; 9.1527 0.93; 8.5274 1.32; 8.5154 1.34; 7.9745 0.49; 7.9523 1.13; 7.9334 3.26; 7.9153 4.04; 7.9112 3.26; 7.907 3.79; 7.892 1.18; 7.8879 0.68; 7.7643 1.05; 7.7596 1.01; 7.745 1.96; 7.7405 1.87; 7.7258 1.18; 7.7213 1.21; 7.5333 2.07; 7.5294 2.07; 7.5155 1.91; 7.5114 1.86; 7.3459 1.98; 7.3266 1.85; 7.267 1.03; 7.2523 1.16; 7.2485 1.12; 7.2365 0.95; 6.4553 0.41; 6.4451 3.6; 5.6879 3.74; 5.2141 2.46; 4.9318 0.43; 4.6527 4.53; 4.6378 4.49; 4.4703 0.34; 4.4591 0.34; 4.4531 0.34; 4.4312 0.34; 4.4231 0.38; 4.4084 0.34; 4.0704 0.35; 4.0466 0.55; 4.0285 0.47; 4.0113 0.32; 3.2924 0.41; 3.253 0.48; 3.2391 0.5; 3.2149 0.51; 3.1754 0.9; 3.1131 698.659973; 3.0635 1.52; 3.0541 1.1; 2.8259 0.36; 2.6665 |

-continued

| Ex. | NMR data |
|---|---|
|  | 0.47; 2.6622 0.8; 2.6574 1.17; 2.6525 0.88; 2.6479 0.51; 2.5265 2.5; 2.5104 3.69; 2.4975 62.919998; 2.4928 125.989998; 2.4882 174.610001; 2.4835 123.220001; 2.4788 60.23; 2.424 0.37; 2.3199 0.77; 2.315 1.17; 2.3103 0.73; 2.3056 0.43; 2.2796 0.64; 2.2199 16; 2.2188 15.84; 2.04 4.06; 2.0252 0.8; 2.0205 0.91; 2.0144 0.96; 1.9866 1.12; 1.974 1.86; 1.8282 0.6; 1.8141 0.65; 1.7877 0.53; 1.2465 0.35; 1.195 0.5; 1.1773 0.74; 1.1594 0.32; −0.0001 9.26 |
| I-26 | [DMSO-$d_6$] 9.2831 0.83; 9.2725 1.69; 9.2618 0.84; 7.9515 1.45; 7.9388 3.89; 7.9261 3.11; 7.9085 3.13; 7.9066 3.36; 7.8958 1.78; 7.8938 1.54; 7.5371 2.25; 7.5353 2.28; 7.5244 2.22; 7.5226 2.08; 7.3837 2.71; 7.3816 2.75; 7.3752 2.83; 7.3731 2.75; 7.035 1.92; 7.0332 1.97; 7.0293 2.28; 7.0276 2.13; 6.9681 2.71; 6.9623 2.42; 6.9596 2.58; 6.9539 2.18; 6.5089 4.29; 5.7639 0.98; 5.3204 0.99; 5.2918 2.95; 5.262 2.9; 5.2336 0.98; 4.8937 0.42; 4.6724 2.29; 4.6689 2.26; 4.6621 2.21; 4.6584 2.27; 4.4915 0.74; 4.4709 0.88; 4.0458 0.91; 4.0339 3.13; 4.0283 0.77; 4.022 3.15; 4.0101 1.49; 3.3508 317.170013; 3.3274 0.65; 3.2479 0.48; 3.2438 0.55; 3.2254 0.94; 3.2223 0.96; 3.2043 0.57; 3.2004 0.47; 3.0708 0.49; 3.0648 0.32; 3.0568 0.6; 3.0509 1.04; 3.0449 0.59; 3.037 0.35; 3.0311 0.55; 2.7775 0.46; 2.7734 0.53; 2.7563 0.96; 2.7521 0.96; 2.7349 0.55; 2.731 0.52; 2.6185 0.45; 2.6154 0.6; 2.6124 0.43; 2.5429 2.31; 2.5244 1.24; 2.5214 1.65; 2.5182 1.9; 2.5094 34.220001; 2.5064 72.040001; 2.5034 97.400002; 2.5004 69.779999; 2.4974 31.370001; 2.3903 0.42; 2.3873 0.57; 2.3843 0.41; 2.2593 0.68; 2.2085 16; 2.0779 0.79; 1.9905 12.04; 1.9714 0.6; 1.9501 0.85; 1.9253 0.63; 1.9045 0.82; 1.8677 0.32; 1.8535 0.66; 1.8471 0.7; 1.8327 0.64; 1.8262 0.61; 1.8123 0.4; 1.8071 0.45; 1.7932 0.68; 1.7864 0.7; 1.7723 0.62; 1.7656 0.61; 1.3968 0.42; 1.1862 3.29; 1.1743 6.65; 1.1624 3.24; 0.0053 0.42; 0 11.28; −0.0056 0.33 |
| I-27 | [DMSO-$d_6$] 9.0765 4.44; 9.0749 4.27; 8.6424 2.55; 8.6386 2.71; 8.6307 2.77; 8.6269 2.62; 8.4586 2.55; 8.4548 2.51; 8.4383 2.93; 8.4346 2.55; 8.3662 2.75; 8.3627 2.89; 8.083 3.3; 8.081 3.46; 8.0786 3.27; 8.0516 0.36; 8.0475 0.4; 7.9939 0.39; 7.9908 0.39; 7.6641 2.56; 7.6524 2.55; 7.6439 2.45; 7.6323 2.42; 7.5262 0.42; 7.473 8.02; 7.063 0.35; 6.0013 0.4; 5.9136 10.93; 4.0572 0.31; 4.0395 0.93; 4.0216 0.89; 4.0039 0.33; 3.4018 0.51; 3.3104 335.649994; 2.6744 0.47; 2.6703 0.61; 2.6653 0.48; 2.5401 2.22; 2.5098 36.200001; 2.5055 66.330002; 2.501 85.220001; 2.4967 57.950001; 2.4924 27.18; 2.4731 1.17; 2.3321 0.41; 2.3278 0.59; 2.3233 0.43; 2.3022 1.75; 2.2944 0.8; 2.2276 0.45; 2.1366 1.72; 2.0697 2.1; 1.9871 3.76; 1.7297 15; 1.2367 0.38; 1.193 1.05; 1.1752 2.04; 1.1575 0.96; 0.8898 0.31 |
| I-28 | [DMSO-$d_6$] 10.2242 2.71; 8.0185 1.03; 7.9994 2.94; 7.9806 2.68; 7.9656 2.61; 7.9626 2.81; 7.9466 1.22; 7.9435 0.99; 7.6255 1.81; 7.6228 1.83; 7.6068 1.72; 7.604 1.59; 7.4471 0.64; 7.4423 0.61; 7.4262 1.26; 7.4104 0.67; 7.4049 0.83; 7.389 0.35; 7.2373 2.46; 7.2171 3.8; 7.1966 1.8; 7.1883 0.39; 6.4911 3.88; 5.7474 1.03; 5.3196 0.37; 5.2785 3.09; 5.262 3.04; 5.2201 0.39; 4.5143 0.68; 4.4806 0.7; 4.057 1.5; 4.0392 3.42; 4.0214 3.45; 4.0036 1.08; 3.3013 342.190002; 3.2554 1.09; 3.2259 0.54; 3.1471 0.45; 3.1386 0.35; 3.1172 0.55; 3.1088 0.56; 3.0965 0.4; 3.0895 0.48; 2.814 0.45; 2.7842 0.86; 2.7551 0.49; 2.6738 0.39; 2.6688 0.52; 2.6644 0.41; 2.539 3.03; 2.5221 2.1; 2.5088 29.85; 2.5044 55.360001; 2.4999 71.589996; 2.4956 48.560001; 2.4912 22.75; 2.3312 0.37; 2.3268 0.5; 2.3223 0.36; 2.2155 15; 2.0496 0.79; 2.0178 0.93; 1.9868 13.55; 1.9654 1.03; 1.9337 0.59; 1.9235 0.63; 1.9016 0.73; 1.8915 0.75; 1.8709 0.7; 1.8621 0.7; 1.8383 0.51; 1.83 0.48; 1.3984 0.71; 1.1927 3.66; 1.1749 7.2; 1.1571 3.53; 0.008 0.69; −0.0001 15.66; −0.0083 0.57 |
| I-29 | [$CD_3CN$] 10.7594 3.08; 8.2171 3.16; 8.2057 3.07; 8.0861 6.29; 7.9743 6.2; 7.9689 6.3; 7.794 3.2; 7.7761 3.33; 7.7203 0.61; 7.6467 3.43; 7.564 8.09; 6.3822 4.17; 5.1659 1.64; 5.1243 5.93; 5.0912 4.75; 5.0563 1.88; 4.9785 0.33; 4.6516 2.29; 4.6259 2.46; 4.0502 3.74; 4.012 2.86; 3.7902 1.57; 3.3263 2.47; 3.1973 2.56; 2.8498 2.54; 2.8188 1.75; 2.5164 1.05; 2.424 1.12; 2.2151 16; 2.1535 14.96; 2.0973 6.82; 2.0592 6.13; 1.9718 9.86; 1.9457 15.14; 1.9398 15.57; 1.7908 0.81; 1.7168 0.58; 1.697 0.56; 1.4346 0.6; 1.264 2.1; 1.2209 3.34; 1.2102 4.05; 1.2038 4.44; 1.1866 3.09; 1.0672 0.39; 1.0595 0.38; 1.0528 0.36; 0.8722 0.54 |
| I-30 | [DMSO-$d_6$] 10.4443 1.67; 8.2219 2.6; 8.2176 2.55; 7.8822 2.27; 7.86 2.69; 7.8457 1.82; 7.8253 1.93; 7.8038 1.8; 7.7834 1.96; 7.6127 2.03; 7.6075 1.93; 7.5904 1.74; 7.5854 1.75; 7.4866 0.89; 7.4834 0.94; 7.4696 1.58; 7.4664 1.93; 7.4495 1.44; 7.4461 1.33; 7.4268 1.45; 7.4235 1.65; 7.4065 2.03; 7.4036 1.6; 7.3894 0.85; 7.3865 0.8; 6.5083 3.51; 5.1225 10.98; 5.1068 0.48; 3.1821 0.62; 3.1269 289.040009; 2.6625 0.51; 2.658 0.7; 2.653 0.49; 2.5271 3.02; 2.511 2.55; 2.498 39.41; 2.4934 77.989998; 2.4887 107.190002; 2.484 75.580002; 2.4794 36.740002; 2.3445 16; 2.3434 15.98; 2.32 0.53; 2.3153 0.71; 2.3111 0.46; 2.2267 0.7; 1.4034 0.32; 1.2444 0.6; −0.0001 10.45 |
| I-31 | [DMSO-$d_6$] 12.4662 1.94; 8.9497 2.1; 8.9456 2.22; 8.9393 2.18; 8.9351 2.09; 8.8306 1.99; 8.8272 2.03; 8.8118 2.08; 8.8085 2.04; 8.4402 1.88; 8.4362 1.91; 8.4193 2.09; 8.4153 1.93; 8.1002 0.9; 8.0967 1.25; 8.081 3.51; 8.0775 3.22; 8.0695 3.27; 8.051 3.5; 8.032 1.29; 7.9764 0.39; 7.7268 1.32; 7.7234 1.51; 7.706 2.75; 7.7026 2.54; 7.6683 3.94; 7.6642 2.29; 7.6494 4.57; 7.6295 1.33; 7.6204 2.02; 7.61 2.01; 7.5997 1.94; 7.5893 1.87; 6.4578 3.71; 5.694 0.39; 5.2872 2.44; 4.5359 0.32; 4.5243 0.33; 4.1241 0.33; 4.1174 0.33; 3.4006 0.35; 3.3914 0.35; 3.2822 0.34; 3.2717 0.63; 3.2615 0.44; 3.2547 0.72; 3.2445 1.16; 3.2346 0.76; 3.2268 0.53; 3.2169 0.74; 3.2066 0.47; 3.1295 220.970001; 2.9894 0.36; 2.6593 0.39; 2.5285 1.64; 2.5122 1.28; 2.4993 21.559999; 2.4947 42.860001; 2.49 59.259998; 2.4854 41.900002; 2.4807 20.459999; 2.3167 0.35; 2.2285 16; 2.1501 0.63; 2.1246 0.84; 2.0461 0.78; 2.0353 0.86; 2.0164 1.37; 2.0066 1.45; 1.9838 1.08; 1.9758 1.09; 1.9553 0.51; 1.9446 0.38; 1.403 0.37; −0.0001 4.78 |
| I-32 | [DMSO-$d_6$] 7.9865 0.69; 7.9743 6.79; 7.9675 3.43; 7.9592 3.28; 7.9399 0.73; 7.661 1.6; 7.6564 1.76; 7.6419 1.91; 7.6375 1.98; 7.6208 1.85; 7.6137 1.68; 7.6056 1.71; 7.5987 1.67; 7.5063 1.57; 7.5031 1.53; 7.487 2.13; 7.4835 2.15; 7.428 0.59; 7.4093 1.46; 7.3899 1.09; 7.3801 1.36; 7.3753 1.34; 7.3606 1.46; 7.3563 1.39; 7.342 0.55; 7.3381 0.46; 6.4958 4.04; 6.3436 0.6; 6.3276 2.02; 6.3112 2.02; 6.2951 0.6; 5.7469 2.61; 5.3447 0.62; 5.3028 2.23; 5.2543 2.46; 5.2114 0.72; 4.4589 0.71; 4.4268 0.78; 4.039 0.69; 4.0362 0.68; 4.022 0.54; 4.0006 0.75; 3.374 0.38; 3.3561 0.7; 3.3123 358.790009; 3.2904 5.67; 3.2628 1.18; 3.229 0.59; 3.1415 0.31; 3.1333 0.51; 3.1244 0.41; 3.1135 0.63; 3.1041 1.04; 3.0951 0.68; 3.0838 0.44; 3.0748 0.58; 2.8389 0.46; 2.8063 0.87; 2.7752 0.5; 2.6703 0.39; 2.5404 0.92; 2.51 22.91; 2.5057 42.700001; 2.5012 55.369999; 2.4969 38.07; 2.4926 18.059999; 2.3324 0.3; 2.3279 0.4; 2.2188 15; 2.1978 |

| Ex. | NMR data |
|---|---|
| | 0.73; 2.0698 0.34; 1.9872 1.05; 1.9785 0.59; 1.9449 1.26; 1.9092 0.81; 1.8326 0.57; 1.8015 0.5; 1.7915 0.39; 1.673 0.33; 1.6369 9.03; 1.6205 9.17; 1.1754 0.32; 0.008 0.34; −0.0001 7.22 |
| I-33 | [DMSO-d$_6$] 7.9514 1.26; 7.9323 3.34; 7.9132 2.83; 7.8905 2.85; 7.8877 3.05; 7.8714 1.5; 7.5834 2.16; 7.5807 2.12; 7.5642 1.97; 7.5616 1.87; 6.4975 3.87; 6.044 0.55; 6.0347 0.96; 6.0204 0.7; 6.0115 1.15; 6.0024 0.63; 5.8189 1; 5.8102 1.03; 5.8048 0.62; 5.7934 0.78; 5.7849 0.82; 5.7467 1.15; 5.4357 1.04; 5.3472 0.77; 5.3044 2.37; 5.2491 2.39; 5.2056 0.79; 4.458 0.69; 4.4275 0.73; 4.0276 0.71; 3.9947 0.73; 3.408 0.32; 3.3977 0.39; 3.3068 845.460022; 3.283 23.370001; 3.2506 1.5; 3.218 0.79; 3.2105 0.71; 3.1111 0.53; 3.1009 0.42; 3.0906 0.71; 3.083 1.1; 3.0749 0.69; 3.063 0.47; 3.0533 0.58; 3.0437 0.37; 2.8191 0.51; 2.791 0.84; 2.7581 0.54; 2.6692 0.98; 2.6644 0.66; 2.5394 2.27; 2.5223 3.58; 2.5091 57.450001; 2.5047 108.660004; 2.5002 142.169998; 2.4958 98.309998; 2.4915 47.139999; 2.4498 0.52; 2.3315 0.8; 2.3269 1; 2.3226 0.76; 2.2215 15; 2.1996 0.49; 2.1908 0.3; 2.1442 0.37; 2.1306 0.38; 2.0922 0.79; 2.0841 0.8; 2.0693 1.21; 2.0496 0.98; 2.0382 0.79; 1.9866 0.71; 1.9719 0.84; 1.9617 1.03; 1.9502 1.12; 1.9391 1.47; 1.929 1.98; 1.9077 1.03; 1.8888 0.87; 1.854 0.35; 1.8415 0.58; 1.821 1.29; 1.8132 1.24; 1.7982 1.19; 1.7873 1.29; 1.7712 0.95; 1.7535 0.86; 1.7394 0.64; 1.7307 0.63; 1.7158 0.39; 1.687 0.61; 1.6787 0.72; 1.6655 0.91; 1.6556 0.83; 1.633 0.9; 1.6241 0.88; 1.6016 0.64; 1.2366 0.32; −0.0001 18.1; −0.0083 0.85 |
| I-34 | [DMSO-d$_6$] 15.7097 0.01; 14.017 0.01; 13.2339 0.01; 13.0845 0.01; 10.467 0.01; 7.9955 0.03; 7.9568 0.28; 7.9376 0.77; 7.9186 0.66; 7.8989 0.62; 7.8959 0.74; 7.8797 0.35; 7.8766 0.29; 7.5861 0.43; 7.5831 0.45; 7.5671 0.42; 7.5641 0.4; 7.5535 0.02; 6.679 0.03; 6.6053 0.01; 6.5048 0.81; 5.9782 0.01; 5.7545 2.1; 5.354 0.17; 5.3115 0.48; 5.2581 0.5; 5.2157 0.17; 5.2001 0.03; 5.1553 0.01; 4.9804 0.06; 4.9708 0.12; 4.9582 0.14; 4.9486 0.23; 4.9388 0.15; 4.9266 0.11; 4.917 0.06; 4.4588 0.13; 4.4266 0.14; 4.1879 0.01; 4.1623 0.01; 4.0665 0.01; 4.0379 0.09; 4.0272 0.12; 4.0205 0.12; 3.9925 0.13; 3.9195 0.04; 3.8262 0.01; 3.6015 0.01; 3.5388 0.01; 3.5219 0.01; 3.5088 0.01; 3.4344 0.19; 3.385 0.16; 3.3766 0.1; 3.3348 188.910004; 3.3112 2.07; 3.2875 0.14; 3.2845 0.3; 3.2474 0.2; 3.2351 0.09; 3.2195 0.12; 3.1626 0.02; 3.1575 0.02; 3.1206 0.05; 3.1129 0.09; 3.1041 0.07; 3.0928 0.11; 3.0835 0.18; 3.0747 0.11; 3.0639 0.07; 3.0546 0.1; 3.0076 0.01; 2.8892 0.01; 2.8207 0.09; 2.7939 0.16; 2.7892 0.16; 2.7632 0.09; 2.6807 0.04; 2.676 0.1; 2.6713 0.14; 2.6668 0.1; 2.6067 0.02; 2.6026 0.02; 2.5434 0.03; 2.5248 0.36; 2.5202 0.51; 2.5115 6.91; 2.5069 15.49; 2.5023 21.860001; 2.4977 15.84; 2.4931 7.32; 2.4518 0.05; 2.4473 0.05; 2.3804 0.03; 2.3387 0.05; 2.3338 0.1; 2.3292 0.14; 2.3246 0.1; 2.3207 0.05; 2.2752 0.01; 2.2468 0.02; 2.2214 2.99; 2.2202 2.94; 2.202 0.16; 2.1963 0.06; 2.1478 0.01; 2.1006 0.01; 2.0734 0.84; 2.0583 0.02; 1.9887 0.12; 1.9597 0.1; 1.9269 0.39; 1.89 0.35; 1.8588 0.06; 1.8466 0.06; 1.8254 0.11; 1.8173 0.12; 1.7946 0.1; 1.7844 0.11; 1.7541 0.2; 1.7479 0.2; 1.7317 0.22; 1.7232 0.22; 1.6689 0.05; 1.6577 0.05; 1.6371 0.11; 1.627 0.12; 1.6054 0.12; 1.5958 0.19; 1.5871 0.13; 1.571 0.24; 1.564 0.34; 1.5485 0.25; 1.5397 0.38; 1.5176 0.22; 1.509 0.19; 1.461 0.08; 1.4526 0.12; 1.4369 0.14; 1.4284 0.25; 1.4202 0.18; 1.4118 0.12; 1.4035 0.22; 1.3957 0.23; 1.3794 0.09; 1.3715 0.12; 1.3638 0.1; 1.3529 0.11; 1.345 0.07; 1.3289 0.11; 1.324 0.12; 1.306 0.08; 1.2985 0.1; 1.2744 0.04; 1.2487 0.02; 1.2347 0.05; 1.1926 0.04; 1.1748 0.07; 1.1679 0.01; 1.1646 0.01; 1.157 0.04; 1.1456 0.02; 1.1207 0.01; 1.0656 0.01; 1.0524 0.01; 0.8897 0.07; 0.8704 0.01; 0.852 0.01; 0.8483 0.01; 0.7232 0.01; 0.1461 0.01; 0.008 0.06; −0.0001 2.14; −0.0084 0.07; −2.6982 0.01 |
| I-35 | $^1$H NMR (DMSO-d$_6$, 400 MHz): d$_{ppm}$: 1.54-1.64 (m, 1H), 1.74-2.12 (m, 7H), 2.21 (s, 3H), 2.72-2.92 (m, 3H), 3.04-3.11 (m, 1H), 3.23 (m, 1H), 3.98-4.02 (m, 1H), 4.41-4.44 (m, 1H), 5.22 (d, 1H), 5.31 (d, 1H), 6.17 (t, 1H), 6.49 (s, 1H), 7.17-7.33 (m, 4H), 7.56 (dd, 1H), 7.85-7.93 (m, 2H) |
| I-36 | [DMSO-d$_6$] 8.0029 0.58; 7.9836 3.01; 7.975 3.42; 7.9683 7.59; 7.9558 0.83; 7.637 1.83; 7.63 1.85; 7.6206 2.74; 7.6148 1.9; 7.6049 2.24; 7.6007 2.26; 7.5783 1.64; 7.5756 1.74; 7.558 2.22; 7.5556 2.29; 7.4674 0.98; 7.463 1.07; 7.4486 1.93; 7.4442 1.79; 7.4286 1.37; 7.4241 1.21; 7.3932 1.69; 7.39 1.68; 7.3743 2.31; 7.3711 2.25; 7.3555 0.92; 7.3523 0.88; 6.4881 3.83; 5.7471 7.85; 5.3503 0.77; 5.3385 0.31; 5.3048 12.29; 5.252 2.39; 5.2095 0.76; 4.6291 0.42; 4.6101 0.45; 4.4725 0.69; 4.4377 0.73; 4.0574 0.36; 4.0395 1.31; 4.0219 1.29; 4.0039 0.93; 3.3085 325.380005; 3.2851 4.52; 3.2482 1.06; 3.2174 0.58; 3.1386 0.49; 3.1287 0.36; 3.1177 0.62; 3.109 1.02; 3.1004 0.61; 3.0893 0.42; 3.0797 0.57; 3.0711 0.32; 2.814 0.51; 2.7871 0.89; 2.7823 0.89; 2.7563 0.5; 2.6748 0.41; 2.6701 0.54; 2.6657 0.41; 2.5402 0.93; 2.5233 2.39; 2.5099 29.09; 2.5056 53.060001; 2.5011 68.040001; 2.4968 46.259998; 2.4925 21.75; 2.3324 0.35; 2.3279 0.45; 2.3232 0.33; 2.2172 15; 2.1966 1.08; 2.1711 0.41; 2.0297 0.61; 1.9873 3.74; 1.9698 0.64; 1.9364 1.42; 1.9087 1.51; 1.8693 0.42; 1.8482 0.61; 1.8392 0.64; 1.8172 0.55; 1.8084 0.49; 1.6748 0.32; 1.6544 0.58; 1.6447 0.62; 1.6234 0.54; 1.6133 0.56; 1.4209 0.72; 1.413 1.2; 1.1932 0.94; 1.1753 1.91; 1.1576 0.94; 0.7746 0.4; 0.7551 0.81; 0.7364 0.38; −0.0001 1.77 |
| I-37 | [DMSO-d$_6$] 7.9713 0.31; 7.9522 0.87; 7.9333 0.8; 7.9189 0.78; 7.9157 0.86; 7.8997 0.38; 7.5978 0.54; 7.5947 0.53; 7.5791 0.52; 7.5759 0.46; 6.4965 0.98; 5.7469 0.89; 5.2939 0.64; 5.2492 0.63; 4.0149 3.01; 3.3071 119.559998; 3.2838 1.37; 2.5229 0.66; 2.5095 8.77; 2.5051 16.190001; 2.5006 20.950001; 2.4963 14.3; 2.4919 6.83; 2.2174 3.79; 1.003 15; 0.8309 0.96; −0.0001 1.55 |
| I-38 | [DMSO-d$_6$] 7.9598 1.16; 7.9406 3.12; 7.9216 2.6; 7.9006 2.79; 7.8979 3.03; 7.8816 1.45; 7.8788 1.22; 7.5888 2.04; 7.5861 2.02; 7.5697 1.91; 7.5672 1.81; 6.4979 3.86; 5.7468 3.75; 5.3395 0.75; 5.2977 2.43; 5.2517 2.59; 5.2086 0.72; 4.4535 0.71; 4.4225 0.76; 4.1379 4.1; 4.1225 4.34; 4.0394 0.51; 4.022 0.82; 3.9935 0.76; 3.3089 409.480011; 3.2856 5.5; 3.2527 1.21; 3.2232 0.66; 3.1157 0.52; 3.1072 0.41; 3.096 0.62; 3.0865 1.04; 3.0782 0.65; 3.0655 0.42; 3.0573 0.55; 2.8296 0.5; 2.8002 0.89; 2.7709 0.51; 2.6743 0.38; 2.6696 0.5; 2.6653 0.38; 2.5399 0.82; 2.5094 30.799999; 2.5053 55.790001; 2.5009 71.300003; 2.4967 49.639999; 2.332 0.39; 2.3276 0.5; 2.3232 0.38; 2.2214 15; 2.2011 0.97; 1.987 0.93; 1.9653 0.59; 1.9296 1.42; 1.9084 0.69; 1.8925 0.9; 1.8551 0.31; 1.8466 0.36; 1.8236 0.65; 1.8153 0.69; 1.7783 1.98; 1.7635 1.5; 1.7513 2.59; 1.7436 2.46; 1.7262 1.79; 1.7177 1.59; 1.7014 1.49; 1.6927 1.75; 1.656 0.98; 1.6432 1.13; 1.6324 1.29; 1.6027 0.7; 1.5715 0.33; 1.2968 0.38; 1.2654 1.13; 1.2349 1.74; 1.2026 1.61; 1.175 1.07; 1.1656 0.58; 1.1576 0.44; 1.1425 0.59; 1.1352 0.36; 1.0905 0.59; 1.0605 1.43; 1.0301 1.17; 1.0038 0.36; −0.0001 1.12 |

-continued

| Ex. | NMR data |
|---|---|
| I-39 | [DMSO-d$_6$] 7.9606 1.26; 7.9415 3.46; 7.9224 2.86; 7.8999 2.91; 7.897 3.15; 7.8806 1.55; 7.8779 1.28; 7.5884 2.16; 7.5856 2.11; 7.5692 2.06; 7.5665 1.85; 6.498 3.85; 5.8704 0.4; 5.8539 0.77; 5.8452 0.46; 5.837 0.41; 5.8281 1.18; 5.8112 1.23; 5.8021 0.48; 5.7943 0.46; 5.7855 0.95; 5.769 0.46; 5.7464 6.68; 5.3392 0.7; 5.2972 2.48; 5.2513 2.47; 5.209 0.68; 5.061 0.67; 5.0569 1.41; 5.0518 1.54; 5.0479 0.74; 5.0179 0.6; 5.014 1.29; 5.0089 1.39; 5.0049 0.66; 5.0019 0.1; 4.9805 1.46; 4.9778 1.34; 4.9752 1.31; 4.955 1.4; 4.9523 1.25; 4.9497 1.2; 4.4593 0.68; 4.4256 0.72; 4.3263 2.74; 4.3097 5.87; 4.2932 2.8; 4.0258 0.65; 3.9922 0.71; 3.3127 556.960022; 3.289 12.16; 3.2464 1.25; 3.2171 0.69; 3.1129 0.56; 3.1034 0.43; 3.0923 0.64; 3.0838 1.04; 3.0742 0.66; 3.063 0.45; 3.0536 0.59; 3.045 0.34; 2.8188 0.47; 2.7911 0.87; 2.7598 0.5; 2.674 0.36; 2.67 0.49; 2.6658 0.37; 2.5401 1.1; 2.5232 1.71; 2.5098 28.73; 2.5054 54.419998; 2.5009 71.5; 2.4965 49.540001; 2.4922 23.84; 2.3321 0.43; 2.3276 0.53; 2.3232 0.37; 2.2219 15; 2.2018 0.7; 2.1276 0.94; 2.1096 2.33; 2.0919 2.43; 2.0741 1.1; 2.0696 1.18; 1.9624 0.59; 1.9291 1.33; 1.892 0.78; 1.8453 0.32; 1.8243 0.6; 1.8174 0.64; 1.7938 0.56; 1.785 0.55; 1.7639 0.77; 1.7473 1.81; 1.7295 2.17; 1.7095 1.95; 1.693 0.79; 1.6651 0.34; 1.6431 0.62; 1.6321 0.64; 1.6113 0.57; 1.6028 0.6; 1.5322 0.78; 1.5125 2.02; 1.4999 1.16; 1.4941 2.59; 1.4751 1.56; 1.457 0.51; 1.3981 0.32; 0.008 0.33; −0.0001 8.86; −0.0082 0.4 |
| I-40 | [DMSO-d$_6$] 7.9596 1.58; 7.9468 4.09; 7.9339 2.87; 7.9012 3.08; 7.8996 3.32; 7.8884 2.05; 7.8868 1.95; 7.5941 2.39; 7.5927 2.46; 7.5812 2.4; 7.5798 2.28; 7.5268 0.5; 7.2074 0.34; 6.5117 4.34; 5.7617 1.29; 5.3489 1.31; 5.3204 2.66; 5.2627 2.68; 5.2342 1.3; 4.4576 0.75; 4.4356 0.77; 4.3061 2.54; 4.295 5.49; 4.2839 2.62; 4.0194 0.73; 3.9965 0.75; 3.4153 0.49; 3.4095 0.56; 3.3781 809.320007; 3.3548 4.71; 3.267 0.46; 3.2632 0.55; 3.2422 0.96; 3.2242 0.69; 3.2198 0.52; 3.1025 0.49; 3.0965 0.32; 3.0888 0.58; 3.0827 1.04; 3.0767 0.6; 3.0693 0.35; 3.0629 0.56; 2.8069 0.45; 2.8026 0.53; 2.7854 0.97; 2.7814 0.97; 2.7642 0.56; 2.7601 0.46; 2.6178 0.36; 2.5268 0.69; 2.5237 0.91; 2.5205 1.05; 2.5117 21.16; 2.5087 45.279999; 2.5057 62.029999; 2.5027 44.830002; 2.4997 20.32; 2.3896 0.36; 2.2195 16; 2.2018 1.03; 1.9509 0.59; 1.9304 0.84; 1.9119 0.72; 1.8915 0.77; 1.8199 0.65; 1.8135 0.71; 1.799 0.61; 1.7926 0.59; 1.7346 0.53; 1.7233 1.76; 1.7116 2.28; 1.6989 1.92; 1.6876 0.69; 1.6471 0.35; 1.6332 0.68; 1.6264 0.72; 1.6124 0.74; 1.6057 0.7; 1.5918 0.37; 1.4107 0.33; 1.4005 1.08; 1.396 0.87; 1.3869 1.66; 1.3748 1.4; 1.3629 0.81; 1.3531 0.66; 1.341 1.25; 1.3304 1.4; 1.3163 1.07; 1.3053 0.53; 1.3014 0.52; 1.296 0.64; 1.2862 1.31; 1.2833 1.3; 1.2759 2.63; 1.2721 4.45; 1.2669 3.46; 1.2605 2.58; 1.2504 0.72; 0.8682 3.04; 0.8569 8.31; 0.8451 3.41; 0 3.37 |
| I-41 | [DMSO-d$_6$] 7.9706 1.32; 7.9514 3.65; 7.9323 3.04; 7.9096 2.92; 7.9067 3.33; 7.8903 1.69; 7.8875 1.37; 7.6002 2.18; 7.5973 2.17; 7.5811 2.07; 7.5782 1.89; 6.4979 3.84; 5.7467 0.63; 5.3477 0.74; 5.3043 2.48; 5.252 2.42; 5.2092 0.75; 4.4634 0.79; 4.4438 3.63; 4.4357 3.18; 4.4323 4.33; 4.4283 3.15; 4.4204 3.91; 4.0308 0.69; 3.9989 0.7; 3.6794 3.54; 3.6714 2.49; 3.6676 3.67; 3.6641 2.51; 3.656 3.26; 3.4146 0.38; 3.3883 0.63; 3.3497 1.72; 3.3068 906.27002; 3.2515 1.57; 3.218 0.83; 3.1342 0.36; 3.1201 0.62; 3.0995 0.68; 3.0911 1.09; 3.082 0.69; 3.0715 0.47; 3.0613 0.59; 2.8163 0.52; 2.7833 0.89; 2.7696 0.3; 2.7572 0.53; 2.6739 0.93; 2.6695 1.19; 2.6647 0.9; 2.5804 0.4; 2.5393 1.85; 2.5225 5.11; 2.5091 68.019997; 2.5047 125.610001; 2.5002 162.800003; 2.4959 110.949997; 2.4915 52.77; 2.3316 0.82; 2.327 1.11; 2.3224 0.87; 2.2438 0.32; 2.2234 15; 2.2021 0.75; 2.0693 0.5; 1.9869 0.31; 1.9637 0.6; 1.9281 1.38; 1.8892 0.81; 1.8507 0.32; 1.8298 0.6; 1.8201 0.64; 1.7983 0.56; 1.7893 0.51; 1.6406 0.64; 1.6292 0.61; 1.6078 0.54; 1.5994 0.55; −0.0001 5.51 |
| I-42 | [DMSO-d$_6$] 7.9745 0.43; 7.9636 1.21; 7.9445 3.28; 7.9257 3.12; 7.9135 3.04; 7.9102 3.35; 7.8943 1.4; 7.891 1; 7.6849 0.73; 7.6681 0.92; 7.6634 1.55; 7.6469 1.56; 7.6422 1; 7.6253 0.8; 7.606 2.17; 7.6028 2.09; 7.5873 2.02; 7.5841 1.8; 7.3492 0.81; 7.3427 0.87; 7.3254 1.04; 7.3231 1.1; 7.3191 1.15; 7.2994 0.78; 7.2931 0.8; 7.1709 0.68; 7.1667 0.65; 7.1517 1.24; 7.1495 1.31; 7.1455 1.15; 7.1304 0.61; 7.1283 0.61; 7.124 0.54; 6.4942 4.04; 5.7468 1.28; 5.4069 7.38; 5.3392 0.86; 5.2971 2.41; 5.2451 2.42; 5.2028 0.73; 4.4516 0.7; 4.4203 0.77; 4.0216 0.72; 3.9862 0.72; 3.3139 408.269989; 3.2903 8.86; 3.2752 0.9; 3.266 0.82; 3.2377 0.95; 3.207 0.51; 3.1092 0.51; 3.1009 0.38; 3.0886 0.61; 3.0795 0.98; 3.07 0.6; 3.0594 0.39; 3.0503 0.53; 2.8083 0.5; 2.7756 0.88; 2.7499 0.49; 2.6706 0.37; 2.5406 0.9; 2.5236 1.43; 2.5103 21.370001; 2.506 39.959999; 2.5015 51.98; 2.4971 35.59; 2.4927 16.84; 2.328 0.35; 2.2134 15; 2.1991 1.02; 2.0699 0.56; 1.9873 0.34; 1.9489 0.62; 1.9162 1.37; 1.8773 0.77; 1.8378 0.35; 1.8171 0.6; 1.8073 0.61; 1.786 0.54; 1.7768 0.48; 1.647 0.34; 1.637 0.61; 1.6205 0.95; 1.5949 0.58; 1.5857 0.55; 0.008 0.31; −0.0001 7.22 |
| I-43 | $^1$H NMR (DMSO-d$_6$, 400 MHz): d$_{ppm}$: 1.57-1.60 (m, 1H), 1.77-1.80 (m, 1H), 1.86-1.92 (m, 2H), 2.21 (s, 3H), 2.74-2.79 (m, 1H), 3.04-3.09 (m, 1H), 3.20-3.25 (m, 1H), 3.98-4.00 (m, 1H), 4.42-4.44 (m, 1H), 5.23 (d, 1H), 5.32 (d, 1H), 5.40 (s, 2H), 6.50 (s, 1H), 7.30-7.33 (m, 2H), 7.59-7.61 (m, 1H), 7.87-7.95 (m, 2H) |
| I-44 | [DMSO-d$_6$] 7.9637 0.88; 7.9446 2.61; 7.9263 3.49; 7.923 3.23; 7.9189 3.35; 7.9036 1.04; 7.8996 0.61; 7.6004 1.8; 7.5965 1.81; 7.5825 1.72; 7.5785 1.6; 7.4377 1.52; 7.4196 1.81; 7.295 0.31; 7.2914 0.32; 7.2761 1.16; 7.2729 1.18; 7.2601 3.79; 7.2565 4.05; 7.2391 1.75; 7.233 1.01; 7.2208 1.29; 7.2147 1.02; 7.2045 0.46; 7.1984 0.44; 6.4943 3.56; 5.7469 4.21; 5.396 9.5; 5.3351 0.68; 5.2922 2.29; 5.2466 2.28; 5.2041 0.66; 4.4505 0.64; 4.4185 0.71; 4.0214 0.76; 3.9845 0.69; 3.3089 268.51001; 3.2855 3.52; 3.2412 0.96; 3.2112 0.55; 3.1131 0.47; 3.1045 0.35; 3.0931 0.59; 3.0839 0.96; 3.0755 0.58; 3.0639 0.39; 3.0548 0.51; 3.0459 0.3; 2.8145 0.46; 2.7831 0.82; 2.7546 0.49; 2.6699 0.37; 2.5397 0.6; 2.5093 21.549999; 2.5051 38.93; 2.5007 49.619999; 2.4965 34.450001; 2.3787 15; 2.3275 0.39; 2.2126 13.81; 2.2009 1.15; 1.987 0.75; 1.9547 0.54; 1.9213 1.29; 1.9086 1.06; 1.8854 0.75; 1.8199 0.54; 1.8107 0.58; 1.7886 0.52; 1.7797 0.49; 1.6375 0.54; 1.6284 0.57; 1.6069 0.52; 1.5975 0.52; 1.1751 0.38; −0.0001 1.21 |
| I-45 | $^1$H NMR (DMSO-d$_6$, 400 MHz): d$_{ppm}$: 1.60-1.66 (m, 1H), 1.80-1.86 (m, 1H), 1.89-1.98 (m, 2H), 2.21 (s, 3H), 2.75-2.82 (m, 1H), 3.06-3.12 (m, 1H), 3.24 (m, 1H), 3.99-4.02 (m, 1H), 4.42-4.45 (m, 1H), 5.22 (d, 1H), 5.31 (d, 1H), 5.54 (s, 2H), 6.49 (s, 1H), 7.59-7.62 (m, 2H), 7.73-7.83 (m, 3H), 7.91-7.98 (m, 2H) |
| I-46 | [DMSO-d$_6$] 7.9801 0.83; 7.9608 2.88; 7.9462 3.99; 7.9439 5.23; 7.9416 4.54; 7.9274 0.92; 7.6415 1.41; 7.6344 0.97; 7.6302 1.5; 7.6262 1.53; 7.6191 3.21; 7.6145 2.18; 7.6025 1.8; 7.5974 1.67; 7.5492 1.43; 7.5419 1.11; 7.5379 1.52; 7.5323 0.97; 7.526 2.02; 7.4389 |

-continued

| Ex. | NMR data |
|---|---|
| | 0.59; 7.4352 0.47; 7.4275 3.43; 7.4205 2.12; 7.4168 2.61; 7.4145 2.38; 7.4105 2.02; 7.4039 3.56; 7.392 0.36; 6.4933 3.9; 5.7472 1.56; 5.4637 10.59; 5.3401 0.79; 5.2979 2.45; 5.2483 2.45; 5.2057 0.71; 4.4552 0.71; 4.4226 0.74; 4.0226 0.69; 3.9907 0.72; 3.3709 0.34; 3.3061 395.619995; 3.2823 12.49; 3.2443 1.05; 3.2163 0.58; 3.1255 0.5; 3.1174 0.37; 3.1047 0.61; 3.0954 1; 3.0869 0.6; 3.0762 0.41; 3.066 0.53; 2.8177 0.48; 2.7867 0.9; 2.7593 0.49; 2.6742 0.37; 2.6696 0.51; 2.6647 0.37; 2.5396 1.24; 2.5093 31.139999; 2.5049 58.419998; 2.5004 76.18; 2.4961 52.34; 2.4917 24.84; 2.3316 0.42; 2.3274 0.53; 2.3225 0.39; 2.2122 15; 2.1978 0.85; 2.0696 1.4; 2.0496 0.33; 1.987 0.32; 1.9646 0.57; 1.9316 1.34; 1.8935 0.79; 1.8542 0.32; 1.8319 0.6; 1.8237 0.62; 1.8014 0.54; 1.7924 0.54; 1.6639 0.31; 1.6441 0.6; 1.6338 0.61; 1.6129 0.57; 1.6041 0.55; 1.2363 0.44; 0.0079 0.62; −0.0001 15.04; −0.0084 0.67 |
| I-47 | $^1$H NMR (DMSO-$d_6$, 400 MHz): $d_{ppm}$: 1.56-1.65 (m, 1H), 1.78-1.84 (m, 1H), 1.88-1.95 (m, 2H), 2.21 (s, 3H), 2.74-2.80 (m, 1H), 3.05-3.11 (m, 1H), 3.23 (m, 1H), 3.98-4.01 (m, 1H), 4.41-4.45 (m, 1H), 5.22 (d, 1H), 5.31 (d, 1H), 5.44 (s, 2H), 6.49 (s, 1H), 7.24-7.29 (m, 2H), 7.41-7.47 (m, 1H), 7.56-7.60 (m, 2H), 7.90-7.96 (m, 2H) |
| I-48 | [DMSO-$d_6$] 7.9521 1.29; 7.9328 3.36; 7.9136 2.63; 7.8818 2.78; 7.8794 2.97; 7.8627 1.63; 7.8602 1.41; 7.5994 2.2; 7.5972 2.17; 7.5801 2.12; 7.5776 2.12; 7.56 0.86; 7.5556 0.81; 7.5388 1.61; 7.522 0.81; 7.5177 0.92; 7.5008 0.43; 7.2209 0.45; 7.2114 2.43; 7.1914 3.73; 7.1791 0.43; 7.171 2.06; 7.1616 0.3; 6.4935 3.93; 5.7476 2.08; 5.4531 7.2; 5.336 0.73; 5.293 2.35; 5.2407 2.35; 5.1981 0.72; 4.4452 0.67; 4.413 0.71; 4.0128 0.65; 3.9778 0.7; 3.3118 191.509995; 3.2881 6.9; 3.2604 0.65; 3.2291 0.92; 3.2013 0.52; 3.0981 0.48; 3.0889 0.37; 3.0779 0.6; 3.0687 0.97; 3.0597 0.59; 3.0486 0.38; 3.0393 0.54; 2.8015 0.46; 2.7734 0.86; 2.7411 0.5; 2.541 0.55; 2.5106 13.11; 2.5063 24.59; 2.5019 32; 2.4975 22.16; 2.4932 10.62; 2.2119 15; 1.9877 0.42; 1.9381 0.56; 1.9064 1.37; 1.868 0.77; 1.8246 0.31; 1.8024 0.57; 1.7944 0.62; 1.7717 0.53; 1.7634 0.49; 1.6117 0.56; 1.602 0.62; 1.5814 0.55; 1.5712 0.54; −0.0001 3.7 |
| I-49 | [DMSO-$d_6$] 8.3741 1.66; 8.3724 1.72; 8.3662 1.71; 8.3645 1.68; 7.9681 1.12; 7.9554 3.23; 7.943 3.55; 7.9381 3.3; 7.9357 3.68; 7.9253 1.35; 7.9229 0.92; 7.6725 1.6; 7.6713 1.62; 7.6599 1.73; 7.6586 1.7; 7.613 2.07; 7.6106 2.08; 7.6007 2.06; 7.5984 1.96; 7.3093 1.77; 7.3013 1.77; 7.2966 1.7; 7.2886 1.62; 6.5085 4.22; 5.7615 3.08; 5.4852 10.75; 5.3427 1.28; 5.3141 2.57; 5.256 2.53; 5.2275 1.26; 4.567 0.34; 4.5581 0.33; 4.4508 0.72; 4.4288 0.74; 4.0101 0.7; 3.9874 0.73; 3.4428 0.41; 3.427 0.41; 3.4016 2.13; 3.3764 1459.030029; 3.3531 9.64; 3.3448 0.83; 3.3364 0.45; 3.3277 0.32; 3.2554 0.48; 3.2514 0.56; 3.2303 0.96; 3.2122 0.58; 3.2081 0.5; 3.1033 0.49; 3.0895 0.6; 3.0834 1.04; 3.0773 0.6; 3.0696 0.35; 3.0635 0.55; 2.7926 0.43; 2.7883 0.52; 2.771 0.95; 2.7672 0.96; 2.7499 0.55; 2.7458 0.45; 2.6202 0.56; 2.6171 0.75; 2.6141 0.53; 2.5261 1.64; 2.523 2.19; 2.5198 2.6; 2.511 44.549999; 2.5081 93.360001; 2.5051 126.209999; 2.5021 90.669998; 2.4991 41.110001; 2.3937 16; 2.3063 1.03; 2.2851 0.32; 2.2095 15.62; 2.2002 0.59; 2.0772 0.62; 1.9415 0.58; 1.9215 0.84; 1.9087 0.7; 1.9044 0.71; 1.8832 0.75; 1.832 0.32; 1.8181 0.65; 1.8117 0.69; 1.7971 0.61; 1.7907 0.58; 1.6238 0.64; 1.617 0.68; 1.6029 0.65; 1.5963 0.63; 0.8891 0.42; 0 6.03 |
| I-50 | [DMSO-$d_6$] 7.9649 1.19; 7.9457 3.3; 7.9269 3.1; 7.9148 3.02; 7.9116 3.28; 7.8956 1.35; 7.8923 0.92; 7.5999 2.11; 7.5967 2.06; 7.5811 1.97; 7.578 1.72; 7.1453 2.13; 7.1424 2.87; 7.1395 2.09; 7.0844 3.25; 6.4956 3.84; 5.7463 3.57; 5.4866 10.13; 5.3436 0.79; 5.3012 2.34; 5.2458 2.3; 5.2034 0.73; 4.4567 0.69; 4.4229 0.72; 4.0215 0.71; 3.9866 0.73; 3.4292 0.34; 3.4254 0.31; 3.3909 0.51; 3.3127 684.559998; 3.2893 12.01; 3.2696 1.14; 3.2658 1.08; 3.2395 0.99; 3.2063 0.55; 3.1082 0.51; 3.0994 0.37; 3.0879 0.6; 3.0781 0.99; 3.0685 0.95; 3.0581 0.43; 3.0483 0.54; 2.8032 0.47; 2.7773 0.86; 2.7471 0.49; 2.6745 0.45; 2.6698 0.57; 2.6654 0.41; 2.5399 1.45; 2.5231 2.31; 2.5096 35.41; 2.5053 66.639999; 2.5008 87.099998; 2.4964 59.889999; 2.492 28.610001; 2.4485 0.3; 2.3317 0.45; 2.3273 0.61; 2.3228 0.45; 2.2175 15; 2.1951 13.6; 2.1929 13.46; 2.1737 0.41; 2.1592 0.41; 2.0693 0.9; 2.0497 0.33; 1.9445 0.54; 1.9084 1.53; 1.8749 0.79; 1.8488 0.34; 1.8397 0.37; 1.8165 0.6; 1.8083 0.64; 1.7874 0.55; 1.7774 0.53; 1.6518 0.31; 1.6319 0.56; 1.6221 0.6; 1.6015 0.58; 1.5909 0.59; 1.3981 0.39; 1.3889 1.53; 1.3836 0.56; 0.0077 0.41; −0.0001 11.02; −0.0081 0.5 |
| I-51 | [DMSO-$d_6$] 8.2422 2.35; 8.241 2.44; 8.2295 2.92; 8.2282 2.89; 8.1079 2.03; 8.0949 3.76; 8.082 1.97; 8.0647 1.75; 8.0627 1.98; 8.0504 1.98; 7.9458 2.28; 7.932 2.51; 7.9214 1.75; 7.9079 2.06; 7.7582 2.56; 7.7461 2.46; 7.7451 2.41; 7.63 2.51; 7.6171 4.78; 7.6102 0.55; 7.606 2.39; 7.6037 5.45; 7.6012 2.23; 7.5923 0.93; 7.59 1.76; 7.5879 1.68; 7.5789 0.87; 7.5766 0.68; 7.5275 2.82; 7.5262 3.08; 7.5151 2.24; 7.5138 2.13; 6.4963 4.39; 5.7634 7.45; 5.757 0.78; 5.3641 1.37; 5.3356 2.55; 5.2674 2.6; 5.239 1.36; 4.4903 0.75; 4.4681 0.78; 4.0508 0.72; 4.046 0.91; 4.034 1.63; 4.0279 0.78; 4.0222 1.59; 4.0103 0.41; 3.3909 0.63; 3.3798 1.18; 3.3587 788.400024; 3.3352 6.5; 3.3016 0.46; 3.2974 0.55; 3.2763 0.94; 3.2583 0.55; 3.2543 0.44; 3.2143 0.48; 3.2008 0.57; 3.1946 1.03; 3.1887 0.59; 3.1811 0.34; 3.1748 0.54; 2.8413 0.45; 2.8376 0.53; 2.8199 0.96; 2.8162 0.97; 2.7989 0.56; 2.7945 0.46; 2.6189 0.6; 2.616 0.81; 2.613 0.6; 2.525 1.4; 2.5219 1.77; 2.5188 1.86; 2.5098 45.02; 2.5069 96.790001; 2.5039 132.770004; 2.5009 96.639999; 2.498 44.439999; 2.4036 1.08; 2.3908 0.54; 2.3879 0.76; 2.3848 0.53; 2.2008 16; 2.1823 0.44; 2.0778 0.81; 2.0409 0.58; 2.0202 0.87; 2.0153 0.87; 2.01 0.81; 1.9906 5.4; 1.9842 0.81; 1.9204 0.62; 1.9142 0.69; 1.8994 0.6; 1.8932 0.58; 1.7048 0.66; 1.6979 0.71; 1.684 0.66; 1.6773 0.65; 1.1863 1.33; 1.1744 2.65; 1.1626 1.3; 0.8891 0.34; 0 4.47 |
| I-52 | $^1$H NMR (DMSO-$d_6$, 400 MHz): $d_{ppm}$: 1.65-1.71 (m, 1H), 1.87-2.06 (m, 3H), 2.21 (s. 3H), 2.78-2.84 (m, 1H), 3.14-3.24 (m, 1H), 3.28 (m, 1H), 4.02-4.05 (m, 1H), 4.45-4.49 (m, 1H), 5.23 (d, 1H), 5.35 (d, 1H), 6.48 (s, 1H), 7.48 (dd, 1H), 7.53-7.60 (m, 2H), 7.70 (d, 1H), 7.85 (d, 1H), 7.94-8.07 (m, 4H), 8.15 (dd, 1H) |
| I-53 | [DMSO-$d_6$] 7.9897 1.65; 7.9703 3.74; 7.9509 2.3; 7.7561 2.43; 7.7542 2.7; 7.737 2.27; 7.735 2.25; 7.6569 2.3; 7.6551 2.33; 7.6374 2.17; 6.5032 3.84; 5.3756 0.9; 5.333 2.06; 5.2451 2.06; 5.2025 0.91; 5.0285 0.64; 4.456 0.7; 4.4231 0.74; 4.0396 0.76; 4.0088 0.74; 3.514 0.98; 3.5058 0.87; 3.4877 0.64; 3.3228 1112.77002; 2.2362 1.4; 3.1707 0.39; 3.1432 0.38; 3.1333 0.53; 3.1251 0.74; 3.1157 0.59; 3.105 0.83; 3.0964 1.21; 3.0884 0.81; 3.0771 0.58; 3.0676 0.73; 3.0585 0.47; 2.8507 0.56; 2.8177 0.93; 2.792 0.6; 2.675 0.84; 2.6705 1.11; 2.666 0.84; 2.6613 0.47; 2.5237 4.81; 2.5103 60.290001; 2.5059 111.529999; 2.5014 144.630005; 2.497 98.989998; 2.4926 47.119999; 2.3375 0.44; 2.3326 0.79; 2.3282 1.06; 2.3237 0.78; 2.3191 0.45; 2.2518 1.17; 2.2295 15; 2.2043 |

-continued

| Ex. | NMR data |
|---|---|
| | 0.71; 2.1918 0.31; 2.0689 0.63; 1.9983 0.64; 1.9869 1.1; 1.9535 1.72; 1.9404 1.66; 1.9181 2.49; 1.8523 0.39; 1.8309 0.64; 1.8207 0.64; 1.7986 0.6; 1.7903 0.58; 1.7685 0.37; 1.7583 0.41; 1.7206 1.61; 1.7084 1.42; 1.6956 1.42; 1.6629 0.74; 1.6534 0.73; 1.6223 1.04; 1.6002 0.82; 1.5888 0.85; 1.5109 0.51; 1.4833 1.37; 1.4577 3.01; 1.4354 2.76; 1.4108 1.31; 1.3983 2.88; 1.3834 0.49; 1.332 0.3; 1.3232 0.39; 1.2979 0.68; 1.2748 0.6; 1.2371 0.4; 1.1752 0.4; −0.0001 3.08 |
| I-54 | [DMSO-$d_6$] 7.9958 1.59; 7.9765 3.66; 7.957 2.24; 7.7668 2.66; 7.7495 2.18; 7.7476 2.23; 7.6649 2.4; 7.647 2.16; 6.4983 3.9; 5.3675 0.82; 5.325 2.13; 5.2501 2.2; 5.208 0.83; 4.4524 0.66; 4.4181 0.72; 4.0396 0.67; 4.0087 0.7; 3.301 372.799988; 3.2463 1.05; 3.1365 0.63; 3.1285 0.46; 3.1174 0.72; 3.108 1.13; 3.0994 0.72; 3.0878 0.5; 3.0787 0.65; 3.0704 0.42; 2.9606 2.51; 2.9424 4.16; 2.924 2.62; 2.8901 0.37; 2.8636 0.53; 2.8318 0.9; 2.8053 0.53; 2.6736 0.55; 2.669 0.69; 2.6646 0.51; 2.5392 3.73; 2.5223 2.55; 2.5089 38.990002; 2.5046 72.800003; 2.5001 94.620003; 2.4957 64.830002; 2.4914 30.879999; 2.331 0.55; 2.3267 0.69; 2.3223 0.53; 2.2459 0.93; 2.2278 15; 2.2022 0.56; 2.1989 0.42; 2.0497 0.39; 2.01 0.62; 1.9868 0.95; 1.9714 1.19; 1.9341 0.82; 1.8681 0.32; 1.8608 0.36; 1.8368 0.61; 1.83 0.65; 1.8075 0.58; 1.7983 0.54; 1.7046 0.31; 1.6946 0.35; 1.6736 0.61; 1.6644 0.68; 1.6425 0.65; 1.6307 0.91; 1.6127 1.64; 1.5937 2.28; 1.5759 1.74; 1.5567 0.75; 1.3934 1; 1.3745 1.55; 1.3537 1.45; 1.3382 1.34; 1.3215 1.48; 1.3067 2; 1.2922 2.81; 1.2857 2.78; 1.2703 5.35; 1.2536 2.64; 0.8803 2.62; 0.8636 8.07; 0.8461 3.07; 0.008 0.63; −0.0001 13.19; −0.0084 0.47 |
| I-55 | [DMSO-$d_6$] 7.5352 8.02; 7.5298 8.51; 7.5203 8.1; 7.4995 10.36; 7.3962 1.02; 7.3916 0.82; 7.3851 6.04; 7.3797 5.68; 7.3644 4.43; 7.359 4.15; 3.9416 1.4; 3.808 15.74; 3.7883 16; 3.1254 38.93; 2.8231 3.71; 2.8034 7.91; 2.7836 3.39; 2.5294 0.4; 2.5004 4.72; 2.4958 9.28; 2.4911 12.7; 2.4864 8.95; 2.4818 4.36; −0.0001 1.07 |
| I-56 | [DMSO-$d_6$] 8.0111 1.32; 7.9918 2.94; 7.9724 1.78; 7.8092 2.24; 7.7902 1.88; 7.6747 2.04; 7.655 1.84; 7.3665 1.4; 7.3503 1.65; 7.3462 1.34; 7.2065 0.7; 7.1981 2.17; 7.1947 2.72; 7.1889 2.73; 7.1831 3.1; 7.1791 2.53; 7.1718 1.72; 7.1658 1.35; 7.1611 1.31; 7.1551 1.37; 7.1476 1.02; 7.1386 0.78; 7.1323 0.53; 6.5123 0.56; 6.4621 3.23; 5.7472 0.41; 5.3497 0.79; 5.3072 1.72; 5.2139 1.71; 5.1722 0.77; 5.008 0.91; 4.4255 0.62; 4.394 0.7; 4.2304 8.26; 4.0572 0.88; 4.0394 2.49; 4.0216 2.75; 4.004 1.35; 3.9744 0.66; 3.3038 196.100006; 3.238 1.08; 3.2078 0.59; 3.1134 0.47; 3.103 0.35; 3.0942 0.62; 3.0851 0.89; 3.0755 0.57; 3.0657 0.38; 3.0558 0.5; 2.8253 0.47; 2.7986 0.81; 2.7659 0.49; 2.674 0.58; 2.6694 0.72; 2.6648 0.56; 2.5394 1.27; 2.5088 43.200001; 2.5047 76.82; 2.5003 96.32; 2.4961 66.199997; 2.3351 15; 2.3038 0.4; 2.282 0.44; 2.2506 2.36; 2.2121 0.35; 2.2005 0.43; 2.1894 0.69; 2.1714 12.98; 2.0695 0.59; 1.9869 10.78; 1.9424 1.22; 1.9082 0.98; 1.8029 0.56; 1.7804 0.48; 1.7717 0.47; 1.6208 0.51; 1.6115 0.53; 1.5898 0.48; 1.5808 0.48; 1.3983 2.91; 1.1928 2.79; 1.175 5.54; 1.1573 2.71; −0.0001 6.83; −0.008 0.33 |
| I-57 | $^1$H NMR (DMSO-$d_6$, 400 MHz): $d_{ppm}$: 1.54-1.68 (m, 1H), 1.71-1.86 (m, 1H), 1.90-2.01 (m, 2H), 2.19 (s, 3H), 2.75-2.84 (m, 1H), 3.04-3.16 (m, 1H), 3.95-4.06 (m, 1H), 4.32 (s, 2H). 4.39-4.46 (m, 1H), 5.20 (d, 1H), 5.33 (d, 1H), 6.47 (s, 1H), 7.28-7.37 (m, 2H), 7.45-7.51 (m, 1H), 7.56-7.61 (m, 1H), 7.67 (d, 1H), 7.80 (d, 1H), 8.00 (dd, 1H) |
| I-58 | [DMSO-$d_6$] 8.0208 1.64; 8.0014 3.54; 7.9821 2.15; 7.8185 2.59; 7.8166 2.56; 7.7993 2.24; 7.6909 2.39; 7.6711 2.15; 7.4519 0.36; 7.4353 0.84; 7.4315 0.77; 7.4141 1.58; 7.3978 0.88; 7.3932 0.93; 7.3762 0.41; 7.1606 0.48; 7.1511 2.5; 7.1311 3.71; 7.1222 0.68; 7.1109 1.95; 7.1012 0.38; 6.517 0.49; 6.4735 3.74; 5.3601 0.87; 5.3179 1.96; 5.2193 1.91; 5.1771 0.89; 5.0255 0.97; 4.4325 0.7; 4.3994 0.74; 4.2785 6.79; 4.0392 0.42; 4.0216 0.88; 4.0045 0.53; 3.9811 0.72; 3.3022 366.459991; 3.2405 1.19; 3.2116 0.63; 3.1199 0.53; 3.0989 0.63; 3.0908 1.02; 3.0819 0.62; 3.0702 0.42; 3.061 0.54; 2.8281 0.51; 2.7994 0.88; 2.7676 0.52; 2.6739 0.75; 2.6694 0.95; 2.6648 0.75; 2.5652 0.46; 2.5225 4.54; 2.5091 59.200001; 2.5048 107.709999; 2.5004 137.470001; 2.496 94.580002; 2.4918 45.470001; 2.3317 0.75; 2.3271 0.98; 2.3225 0.74; 2.2525 1.95; 2.1846 15; 2.0698 0.72; 1.987 1.91; 1.9464 1.38; 1.9293 0.66; 1.9081 1.15; 1.8413 0.38; 1.8369 0.38; 1.8043 0.59; 1.7787 0.53; 1.7749 0.54; 1.6172 0.58; 1.6078 0.6; 1.5858 0.56; 1.5769 0.55; 1.1931 0.46; 1.1751 0.84; 1.1572 0.45; 0.008 0.61; −0.0001 14.2; −0.0083 0.67 |
| I-59 | [DMSO-$d_6$] 8.0097 1.61; 8.002 0.33; 7.9904 3.54; 7.971 2.2; 7.9521 0.43; 7.8087 0.47; 7.7981 2.67; 7.7809 2.35; 7.6766 2.34; 7.6587 2.12; 7.445 2.33; 7.4311 2.85; 7.4231 3.11; 7.415 1.54; 7.4094 2.86; 7.1655 2.92; 7.1603 1.44; 7.1432 5.11; 7.126 1.18; 7.121 2.51; 6.6595 0.36; 6.5185 1.92; 6.4805 3.61; 5.3506 0.9; 5.3083 2.12; 5.2304 2.06; 5.1877 0.88; 5.0297 5.81; 4.4341 0.74; 4.3977 0.9; 4.2148 8.98; 4.1909 0.57; 4.057 0.61; 4.0393 1.72; 4.0214 2.18; 4.0037 0.9; 3.9996 0.6; 3.9862 0.83; 3.7243 0.42; 3.4793 0.44; 3.4547 0.53; 3.4368 0.66; 3.3792 1.57; 3.3045 643.530029; 3.2188 1.17; 3.1682 0.35; 3.1233 0.64; 3.0942 1.15; 3.0837 0.77; 3.0653 0.77; 2.8905 2.33; 2.8407 0.57; 2.8091 0.96; 2.7841 0.61; 2.7319 1.9; 2.6735 1.54; 2.669 2; 2.6647 1.52; 2.5888 0.49; 2.5223 9.6; 2.5089 118.849998; 2.5046 218.559998; 2.5002 282.119995; 2.4958 194.5; 2.4915 93.57; 2.4132 0.49; 2.3989 0.43; 2.3897 0.36; 2.3527 0.41; 2.3314 1.47; 2.327 2.03; 2.322 1.51; 2.2528 8.24; 2.196 15; 2.1706 0.42; 2.1435 0.35; 2.0695 1.46; 1.9868 7.12; 1.9506 1.36; 1.9078 1.11; 1.8493 0.41; 1.8455 0.51; 1.8141 0.68; 1.8064 0.67; 1.7823 0.62; 1.7639 0.35; 1.681 0.38; 1.6706 0.36; 1.6471 0.71; 1.6384 0.65; 1.6139 0.65; 1.6058 0.62; 1.5818 0.34; 1.3984 1.48; 1.236 0.47; 1.1928 1.83; 1.175 3.54; 1.1572 1.76; 0.8898 0.36; 0.0079 1.55; −0.0001 35.349998; −0.0084 1.56 |
| I-60 | $^1$H NMR (DMSO-$d_6$, 400 MHz): $d_{ppm}$: 1.70-1.81 (m, 1H), 1.89-1.98 (m, 1H), 2.02-2.14 (m, 2H), 2.23 (s, 3H), 2.85-2.96 (m, 1H), 4.02-4.11 (m, 1H), 4.46-4.54 (m, 1H), 5.25 (d, 1H), 5.37 (d, 1H), 6.49 (s, 1H), 7.55-7.64 (m, 3H), 7.70-7.84 (m, 3H), 8.00-8.17 (m, 4H) |
| I-61 | [DMSO-$d_6$] 10.0221 0.33; 8.1672 3.41; 8.0589 1.9; 8.0551 0.36; 8.046 4.11; 8.0399 3.08; 8.0331 2.72; 8.0253 3.43; 8.0204 2.15; 8.0071 2.03; 7.9954 1.79; 7.9826 1.87; 7.9525 0.37; 7.8063 2.73; 7.805 2.98; 7.7936 2.61; 7.7923 2.67; 7.7676 2.57; 7.7665 2.52; 7.7545 2.6; 7.6452 0.94; 7.6427 0.99; 7.6337 2.23; 7.6314 2; 7.6209 3.44; 7.6177 3.46; 7.6072 1.77; 7.605 1.9; 7.5959 0.88; 7.5935 0.73; 7.5783 2.35; 7.5754 2.23; 7.5642 2.3; 7.5613 2.28; 6.5232 0.48; 6.5114 4.49; 5.7644 0.4; 5.4049 1.44; 5.3764 2.39; 5.2857 2.37; 5.2572 1.45; 4.4892 0.74; 4.4674 0.79; 4.0801 0.71; 4.057 0.76; 4.046 1.2; 4.0341 3.29; 4.0222 3.32; 4.0104 1.09; 3.3513 |

-continued

| Ex. | NMR data |
|---|---|
| | 293.450012; 3.3278 6.66; 3.3184 1.41; 3.2974 0.73; 3.2118 0.54; 3.2055 0.39; 3.1985 0.65; 3.1925 1.1; 3.1864 0.68; 3.1794 0.42; 3.1729 0.63; 3.1674 0.35; 2.8967 0.46; 2.8908 1.34; 2.8758 0.95; 2.8719 0.99; 2.8546 0.78; 2.8506 0.52; 2.7314 0.87; 2.7306 0.86; 2.6188 0.61; 2.6157 0.84; 2.6127 0.61; 2.5248 1.56; 2.5217 2.1; 2.5186 2.43; 2.5097 52.360001; 2.5068 111.389999; 2.5037 151.720001; 2.5007 109.730003; 2.4978 50.18; 2.3936 0.35; 2.3906 0.69; 2.3876 1; 2.3848 0.75; 2.2551 0.63; 2.2474 2.16; 2.2331 16; 2.2203 0.95; 2.1957 1.19; 2.1916 0.33; 2.0783 0.91; 2.0605 0.85; 2.035 0.72; 2.0139 0.8; 1.9953 0.51; 1.9907 14.64; 1.9387 0.33; 1.9247 0.63; 1.9183 0.7; 1.9105 0.81; 1.9038 0.63; 1.8978 0.6; 1.756 0.33; 1.7418 0.63; 1.7354 0.68; 1.7213 0.65; 1.7148 0.62; 1.3968 0.73; 1.2332 0.53; 1.1863 3.96; 1.1745 7.96; 1.1626 3.9; 0.8889 0.37; 0.0053 0.37; 0 10.79; −0.0056 0.36 |
| I-62 | [DMSO-$d_6$] 8.0443 1.66; 8.0249 3.58; 8.0056 2.22; 7.7822 2.75; 7.7649 2.29; 7.7403 2.49; 7.7207 2.24; 7.5267 1.48; 7.5089 11.54; 7.5049 12.24; 7.4955 1.98; 7.4865 1.26; 6.4975 3.84; 5.3819 0.85; 5.3402 2.21; 5.2638 2.1; 5.2206 0.91; 4.4812 0.74; 4.4453 0.82; 4.0704 0.77; 4.0668 0.7; 4.057 1.02; 4.0393 2.52; 4.0214 1.96; 4.0037 0.67; 3.622 0.33; 3.5932 0.36; 3.549 0.47; 3.4748 0.69; 3.4591 0.77; 3.3172 2088.639893; 3.2284 0.73; 3.2065 0.68; 3.1963 0.75; 3.1889 0.69; 3.1764 0.91; 3.168 1.31; 3.1571 0.81; 3.1379 0.72; 3.13 0.44; 2.891 0.55; 2.8864 0.4; 2.8605 0.9; 2.8351 0.57; 2.6745 1.42; 2.6699 1.89; 2.6656 1.43; 2.5393 2.21; 2.5231 8.84; 2.5097 112.940002; 2.5054 208.210007; 2.501 268.640015; 2.4966 185.160004; 2.4923 88.660006; 2.4149 0.43; 2.3458 0.3; 2.3366 0.8; 2.3323 1.37; 2.3278 1.94; 2.3232 1.33; 2.2512 0.51; 2.2298 15; 2.1963 0.68; 2.0849 0.99; 2.0689 1.67; 2.0301 1.23; 1.9868 8.63; 1.9278 0.35; 1.9214 0.43; 1.9081 0.67; 1.892 0.68; 1.87 0.57; 1.7514 0.32; 1.7468 0.31; 1.7257 0.6; 1.7158 0.7; 1.6947 0.6; 1.683 0.58; 1.3984 0.5; 1.2355 0.33; 1.1928 2.1; 1.175 4.43; 1.1573 2.19; 0.8899 0.37; 0.008 0.36; −0.0001 8.21 |
| I-63 | $^1$H NMR (DMSO-$d_6$, 400 MHz): $d_{ppm}$: 1.63-1.77 (m, 1H), 1.80-1.93 (m, 1H), 1.97-2.09 (m, 2H), 2.23 (s, 3H), 2.80-2.91 (m, 1H), 3.13-3.21 (m, 1H), 4.01-4.09 (m, 1H), 4.41-4.49 (m, 1H), 5.24 (d, 1H), 5.36 (d, 1H), 6.51 (s, 1H), 7.20-7.25 (m, 1H), 7.32-7.36 (m, 1H), 7.75 (d, 1H), 7.79 (d, 1H), 7.88-7.92 (m, 1H), 8.04 (dd, 1H) |
| I-64 | [CD$_3$CN] 7.643 1.14; 7.6247 1.4; 7.6216 1.8; 7.6033 1.24; 6.816 1.65; 6.8013 0.85; 6.7946 1.63; 6.7802 0.68; 6.7553 1.84; 6.7372 1.76; 6.3977 3.28; 5.4459 1.89; 5.0811 9.19; 3.6526 2.7; 3.6409 4.64; 3.6288 2.62; 3.6144 2.88; 3.5995 2.12; 3.5821 1.91; 3.5737 1.88; 3.5667 1.96; 3.5238 0.38; 3.5026 0.44; 3.4941 0.72; 3.4859 0.44; 3.4646 0.41; 2.8852 11.79; 2.7805 4.45; 2.2311 15; 2.1577 95.870003; 1.9713 0.86; 1.9629 0.48; 1.9511 6.77; 1.945 12.7; 1.9388 18.129999; 1.9326 12.53; 1.9265 6.48; 1.8539 0.43; 1.8217 0.47; 1.746 1.35; 1.728 2.25; 1.6912 0.84; 1.6574 0.3; 1.6289 0.35; 1.5905 0.78; 1.5699 0.81; 1.5567 0.94; 1.5461 0.96; 1.5263 1.08; 1.4399 0.45; 1.4078 0.39; 1.2035 0.43; 1.1857 0.33; 1.0801 1.09; 1.0686 1.57; 1.045 0.54; −0.0001 1 |
| I-65 | [CD$_3$CN] 8.5608 0.71; 7.7333 1.65; 7.7149 2.07; 7.712 2; 7.6936 1.91; 7.4371 3.22; 7.4307 1.2; 7.4188 3.5; 7.4121 1.81; 7.3998 0.33; 7.3892 1.05; 7.3823 1.15; 7.3659 1.57; 7.3117 0.45; 7.3068 0.7; 7.2931 2; 7.2883 1.95; 7.2849 1.89; 7.2772 3.26; 7.27 1.5; 7.2665 1.48; 7.2613 1.18; 7.2477 0.41; 6.9833 2.59; 6.9619 2.45; 6.401 3.23; 5.0955 10.18; 5.0018 0.37; 4.6662 4.51; 4.6501 4.44; 4.0685 0.49; 4.0507 0.46; 3.7585 1.38; 3.7464 2.17; 3.7323 2.06; 3.6566 8.02; 3.6388 3.05; 3.6309 2.24; 3.6251 2.38; 3.613 1.42; 3.6005 0.67; 3.0292 0.66; 2.8985 0.54; 2.2718 0.33; 2.2367 15; 2.2136 1.3; 2.1556 377.309998; 2.1129 1.25; 2.1065 1.14; 2.1004 0.9; 2.0722 0.44; 1.9715 3.01; 1.9515 26.77; 1.9453 49.98; 1.9392 70.379997; 1.933 48.59; 1.9268 25.1; 1.7739 0.36; 1.7678 0.49; 1.7616 0.3; 1.2707 0.79; 1.2216 0.66; 1.2037 1.17; 1.186 0.59; 0.0078 1.98; −0.0001 36.900002; −0.0083 1.74 |
| I-66 | [CD$_3$CN] 8.3549 0.65; 7.6997 2.17; 7.6876 2.49; 7.6855 2.4; 7.6734 2.46; 7.4128 2.78; 7.4119 2.83; 7.4007 2.64; 7.3998 2.47; 7.3577 0.4; 7.3468 0.78; 7.3437 0.79; 7.3358 0.47; 7.3328 1.54; 7.3298 0.51; 7.3219 0.77; 7.3188 0.87; 7.3078 0.41; 6.9948 1.98; 6.9884 0.37; 6.9812 3.52; 6.974 0.4; 6.9675 1.84; 6.9476 2.65; 6.9342 2.62; 6.4049 3.34; 5.4493 0.52; 5.0965 10.94; 4.6663 3.84; 4.6561 3.86; 4.0652 0.65; 4.0534 0.69; 3.7191 1.39; 3.7108 1.99; 3.7073 1.55; 3.7018 1.99; 3.6578 0.93; 3.652 1.91; 3.6467 1.55; 3.6415 2.24; 3.6189 3.89; 3.6095 3.39; 3.6021 2.19; 2.235 16; 2.234 15.75; 2.2154 0.61; 2.2128 0.37; 2.2081 0.83; 2.2002 2.38; 2.1877 906.52002; 2.1569 0.66; 2.1544 0.53; 2.1465 0.41; 2.0566 0.52; 2.0526 0.75; 2.0484 0.53; 1.9733 3.07; 1.9663 1.41; 1.9582 1.44; 1.954 2.05; 1.9502 47.91; 1.9461 94.529999; 1.942 140.320007; 1.9379 95.580002; 1.9338 48.73; 1.925 1.35; 1.8313 0.52; 1.8272 0.77; 1.8231 0.5; 1.2161 0.83; 1.2043 1.72; 1.1924 0.85; 0 1.02 |
| I-67 | [CD$_3$CN] 8.5455 0.66; 7.7204 1.66; 7.7021 2.13; 7.6991 2.08; 7.6808 2; 7.4433 2.7; 7.4252 2.33; 7.2691 1.77; 7.266 1.87; 7.2563 1.97; 7.2532 1.96; 7.0342 1.42; 7.0321 1.52; 7.0259 1.79; 7.0236 1.74; 6.9639 2.34; 6.9591 3; 6.9554 2.22; 6.9512 2.09; 6.9424 1.84; 6.9381 2.64; 6.3998 3.24; 5.0927 10.41; 4.7285 4.42; 4.7125 4.34; 3.7412 1.32; 3.7298 2.1; 3.7157 2.08; 3.6452 5.05; 3.6412 5.18; 3.628 3.64; 3.6199 2.59; 3.6138 2.55; 3.6019 1.42; 2.2334 15; 2.1507 225.710007; 2.1123 0.61; 2.1063 0.59; 2.1001 0.45; 2.0939 0.32; 1.963 1.02; 1.9512 15.17; 1.9451 28.6; 1.9389 41; 1.9327 28.370001; 1.9265 14.67; −0.0001 2.75 |
| I-68 | [CD$_3$CN] 7.6945 1.56; 7.676 2.04; 7.6731 1.98; 7.6547 1.86; 7.3922 2.77; 7.3741 2.39; 6.9795 2.62; 6.9581 2.48; 6.4009 3.3; 6.0462 0.48; 6.0376 0.82; 6.0277 0.54; 6.0241 0.6; 6.0212 0.62; 6.0143 1.03; 6.0054 0.59; 6.0028 0.55; 5.8321 0.46; 5.8267 0.9; 5.8227 0.84; 5.8181 0.94; 5.8125 0.52; 5.807 0.42; 5.8015 0.72; 5.7978 0.65; 5.7928 0.74; 5.7874 0.38; 5.4464 4.98; 5.093 10.07; 3.7153 1.22; 3.7046 2.08; 3.697 1.84; 3.6914 2.02; 3.6626 2.12; 3.6476 2.9; 3.6334 2.66; 3.621 5.18; 2.3375 0.68; 2.2642 0.63; 2.2358 15; 2.1674 99.370003; 2.1219 1.28; 2.1171 1.28; 2.1127 1.24; 2.1073 1.31; 2.1027 1; 2.088 0.59; 2.0826 0.57; 2.0736 0.77; 2.0685 0.83; 2.0643 0.84; 2.0604 0.83; 2.0516 0.72; 2.0424 0.58; 2.0372 0.43; 2.019 0.44; 2.0099 0.64; 2.0022 0.62; 1.9971 0.57; 1.986 0.66; 1.9766 1.08; 1.9718 1.41; 1.9641 1.54; 1.9519 11.31; 1.9457 20.530001; 1.9396 28.68; 1.9334 19.76; 1.9273 10.19; 1.877 0.45; 1.8694 0.59; 1.8645 0.6; 1.8564 1.01; 1.8493 0.95; 1.8364 1.06; 1.8277 0.96; 1.8235 1.02; 1.8154 0.9; 1.809 0.99; 1.8015 0.87; 1.794 0.6; 1.777 0.37; 1.7684 0.4; 1.7411 0.32; 1.7369 0.32; 1.7262 0.64; 1.7175 0.7; 1.7112 0.63; 1.7055 0.71; 1.6973 0.61; 1.6922 0.56; 1.6844 0.53; 1.6705 0.41; 1.6639 0.31; 1.4256 0.41; 1.2745 0.3; 1.2571 0.34; 0.0078 0.81; −0.0001 14.45; −0.0082 0.63 |

-continued

| Ex. | NMR data |
|---|---|
| I-69 | [CD$_3$CN] 7.6996 1.68; 7.6813 2.18; 7.6782 1.77; 7.6599 1.8; 7.4011 2.68; 7.3828 2.27; 6.9818 2.52; 6.9603 2.28; 6.402 2.97; 5.4468 1.38; 5.1335 0.3; 5.0943 9.8; 4.9934 0.35; 4.9843 0.62; 4.972 0.69; 4.9622 1.09; 4.9526 0.67; 4.9403 0.47; 4.0868 0.47; 4.0689 1.33; 4.0511 1.31; 4.0332 0.45; 3.721 1.37; 3.7103 2.11; 3.703 1.77; 3.6967 2.07; 3.6644 2.01; 3.6492 2.9; 3.6358 2.83; 3.6259 4.43; 3.6121 2.27; 2.2638 0.81; 2.2371 15; 2.2358 14.28; 2.1696 194.880005; 1.9719 6.43; 1.9637 1.42; 1.952 16.58; 1.9459 30.700001; 1.9397 42.950001; 1.9335 29.32; 1.9273 15.12; 1.9009 1; 1.8147 0.5; 1.8076 0.66; 1.7995 0.81; 1.7914 0.9; 1.7808 0.97; 1.7744 1.17; 1.7681 1.19; 1.762 0.88; 1.6227 0.47; 1.6141 0.5; 1.5986 1.2; 1.5911 1.51; 1.5827 1.08; 1.5752 1.22; 1.568 1.78; 1.5595 1.33; 1.5447 0.94; 1.5373 0.8; 1.4993 0.46; 1.4911 0.59; 1.4755 0.75; 1.4672 1.33; 1.4586 0.84; 1.4513 0.59; 1.4428 1.21; 1.4348 1.21; 1.4184 0.47; 1.4096 0.77; 1.4047 0.74; 1.394 0.37; 1.3786 0.54; 1.3721 0.54; 1.3626 0.3; 1.3558 0.32; 1.348 0.41; 1.2217 1.61; 1.2039 3.16; 1.1861 1.56; −0.0001 0.85 |
| I-70 | [CD$_3$CN] 7.6784 1.67; 7.66 2.13; 7.6569 2.07; 7.6385 2; 7.3686 3.59; 7.3499 3.31; 7.2717 0.48; 7.2683 0.5; 7.2516 1.18; 7.235 1.48; 7.2313 1.3; 7.1948 2.32; 7.1804 1.76; 7.1784 1.8; 7.1632 0.64; 6.9765 2.48; 6.9556 2.37; 6.3985 3.13; 6.2034 0.85; 6.1923 1.77; 6.1811 0.92; 5.4463 9.51; 5.0837 9.83; 3.7019 1.17; 3.6919 1.98; 3.6845 1.76; 3.6786 1.95; 3.6503 2.05; 3.635 2.73; 3.6202 2.54; 3.6085 4.54; 3.5962 2.5; 2.9525 0.32; 2.9388 0.61; 2.926 0.35; 2.9097 0.63; 2.8964 1.08; 2.8841 0.51; 2.8375 0.6; 2.8156 0.81; 2.8017 0.63; 2.7733 0.41; 2.2654 0.56; 2.231 15; 2.2297 14.62; 2.2211 1.69; 2.1709 322.059998; 2.1204 0.91; 2.1131 1.2; 2.1069 1.02; 2.1005 2.54; 2.0888 3.32; 2.0817 1.8; 2.0785 1.89; 2.0655 0.71; 2.0629 0.69; 2.0508 0.76; 2.0422 0.68; 2.0292 0.77; 2.0222 0.4; 2.0164 0.43; 2.0083 0.46; 1.9951 0.35; 1.9718 1.2; 1.9636 1.26; 1.9518 18.07; 1.9457 33.990002; 1.9395 48.080002; 1.9333 32.689999; 1.9271 16.52; 1.9075 0.67; 1.9041 0.56; 1.8943 0.92; 1.882 0.74; 1.8741 0.48; 1.8686 0.51; 1.8586 0.37; 1.8518 0.36; 1.7679 0.37; 1.4369 0.33; 1.2038 0.37; −0.0001 0.87 |
| I-71 | [CD$_3$CN] 7.6955 2.14; 7.6833 2.47; 7.6813 2.44; 7.6691 2.45; 7.3982 2.88; 7.3975 2.95; 7.3861 2.73; 7.3853 2.63; 6.9844 2.79; 6.9707 2.72; 6.4045 3.44; 5.8951 0.39; 5.884 0.8; 5.8781 0.43; 5.8729 0.41; 5.8669 1.22; 5.8556 1.23; 5.8496 0.46; 5.8444 0.45; 5.8385 0.9; 5.8273 0.44; 5.4489 2.26; 5.0958 11.15; 5.0614 0.58; 5.0588 1.36; 5.0552 1.48; 5.0526 0.7; 5.0329 0.56; 5.0303 1.28; 5.0267 1.38; 5.0241 0.65; 4.9762 0.69; 4.9742 1.32; 4.9724 1.21; 4.9706 1.27; 4.9686 0.66; 4.9592 0.63; 4.9572 1.29; 4.9554 1.17; 4.9536 1.22; 4.9516 0.63; 4.2992 3.51; 4.2883 7.4; 4.2774 3.61; 3.7132 1.31; 3.7052 2.01; 3.7013 1.52; 3.6959 2.09; 3.666 0.97; 3.6591 1.98; 3.6539 1.57; 3.6486 2.14; 3.6281 2.38; 3.622 3.75; 3.6112 3.21; 3.6048 1.19; 2.2363 15.97; 2.2353 16; 2.1791 99.779999; 2.154 0.95; 2.1518 1.19; 2.1496 0.83; 2.1396 2.19; 2.1275 2.2; 2.118 0.7; 2.1159 1.05; 2.1136 0.67; 1.966 0.38; 1.9577 0.34; 1.9537 0.39; 1.9499 10.85; 1.9458 21.5; 1.9417 32.009998; 1.9376 21.870001; 1.9335 11.18; 1.7788 0.67; 1.7678 1.84; 1.7633 0.49; 1.7559 1.86; 1.7537 1.58; 1.7424 2.07; 1.7315 0.88; 1.5659 0.78; 1.553 1.93; 1.5447 0.88; 1.5407 2.79; 1.5314 0.65; 1.5279 1.62; 1.5156 0.62; 0 0.73 |
| I-72 | [CD$_3$CN] 7.7112 1.74; 7.6928 2.23; 7.6898 2.1; 7.6714 2.11; 7.6131 1.12; 7.6059 0.89; 7.6021 1.17; 7.5957 0.82; 7.5899 1.34; 7.489 1.2; 7.4833 0.75; 7.4764 1.23; 7.4727 1.07; 7.4658 1.78; 7.4564 0.33; 7.4387 2.83; 7.4209 2.48; 7.3977 0.56; 7.3852 2.68; 7.3831 2.52; 7.3791 1.8; 7.3724 3.21; 7.3661 1.46; 7.362 1.91; 7.3599 1.66; 7.3474 0.3; 7.0106 2.68; 6.9894 2.53; 6.4 3.26; 5.4461 1.7; 5.4369 10.67; 5.0903 10.48; 4.0865 0.48; 4.0686 1.44; 4.0508 1.47; 4.033 0.49; 3.728 1.26; 3.7167 2.08; 3.7097 1.74; 3.703 2.15; 3.6492 3.21; 3.6332 5.13; 3.6101 1.97; 2.2637 0.32; 2.2343 15; 2.2333 14.79; 2.1631 160.529999; 2.1133 0.36; 2.1069 0.37; 1.9717 6.81; 1.9635 0.87; 1.9518 10.14; 1.9456 19.1; 1.9395 27.18; 1.9333 18.709999; 1.9271 9.63; 1.2216 1.76; 1.2038 3.44; 1.186 1.71; −0.0001 1.47 |
| I-73 | [CD$_3$CN] 7.7 1.54; 7.6815 2.03; 7.6787 1.84; 7.6602 1.72; 7.5755 0.71; 7.5567 1.32; 7.5373 0.69; 7.4388 0.45; 7.4341 0.48; 7.4125 3.14; 7.3997 1.21; 7.3943 2.68; 7.386 0.48; 73816 0.36; 7.2517 1.08; 7.233 1.73; 7.2138 0.77; 7.1936 1.01; 7.1685 1.12; 7.147 0.75; 6.9995 2.65; 6.9781 2.38; 6.3985 3.23; 5.4458 2.26; 5.4052 7.6; 5.0863 9.83; 4.0862 0.4; 4.0684 1.05; 4.0506 1.08; 4.0327 0.36; 3.7127 1.41; 3.702 2.25; 3.6949 1.95; 3.6886 2.24; 3.6567 2.14; 3.6417 3.12; 3.6177 4.94; 3.604 2.75; 2.2644 0.5; 2.2316 15; 2.2093 0.63; 2.144 198.509995; 2.1063 0.78; 2.1002 0.63; 1.9713 5.43; 1.9512 22.66; 1.9451 42.16; 1.9389 59.060001; 1.9327 40.669998; 1.9265 20.790001; 1.2712 0.3; 1.2215 1.25; 1.2037 2.41; 1.1859 1.16; −0.0001 34.84; −0.0083 1.88 |
| I-74 | [CD$_3$CN] 7.6805 1.75; 7.6621 2.19; 7.6591 2.11; 7.6407 2.07; 7.4939 0.37; 7.4774 0.78; 7.4727 0.77; 7.4608 0.54; 7.4563 1.55; 7.4517 0.58; 7.4397 0.78; 7.4351 0.9; 7.4186 0.45; 7.3661 2.75; 7.3484 2.44; 7.0796 0.39; 7.0701 2.15; 7.0621 0.45; 7.0584 0.5; 7.05 3.29; 7.0412 0.53; 7.0375 0.43; 7.0296 1.91; 7.02 0.35; 6.984 2.67; 6.9626 2.53; 6.3967 3.24; 5.446 4.21; 5.4294 7.29; 5.0805 10.39; 4.0686 0.78; 4.0508 0.8; 3.6929 1.24; 3.6821 2.09; 3.6738 1.83; 3.6686 1.89; 3.653 1.33; 3.6435 2.17; 3.6282 2.73; 3.6144 2.32; 3.608 2.37; 3.599 4.06; 3.5904 2.73; 3.5816 1.98; 3.572 0.99; 2.2649 0.41; 2.2291 15; 2.2281 14.7; 2.1566 161.330002; 1.9716 3.86; 1.9634 0.89; 1.9517 10.4; 1.9456 19.41; 1.9394 27.459999; 1.9332 18.780001; 1.927 9.5; 1.2216 0.95; 1.2038 1.86; 1.1859 0.92; −0.0001 1.46 |
| I-75 | [CD$_3$CN] 8.0035 1.32; 8.0012 1.66; 7.989 1.59; 7.9809 1.4; 7.9677 1.48; 7.9659 1.32; 7.8866 1.87; 7.8728 2.04; 7.8303 1.73; 7.8181 2.19; 7.816 2; 7.8038 2.23; 7.7093 3.18; 7.6973 2.58; 7.6054 0.55; 7.603 0.72; 7.5921 3.16; 7.5798 4.41; 7.5784 4.22; 7.5686 0.77; 7.5661 3.41; 7.5551 0.69; 7.5528 0.58; 7.4331 2.21; 7.4317 2.34; 7.4207 1.9; 7.4192 1.9; 7.1308 2.82; 7.1166 2.73; 6.4034 3.45; 5.1025 11.05; 4.0768 1.28; 4.065 3.89; 4.0531 3.93; 4.0413 1.32; 3.8026 1.48; 3.7944 2.04; 3.7911 1.56; 3.7852 1.96; 3.6972 14.32; 3.6769 0.45; 3.6695 2.06; 3.6637 1.56; 3.6604 2.08; 3.652 1.5; 2.2562 0.62; 2.2376 16; 2.2298 0.95; 2.1889 47.09; 1.973 17.540001; 1.9659 0.34; 1.9575 0.56; 1.9533 0.58; 1.9496 12.03; 1.9455 23.690001; 1.9414 35; 1.9373 23.969999; 1.9332 12.15; 1.2158 4.61; 1.204 9.24; 1.1921 4.59; 0 1.57 |
| I-76 | [CD$_3$CN] 7.9981 2.35; 7.9833 2.45; 7.9653 1.42; 7.9521 1.49; 7.914 1.48; 7.9008 1.59; 7.7988 1.99; 7.7867 2.46; 7.7845 2.24; 7.7723 2.47; 7.7417 2.3; 7.738 2.35; 7.6415 3.02; 7.641 3.07; 7.6295 2.66; 7.5836 0.63; 7.5812 0.75; 7.5721 1.58; 7.5698 1.49; 7.5593 1.77; 7.5567 2.65; 7.554 1.92; 7.5454 0.79; 7.5436 1.51; 7.5413 1.54; 7.5322 0.72; 7.5298 0.59; 7.4184 2.02; 7.4145 1.97; 7.4036 1.92; 7.3997 1.88; 7.0946 2.74; 7.0941 2.74; 7.0803 2.71; 6.4044 3.42; 5.4485 |

-continued

| Ex. | NMR data |
|---|---|
|  | 2.77; 5.1029 10.93; 4.0768 0.79; 4.065 2.36; 4.0531 2.39; 4.0413 0.8; 3.7776 1.39; 3.7693 1.97; 3.766 1.53; 3.7602 1.87; 3.6962 0.65; 3.6826 4.92; 3.6805 4.97; 3.6664 0.86; 3.6599 2.22; 3.6539 1.58; 3.6507 2.05; 3.6424 1.4; 2.2387 16; 2.2377 15.54; 2.231 0.53; 2.1877 205.589996; 2.1704 0.39; 1.973 11.04; 1.9575 0.34; 1.9532 0.52; 1.9495 10.74; 1.9454 21.02; 1.9413 31.040001; 1.9372 20.91; 1.9331 10.45; 1.2157 3.09; 1.2038 6.17; 1.192 3.04; 0 0.66 |
| I-77 | [DMSO-d$_6$] 7.9572 0.34; 7.9403 0.32; 7.9197 0.32; 7.8143 0.32; 7.767 6.7; 7.7477 15; 7.7283 9.35; 7.6104 8.82; 7.591 6.66; 7.568 0.49; 7.5463 0.49; 7.5265 0.47; 7.4921 0.59; 7.478 0.5; 7.471 0.71; 7.4443 2.48; 7.4348 2.73; 7.43 3.07; 7.4207 3.58; 7.4071 2.68; 7.3922 2.79; 7.3832 3.05; 7.3448 6.76; 7.3305 2.72; 7.3239 4.21; 7.3104 2.97; 7.2953 3.22; 7.2557 6.32; 7.2418 6.09; 7.2319 10.69; 7.2226 6.55; 7.2109 14.24; 7.197 10.65; 7.1834 7.76; 7.1774 10.01; 7.1483 0.39; 7.0775 5.68; 7.0475 13.97; 7.0274 0.62; 6.9337 12.78; 6.9117 7; 5.7474 2.18; 5.4531 0.67; 5.4217 1.47; 5.4028 0.72; 5.3776 5.66; 5.3568 11.6; 5.3101 1.55; 4.2714 2.43; 4.0392 0.43; 4.0215 0.36; 4.0018 0.37; 3.8746 2.05; 3.8529 2.32; 3.5195 0.32; 3.4854 0.32; 3.4652 0.79; 3.4219 0.6; 3.3947 0.91; 3.3118 313.070007; 3.2928 100.93; 3.2029 0.61; 3.1822 0.73; 3.1258 0.56; 3.102 2.36; 3.0678 4.03; 3.0371 2.97; 2.9435 0.49; 2.8499 0.88; 2.8114 0.44; 2.7847 0.41; 2.7524 0.4; 2.7307 2.09; 2.7212 1.64; 2.7103 2.55; 2.7022 4.24; 2.6928 2.55; 2.6733 3.7; 2.6688 3.33; 2.664 2.68; 2.6224 2.24; 2.5901 4.18; 2.564 2.67; 2.5388 11.41; 2.5219 7.7; 2.5084 118.080002; 2.5041 222.740005; 2.4996 292.51001; 2.4953 202.589996; 2.4909 97.57; 2.4468 1.15; 2.418 0.79; 2.3793 0.58; 2.3354 0.99; 2.3312 1.52; 2.3266 2.01; 2.322 1.62; 2.2907 0.42; 2.2371 0.35; 2.0843 0.31; 2.0693 2.93; 2.0493 1.05; 2.0081 0.38; 1.9866 1.3; 1.9581 0.45; 1.9067 0.33; 1.6641 0.34; 1.6408 0.35; 1.6173 0.33; 1.5282 1.5; 1.5025 3; 1.4756 2.17; 1.4394 1.73; 1.4075 3.15; 1.3983 3.3; 1.3749 2.29; 1.3345 1.61; 1.3111 1.44; 1.292 1.15; 1.271 1.08; 1.2598 0.96; 1.2366 1.88; 1.2072 1.34; 1.1992 1.36; 1.1748 1.41; 1.1624 1.09; 1.1381 1.41; 1.1308 1.34; 1.1109 1.72; 1.0983 1.32; 1.0703 1.21; 1.0564 0.88; 1.0494 0.78; 1.0263 1.28; 1.0172 1.4; 0.9927 1.23; 0.9853 1.31; 0.9628 0.64; 0.9534 0.49; 0.8904 0.44; 0.008 1.42; −0.0001 32.599998; −0.0085 1.33; −2.2704 0.34 |
| I-78 | [DMSO-d$_6$] 7.8679 1.41; 7.8617 0.69; 7.8486 2.98; 7.8423 1.37; 7.8292 1.72; 7.8229 0.75; 7.3891 2.05; 7.3691 2.66; 7.3527 2.53; 7.3477 2.01; 7.3353 2.17; 7.3287 1.13; 7.3121 0.54; 7.2984 1.12; 7.1786 1.06; 7.1649 2.58; 7.1538 1.33; 7.0451 0.53; 7.0315 1.32; 7.0242 1.38; 7.0176 2.79; 6.8979 3.78; 6.8817 1.39; 5.747 6.02; 5.458 0.31; 5.4158 0.91; 5.3834 2.21; 5.3543 3; 5.3119 0.74; 4.4274 0.88; 4.3946 0.93; 4.3199 0.4; 4.057 0.45; 4.0392 1.3; 4.0214 1.66; 4.0038 1.15; 3.9766 0.93; 3.3892 0.5; 3.3808 0.45; 3.3602 1.05; 3.3028 353.709991; 3.2809 3.34; 3.2638 1.22; 3.2263 1.34; 3.1983 0.73; 3.0598 0.6; 3.0513 0.49; 3.0305 1.14; 3.0115 0.48; 3.0018 0.64; 2.8726 15; 2.7953 0.71; 2.7618 1.42; 2.7508 6.34; 2.7369 0.82; 2.6736 0.46; 2.6693 0.53; 2.6645 0.4; 2.5391 1.21; 2.5221 2.27; 2.5088 33.290001; 2.5045 61.48; 2.5 79.449997; 2.4957 54.490002; 2.4914 26.040001; 2.3311 0.43; 2.3266 0.56; 2.3222 0.44; 2.0694 0.32; 1.9867 5.57; 1.9339 0.72; 1.9076 1.78; 1.9028 1.79; 1.8673 1.03; 1.8245 0.93; 1.7953 1.35; 1.7638 0.9; 1.754 0.83; 1.7452 0.81; 1.7088 2.31; 1.6801 2.37; 1.6539 1.3; 1.614 0.95; 1.6048 1.2; 1.5737 1.79; 1.5424 1.59; 1.5039 1.16; 1.4673 0.95; 1.3768 0.56; 1.3449 0.51; 1.1927 1.56; 1.1749 3.17; 1.1571 1.61; 1.1404 0.33; 1.0504 0.42; 1.0222 0.64; 0.9923 1.22; 0.9632 1.12; 0.9304 0.82; 0.8906 0.32; −0.0001 4.17 |
| I-79 | $^1$H NMR (DMSO-d$_6$, 400 MHz): d$_{ppm}$: [7.90 (t), 7.84 (t)] (1H), [7.67 (d), 7.58 (d)] (1H), 7.55-7.30 (m, 4H), 7.20-7.15 (m, 1H), 7.03 (t, 1H), 6.94-6.86 (m, 1H), [5.40 (q), 5.34 (s)] (2H), 4.80-4.60 (m, 2H), [4.42 (d), 4.29 (d)] (1H), [4.01 (d), 3.88 (d)] (1H), 3.40-2.40 (m, 3H), [3.02 (s), 2.97 (s)] (3H), 2.01-1.20 (m, 4H) |
| I-80 | [DMSO-d$_6$] 8.5633 0.86; 8.5531 0.79; 8.4858 1.25; 8.4759 1.21; 7.9137 0.74; 7.8942 1.57; 7.8747 0.92; 7.8363 1.72; 7.8267 0.4; 7.8169 3.43; 7.7976 1.95; 7.7884 0.88; 7.7841 0.78; 7.7695 1.47; 7.7649 1.42; 7.7504 0.84; 7.7462 0.81; 7.4873 1.41; 7.477 2.07; 7.4692 1.3; 7.4594 1.92; 7.4294 1.18; 7.4114 1.09; 7.3706 1.07; 7.3511 1.14; 7.3407 1.96; 7.3191 2.95; 7.3096 2.81; 7.2895 1.58; 7.256 0.91; 7.2455 1; 7.2379 0.99; 7.2271 0.89; 7.1854 3.4; 7.1773 1.54; 7.1604 0.71; 7.0498 3.14; 7.0434 0.98; 7.0244 1.49; 6.9189 2.47; 6.9005 1.48; 6.8882 0.76; 5.7463 0.67; 5.4629 0.38; 5.4196 1.05; 5.4013 0.51; 5.358 2.96; 5.3251 1.98; 5.2813 0.42; 4.7705 3.38; 4.69 5.81; 4.438 0.42; 4.4091 0.39; 4.3041 0.59; 4.2727 0.6; 4.0393 0.72; 4.0215 0.9; 4.0036 0.38; 3.9856 0.48; 3.8907 0.62; 3.8526 0.65; 3.464 0.32; 3.4549 0.36; 3.4281 0.44; 3.3941 0.7; 3.3109 1092.949951; 3.2872 78.389999; 3.2445 1.09; 3.2165 0.52; 3.2019 0.48; 3.195 0.33; 3.1339 0.51; 3.1005 0.95; 3.0705 0.77; 3.0621 0.86; 3.0534 0.56; 3.0227 15; 3.0203 10.04; 2.8908 0.5; 2.8585 0.79; 2.8306 0.5; 2.8195 0.46; 2.7854 0.51; 2.778 0.54; 2.7495 0.35; 2.6742 0.96; 2.6695 1.38; 2.665 1.2; 2.6266 0.82; 2.5983 0.58; 2.5397 2.17; 2.5225 4.87; 2.5092 73.919998; 2.5049 138.350006; 2.5005 180.330002; 2.4961 124.330002; 2.4918 59.540001; 2.4339 0.46; 2.3319 0.97; 2.3268 1.22; 2.3226 0.94; 2.0691 1.01; 2.0497 0.44; 1.9867 2.92; 1.9365 0.73; 1.9066 0.5; 1.8233 0.42; 1.7952 0.35; 1.7842 0.31; 1.7418 0.55; 1.7066 0.69; 1.6699 0.66; 1.6328 0.75; 1.5991 0.38; 1.5099 0.53; 1.4888 0.45; 1.4816 0.47; 1.3981 0.45; 1.2923 0.33; 1.2591 0.58; 1.2364 0.84; 1.1926 0.79; 1.175 1.54; 1.1571 0.84; 0.0078 0.91; −0.0001 21.77; −0.0086 0.99 |
| I-81 | [DMSO-d$_6$] 7.9305 1.18; 7.9111 2.47; 7.8918 1.46; 7.5805 2.36; 7.5614 2.19; 7.4442 1.78; 7.425 1.77; 7.3909 0.36; 7.2964 1.82; 7.1629 4.1; 7.1518 2.02; 7.0295 2.79; 7.0158 5.64; 6.998 0.99; 6.9195 2.66; 6.9164 2.85; 6.8951 5.41; 6.8799 2.4; 6.8419 0.4; 6.7688 0.39; 6.7646 0.4; 6.7512 0.4; 6.7467 0.4; 5.747 10.97; 5.4114 0.47; 5.3693 2.44; 5.3444 3.18; 5.303 0.59; 4.3064 2.99; 4.0568 1.14; 4.039 3.42; 4.0212 3.45; 4.0034 1.21; 3.9336 0.76; 3.8847 2.16; 3.3006 528.530029; 3.2769 15.56; 3.2312 0.99; 3.1978 1.22; 3.1689 0.72; 3.0262 0.59; 3.0007 0.82; 2.7841 0.62; 2.754 1.08; 2.7261 0.62; 2.6774 0.38; 2.6732 0.69; 2.6687 0.92; 2.6641 0.67; 2.5387 2.37; 2.5219 3.35; 2.5085 54.509998; 2.5041 101.230003; 2.4996 130.699997; 2.4953 89.199997; 2.491 42.59; 2.4104 0.3; 2.3356 0.46; 2.3309 0.76; 2.3263 1.2; 2.3217 0.76; 2.2692 1.05; 2.0493 0.39; 1.9866 15; 1.907 0.43; 1.8501 0.93; 1.8234 0.82; 1.8109 0.73; 1.8072 0.72; 1.764 0.39; 1.7089 0.48; 1.6584 0.31; 1.5016 0.5; 1.4822 0.49; 1.3984 0.66; 1.1925 4.13; 1.1748 8.13; 1.157 4.02; 0.0078 0.44; −0.0001 10.13; −0.0084 0.41 |
| I-82 | [DMSO-d$_6$] 8.922 1.21; 8.9026 1.23; 7.9555 1.52; 7.9362 3.68; 7.9169 2.45; 7.8435 3.09; 7.8262 2.18; 7.5688 1.83; 7.565 2.08; 7.5587 2.81; 7.55 2.28; 7.5462 2.34; 7.5397 2.53; 7.4464 1.7; 7.427 |

-continued

| Ex. | NMR data |
|---|---|
| | 2.18; 7.3572 0.69; 7.3384 1.54; 7.3222 2.43; 7.2964 1.39; 7.2776 1.65; 7.2588 0.63; 7.1889 3.41; 7.1651 1.66; 7.0555 1.7; 7.0291 3.78; 6.9105 3.49; 6.8932 1.87; 5.7468 0.56; 5.5048 0.32; 5.487 1.22; 5.4683 2.1; 5.4496 1.3; 5.4303 1.98; 5.3808 2.59; 5.3382 0.75; 4.4932 0.79; 4.4592 0.82; 4.0574 1.79; 4.0396 3.75; 4.0218 3.98; 4.004 1.19; 3.3102 325.160004; 3.2677 1.49; 3.2374 0.7; 3.15 0.55; 3.1293 0.72; 3.1208 1.13; 3.1127 0.7; 3.1002 0.46; 3.0911 0.61; 2.8347 0.55; 2.805 1.01; 2.775 0.56; 2.6701 0.4; 2.54 0.89; 2.5096 22.719999; 2.5053 41.68; 2.5009 53.59; 2.4966 36.98; 2.3275 0.38; 2.0696 0.61; 2.0501 0.78; 2.019 1.34; 1.9872 15; 1.9 0.32; 1.8698 0.69; 1.8386 0.64; 1.779 0.32; 1.7474 0.69; 1.7158 0.63; 1.5468 7.04; 1.5293 7.01; 1.193 3.91; 1.1752 7.84; 1.1574 3.81; −0.0001 2.21 |
| I-83 | [DMSO-$d_6$] 8.1932 4.31; 8.1784 4.42; 7.9457 4.71; 7.9329 11.59; 7.9201 7.93; 7.8799 8.52; 7.8783 8.86; 7.8671 6.02; 7.8655 5.64; 7.8462 0.35; 7.8446 0.34; 7.5272 6.54; 7.5258 6.6; 7.5144 6.45; 7.5129 6.09; 7.2847 3.28; 7.1957 7.29; 7.1348 3.81; 7.1069 3.65; 7.0442 9.52; 6.9536 4.54; 6.9234 8.96; 5.7641 1.45; 5.4623 1.83; 5.4542 1.73; 5.4336 3.49; 5.4257 3.46; 5.3771 6.81; 5.3486 3.19; 5.3195 0.39; 4.4643 2.06; 4.4425 2.12; 4.0459 1.45; 4.0341 5.85; 4.0222 5.74; 4.0104 5.62; 4.0006 2.45; 3.9862 1.08; 3.3995 0.36; 3.386 0.62; 3.372 1.65; 3.3511 918.869995; 3.3276 2.16; 3.3181 0.66; 2.2633 1.41; 3.2594 1.62; 3.2382 2.75; 3.2197 1.58; 3.2158 1.32; 3.1005 0.75; 3.0948 1.38; 3.0891 0.9; 3.0808 1.66; 3.0749 2.91; 3.0691 1.66; 3.061 0.97; 3.0551 1.52; 3.0492 0.81; 3.0369 1.1; 2.891 0.33; 2.8487 0.86; 2.795 1.37; 2.7739 2.7; 2.7529 1.4; 2.6216 0.61; 2.6188 1.3; 2.6157 1.77; 2.6127 1.28; 2.6097 0.61; 2.5432 7.01; 2.5248 3.5; 2.5217 4.53; 2.5186 4.94; 2.5097 100.57; 2.5067 216.080002; 2.5037 295.079987; 2.5007 212.289993; 2.4977 95.790001; 2.3936 0.62; 2.3906 1.29; 2.3876 1.75; 2.3846 1.26; 2.3816 0.57; 2.0782 3.04; 2.0532 0.43; 1.9956 1.91; 1.9907 16; 1.9752 2.1; 1.9508 1.64; 1.9292 1.86; 1.8402 0.65; 1.8358 0.74; 1.8196 1.65; 1.8151 1.7; 1.7991 1.51; 1.7942 1.46; 1.778 0.56; 1.7728 0.51; 1.7089 0.7; 1.7046 0.62; 1.689 1.65; 1.6728 1.28; 1.6679 1.55; 1.6632 1.21; 1.6524 0.52; 1.6483 0.58; 1.6425 0.45; 1.6004 0.79; 1.5961 0.86; 1.5865 1.38; 1.5773 1.73; 1.5736 1.68; 1.5643 1.56; 1.5534 0.75; 1.5197 1.74; 1.5091 2.23; 1.4967 1.8; 1.4859 1.23; 1.4743 0.58; 1.3969 0.69; 1.2682 11.74; 1.2634 10.77; 1.2345 1.49; 1.1903 12.62; 1.1866 14.36; 1.1793 13.43; 1.1763 13.3; 1.1746 14.18; 1.1684 1.68; 1.1627 4.46; 1.1577 0.79; 1.0669 0.32; 0.8495 6.03; 0.8444 10.99; 0.8385 10.87; 0.8335 5.4; 0.8275 3.61; 0.0054 1.17; 0 35.220001; −0.0056 1.1 |
| I-84 | [DMSO-$d_6$] 16.9338 0.52; 16.757601 0.52; 16.381001 0.58; 8.7368 2.49; 8.7169 2.45; 7.9996 0.58; 7.9852 1.31; 7.9662 6.89; 7.9589 7.84; 7.9514 15; 7.9397 1.52; 7.5527 0.91; 7.5405 3.9; 7.5334 3.85; 7.5265 3.77; 7.519 3.55; 7.339 0.54; 7.3012 3.27; 7.2845 5.67; 7.2628 3.25; 7.2549 1.87; 7.2436 2.85; 7.2333 3.63; 7.2222 2.44; 7.2146 2.75; 7.197 11.97; 7.165 0.61; 7.1448 2.98; 7.1298 5.86; 7.0083 5.91; 6.9965 3.13; 6.8845 7.62; 6.872 3.15; 5.7468 4.31; 5.6044 1.09; 5.5817 3.27; 5.5604 3.43; 5.5378 1.15; 5.4167 1.57; 5.374 7.5; 5.3339 5.39; 5.3077 0.68; 5.2902 1.49; 4.4306 2.09; 4.3992 2.13; 4.0568 1.23; 4.0391 3.38; 4.0212 3.57; 4.0039 2.7; 3.9692 2.02; 3.9647 2.13; 3.6742 0.55; 3.5839 0.57; 3.5377 0.71; 3.5252 0.57; 3.4963 0.71; 3.4731 0.76; 3.408 1.27; 3.3858 1.74; 3.3033 2034.709961; 3.2368 2.56; 3.2 2.98; 3.1801 1.23; 3.1691 1.75; 3.1566 0.92; 3.1415 0.61; 3.1358 0.6; 3.0815 1.09; 3.0751 1.45; 3.044 3.91; 3.0228 2.41; 3.0121 3.36; 3.0057 3; 2.99 2.22; 2.9831 2.25; 2.9201 1.39; 2.8998 2.86; 2.8789 2.26; 2.8603 1.81; 2.841 1.02; 2.7681 1.43; 2.7363 2.52; 2.7081 1.48; 2.6682 2.81; 2.6489 0.59; 2.6421 0.56; 2.5389 8.32; 2.5 426.429993; 2.4403 1.93; 2.4054 0.8; 2.3574 0.63; 2.3261 2.84; 2.1474 1.19; 2.1238 2.56; 2.1169 1.35; 2.1023 2.55; 2.0931 2.36; 2.0847 1.75; 2.0696 3.36; 2.0599 0.67; 2.0493 1.98; 1.9867 14.85; 1.9427 3.05; 1.9078 2.67; 1.8239 1.36; 1.8007 1.86; 1.7792 1.3; 1.7679 1.1; 1.7329 0.67; 1.6803 1.6; 1.6675 1.34; 1.6485 1.39; 1.6364 1.21; 1.6154 0.77; 1.3998 0.66; 1.2917 0.76; 1.2362 0.89; 1.1926 3.57; 1.1749 7.03; 1.157 3.59; 1.0456 1.33; 1.0292 1.25; −0.0001 77.949997; −3.6563 0.61 |
| I-85 | [DMSO-$d_6$] 8.6033 1.62; 8.5882 2.85; 8.5719 1.42; 7.9373 2.65; 7.9181 6.81; 7.8991 5.33; 7.8714 5.66; 7.8687 6.18; 7.8524 3.18; 7.8497 2.81; 7.5104 4.4; 7.5078 4.39; 7.4913 4.08; 7.4889 3.89; 7.317 2.69; 7.1835 6.06; 7.1651 2.93; 7.05 3.05; 7.029 6.76; 6.9076 6.07; 6.8931 3.25; 5.4462 1.11; 5.4262 0.41; 5.4194 0.4; 5.4029 5.09; 5.373 5.08; 5.3316 1.03; 4.4731 1.43; 4.4701 1.46; 4.4378 1.43; 4.0569 0.47; 4.0393 2.19; 4.0216 1.78; 4.0036 1.73; 3.4495 0.35; 3.4334 0.37; 3.3753 1.05; 3.312 134.529999; 3.2758 4.55; 3.2386 2.17; 3.2077 1.18; 3.0876 0.99; 3.0778 0.78; 3.0673 1.34; 3.0585 2.07; 3.0494 1.37; 3.0373 1.27; 3.0288 1.16; 3.0195 0.71; 2.8503 0.45; 2.8054 0.92; 2.7727 1.84; 2.7441 1.04; 2.6736 0.9; 2.6691 1.1; 2.5659 0.3; 2.539 5.95; 2.5085 65.870003; 2.5043 125.209999; 2.4999 165.910004; 2.4956 118.529999; 2.4118 0.4; 2.3312 0.9; 2.3264 1.15; 2.3226 0.85; 2.0697 0.69; 2.0495 0.57; 1.9868 5.46; 1.9625 2.17; 1.9173 1.68; 1.908 1.44; 1.8776 0.6; 1.868 0.67; 1.8485 1.18; 1.8379 1.31; 1.8143 1.19; 1.8044 1.14; 1.7862 0.88; 1.7738 0.96; 1.7534 1.25; 1.7442 1.36; 1.7217 1.15; 1.713 1.17; 1.6906 0.47; 1.6805 0.44; 1.5576 2.36; 1.54 3.49; 1.5229 2.52; 1.3985 0.33; 1.2986 10.41; 1.2922 10.14; 1.2702 7.42; 1.2628 9.95; 1.1927 1.53; 1.175 2.8; 1.1572 1.59; 1.1109 0.32; 1.1014 0.32; 1.0707 0.45; 0.872 4.81; 0.8552 15; 0.8376 5.7; 0.0082 0.64; −0.0001 18.17; −0.0081 0.91 |
| I-86 | [DMSO-$d_6$] 9.2669 0.94; 9.2516 1.95; 9.236 0.96; 7.9744 1.54; 7.9552 4.14; 7.9361 3.2; 7.9058 3.4; 7.9033 3.68; 7.8867 2.02; 7.8841 1.75; 7.625 4.06; 7.6198 4.23; 7.5646 2.61; 7.5624 2.65; 7.5457 2.52; 7.5432 2.33; 7.4236 1.89; 7.4183 1.79; 7.4027 2.85; 7.3973 2.74; 7.3234 4; 7.3029 4.06; 7.1702 3.79; 7.1554 1.88; 7.0368 1.87; 7.0194 4.18; 6.9025 3.66; 6.8836 2.03; 5.7463 1.17; 5.439 0.61; 5.3958 3.08; 5.3673 3.05; 5.3251 0.64; 4.5811 4.29; 4.5654 4.25; 4.4765 0.87; 4.4463 0.87; 4.0572 1.26; 4.0395 4.01; 4.0217 3.59; 4.0039 1.9; 3.3138 479.829987; 3.2902 10.54; 3.2448 1.3; 3.2154 0.73; 3.1145 0.62; 3.1053 0.44; 3.0944 0.76; 3.0847 1.22; 3.0765 0.74; 3.0641 0.51; 3.0554 0.66; 3.047 0.39; 3.038 0.4; 2.8505 0.31; 2.8119 0.58; 2.78 1.05; 2.754 0.61; 2.6746 0.32; 2.6701 0.41; 2.6654 0.32; 2.5401 1; 2.5098 25.139999; 2.5055 46.779999; 2.501 60.709999; 2.4967 41.98; 2.4925 20.18; 2.3321 0.32; 2.3276 0.42; 2.0697 0.31; 2.0496 0.36; 2.0305 0.73; 1.9871 15; 1.9499 0.99; 1.8918 0.35; 1.8667 0.71; 1.8595 0.77; 1.8284 0.9; 1.7989 0.91; 1.7899 0.85; 1.7688 0.66; 1.7591 0.62; 1.3977 0.38; 1.193 3.73; 1.1752 7.31; 1.1574 3.64; 0.0078 0.33; −0.0001 7.08 |
| I-87 | [DMSO-$d_6$] 9.2143 1.96; 9.1984 4.04; 9.1827 1.94; 7.9639 3.2; 7.9448 8.54; 7.9257 6.67; 7.8981 7.31; 7.8958 7.34; 7.8791 4.05; 7.8767 3.24; 7.5483 5.56; 7.5461 5.28; 7.5294 5.29; 7.527 |

-continued

| Ex. | NMR data |
|---|---|
| | 4.67; 7.4201 1.6; 7.3984 3.44; 7.3816 3.46; 7.377 2.12; 7.3598 1.73; 7.3097 3.44; 7.2527 2.06; 7.2462 2.16; 7.2287 2.68; 7.2262 2.78; 7.2225 2.88; 7.2029 2.09; 7.1965 2.19; 7.1763 7.96; 7.1663 3.85; 7.1542 0.42; 7.0785 1.78; 7.072 1.74; 7.0571 3.3; 7.0505 3.29; 7.0431 4.23; 7.0302 9.91; 7.021 0.69; 6.9109 7.46; 6.8945 4.37; 5.755 16; 5.4472 1.68; 5.4046 6.44; 5.3701 6.37; 5.3274 1.71; 5.3134 0.87; 4.5477 7.66; 4.532 7.63; 4.4768 1.77; 4.4446 183; 4.0562 0.51; 4.0383 2.45; 4.0207 1.44; 4.0028 2.06; 3.4316 1.38; 3.3809 1.73; 3.3312 1209.810059; 3.3087 3.99; 3.2648 1.64; 3.2328 2.6; 3.205 1.36; 3.1075 0.66; 3.0987 1.17; 3.09 0.82; 3.078 1.46; 3.0692 2.45; 3.0604 1.45; 3.0486 0.95; 3.0376 2.84; 2.8497 1.58; 2.799 1.18; 2.7726 2.2; 2.767 2.17; 2.741 1.31; 2.6759 0.85; 2.6714 1.13; 2.6668 0.81; 2.6626 0.37; 2.5414 4.41; 2.5245 4.18; 2.5196 6.03; 2.5112 60.82; 2.5068 124.940002; 2.5024 168.600006; 2.4979 120.279999; 2.4935 55.740002; 2.3336 0.86; 2.3292 1.16; 2.3249 0.82; 2.3202 0.41; 2.0735 0.48; 2.0105 1.4; 1.9888 5.03; 1.9738 2.49; 1.9301 2.03; 1.8893 0.67; 1.88 0.77; 1.8579 1.49; 1.8488 1.59; 1.826 1.59; 1.8184 1.87; 1.7882 1.88; 1.7783 1.69; 1.7569 1.42; 1.7472 1.37; 1.7256 0.52; 1.7153 0.42; 1.2357 0.42; 1.1926 1.01; 1.1748 1.96; 1.1571 0.99; −0.0001 6.78 |
| I-88 | [DMSO-$d_6$] 16.7486 0.41; 14.2673 0.39; 13.1161 0.41; 12.3798 0.41; 9.2083 2.89; 9.1974 1.68; 9.0798 0.41; 7.9992 0.43; 7.9762 1.62; 7.957 3.65; 7.938 2.94; 7.9119 4.78; 7.8923 2.29; 7.6743 0.39; 7.6408 0.46; 7.5648 3.59; 7.5451 3.4; 7.5213 0.52; 7.4952 0.63; 7.4736 2.84; 7.4578 3.27; 7.3887 0.41; 7.3602 0.62; 7.3104 15; 7.1671 3.83; 7.1168 0.43; 7.0337 2.22; 7.0173 3.81; 6.9027 5.87; 6.8815 1.95; 5.7468 2.68; 5.4377 1.27; 5.3958 4.41; 5.3675 4.46; 5.3262 1.14; 5.3049 0.42; 4.6157 6.55; 4.6013 6.14; 4.4771 2.05; 4.4475 2.14; 4.0398 3.12; 4.0207 2.54; 4.0084 2.34; 3.7329 0.46; 3.4608 0.39; 3.4394 0.46; 3.3098 371.700012; 3.3049 420.179993; 3.3006 555.710022; 3.2577 3.58; 3.217 1.89; 3.1816 0.55; 3.1661 0.62; 3.1547 0.52; 3.1473 0.57; 3.1155 1.5; 3.0873 2.27; 3.0668 1.42; 2.9673 0.39; 2.9155 0.43; 2.8484 0.6; 2.8194 1.4; 2.7858 2.36; 2.7534 1.36; 2.7425 0.48; 2.6736 1.69; 2.6294 0.42; 2.609 0.43; 2.5588 1.09; 2.5389 4.03; 2.5041 267.200012; 2.436 0.98; 2.403 0.72; 2.3803 0.53; 2.3606 0.53; 2.3586 0.55; 2.3318 1.76; 2.3043 0.45; 2.069 1.1; 2.0356 1.82; 1.9904 6.48; 1.9866 7.58; 1.9548 2.5; 1.9071 0.99; 1.868 1.89; 1.8371 1.89; 1.8195 1.4; 1.7941 2; 1.7889 1.66; 1.7644 1.49; 1.7196 0.63; 1.6829 0.4; 1.292 0.54; 1.2361 0.64; 1.1927 1.58; 1.1752 2.89; 1.1572 1.64; 1.1353 0.39; 1.0391 0.4; 0.8991 0.52; 0.873 0.4; 0.0089 20.620001; 0.0036 23.48; −0.0001 31.66; −0.1512 0.41; −3.1868 0.44 |
| I-89 | $^1$H NMR (DMSO-$d_6$, 400 MHz): d$_{ppm}$: 8.89 (t, 1H), 7.93 (t, 1H), 7.87 (t, 1H), 7.51 (dd, 1H), 7.45-7.32 (m, 1H), 7.17 (t, 1H), 7.08 (t, 2H), 7.02 (t, 1H), 6.90 (s, 1H), 5.38 (q, 2H), 4.62 (d, 2H), 4.44 (d, 1H), 4.00 (d, 1H), 3.30-3.16 (m, 1H), 3.10-3.00 (m, 1H), 2.77 (t, 1H), 2.05-1.89 (m, 2H), 1.87-1.62 (m, 2H) |
| I-90 | [DMSO-$d_6$] 16.369101 0.34; 9.3029 2.5; 9.2879 4.68; 9.2736 2.42; 8.5306 6.08; 8.52 5.96; 7.9723 4.13; 7.9532 11.68; 7.9343 10.12; 7.9147 12.02; 7.8981 5.1; 7.7776 3.59; 7.7735 3.7; 7.7584 7.12; 7.7542 7.23; 7.7394 4.11; 7.7348 4.16; 7.5528 8.37; 7.5364 7.62; 7.3341 8.43; 7.3144 7.75; 7.3016 5.52; 7.2825 4.64; 7.2698 4.93; 7.2648 4.73; 7.2522 4.09; 7.1681 11.44; 7.148 5.51; 7.0346 5.68; 7.0119 12.06; 6.8955 11.98; 6.8761 5.9; 5.739 4.25; 5.4395 1.78; 5.3961 9.72; 5.3668 9.53; 5.3237 1.68; 4.6472 13.75; 4.6325 15; 4.4723 2.83; 4.4386 2.84; 4.4057 0.35; 4.0403 3.12; 4.0214 1.91; 4.0051 2.89; 3.4358 0.32; 3.4235 0.32; 3.3799 0.38; 3.3752 0.61; 3.2827 706.349976; 3.2609 39.23; 3.2273 3.23; 3.1678 0.54; 3.1211 2.16; 3.1008 2.61; 3.0915 4.2; 3.0839 2.59; 3.071 1.65; 3.0628 2.35; 2.8275 1.93; 2.7992 3.48; 2.7696 1.86; 2.6679 1.43; 2.6636 1.27; 2.6124 0.31; 2.5945 0.42; 2.5693 0.56; 2.5377 2.58; 2.503 178.309998; 2.4988 226.889999; 2.4947 162.949997; 2.4262 0.5; 2.4211 0.42; 2.3914 0.38; 2.365 0.32; 2.3252 1.53; 2.0653 1.44; 2.0351 2.36; 1.9997 4.16; 1.9852 5.24; 1.9533 3.21; 1.9076 2.02; 1.9 1.37; 1.8696 2.51; 1.8452 2.31; 1.8392 2.2; 1.8125 1.97; 1.7919 2.5; 1.7823 2.5; 1.7615 2.17; 1.7284 0.85; 1.7199 0.71; 1.2378 0.48; 1.1931 0.49; 1.1752 1.14; 1.1577 0.65; 0.8897 0.47; 0.0193 0.4; −0.0001 23.35 |
| I-91 | [DMSO-$d_6$] 9.2229 2.03; 9.2077 3.69; 9.1925 1.86; 7.9587 2.76; 7.9396 7.96; 7.921 8.15; 7.9121 7.69; 7.9087 8.44; 7.8929 3.08; 7.8895 2.24; 7.5324 5.26; 7.529 5.24; 7.5141 4.94; 7.5107 4.59; 7.3782 5.2; 7.3754 5.16; 7.3656 5.59; 7.3627 5.22; 7.305 3.57; 7.1715 8.06; 7.1618 4.03; 7.038 8.72; 7.026 12.82; 6.9699 6.1; 6.9612 5.21; 6.9573 5.82; 6.9488 4.49; 6.9039 7.91; 6.8898 4.19; 5.7463 12.55; 5.4397 1.53; 5.422 0.42; 5.3974 6.41; 5.3611 6.26; 5.319 1.51; 4.715 0.34; 4.6818 9.45; 4.666 9.27; 4.4715 1.83; 4.4381 1.93; 4.0633 0.41; 4.0571 1.22; 4.0393 4.07; 4.0216 4.81; 4.004 2.32; 3.9954 1.98; 3.5562 0.36; 3.53 0.34; 3.5166 0.33; 3.4914 0.41; 3.4187 0.73; 3.4034 0.88; 3.3116 1540.969971; 3.288 36.91; 3.2616 2.62; 3.2275 2.75; 3.1964 1.54; 3.0854 1.34; 3.0763 1.01; 3.0638 1.73; 3.0556 2.81; 3.049 1.55; 3.0375 1.22; 3.0263 1.49; 2.7924 1.23; 2.762 2.28; 2.7353 1.37; 2.7325 1.37; 2.6697 1.53; 2.6654 1.14; 2.5395 3.47; 2.5092 93.239998; 2.505 172.770004; 2.5006 222.860001; 2.4964 154.990005; 2.3791 0.32; 2.3271 1.51; 2.3227 1.07; 2.0693 0.95; 2.0497 0.69; 1.9869 15; 1.9593 2.96; 1.9162 2.23; 1.8949 0.48; 1.8645 0.81; 1.8354 2.01; 1.8038 1.96; 1.7773 1.94; 1.7679 1.87; 1.7457 1.5; 1.7356 1.44; 1.714 0.62; 1.3987 1; 1.2921 0.39; 1.2359 0.57; 1.1929 3.6; 1.1749 7.14; 1.1572 3.56; 0.891 0.3; 0.0077 1.13; −0.0001 25.040001; −0.0159 0.36 |
| I-92 | [DMSO-$d_6$] 9.1147 0.65; 9.099 1.24; 9.0839 0.57; 7.9573 1.02; 7.9383 2.75; 7.9196 2.74; 7.9084 2.55; 7.905 2.76; 7.8892 1.13; 7.8858 0.78; 7.5316 1.77; 7.5282 1.72; 7.513 1.66; 7.5097 1.5; 7.3036 1.18; 7.2604 2.7; 7.2478 2.82; 7.1701 2.65; 7.1613 1.31; 7.0367 1.38; 7.0254 2.99; 6.9034 2.55; 6.8895 1.47; 6.8254 2.79; 6.8127 2.6; 5.7473 5.03; 5.4396 0.52; 5.3966 2.05; 5.3606 1.99; 5.3179 0.48; 4.6125 3.21; 4.5968 3.14; 4.4702 0.58; 4.436 0.61; 4.0569 0.42; 4.0391 1.45; 4.0214 1.53; 4.0035 0.85; 3.3012 339.890015; 3.2681 0.89; 3.2297 0.82; 3.2007 0.45; 3.0876 0.41; 3.0671 0.52; 3.0583 0.87; 3.0488 0.5; 3.037 0.45; 3.0284 0.48; 2.7968 0.39; 2.7648 0.72; 2.738 0.42; 2.6738 0.36; 2.6691 0.51; 2.6645 0.37; 2.5389 2.94; 2.5219 1.9; 2.5087 30.209999; 2.5043 56.48; 2.4998 73.379997; 2.4955 50.130001; 2.4911 23.84; 2.3306 0.39; 2.3267 0.51; 2.3219 0.41; 2.2471 15; 1.9867 5.22; 1.9621 0.96; 1.9188 0.71; 1.9077 0.61; 1.8396 0.5; 1.8326 0.53; 1.8105 0.5; 1.7997 0.54; 1.7826 0.4; 1.7622 0.58; 1.7538 0.58; 1.7323 0.48; 1.7214 0.44; 1.398 0.35; 1.1926 1.36; 1.1748 2.69; 1.157 1.35; 0.008 0.54; −0.0001 15.01; −0.0083 0.65 |
| I-93 | [DMSO-$d_6$] 10.242 4.36; 8.0238 1.86; 8.0047 5.24; 7.9957 0.33; 7.9858 4.7; 7.9686 4.18; 7.9656 4.95; 7.9495 2.22; 7.9464 1.87; 7.6265 2.82; 7.6235 3.06; 7.6076 2.76; 7.6046 2.72; 7.4679 0.46; 7.452 0.99; 7.4465 0.92; 7.4361 0.76; 7.4308 1.99; 7.4144 1; 7.4097 1.38; 7.3939 0.6; 7.3068 |

| Ex. | NMR data |
|---|---|
| | 2.23; 7.2563 0.41; 7.2518 0.69; 7.2438 4.11; 7.2237 6.14; 7.2033 2.89; 7.1949 0.65; 7.1735 5.24; 7.1592 2.56; 7.0402 2.52; 7.0232 6.25; 6.9052 4.64; 6.8875 2.92; 5.7548 16; 5.4512 0.87; 5.4085 3.85; 5.3795 3.82; 5.3368 0.9; 4.4906 0.94; 4.4577 1.02; 4.0559 1.39; 4.0381 1.83; 4.0203 2.48; 4.0026 0.64; 3.4326 1.57; 3.3831 2.5; 3.3616 0.89; 3.3326 1026.800049; 3.284 2.14; 3.2784 0.67; 3.2498 1.38; 3.2205 0.79; 3.1589 0.39; 3.1501 0.66; 3.1413 0.49; 3.1296 0.8; 3.1206 1.34; 3.1123 0.81; 3.1004 0.53; 3.0915 0.74; 3.0369 0.49; 2.8493 0.36; 2.8143 0.67; 2.7877 1.2; 2.7823 1.21; 2.7569 0.69; 2.6757 0.57; 2.6709 0.77; 2.6664 0.56; 2.5525 0.39; 2.5479 0.35; 2.5413 3.21; 2.5246 2; 2.5199 2.79; 2.5112 39.689999; 2.5066 89.610001; 2.502 127.580002; 2.4973 92.459999; 2.4927 42.41; 2.3335 0.57; 2.3288 0.76; 2.3242 0.6; 2.0734 1.35; 2.0571 0.77; 2.0513 0.88; 2.0268 1.2; 1.9886 7.49; 1.9701 1.16; 1.9414 0.48; 1.9199 0.84; 1.911 0.9; 1.8902 1.02; 1.8815 1.07; 1.8613 1.02; 1.8515 1.07; 1.8303 0.77; 1.8207 0.74; 1.1924 2.05; 1.1746 4.21; 1.1568 2.03; −0.0001 7.15 |
| I-94 | [DMSO-d$_6$] 10.8799 5.86; 8.0813 0.95; 8.062 7.78; 8.0578 7.8; 8.0489 15; 8.0388 1.54; 8.0234 7.97; 8.0041 12.57; 7.9832 4.22; 7.8561 4.34; 7.8356 5.06; 7.7914 0.3; 7.6862 0.83; 7.6762 3.61; 7.6671 3.68; 7.6633 3.44; 7.654 3.8; 7.648 2.25; 7.6343 3.78; 7.6309 3.79; 7.6143 3.37; 7.6098 3.81; 7.6045 7.67; 7.5845 9.01; 7.5653 4.63; 7.2972 3.14; 7.1637 7.01; 7.1366 3.37; 7.0302 3.52; 7.0005 7.69; 6.898 6.72; 6.8646 3.62; 5.7471 0.33; 5.4671 1.09; 5.425 5.76; 5.3994 5.72; 5.3572 1.02; 4.5144 1.51; 4.4828 1.55; 4.0929 1.54; 4.0584 1.61; 4.0394 0.68; 4.0218 0.55; 3.4443 0.32; 3.4166 0.35; 3.4112 0.39; 3.3988 0.43; 3.3654 1.08; 3.3064 899.190002; 3.2645 1.59; 3.2535 1.27; 3.2408 1.38; 3.2337 1.17; 3.2115 2.34; 3.2027 1.52; 3.183 1.26; 3.0725 1.37; 3.0382 0.3; 2.8795 1.09; 2.8503 2.07; 2.8213 1.1; 2.674 0.73; 2.6694 1.07; 2.6651 0.75; 2.66 0.41; 2.5646 0.44; 2.5394 4.15; 2.5224 3.97; 2.5092 63.27; 2.5049 118.889999; 2.5004 155.089996; 2.4961 107.169998; 2.4917 51.209999; 2.4065 0.31; 2.3317 0.78; 2.3273 1.09; 2.3222 0.79; 2.1373 1.24; 2.1041 2.05; 2.0695 1.69; 2.0499 2.15; 2.0124 0.69; 1.987 3.08; 1.9608 1.18; 1.9505 1.12; 1.9279 0.56; 1.9085 1.69; 1.8781 1.29; 1.8713 1.25; 1.8485 1.18; 1.8374 1.06; 1.8173 0.46; 1.806 0.41; 1.3979 0.45; 1.2929 0.41; 1.2351 0.48; 1.1933 0.58; 1.1751 0.97; 1.1575 0.54; 0.8895 0.44; 0.0079 1.04; −0.0001 25.360001; −0.0081 1.05 |
| I-95 | [DMSO-d$_6$] 10.5642 7.41; 8.5177 5.95; 8.06 1.46; 8.0523 16; 8.0473 7.98; 8.0426 7.25; 8.0299 1.33; 7.9662 2; 7.9515 8.76; 7.9447 6.76; 7.9416 6.07; 7.93 1.53; 7.9268 1.65; 7.9102 4.22; 7.9044 4.13; 7.8974 4.3; 7.8912 4.49; 7.6512 0.52; 7.6435 3.76; 7.6385 3.31; 7.6338 3.59; 7.6288 3.59; 7.6209 0.48; 7.5358 2.05; 7.5338 2.05; 7.5244 3.21; 7.5225 4.12; 7.5203 2.26; 7.5107 2.79; 7.5089 2.74; 7.4735 3.08; 7.4718 2.97; 7.4621 2.51; 7.46 4.39; 7.4582 3.12; 7.4487 2.04; 7.4468 1.99; 7.3117 2.46; 7.2227 5.77; 7.1431 2.77; 7.1339 2.83; 7.0525 6.84; 6.9619 3.15; 6.9357 6.5; 5.7624 2.13; 5.492 2.29; 5.4633 4.99; 5.4143 4.98; 5.3857 2.29; 4.5148 1.52; 4.4931 1.54; 4.0803 1.44; 4.0578 1.54; 4.046 0.44; 4.0341 0.73; 4.0222 0.7; 3.5053 0.34; 3.4883 0.33; 3.4862 0.34; 3.476 0.42; 3.4699 0.43; 3.4615 0.45; 3.4581 0.51; 3.4541 0.55; 3.4479 0.69; 3.4414 0.85; 3.4341 1.17; 3.431 1.09; 3.423 1.29; 3.4049 2.2; 3.4009 2.56; 3.3965 3.46; 3.3679 3527.939941; 3.3445 18.950001; 3.3366 1.14; 3.3061 0.68; 3.3003 0.96; 3.283 1.73; 3.2804 1.75; 3.2623 1.02; 3.2577 0.77; 3.2065 0.47; 3.2006 0.86; 3.1944 0.57; 3.1865 1.14; 3.1806 1.96; 3.1748 1.09; 3.167 0.65; 3.1608 0.94; 3.1551 0.47; 2.84 0.93; 2.8363 1.01; 2.8188 1.94; 2.8149 1.92; 2.7975 1.04; 2.7933 0.9; 2.6225 0.82; 2.6196 1.69; 2.6166 2.28; 2.6136 1.63; 2.6106 0.76; 2.5256 4.75; 2.5225 6.28; 2.5193 7.33; 2.5105 133.360001; 2.5076 281.079987; 2.5045 380.359985; 2.5015 271.429993; 2.4985 121.480003; 2.3942 0.68; 2.3914 1.57; 2.3884 2.15; 2.3854 1.51; 2.0775 3.09; 2.0568 1.73; 2.0343 1.33; 2.0127 1.6; 1.9989 0.74; 1.9906 3.4; 1.9846 1.31; 1.978 1.37; 1.9636 1.17; 1.9573 1.13; 1.943 0.4; 1.8432 0.5; 1.8359 0.58; 1.822 1.31; 1.8151 1.37; 1.801 1.29; 1.7943 1.23; 1.7801 0.48; 1.7732 0.39; 1.2324 0.57; 1.1864 0.85; 1.1745 1.71; 1.1626 0.84; 0.889 1.43; 0.0054 0.64; 0 18.02; −0.0056 0.55 |
| I-96 | [DMSO-d$_6$] 12.5396 9.47; 8.9656 6.6; 8.9615 7.39; 8.9552 7.32; 8.951 7.29; 8.8455 6.43; 8.8421 7.25; 8.8267 7.13; 8.8233 7.3; 8.4803 5.95; 8.4762 6.49; 8.4594 6.61; 8.4553 6.39; 8.116 1.1; 8.1109 3.16; 8.0968 14.72; 8.0942 16; 8.0919 13.85; 8.0774 11.16; 8.0582 3.62; 7.7576 4.38; 7.7542 5.13; 7.7368 8.54; 7.7334 8.22; 7.7183 0.46; 7.7024 6.29; 7.6972 6.59; 7.6932 8.56; 7.6855 6.21; 7.6803 6.21; 7.674 8.92; 7.6574 7.03; 7.6538 5.29; 7.647 6.68; 7.6367 6.56; 7.6262 6.65; 7.3362 4.42; 7.2028 10.29; 7.163 4.95; 7.0695 4.95; 7.0271 12.15; 6.9337 9.2; 6.8912 5.61; 5.7559 1.65; 5.5286 2.12; 5.4855 7.45; 5.4473 7.33; 5.4045 2.11; 4.5325 2.01; 4.4991 2.15; 4.1307 1.9; 4.0975 2.06; 3.4355 2.53; 3.4051 1.34; 3.3926 0.61; 3.3847 3.14; 3.3758 3.58; 3.3733 3.58; 3.3698 3.51; 3.3353 2097.399902; 3.2844 2.91; 3.2736 2.02; 3.2646 1.52; 3.2553 2.08; 3.2458 3.2; 3.2362 2.17; 3.2276 1.33; 3.218 1.73; 3.2084 0.95; 3.0382 0.52; 2.982 1.4; 2.9572 2.36; 2.9514 2.45; 2.9261 1.47; 2.8502 0.35; 2.6816 0.51; 2.6772 1.12; 2.6725 1.55; 2.6677 1.12; 2.6631 0.56; 2.5426 6.66; 2.5259 4.48; 2.5212 6.04; 2.5126 80.190002; 2.508 179.720001; 2.5034 254.350006; 2.4988 184.600006; 2.4942 84.769997; 2.4575 0.43; 2.4514 0.48; 2.4476 0.47; 2.3395 0.53; 2.3349 1.14; 2.3303 1.62; 2.3257 1.2; 2.3208 0.55; 2.1694 1.53; 2.1403 2.26; 2.1 1.5; 2.0748 6.31; 2.0524 1.64; 2.0414 0.98; 2.0202 1.72; 2.0117 2.01; 1.9929 2.12; 1.9785 2.25; 1.9644 2.03; 1.9433 1.55; 1.9357 1.42; 1.9135 0.64; 1.9028 0.5; 1.2924 0.44; 1.2312 0.51; 0.008 0.35; −0.0001 12.34; −0.0084 0.39 |
| I-97 | $^1$H NMR (DMSO-d$_6$, 400 MHz): d$_{ppm}$: 0.91 (d, 3H), 1.11-2.05 (m, 13H), 2.75-2.85 (m, 1H), 3.04-3.12 (m, 1H), 3.25 (m, 1H), 3.98-4.02 (m, 1H), 4.40-4.43 (m, 1H), 4.56-4.62 (m, 1H), 5.34 (d, 1H), 5.43 (d, 1H), 6.90 (s, 1H), 7.03 (t, 1H), 7.18 (t, 1H), 7.56 (d, 1H), 7.87-7.97 (m, 2H) |
| I-98 | $^1$H NMR (DMSO-d$_6$, 400 MHz): d$_{ppm}$: 1.54-2.15 (m, 10H), 2.72-2.83 (m, 1H), 3.03-3.12 (m, 1H), 3.24 (m, 1H), 3.97-4.02 (m, 1H), 4.40-4.43 (m, 1H), 5.34 (d, 1H), 5.41-5.46 (m, 2H), 5.78-5.82 (m, 1H), 6.00-6.04 (m, 1H), 6.90 (s, 1H), 7.02 (t, 1H), 7.18 (t, 1H), 7.56 (dd, 1H), 7.87-7.95 (m, 2H) |
| I-99 | $^1$H NMR (DMSO-d$_6$, 400 MHz): d$_{ppm}$: 1.27-1.98 (m, 14H), 2.76-2.84 (m, 1H), 3.02-3.11 (m, 1H), 3.25 (m, 1H), 3.98-4.03 (m, 1H), 4.38-4.43 (m, 1H), 4.91-4.98 (m, 1H), 5.34 (d, 1H), 5.44 (d, 1H), 6.90 (s, 1H), 7.03 (t, 1H), 7.18 (t, 1H), 7.56 (dd, 1H), 7.87-7.95 (m, 2H) |
| I-100 | $^1$H NMR (DMSO-d$_6$, 400 MHz): d$_{ppm}$: 1.54-1.64 (m, 1H), 1.74-2.12 (m, 7H), 2.72-2.92 (m, 3H), 3.04-3.10 (m, 1H), 3.23 (m, 1H), 3.97-4.00 (m, 1H), 4.39-4.42 (m, 1H), 5.33 (d, 1H), 5.42 (d, 1H), 6.17 (t, 1H), 6.90 (s, 1H), 7.02 (t, 1H), 7.04-7.33 (m, 5H), 7.56 (dd, 1H), 7.85-7.93 (m, 2H) |

-continued

| Ex. | NMR data |
|---|---|
| I-101 | [DMSO-d6] 7.9631 3.09; 7.9439 8.57; 7.9248 6.95; 7.9014 7.49; 7.8993 8.19; 7.8825 3.94; 7.8802 3.48; 7.5826 5.82; 7.5806 5.89; 7.5636 5.49; 7.5615 5.19; 7.3158 3.67; 7.1823 8.23; 7.1652 4.12; 7.0489 4.08; 7.0291 8.98; 6.9051 8.27; 6.8933 4.77; 5.8713 0.91; 5.8547 1.89; 5.8458 1.09; 5.8382 1.06; 5.8289 2.93; 5.812 3.01; 5.8029 1.23; 5.7952 1.18; 5.7863 2.25; 5.7697 1.12; 5.7465 9.5; 5.4563 2.44; 5.4144 6.3; 5.3671 6.44; 5.3247 1.85; 5.0569 3.65; 5.0525 3.91; 5.0486 1.85; 5.018 1.53; 5.014 3.33; 5.0096 3.55; 5.0057 1.68; 4.9807 3.69; 4.9783 3.55; 4.976 3.36; 4.9552 3.48; 4.9529 3.35; 4.9506 3.15; 4.4383 1.93; 4.406 2.01; 4.3278 7.05; 4.3113 15; 4.2947 7.34; 4.0213 1.88; 3.9864 1.97; 3.921 0.43; 3.3142 500.690002; 3.2907 19.27; 3.2473 2.8; 3.2177 1.56; 3.1248 0.8; 3.116 1.41; 3.1071 1.03; 3.0957 1.7; 3.0866 2.81; 3.078 1.68; 3.0664 1.1; 3.0574 1.51; 3.0485 0.84; 3.0383 0.44; 2.9421 0.55; 2.8509 0.35; 2.8221 1.32; 2.7945 2.39; 2.7899 2.4; 2.7635 1.36; 2.6754 0.38; 2.6707 0.51; 2.6665 0.38; 2.5407 1.13; 2.506 56.150002; 2.5017 71.639999; 2.4975 50.34; 2.3951 0.31; 2.3327 0.4; 2.3282 0.52; 2.3243 0.38; 2.1278 2.42; 2.1099 6.28; 2.0923 6.54; 2.0744 2.72; 2.0709 2.1; 1.9872 0.78; 1.9664 1.58; 1.9303 3.48; 1.9069 1.35; 1.8921 2.17; 1.8529 0.77; 1.8433 0.86; 1.822 1.67; 1.8133 1.73; 1.7907 1.54; 1.7817 1.48; 1.7655 1.88; 1.7488 5.12; 1.7313 6.03; 1.7112 5.37; 1.6947 2.19; 1.6697 0.75; 1.6601 0.86; 1.639 1.66; 1.6293 1.74; 1.6079 1.58; 1.5982 1.53; 1.5775 0.68; 1.5672 0.57; 1.5325 2.06; 1.5132 5.36; 1.4948 6.92; 1.4759 4.22; 1.4576 1.35; 1.2755 0.31; 1.2362 0.45; 0.8571 0.44; −0.0001 2.46 |
| I-102 | |
| I-103 | [DMSO-d6] 7.9657 1.97; 7.9465 5.56; 7.9276 5.13; 7.9138 5.28; 7.9109 5.75; 7.8947 2.43; 7.8918 1.87; 7.6849 1.25; 7.6677 1.66; 7.6634 2.68; 7.6468 2.7; 7.6423 1.67; 7.6253 1.36; 7.6 3.85; 7.5972 3.79; 7.5813 3.63; 7.5784 3.32; 7.3485 1.44; 7.3421 1.52; 7.3223 2.14; 7.3183 2.37; 7.3161 2.42; 7.3117 2.83; 7.2989 1.47; 7.2926 1.46; 7.1781 5.81; 7.1623 3.28; 7.1497 2.45; 7.1451 2.21; 7.1283 1.21; 7.1241 1.09; 7.0448 2.8; 7.026 5.97; 6.9027 5.57; 6.8901 3.09; 5.7469 3.14; 5.4556 1.71; 5.408 15; 5.3598 4.08; 5.3171 1.32; 4.4309 1.3; 4.3983 1.33; 4.0394 0.65; 4.0214 1.37; 4.0128 1.24; 3.9792 1.32; 3.5682 0.95; 3.3095 558.380005; 3.2858 25.43; 3.2372 1.89; 3.2072 1.02; 3.1201 0.53; 3.1116 0.93; 3.1028 0.69; 3.0909 1.15; 3.0821 1.86; 3.0734 1.12; 3.0619 0.72; 3.0531 1.01; 2.9416 0.4; 2.81 0.9; 2.7782 1.61; 2.7507 0.93; 2.6747 0.53; 2.67 0.7; 2.6656 0.53; 2.54 1.53; 2.5053 76.669998; 2.501 97.25; 2.4968 67.599998; 2.332 0.51; 2.3277 0.67; 2.3233 0.52; 2.0698 0.65; 1.9871 2.33; 1.954 1.07; 1.9183 2.42; 1.8819 1.44; 1.8427 0.5; 1.8345 0.58; 1.811 1.09; 1.8032 1.15; 1.7803 1; 1.7723 0.94; 1.7509 0.39; 1.6541 0.44; 1.6421 0.55; 1.621 1.12; 1.6123 1.14; 1.5913 1.06; 1.5816 1.02; 1.5613 0.39; 1.55 0.32; 1.3976 0.3; 1.236 0.3; 1.1928 0.63; 1.1752 1.17; 1.1574 0.61; 1.1118 1.17; −0.0001 4.89 |
| I-104 | [DMSO-d6] 7.9631 0.38; 7.9556 2.05; 7.9447 0.61; 7.9363 5.52; 7.917 4.07; 7.881 4.66; 7.8789 4.67; 7.8619 2.78; 7.8596 2.37; 7.614 0.34; 7.5956 3.85; 7.5763 3.48; 7.3278 0.44; 7.3113 5.03; 7.2914 4.72; 7.2891 4.59; 7.2687 3.1; 7.2524 0.32; 7.177 5.09; 7.1647 2.53; 7.0436 2.53; 7.0286 5.47; 6.9024 5.24; 6.8928 3.03; 5.747 2.76; 5.5478 0.48; 5.4524 1.33; 5.4088 15; 5.3573 3.68; 5.3147 1.17; 4.4253 1.19; 4.3927 1.24; 4.0575 0.5; 4.0396 1.45; 4.0218 1.86; 4.0042 1.52; 3.9746 1.22; 3.3945 0.35; 3.31 561.539978; 3.2864 23.34; 3.2691 1.59; 3.2317 1.66; 3.2024 0.92; 3.1016 0.87; 3.0924 0.65; 3.0808 1.04; 3.0722 1.66; 3.063 1.01; 3.0515 0.66; 3.0421 0.91; 2.9423 0.32; 2.8046 0.84; 2.7783 1.46; 2.7463 0.83; 2.6749 0.49; 2.6701 0.64; 2.6654 0.48; 2.5404 1.48; 2.5056 72.480003; 2.5012 89.940002; 2.497 60.939999; 2.3325 0.48; 2.328 0.62; 2.3234 0.46; 2.0701 0.63; 1.9873 6.07; 1.9436 1.04; 1.9066 2.3; 1.8717 1.28; 1.8296 0.48; 1.8212 0.54; 1.7991 1.01; 1.7896 1.02; 1.7679 0.91; 1.7597 0.87; 1.738 0.35; 1.6404 0.43; 1.63 0.51; 1.609 0.99; 1.5987 1.04; 1.5775 0.95; 1.5677 0.88; 1.5474 0.36; 1.2367 0.31; 1.1932 1.63; 1.1754 3.23; 1.1576 1.59; 1.112 0.52; −0.0001 4.46 |
| I-105 | $^1$H NMR (DMSO-d6, 400 MHz): d$_{ppm}$: 1.57-1.67 (m, 1H), 1.76-1.85 (m, 1H), 1.89-1.98 (m, 2H), 2.76-2.82 (m, 1H), 3.06-3.12 (m, 1H), 3.24 (m, 1H), 4.02-4.03 (m, 1H), 4.40-4.43 (m, 1H), 5.34 (d, 1H), 5.43 (d, 1H), 5.46 (s, 2H), 6.89 (s, 1H), 7.02 (t, 1H), 7.17 (t, 1H), 7.39-7.44 (m, 2H), 7.51-7.55 (m, 1H), 7.59-7.64 (m, 2H), 7.92-7.98 (m, 2H) |
| I-106 | $^1$H NMR (DMSO-d6, 400 MHz): d$_{ppm}$: 1.55-1.65 (m, 1H), 1.74-1.84 (m, 1H), 1.88-1.98 (m, 2H), 2.75-2.81 (m, 1H), 3.04-3.11 (m, 1H), 3.23 (m, 1H), 3.98-4.03 (m, 1H), 4.40-4.43 (m, 1H), 5.34 (d, 1H), 5.43 (d, 1H), 5.44 (s, 2H), 6.90 (s, 1H), 7.02 (t, 1H), 7.17 (t, 1H), 7.24-7.31 (m, 2H), 7.42-7.47 (m, 1H), 7.56-7.60 (m, 2H), 7.90-7.97 (m, 2H) |
| I-107 | $^1$H NMR (DMSO-d6, 400 MHz): d$_{ppm}$: 1.53-1.64 (m, 1H), 1.72-1.82 (m, H), 1.87-1.94 (m, 2H), 2.74-2.80 (m, 1H), 3.04-3.10 (m, 1H), 3.18-3.26 (m, 1H), 3.97-4.00 (m, 1H), 4.39-4.42 (m, 1H), 5.33 (d, 1H), 5.42 (d, 1H), 5.45 (s, 2H), 6.90 (s, 1H), 7.03 (t, 1H), 7.06-7.31 (m + t, 3H), 7.50-7.59 (m, 2H), 7.86-7.95 (m, 2H) |
| I-108 | (m, 2H), 2.39 (s, 3H), 2.75-2.82 (m, 1H), 3.05-3.12 (m, 1H), 3.24 (m, 1H), 3.98-4.01 (m, 1H), 4.40-4.43 (m, 1H), 5.29 (d, 1H), 5.37 (d, 1H), 5.45 (s, 2H), 6.90 (s, 1H), 7.02 (t, 1H), 7.17 (t, 1H), 7.27-7.30 (m, 1H), 7.58 (dd, 1H), 7.65 (d, 1H), 7.90-7.97 (m, 2H), 8.36 (d, 1H) |
| I-109 | [DMSO-d6] 7.9667 1.21; 7.9476 3.45; 7.9287 3.17; 7.9152 3.32; 7.9123 3.61; 7.8961 1.52; 7.8933 1.17; 7.5939 2.36; 7.5911 2.36; 7.5752 2.23; 7.5723 2.07; 7.3144 1.55; 7.181 3.51; 7.1657 1.78; 7.1417 3.21; 7.0841 3.75; 7.0476 1.74; 7.0297 3.82; 6.9032 3.55; 6.8939 2.17; 5.7471 3.06; 5.4873 11.47; 5.4602 1.01; 5.4179 2.52; 5.361 2.51; 5.3182 0.85; 4.4361 0.83; 4.4039 0.84; 4.0393 0.33; 4.0211 0.84; 4.013 0.78; 3.9806 0.85; 3.3044 253.399994; 3.2807 15.25; 3.2364 1.16; 3.2051 0.64; 3.1184 0.34; 3.11 0.58; 3.1018 0.43; 3.0899 0.71; 3.0807 1.16; 3.0718 0.73; 3.0597 0.47; 3.0508 0.62; 3.0419 0.36; 2.8058 0.57; 2.779 1.02; 2.7477 0.59; 2.6739 0.35; 2.6692 0.47; 2.6648 0.33; 2.5393 1.01; 2.5045 50.09; 2.5002 63.139999; 2.496 43.830002; 2.3316 0.34; 2.327 0.44; 2.3225 0.33; 2.1955 15; 2.1747 0.36; 2.0696 0.37; 1.9868 1.15; 1.9476 0.68; 1.9153 1.57; 1.8791 0.93; 1.8345 0.36; 1.8145 0.69; 1.8053 0.72; 1.7827 0.62; 1.774 0.59; 1.648 0.32; 1.6279 0.68; 1.6176 0.72; 1.596 0.67; 1.587 0.65; 1.1929 0.31; 1.175 0.59; −0.0001 2.68 |
| I-110 | [DMSO-d6] 10.0508 0.5; 8.2376 5.26; 8.22 6.91; 8.11 4.75; 8.0905 8.33; 8.071 4.41; 8.0625 3.92; 8.0578 4.14; 8.0398 4.12; 7.9426 5.38; 7.9301 4.36; 7.9228 7.09; 7.9129 4.07; 7.9078 3.75; 7.8957 0.43; 7.7448 5.9; 7.7264 5.55; 7.6323 5.1; 7.6173 5.65; 7.6133 10.79; 7.6056 5.14; 7.5998 8.68; 7.5933 8.53; 7.5853 3.79; 7.5816 3.92; 7.5682 1.55; 7.5553 0.33; 7.5241 6.55; 7.5223 6.55; 7.5054 4.67; 7.3042 3.25; 7.2908 0.33; 7.1707 7.53; 7.148 3.56; 7.0375 |

| Ex. | NMR data |
| --- | --- |
|  | 3.64; 7.0285 0.67; 7.012 8.05; 6.9141 0.42; 6.8923 7.76; 6.876 3.92; 5.7476 15; 5.4714 1.86; 5.4547 0.93; 5.4294 5.38; 5.3703 5.38; 5.3281 1.93; 4.4716 1.79; 4.4386 1.92; 4.057 2.02; 4.039 2.35; 4.0213 3.31; 4.0037 1.02; 3.9204 0.42; 3.3931 0.37; 3.3808 0.45; 3.3009 489.959991; 3.2779 32.869999; 3.2527 2.25; 3.2275 1.64; 3.2072 1.8; 3.1977 2.65; 3.1892 1.64; 3.1776 1.15; 3.1678 1.54; 3.0364 0.35; 2.8561 1.26; 2.8241 2.24; 2.7979 1.26; 2.6731 1.19; 2.6689 1.54; 2.6642 1.2; 2.5389 3.26; 2.5041 175.110001; 2.4998 221.259995; 2.4956 153.389999; 2.4569 1.39; 2.3948 0.5; 2.3878 0.39; 2.3308 1.19; 2.3266 1.53; 2.322 1.15; 2.0695 1.89; 2.0499 1.66; 2.0206 3.47; 1.9867 8.48; 1.9517 0.76; 1.9413 0.84; 1.9188 1.55; 1.9096 1.71; 1.8863 1.39; 1.8567 0.63; 1.7444 0.73; 1.7334 0.79; 1.7116 1.49; 1.7025 1.53; 1.6816 1.39; 1.6717 1.36; 1.6509 0.55; 1.2356 0.48; 1.1926 1.8; 1.1749 3.48; 1.1571 1.7; 1.1113 0.3; 0.8893 0.32; −0.0001 11.24 |
| I-111 |  |
| I-112 | [DMSO-$d_6$] 7.9914 0.95; 7.9721 2.21; 7.9618 0.31; 7.9528 1.65; 7.7551 1.56; 7.738 1.4; 7.736 1.31; 7.6543 1.35; 7.6525 1.37; 7.6346 1.28; 7.3186 0.77; 7.1849 1.86; 7.1651 0.95; 7.0516 1.04; 7.0291 2.1; 6.9062 1.86; 6.8932 1.17; 5.4913 0.5; 5.4481 1.12; 5.3621 1.12; 5.3198 0.49; 4.4357 0.41; 4.4034 0.42; 4.0335 0.38; 4.0004 0.44; 3.9668 0.76; 3.6827 0.75; 3.5166 0.59; 3.5079 0.56; 3.2997 485.100006; 3.2363 0.7; 3.1266 0.42; 3.1176 0.36; 3.1064 0.49; 3.0985 0.71; 3.0891 0.51; 3.0785 0.38; 3.0686 0.46; 3.0597 0.36; 2.8902 1.78; 2.8501 0.4; 2.8249 0.57; 2.794 0.37; 2.7317 1.39; 2.6735 0.75; 2.6687 1; 2.6642 0.76; 2.6602 0.43; 2.5389 3.1; 2.5219 4.64; 2.5086 56.009998; 2.5042 102.040001; 2.4998 130.990005; 2.4954 89.459999; 2.4911 42.91; 2.3311 0.72; 2.3265 0.92; 2.3219 0.68; 2.3179 0.39; 2.0693 2.34; 2.0493 0.46; 2.0063 0.44; 1.9864 0.59; 1.9549 1.14; 1.9408 1.17; 1.9192 1.76; 1.9077 1.34; 1.8294 0.41; 1.8217 0.43; 1.7985 0.39; 1.7924 0.39; 1.7593 0.32; 1.7222 1.19; 1.71 1.09; 1.698 1.05; 1.6572 0.56; 1.6488 0.54; 1.6182 0.82; 1.5971 0.68; 1.5871 0.71; 1.5113 0.39; 1.4808 0.97; 1.4584 2.04; 1.4364 1.96; 1.3984 15; 1.3161 0.41; 1.2926 0.6; 1.2669 0.53; 1.2364 0.76; 0.0079 0.65; −0.0001 13.57; −0.0084 0.56 |
| I-113 | [DMSO-$d_6$] 8.0478 1.13; 8.0344 0.66; 8.0234 3.1; 8.015 1.53; 8.0041 6.81; 7.9958 1.14; 7.9847 4.32; 7.9658 0.3; 7.9516 0.36; 7.8209 4.88; 7.8189 4.96; 7.8018 4.31; 7.6886 4.78; 7.6709 4.2; 7.669 4.11; 7.5361 1.7; 7.4473 0.91; 7.4304 1.94; 7.4265 1.95; 7.4094 3.59; 7.3922 2.31; 7.3886 2.44; 7.3714 1.32; 7.3627 0.63; 7.3541 0.42; 7.2883 2.59; 7.2116 0.36; 7.1897 0.52; 7.1844 0.74; 7.1547 7.18; 7.1503 4.63; 7.1461 5.51; 7.1258 8.02; 7.1054 5.63; 7.0834 1.76; 7.0706 0.76; 7.0543 0.94; 7.049 1.45; 7.0314 0.93; 7.0212 3.33; 7.0142 6.48; 6.9898 1.12; 6.9593 0.4; 6.9494 0.99; 6.9301 0.53; 6.9186 0.68; 6.9141 0.78; 6.8908 5.37; 6.8783 3.19; 6.8161 0.49; 5.4693 1.52; 5.4268 3.35; 5.3881 0.44; 5.3647 0.32; 5.341 3.4; 5.2984 1.43; 4.4608 0.44; 4.4418 0.44; 4.4116 1.34; 4.3803 1.35; 4.3213 0.34; 4.2807 15; 4.2604 1.04; 4.2216 2.12; 4.1995 0.58; 4.173 0.69; 4.16 0.51; 4.0112 1.44; 3.9766 1.53; 3.9673 3.89; 3.919 0.72; 3.8284 0.33; 3.8228 0.37; 3.7194 0.47; 3.7089 0.42; 3.7003 0.36; 3.6831 3.15; 3.6319 0.41; 3.5316 0.34; 3.5252 0.34; 3.3023 1356.869995; 3.2435 2.42; 3.2105 1.3; 3.1861 0.59; 3.1824 0.58; 3.1469 0.55; 3.1175 1.27; 3.098 1.75; 3.0898 2.34; 3.0814 1.46; 3.0689 1.13; 3.0608 1.38; 2.8904 2.06; 2.8296 0.95; 2.8033 1.64; 2.7987 1.63; 2.7723 1.02; 2.7318 1.74; 2.6738 1.97; 2.6692 2.63; 2.6647 1.97; 2.6599 1.11; 2.5393 8.28; 2.5223 12.71; 2.509 154.240005; 2.5046 280.290009; 2.5002 358.350006; 2.4958 244.440002; 2.4915 116.559998; 2.3848 0.32; 2.3315 1.94; 2.3269 2.55; 2.3223 1.86; 2.1581 0.35; 2.0696 4.13; 2.0497 1.13; 1.9869 1.62; 1.9568 2.65; 1.9241 1.57; 1.908 1.26; 1.879 0.32; 1.8459 0.57; 1.8368 0.66; 1.8051 1.14; 1.7824 1.01; 1.7737 1.01; 1.7528 0.51; 1.7428 0.5; 1.7044 0.38; 1.6769 0.57; 1.6709 0.55; 1.6412 0.83; 1.6125 1.19; 1.6025 1.21; 1.581 1.08; 1.5703 1.01; 1.5513 0.5; 1.3983 9.48; 1.292 0.31; 1.2363 1.35; 1.1752 0.45; 1.159 0.32; 0.0079 1.57; −0.0001 35.639999; −0.0084 1.65 |
| I-114 | [DMSO-$d_6$] 9.6017 0.33; 8.1606 5.17; 8.1352 0.41; 8.1095 0.44; 8.0615 2.97; 8.0419 7.49; 8.0224 6.02; 8.0165 6.75; 7.9962 4.52; 7.9771 2.69; 7.9717 2.48; 7.9517 0.56; 7.9265 0.41; 7.9156 0.39; 7.8933 0.47; 7.8786 0.35; 7.8063 4.36; 7.8045 4.66; 7.7872 4.01; 7.7852 3.8; 7.7577 4.11; 7.7384 3.65; 7.6801 0.3; 7.6484 1.04; 7.6445 1.28; 7.6315 3.33; 7.6274 3.02; 7.621 3.31; 7.6145 6.1; 7.6076 3.15; 7.6019 2.84; 7.5975 2.78; 7.5795 4.2; 7.5751 3.51; 7.5581 3.39; 7.5538 3.31; 7.5315 0.47; 7.5146 0.38; 7.4141 1.13; 7.3286 2.31; 7.2815 2.33; 7.2084 0.34; 7.1949 5.14; 7.1778 1.34; 7.1595 2.74; 7.1484 1.41; 7.1394 0.36; 7.0617 2.45; 7.0418 2.61; 7.0235 5.86; 6.9655 0.32; 6.926 2.15; 6.9057 4.99; 6.9028 5.06; 6.8876 2.81; 5.5081 1.34; 5.4946 0.33; 5.4654 3.27; 5.4123 0.34; 5.3886 3.63; 5.3464 1.33; 5.1344 6.42; 4.4717 1.25; 4.435 1.26; 4.0839 1.23; 4.0684 0.86; 4.0461 1.29; 4.0034 0.34; 3.853 0.98; 3.8147 0.3; 3.786 0.34; 3.7719 0.3; 3.7084 0.8; 3.6824 0.44; 3.6768 0.4; 3.6204 0.49; 3.5967 0.51; 3.5769 0.52; 3.5508 0.62; 3.5071 0.7; 3.4947 0.79; 3.4095 1.61; 3.3006 2024.209961; 3.2254 2.1; 3.2057 1.84; 3.1948 2.26; 3.1671 1.31; 3.1466 0.85; 3.1352 0.42; 3.0366 0.45; 2.9438 0.45; 2.9144 0.9; 2.8898 3.64; 2.8495 1.06; 2.7963 0.3; 2.782 0.37; 2.7306 2.13; 2.6778 2.16; 2.6733 3.88; 2.6688 5.15; 2.6642 3.93; 2.6206 0.83; 2.5388 16.76; 2.5219 24.73; 2.5085 303.920013; 2.5042 554.929993; 2.4997 714.030029; 2.4953 487.720001; 2.4909 234.240005; 2.3986 0.89; 2.3938 0.77; 2.386 0.73; 2.3358 2.07; 2.3309 3.95; 2.3264 5.07; 2.3217 3.77; 2.3171 2.05; 2.2808 0.34; 2.2694 0.38; 2.2541 0.33; 2.0969 1.14; 2.0843 1.39; 2.0692 15; 2.0493 3.48; 2.0189 1.35; 1.9867 1.77; 1.9554 0.85; 1.9251 1.03; 1.9192 1.03; 1.8967 1; 1.862 0.45; 1.7687 0.55; 1.7479 1.05; 1.7401 1.1; 1.7144 1.01; 1.685 0.48; 1.6737 0.42; 1.3984 1.99; 1.2918 0.45; 1.2592 0.4; 1.2486 0.48; 1.2367 1.79; 1.193 0.5; 1.1748 1.1; 1.1571 0.62; 0.0081 2.37; −0.0001 58.860001; −0.0084 2.72 |
| I-115 | [DMSO-$d_6$] 7.9623 2.3; 7.9431 6.31; 7.9239 4.96; 7.897 5.4; 7.8949 6.01; 7.878 2.98; 7.8758 2.75; 7.5815 4.19; 7.5794 4.34; 7.5625 3.96; 7.5603 3.85; 7.3155 2.65; 7.1821 5.94; 7.1644 2.95; 7.0487 2.93; 7.0284 6.46; 6.9042 5.95; 6.8925 3.46; 5.7467 7.25; 5.4573 1.53; 5.4151 4.53; 5.3676 4.59; 5.325 1.33; 4.4391 1.38; 4.4066 1.44; 4.3137 4.95; 4.307 1.63; 4.2971 10.78; 4.2805 5.61; 4.04 0.36; 4.0218 1.41; 3.9869 1.4; 3.3945 0.7; 3.3784 1.5; 3.3652 1.58; 3.3621 1.31; 3.3487 1.46; 3.3138 354.920013; 3.29 14.59; 3.2463 2.01; 3.2181 1.12; 3.1239 0.56; 3.1153 1.01; 3.1062 0.73; 3.0951 1.23; 3.086 2; 3.0771 1.22; 3.066 0.79; 3.0567 1.09; 3.0484 0.61; 2.9418 0.47; 2.8217 0.96; 2.7952 1.72; 2.7909 1.71; 2.7634 0.97; 2.6707 0.36; 2.5409 0.79; 2.5061 40.939999; 2.5017 53.060001; 2.4975 37.619999; 2.3284 0.36; 1.9874 0.78; 1.9671 1.11; 1.931 2.5; 1.894 1.55; 1.8528 0.54; 1.8429 0.62; 1.8206 1.17; 1.8122 1.23; 1.7897 1.07; 1.7815 1.05; 1.75 |

-continued

| Ex. | NMR data |
|---|---|
|  | 1.23; 1.733 3.14; 1.7157 4.41; 1.6971 3.6; 1.6803 1.37; 1.6719 0.64; 1.6601 0.64; 1.6387 1.19; 1.6289 1.25; 1.608 1.12; 1.5984 1.09; 1.5772 0.47; 1.5676 0.39; 1.4111 2.01; 1.4045 2.28; 1.3946 3.16; 1.39 3.1; 1.3709 3.19; 1.357 3.01; 1.3498 3.11; 1.3359 2.87; 1.3116 2.76; 1.2752 9.03; 1.268 8.69; 1.2583 6.79; 1.1757 0.41; 0.8744 5.55; 0.8575 15; 0.8401 5.76; −0.0001 2.29 |
| I-116 | [DMSO-$d_6$] 7.9759 1.08; 7.9568 3.1; 7.9381 3.15; 7.928 3.03; 7.9246 3.36; 7.9088 1.27; 7.9053 0.9; 7.6076 2.08; 7.6043 2.04; 7.5891 1.99; 7.5857 1.82; 6.4983 3.89; 5.7474 3.2; 5.3495 0.73; 5.3075 2.33; 5.2525 2.4; 5.2103 0.77; 5.0948 0.34; 5.0801 0.64; 5.0733 0.54; 5.0682 0.7; 5.0588 0.73; 5.0468 0.7; 5.033 0.32; 5.0205 0.3; 4.7714 0.3; 4.7595 0.33; 4.7506 0.39; 4.7459 0.43; 4.7386 0.41; 4.7243 0.34; 4.6322 0.36; 4.6191 0.44; 4.6115 0.4; 4.6072 0.4; 4.4653 0.68; 4.4331 0.71; 4.039 0.62; 4.0319 0.65; 3.9972 0.69; 3.3025 200.820007; 3.2787 8.31; 3.2532 1.08; 3.2221 0.57; 3.1226 0.49; 3.1139 0.36; 3.1017 0.63; 3.0931 0.98; 3.0836 0.6; 3.0736 0.41; 3.0637 0.56; 2.8218 0.47; 2.7906 0.84; 2.7638 0.49; 2.6695 0.33; 2.5394 0.76; 2.5223 1.28; 2.5091 21.08; 2.5047 39.849998; 2.5002 52.16; 2.4958 36.189999; 2.4915 17.42; 2.3272 0.38; 2.2236 15; 2.2126 1.02; 2.2018 0.45; 2.1982 0.41; 2.1311 0.41; 2.1102 0.64; 2.0697 1.21; 2.0616 0.6; 2.0498 0.75; 2.0351 0.6; 2.0261 0.65; 1.987 0.65; 1.9692 0.58; 1.9338 1.36; 1.8964 0.79; 1.8589 0.32; 1.8495 0.36; 1.8292 0.61; 1.82 0.66; 1.7977 0.55; 1.7879 0.54; 1.6908 1.09; 1.6784 1.17; 1.6692 1.15; 1.6461 0.85; 1.6358 0.85; 1.6155 0.9; 1.6039 1.01; 1.5739 0.63; 1.5453 0.44; 1.5224 0.58; 1.5158 0.62; 1.4898 0.63; 1.4651 0.36; 1.4568 0.32; 1.4026 0.73; 1.3799 1.16; 1.3587 1.04; 1.3339 0.48; 0.008 0.43; −0.0081 0.5 |
| I-117 | [DMSO-$d_6$] 7.7213 0.38; 7.7028 0.51; 7.7 0.48; 7.6816 0.44; 7.3196 1.14; 7.3016 1.29; 7.2576 0.49; 7.2394 0.43; 7.2356 0.34; 7.2024 0.42; 7.1871 0.96; 7.1718 1.07; 7.1604 0.42; 7.1324 0.62; 7.111 0.58; 7.0388 0.37; 7.0243 0.8; 6.9091 0.75; 6.8884 0.39; 6.1265 0.51; 5.7466 0.32; 5.4148 1.7; 4.0394 0.32; 4.0216 0.32; 3.6729 0.54; 3.6403 0.56; 3.6273 0.52; 3.5715 2.19; 3.304 59.509998; 3.2806 0.86; 2.8565 0.31; 2.5087 5.73; 2.5046 10.22; 2.5002 12.91; 2.4959 8.94; 2.0467 0.34; 2.0365 0.31; 1.9867 1.57; 1.3982 15; 1.1929 0.39; 1.175 0.76; 1.1573 0.38; −0.0001 2.11 |
| I-118 | [DMSO-$d_6$] 7.7293 1.55; 7.7107 2.07; 7.7079 1.98; 7.6894 1.82; 7.3091 3.88; 7.3049 2.46; 7.291 3.62; 7.2842 3.11; 7.2613 1.92; 7.1454 2.54; 7.1239 2.4; 6.5001 3.92; 5.3644 7.03; 5.2968 7.9; 3.6674 2.44; 3.6394 2.53; 3.5737 9.94; 3.4286 0.32; 3.3057 570.400024; 2.6739 0.64; 2.6694 0.82; 2.6648 0.62; 2.5395 3.63; 2.5087 50.369999; 2.5047 87.110001; 2.5004 107.690002; 2.4962 74.57; 2.3316 0.63; 2.3271 0.8; 2.3226 0.61; 2.2586 0.55; 2.2128 15; 2.0694 0.53; 2.0497 0.34; 1.9869 0.78; 1.2926 0.32; 1.2373 0.38; 1.175 0.42; 1.0455 0.31; −0.0001 4.64 |
| I-119 | [DMSO-$d_6$] 7.7752 2.4; 7.7567 3.16; 7.7538 3.14; 7.7355 2.91; 7.3125 2.02; 7.2006 4.82; 7.1954 5.82; 7.1785 11.49; 7.1652 2.56; 7.0461 2.5; 7.0291 5.07; 6.9152 4.74; 6.8932 2.52; 5.7463 2.86; 5.4289 10.86; 5.3885 0.47; 4.0394 0.8; 4.0217 0.8; 4.0037 0.32; 3.7126 3.62; 3.6836 3.66; 3.6023 15; 3.5432 0.34; 3.5311 0.34; 3.4683 1.55; 3.4605 1.35; 3.4348 0.78; 3.4169 0.59; 3.406 0.66; 3.3905 0.83; 3.3082 654.059998; 3.2035 0.41; 2.6742 0.73; 2.6694 0.93; 2.6651 0.69; 2.5395 4.73; 2.5089 57.009998; 2.5048 100.760002; 2.5004 126.889999; 2.4962 88.5; 2.3315 0.71; 2.3273 0.9; 2.3224 0.67; 2.0691 1.32; 2.0495 0.41; 1.9868 3.43; 1.9352 1.38; 1.9235 2.03; 1.9117 2.65; 1.9034 2.8; 1.7131 2.57; 1.7036 2.35; 1.6912 1.87; 1.7068 0.31; 1.6096 1.09; 1.579 1.24; 1.485 0.83; 1.4785 0.75; 1.4539 2.8; 1.429 5.46; 1.3984 5.14; 1.3726 0.76; 1.2919 1.23; 1.262 1.04; 1.2365 0.93; 1.1929 1.06; 1.1751 2.03; 1.1575 1.13; −0.0001 6.46 |
| I-120 | [DMSO-$d_6$] 8.1249 1.46; 8.1056 1.8; 8.0876 0.9; 8.0613 0.96; 8.0503 0.93; 8.0381 1.01; 7.8293 1.06; 7.808 2.4; 7.7895 2.38; 7.6313 1.46; 7.6261 0.68; 7.6133 3.22; 7.6021 1.87; 7.5931 2.28; 7.3302 0.89; 7.3118 1.6; 7.2903 1.49; 7.1969 1.91; 7.1798 2.1; 7.1727 1.06; 7.1622 1.94; 7.0636 0.95; 7.0366 1.91; 6.9228 1.88; 6.9009 0.94; 5.4608 4.25; 4.0392 0.73; 4.0214 0.73; 3.8508 1.35; 3.7419 1.89; 3.7303 1.97; 3.7201 1.59; 3.6808 1.51; 3.4192 0.69; 3.4085 0.8; 3.4029 0.87; 3.3095 650.429993; 3.2127 0.32; 3.1995 0.3; 2.6694 0.84; 2.6651 0.63; 2.5394 2.24; 2.5089 56.82; 2.5048 99.25; 2.5004 123.519997; 2.4962 85.459999; 2.3315 0.69; 2.3271 0.9; 2.3226 0.67; 2.0691 0.54; 1.9867 2.87; 1.3984 15; 1.2366 0.34; 1.1928 0.84; 1.1749 1.57; 1.1571 0.81; −0.0001 14.7 |
| I-121 | [DMSO-$d_6$] 8.0457 2.09; 8.0263 4.62; 8.007 2.81; 7.7842 3.53; 7.7669 3.06; 7.7651 2.92; 7.7366 3.26; 7.717 3.01; 7.5274 2.3; 7.5198 3.5; 7.5104 13.7; 7.5057 15; 7.4875 2.13; 7.4146 1.21; 7.3985 0.32; 7.3951 0.32; 7.3238 1.84; 7.2819 2.2; 7.1904 3.98; 7.178 1.27; 7.1597 1.96; 7.1491 1.18; 7.057 2; 7.0422 2.39; 7.0238 4.35; 6.9263 2.03; 6.906 4.34; 6.8879 2.19; 5.7467 4.55; 5.4993 1.07; 5.4568 2.64; 5.3802 2.58; 5.3375 1.08; 5.1329 6.09; 4.4596 0.96; 4.4268 0.98; 4.0667 0.94; 4.0575 1.1; 4.0395 2.3; 4.0218 1.94; 4.004 0.6; 3.4728 0.34; 3.3084 46.98; 3.2069 0.9; 3.1987 1.16; 3.1788 1.14; 3.1698 1.6; 3.1616 1.05; 3.1496 0.74; 3.1411 0.9; 2.8906 0.8; 2.8688 1.23; 2.8364 0.71; 2.7323 0.31; 2.6743 0.41; 2.6699 0.5; 2.6651 0.38; 2.5398 2.85; 2.5093 28.290001; 2.5051 49.52; 2.5007 61.889999; 2.4964 42.369999; 2.3321 0.32; 2.3274 0.42; 2.323 0.31; 2.0694 0.97; 2.0494 1.2; 2.037 1.42; 1.987 7.21; 1.9204 0.4; 1.9082 0.47; 1.8996 0.79; 1.89 0.81; 1.8689 0.7; 1.8598 0.68; 1.7531 0.34; 1.7438 0.45; 1.7219 0.79; 1.7135 0.81; 1.6916 0.73; 1.6828 0.69; 1.398 8.28; 1.2927 0.31; 1.2365 0.38; 1.1929 1.77; 1.1752 3.47; 1.1574 1.76; −0.0001 5.57 |
| I-122 | [DMSO-$d_6$] 7.8212 0.82; 7.8029 1.06; 7.7999 1.07; 7.7816 0.97; 7.5083 0.57; 7.4898 15; 7.3831 0.31; 7.3228 0.73; 7.2763 1.41; 7.2548 1.32; 7.2141 1.75; 7.196 1.79; 7.1896 1.7; 7.1696 0.81; 7.0563 0.83; 7.0336 1.69; 6.9204 1.63; 6.8977 0.85; 5.7462 2.19; 5.4482 3.71; 4.0396 0.36; 4.0218 0.36; 3.7912 1.11; 3.7845 1.1; 3.7069 1.22; 3.6635 1.58; 3.6473 1.55; 3.3119 78.5; 3.1933 0.39; 2.5399 0.69; 2.5053 16.85; 2.501 21.1; 2.4968 14.76; 1.9871 1.48; 1.193 0.42; 1.1752 0.8; 1.1574 0.42; −0.0001 0.98 |
| I-123 | [DMSO-$d_6$] 8.0598 1.57; 8.0403 3.39; 8.0209 2.08; 7.9034 2.25; 7.9003 2.29; 7.8902 2.33; 7.8871 2.12; 7.8037 2.61; 7.7864 2.22; 7.7572 2.42; 7.7379 2.19; 7.7261 0.33; 7.3383 2.32; 7.3352 2.4; 7.3293 2.88; 7.3263 2.68; 7.3203 1.52; 7.2536 0.41; 7.2386 2.61; 7.2296 2.36; 7.2253 2.46; 7.2164 2.13; 7.187 2.94; 7.1586 1.47; 7.1134 0.73; 7.068 0.35; 7.0537 1.46; 7.0224 3.17; 6.9954 0.32; 6.9024 2.84; 6.8864 1.57; 5.4945 0.76; 5.4511 1.98; 5.3762 1.91; 5.3346 0.82; 4.4475 0.81; 4.4146 0.75; 4.0575 0.78; 4.0217 0.92; 3.9035 0.31; 3.7432 0.32; 3.7219 0.35; 3.7124 0.33; 3.6743 0.36; 3.6448 0.41; 3.6259 0.43; 3.5902 0.5; 3.5826 0.48; 3.5722 0.51; 3.555 0.58; 3.459 1.15; 3.3095 2849.459961; 3.2861 38.669998; 3.203 1.37; 3.1966 1.29; 3.1775 1.1; 3.1682 1.4; 3.1401 0.83; 3.1034 0.34; 3.0946 0.31; 3.0832 |

-continued

| Ex. | NMR data |
|---|---|
| | 0.31; 3.0365 0.42; 2.8902 0.87; 2.86 0.98; 2.83 0.65; 2.7307 0.44; 2.6739 2.18; 2.6692 2.86; 2.6648 2.13; 2.5394 5.95; 2.509 170.830002; 2.5048 302.220001; 2.5003 379.850006; 2.496 260.809998; 2.4247 0.85; 2.4009 0.53; 2.3316 2.07; 2.3272 2.74; 2.3225 1.96; 2.2102 0.43; 2.0689 1.93; 2.0568 0.58; 2.0492 1; 2.0281 1.1; 1.9866 1.49; 1.9074 1.32; 1.8782 0.66; 1.8568 0.58; 1.8264 0.34; 1.7418 0.33; 1.697 0.7; 1.6742 0.66; 1.646 0.3; 1.3984 15; 1.2925 0.66; 1.2359 1.03; 1.1753 0.42; 1.1573 0.36; 1.0704 0.3; 0.8902 1.14; 0.0079 3.47; −0.0001 68.889999; −0.0083 3.35 |
| I-124 | [DMSO-d$_6$] 8.5809 0.36; 8.5708 0.34; 7.8847 3.08; 7.8818 3; 7.8716 3.13; 7.8686 2.94; 7.8298 2.16; 7.8115 2.87; 7.8083 2.81; 7.7901 2.61; 7.7746 0.68; 7.7696 0.7; 7.7635 0.64; 7.7583 0.61; 7.7256 1.18; 7.4147 1.71; 7.4025 0.43; 7.3916 0.33; 7.3882 0.41; 7.3834 0.38; 7.3689 0.37; 7.32 2.17; 7.3111 3.32; 7.3081 3.39; 7.3022 4.28; 7.2991 4.42; 7.2945 4.37; 7.2818 3.91; 7.2729 3.59; 7.2439 0.45; 7.226 6.14; 7.2161 3.85; 7.2116 5.14; 7.2096 5.25; 7.203 3.39; 7.1867 4.19; 7.1779 2.23; 7.1682 2.3; 7.1491 2.01; 7.1302 1.16; 7.1139 2.33; 7.1091 1.15; 7.1024 1.08; 7.0934 0.43; 7.0669 0.37; 7.0536 2.1; 7.0421 3.8; 7.0322 4.66; 6.9947 0.51; 6.9196 4.76; 6.9065 2.16; 6.8963 2.21; 5.7464 0.55; 5.4445 9.32; 5.1351 9.57; 4.0572 1.3; 4.0395 3.65; 4.0217 3.63; 4.0039 1.31; 3.8527 0.32; 3.7797 2.94; 3.7731 2.91; 3.701 3.24; 3.6568 4.25; 3.6415 4.15; 3.5731 0.38; 3.5451 0.33; 3.5214 0.36; 3.4963 0.41; 3.307 81.07; 3.2036 3.34; 3.0374 0.62; 2.8506 0.53; 2.6738 0.6; 2.6695 0.78; 2.6648 0.59; 2.5395 3.28; 2.5047 74.510002; 2.5004 90.870003; 2.4963 62.459999; 2.3317 0.46; 2.3272 0.6; 2.3226 0.43; 2.211 2.69; 2.0692 0.36; 1.9869 15; 1.9084 0.44; 1.3983 1.24; 1.2926 0.34; 1.2371 0.68; 1.1929 4.22; 1.1751 8.17; 1.1574 4.06; −0.0001 4.5 |
| I-125 | [DMSO-d$_6$] 7.8007 2.47; 7.7825 3.34; 7.7794 2.98; 7.7611 2.84; 7.4421 0.77; 7.4247 1.38; 7.4201 1.26; 7.4038 2.53; 7.3872 1.36; 7.3829 1.52; 7.3661 0.74; 7.2978 2.12; 7.2511 5.11; 7.2332 8.43; 7.2117 3.81; 7.1645 4.91; 7.156 2.89; 7.1435 3.92; 7.1237 5.74; 7.1034 3.05; 7.0315 2.47; 7.0199 4.92; 6.9062 4.61; 6.8841 2.34; 5.4028 10.71; 4.2406 10.93; 4.0393 0.35; 3.8587 0.31; 3.8225 0.32; 3.8 0.34; 3.7821 0.34; 3.771 0.37; 3.7665 0.35; 3.6845 4.07; 3.6608 4.04; 3.5816 15; 3.509 0.69; 3.4531 0.94; 3.3093 1444.550049; 3.2089 0.47; 2.6738 1.33; 2.6695 1.7; 2.665 1.32; 2.5396 4.75; 2.5091 113.230003; 2.5049 199.759995; 2.5005 250.399994; 2.4962 172.940002; 2.3806 0.34; 2.3708 0.33; 2.3316 1.42; 2.3274 1.81; 2.3227 1.31; 2.0692 1.25; 1.9868 1.01; 1.3983 13.56; 1.2359 0.75; 1.1928 0.42; 1.175 0.59; 1.157 0.33; −0.0001 46.560001; −0.0084 2.6; −0.1508 0.31 |
| I-126 | [DMSO-d$_6$] 8.0182 0.56; 7.999 1.25; 7.9796 0.86; 7.8112 0.88; 7.794 0.83; 7.7736 0.31; 7.6848 0.85; 7.6654 0.79; 7.5829 0.65; 7.5741 0.73; 7.5687 0.65; 7.5596 0.75; 7.4907 0.59; 7.4811 0.57; 7.476 0.75; 7.4674 0.75; 7.3435 0.32; 7.3339 1.7; 7.3255 1.49; 7.3192 1.48; 7.3105 1.52; 7.3031 0.53; 7.2931 0.54; 7.1593 1.08; 7.1509 0.57; 7.026 0.59; 7.0146 1.12; 6.8927 1.06; 6.8789 0.6; 5.468 0.32; 5.4243 0.65; 5.3423 0.65; 5.3001 0.3; 4.3211 3.65; 4.3084 1.18; 3.9809 0.31; 3.4079 0.54; 3.3001 641.619995; 3.2767 10.26; 3.0928 0.41; 3.0373 0.33; 2.8493 0.31; 2.8094 0.43; 2.7779 0.32; 2.6733 1.04; 2.6687 1.33; 2.6641 0.99; 2.6056 0.32; 2.5933 0.38; 2.5915 0.4; 2.5388 2.8; 2.5084 82.190002; 2.5041 145.470001; 2.4997 182.970001; 2.4954 125.709999; 2.3308 0.97; 2.3265 1.31; 2.322 0.94; 2.318 0.54; 2.0693 0.73; 1.9865 0.4; 1.9646 0.47; 1.9234 0.36; 1.9072 0.4; 1.8036 0.35; 1.7766 0.33; 1.3985 15; 1.2923 0.33; 1.2369 0.62; 0.8903 0.36; 0.0079 1.74; −0.0001 35.150002; −0.0083 1.8 |
| I-127 | [DMSO-d$_6$] 7.7962 2.13; 7.7777 3.02; 7.7753 3.02; 7.7566 2.64; 7.5678 2.27; 7.559 2.47; 7.5547 2.22; 7.5445 2.76; 7.4854 2.11; 7.4753 2.01; 7.4709 2.53; 7.4622 2.86; 7.3385 1.12; 7.3294 6.08; 7.3206 4.8; 7.3151 4.86; 7.306 5.43; 7.3002 3.09; 7.2704 2.3; 7.2645 0.39; 7.2464 4.69; 7.2278 8.03; 7.206 3.84; 7.1666 4.41; 7.1573 2.45; 7.048 0.33; 7.0335 2.29; 7.0212 4.52; 6.9072 4.72; 6.8853 2.43; 5.7467 1.89; 5.407 10.47; 5.308 0.36; 4.2838 15; 4.0575 0.81; 4.0398 2.33; 4.022 2.35; 4.0043 0.82; 3.9628 0.49; 3.6936 3.75; 3.6648 3.76; 3.5863 14.92; 3.5123 0.5; 3.4248 0.52; 3.3101 218.339996; 3.0381 0.78; 2.8511 0.66; 2.6749 0.37; 2.6702 0.46; 2.6659 0.36; 2.5401 1.9; 2.5052 49.459999; 2.5012 60.130001; 2.3277 0.45; 1.9873 9.62; 1.3977 0.33; 1.2357 0.48; 1.1932 2.68; 1.1754 5.16; 1.1576 2.62; −0.0001 1.82 |
| I-128 | [DMSO-d$_6$] 8.0129 2.61; 8.0057 1.07; 7.9935 5.1; 7.9866 0.6; 7.9741 3.1; 7.9536 0.32; 7.803 4.15; 7.7841 3.46; 7.7657 0.3; 7.7463 0.34; 7.6779 3.8; 7.6583 3.21; 7.5241 1.06; 7.4455 3.99; 7.4398 2.33; 7.4316 4.71; 7.4239 4.5; 7.4156 2.56; 7.41 3.72; 7.3826 0.35; 7.3022 2.05; 7.2726 0.38; 7.2587 0.5; 7.236 0.49; 7.1687 6.03; 7.1644 5.12; 7.1552 3.4; 7.1422 7.6; 7.1255 2.24; 7.1201 3.66; 7.1049 0.48; 7.0816 0.36; 7.0583 0.56; 7.0355 2.26; 7.0192 4.89; 6.9502 0.41; 6.8989 4.2; 6.8833 1.96; 5.7475 0.48; 5.467 1.22; 5.424 2.89; 5.3493 2.81; 5.3076 1.17; 4.4123 1.16; 4.3823 1.13; 4.2177 13.71; 4.1995 0.99; 4.1558 1.23; 4.0577 1.27; 4.0398 3.6; 4.022 4.15; 4.0043 1.8; 3.9802 1.09; 3.6443 0.31; 3.306 563.599976; 3.2836 5.67; 3.2511 1.33; 3.2238 0.68; 3.1242 0.74; 3.0955 1.58; 3.0866 1.04; 3.0666 1; 3.0385 0.45; 2.8506 0.85; 2.813 1.23; 2.7869 0.68; 2.6701 0.79; 2.6655 0.56; 2.5398 1.43; 2.5095 53.189999; 2.5053 95.830002; 2.501 121.959999; 2.4967 85.239998; 2.3321 0.66; 2.3274 0.9; 2.0697 0.31; 1.9873 15; 1.9619 1.88; 1.9226 1.4; 1.8356 0.56; 1.8064 1.05; 1.7835 0.93; 1.6637 0.58; 1.6349 1.14; 1.6137 1.14; 1.5823 0.55; 1.3981 1.65; 1.236 0.8; 1.1931 3.88; 1.1754 7.74; 1.1576 3.95; 0.008 0.53; −0.0001 19.790001 |
| I-129 | [DMSO-d$_6$] 7.9982 2.53; 7.9789 5.61; 7.9596 3.43; 7.769 4.12; 7.7514 3.74; 7.6638 3.9; 7.6446 3.54; 7.601 0.89; 7.3179 2.06; 7.2817 0.36; 7.223 0.36; 7.1841 4.96; 7.1634 2.51; 7.1428 0.33; 7.0877 0.64; 7.0506 3.18; 7.0275 5.22; 6.9505 0.41; 6.9055 4.95; 6.8915 2.76; 5.4809 1.31; 5.4381 3.29; 5.3659 3.33; 5.324 1.38; 5.1352 0.56; 4.431 1.18; 4.3985 1.2; 4.2899 0.37; 4.2629 0.35; 4.2473 0.37; 4.0368 1.1; 4.0048 1.18; 3.5736 0.38; 3.4753 0.47; 3.4263 0.68; 3.4075 0.94; 3.3051 1051.73999; 3.2462 2.1; 3.1968 0.7; 3.1912 0.66; 3.1405 1.23; 3.1199 1.41; 3.1103 2; 3.0894 0.98; 3.0832 1.17; 3.0371 0.46; 2.9617 4.1; 2.9434 6.82; 2.9252 4.55; 2.8914 0.96; 2.8737 1.24; 2.8394 1.58; 2.808 1.04; 2.7781 0.35; 2.7719 0.35; 2.7453 0.31; 2.7374 0.36; 2.7237 0.35; 2.7096 0.39; 2.6894 0.56; 2.6783 0.95; 2.6738 1.57; 2.6695 1.88; 2.6648 1.42; 2.6372 0.41; 2.624 0.46; 2.6016 0.61; 2.5393 3.54; 2.509 103.199997; 2.5049 182.690002; 2.5005 229.910004; 2.4962 159.270004; 2.3869 0.42; 2.3771 0.4; 2.3518 0.37; 2.3274 1.74; 2.3226 1.34; 2.2703 0.35; 2.2527 0.48; 2.2359 0.33; 2.0697 1.08; 2.0495 0.49; 2.0181 1.18; 2.0128 1.16; 1.983 2.02; 1.9372 1.42; 1.8569 0.62; 1.837 1.15; 1.828 1.15; 1.7963 1.03; 1.7664 0.66; 1.7457 0.52; 1.727 0.52; 1.7011 0.81; 1.6948 0.85; 1.69 0.83; 1.6676 1.37; 1.6599 1.49; 1.6313 2.06; 1.6128 3.17; 1.5951 4.47; 1.5765 3.58; 1.5585 1.76; 1.536 0.76; 1.4846 0.49; 1.4672 0.47; 1.3758 |

| Ex. | NMR data |
|---|---|
| | 3.46; 1.3536 3.49; 1.3383 3.36; 1.2923 6.99; 1.2707 12.81; 1.238 6.64; 1.1123 0.38; 1.0707 0.31; 0.8803 5.34; 0.864 15; 0.8466 7.25; 0.8215 1.95; 0.804 0.9; 0.1466 0.36; 0.0305 0.4; 0.0079 3.52; −0.0001 61.439999; −0.0083 2.9 |
| I-130 | [DMSO-$d_6$] 9.6025 0.45; 7.7813 3.03; 7.7624 4.02; 7.7418 3.35; 7.3129 2.67; 7.2907 0.31; 7.2833 0.32; 7.2069 8.55; 7.1882 12.69; 7.1798 6.44; 7.165 3.02; 7.0464 3.29; 7.0291 6.2; 6.9634 0.41; 6.9552 0.31; 6.9157 6.3; 6.8932 3.09; 6.2886 0.33; 5.7463 0.67; 5.4306 14.4; 5.389 0.78; 3.7201 4.57; 3.6828 4.72; 3.6718 4.45; 3.6115 15; 3.5422 0.57; 3.4923 0.54; 3.4764 0.6; 3.4286 0.83; 3.3054 1108.430054; 3.1645 0.45; 3.1479 0.44; 3.1233 0.3; 3.0899 0.31; 2.9257 4.7; 2.9076 7.99; 2.8892 4.89; 2.6957 0.58; 2.674 1.56; 2.6693 1.87; 2.6472 0.4; 2.6429 0.38; 2.6255 0.45; 2.5936 0.69; 2.5393 8.51; 2.5046 199.830002; 2.5004 250.910004; 2.4964 181.169998; 2.4062 0.54; 2.3988 0.52; 2.3579 0.39; 2.3445 0.36; 2.331 1.43; 2.3273 1.81; 2.3231 1.35; 2.0691 1.44; 2.05 0.74; 1.9871 1.03; 1.761 0.39; 1.6097 0.98; 1.5929 2.9; 1.5742 4.54; 1.5559 3.59; 1.5374 1.43; 1.4553 0.31; 1.4219 0.4; 1.3971 1.09; 1.3669 3.29; 1.3444 3.15; 1.3306 2.99; 1.2894 6.18; 1.2662 11.51; 1.1756 0.8; 1.1586 0.88; 1.109 0.31; 1.0704 0.4; 0.8793 5.51; 0.8626 14.81; 0.8451 6.44; −0.0001 8.31 |
| I-131 | [DMSO-$d_6$] 7.935 1.21; 7.9159 3.38; 7.8969 2.98; 7.8797 2.58; 7.8765 2.98; 7.8605 1.31; 7.8573 1.04; 7.5468 1.9; 7.5436 1.93; 7.5278 1.77; 7.5247 1.7; 7.2873 1.38; 7.1535 2.89; 7.1114 1.55; 7.0196 1.45; 6.9815 0.38; 6.9751 3.28; 6.8686 0.34; 6.8562 2.31; 6.8457 0.4; 6.8388 1.72; 5.4078 0.45; 5.3618 0.75; 5.3387 0.75; 5.0738 0.53; 4.3828 2.07; 4.365 6.05; 4.3473 6.16; 4.3296 2.02; 4.0653 1.22; 4.0475 3.53; 4.0298 3.62; 4.012 1.36; 3.116 5.44; 3.089 1.79; 3.0795 1.02; 3.0692 0.64; 3.0597 0.73; 3.0504 0.44; 2.5113 0.33; 2.4984 5.18; 2.4937 10.27; 2.489 14.17; 2.4843 9.92; 2.4796 4.78; 1.9746 16; 1.9351 0.88; 1.3543 6.16; 1.3366 12.71; 1.3189 6.02; 1.1955 4.41; 1.1777 8.82; 1.16 4.32; −0.0001 0.7 |
| I-132 | [DMSO-$d_6$] 7.9336 1.39; 7.9145 3.84; 7.8955 3.34; 7.878 2.94; 7.8748 3.37; 7.8588 1.48; 7.8556 1.17; 7.5505 2.15; 7.5474 2.15; 7.5315 1.98; 7.5285 1.9; 6.4666 0.54; 6.4507 3.37; 5.2826 0.6; 5.2367 0.8; 5.2125 0.83; 4.9763 1.54; 4.3816 2.35; 4.3638 7; 4.3461 7.13; 4.3284 2.34; 4.0653 1.04; 4.0476 2.8; 4.0298 2.83; 4.0121 1.11; 3.9191 0.34; 3.6401 0.37; 3.6236 0.93; 3.607 1.23; 3.5906 0.95; 3.5738 0.42; 3.2438 0.41; 3.1211 10.63; 3.1025 4.7; 3.0853 2.64; 3.077 1.51; 3.0662 0.98; 3.0565 1.04; 3.0472 0.68; 2.8889 0.54; 2.7351 0.4; 2.7339 0.39; 2.5123 0.42; 2.5073 0.62; 2.4994 6.88; 2.4947 13.79; 2.49 19.15; 2.4853 13.46; 2.4806 6.51; 2.2594 2.17; 2.2578 2.11; 2.2364 16; 2.235 15.43; 2.209 0.97; 2.2019 1.4; 1.9747 12.22; 1.9313 1.08; 1.9032 0.48; 1.8115 0.32; 1.6561 0.32; 1.353 7.01; 1.3353 14.7; 1.3175 7.6; 1.3104 4.69; 1.3041 7.89; 1.2921 8.28; 1.2877 7.97; 1.2738 2.87; 1.1956 3.42; 1.1778 6.63; 1.1601 3.29 |
| I-133 | [DMSO-$d_6$] 8.0141 1.26; 7.9945 2.68; 7.975 1.61; 7.9486 0.41; 7.811 1.95; 7.7923 1.75; 7.7697 0.41; 7.7558 0.35; 7.6748 1.76; 7.6551 1.58; 7.6232 0.32; 7.5071 0.49; 7.3666 1.42; 7.35 1.96; 7.3462 1.57; 7.3182 0.33; 7.2847 1.16; 7.2674 0.36; 7.2621 0.37; 7.2581 0.37; 7.2431 0.37; 7.1907 3.08; 7.1858 3.26; 7.1791 3.84; 7.175 3.25; 7.1689 2.65; 7.1516 4.37; 7.1464 2.95; 7.1086 1.12; 7.0983 0.81; 7.0857 0.65; 7.0663 0.55; 7.0569 0.53; 7.0409 0.5; 7.0348 0.49; 7.0185 1.4; 7.0105 2.35; 6.9927 0.37; 6.9838 0.46; 6.9408 0.41; 6.8883 2.35; 6.8745 1.41; 6.8168 0.34; 5.462 0.65; 5.4201 1.45; 5.3351 1.33; 5.3058 0.42; 5.294 0.65; 4.4066 0.66; 4.3736 0.6; 4.2322 7.52; 4.205 1.19; 4.1646 0.64; 4.145 0.33; 4.1298 0.31; 4.1145 0.32; 4.0599 0.32; 4.0037 0.68; 3.9804 0.51; 3.9705 0.7; 3.8099 0.31; 3.7728 0.38; 3.7361 0.38; 3.5109 0.33; 3.4825 0.33; 3.4709 0.37; 3.4639 0.46; 3.4592 0.43; 3.4147 0.67; 3.3774 1.35; 3.3021 1350.109985; 3.2427 2.19; 3.2232 1.26; 3.1767 0.71; 3.1642 0.69; 3.1451 0.55; 3.1107 0.71; 3.093 0.84; 3.0843 1.04; 3.0556 0.82; 3.0372 1.02; 3.0062 0.49; 2.9834 0.38; 2.951 0.32; 2.9243 0.4; 2.9023 0.32; 2.8904 0.33; 2.8497 0.61; 2.8292 0.57; 2.8206 0.48; 2.797 0.85; 2.7723 0.62; 2.7408 0.33; 2.6734 1.73; 2.669 2.19; 2.6645 1.68; 2.6598 1.02; 2.6422 0.41; 2.6337 0.44; 2.5389 4.55; 2.5085 138.130005; 2.5043 243.25; 2.4999 304.350006; 2.4956 209.149994; 2.4057 0.73; 2.3909 0.68; 2.3784 0.73; 2.3711 0.69; 2.3365 15; 2.3054 0.86; 2.2874 0.87; 2.263 1.45; 2.2496 0.68; 2.2316 0.5; 2.2139 0.57; 2.1897 0.81; 2.1782 0.74; 2.1484 0.38; 2.1001 0.3; 2.0692 1.06; 2.0495 0.48; 2.0087 0.4; 1.9955 0.67; 1.9866 1.17; 1.9569 1.21; 1.9234 0.9; 1.915 0.86; 1.8808 0.36; 1.863 0.4; 1.8421 0.56; 1.8124 0.68; 1.7819 0.56; 1.7512 0.4; 1.7448 0.35; 1.637 0.55; 1.6286 0.49; 1.6066 0.7; 1.5827 0.75; 1.5546 0.42; 1.5302 0.33; 1.5175 0.32; 1.2922 0.47; 1.2369 1.05; 1.1918 0.36; 1.1755 0.49; 1.158 0.37; 0.1458 0.34; 0.0079 4.28; −0.0001 78.559998; −0.0084 3.78; −0.1497 0.31 |
| I-134 | [DMSO-$d_6$] 7.9329 1.44; 7.9137 4.02; 7.8948 3.59; 7.8783 3; 7.875 3.53; 7.8591 1.51; 7.8558 1.18; 7.5498 2.16; 7.5466 2.2; 7.5308 1.99; 7.5277 1.93; 6.4511 3.39; 5.2797 0.62; 5.2353 0.75; 5.2076 0.76; 4.3818 2.39; 4.3641 7.41; 4.3464 7.39; 4.3286 2.44; 4.0655 0.46; 4.0477 1.14; 4.03 1.17; 4.0122 0.52; 3.1211 70.699997; 3.0948 0.89; 3.0853 1.21; 3.0757 0.7; 3.0656 0.45; 3.0559 0.64; 3.0467 0.37; 2.4992 5.25; 2.4945 10.96; 2.4898 15.57; 2.4851 10.96; 2.4804 5.33; 2.2363 15.98; 2.2348 16; 2.2019 0.4; 1.9748 4.82; 1.9612 0.78; 1.9484 0.78; 1.9321 1; 1.9028 0.4; 1.3531 7.41; 1.3354 15.56; 1.3177 7.29; 1.1957 1.29; 1.1779 2.52; 1.1602 1.28 |
| I-135 | [DMSO-$d_6$] 7.9292 3.08; 7.9102 8.73; 7.892 10.95; 7.8876 9.26; 7.8835 10.43; 7.8684 3.35; 7.8643 1.95; 7.5328 5.88; 7.5288 5.78; 7.5147 5.28; 7.5107 5.09; 7.3779 0.54; 7.2937 4.43; 7.2448 1.11; 7.1598 9.4; 7.1235 0.85; 7.1161 4.85; 7.0259 4.72; 6.9873 1.58; 6.9797 10.3; 6.8855 0.96; 6.8624 7.73; 6.8514 1.29; 6.8434 5.22; 5.4154 1.22; 5.3619 3.41; 5.3523 3.38; 5.1052 3.1; 4.426 0.73; 4.0676 1.47; 4.0499 3.67; 4.0321 3.8; 4.0143 1.73; 3.9226 0.78; 3.2536 0.71; 3.1226 0.87; 3.1133 1.47; 3.1037 1.04; 3.0936 1.75; 3.0843 2.89; 3.0748 1.69; 3.0648 1.12; 3.0552 1.6; 3.0457 0.92; 2.8208 0.69; 2.5158 0.37; 2.5032 4.18; 2.4985 8.1; 2.4938 11; 2.4891 7.66; 2.4845 3.71; 1.9758 16; 1.945 2.93; 1.9072 13.84; 1.8247 0.8; 1.8126 0.84; 1.7795 0.68; 1.7449 0.77; 1.7088 0.82; 1.1963 3.83; 1.1786 7.5; 1.1608 3.71; −0.0001 0.92 |
| I-136 | [DMSO-$d_6$] 7.9269 1.21; 7.9078 3.4; 7.8893 3.75; 7.8817 3.19; 7.878 3.68; 7.8625 1.31; 7.8588 0.86; 7.5358 2.1; 7.5322 2.11; 7.5175 1.9; 7.5138 1.84; 6.4688 0.53; 6.4502 3.48; 5.282 0.48; 5.2281 1.26; 5.2181 1.27; 4.9845 1.89; 4.0663 0.65; 4.0485 1.57; 4.0307 1.59; 4.013 0.7; 3.9197 0.34; 3.1169 0.35; 3.1075 0.58; 3.0982 0.41; 3.0881 0.67; 3.0786 1.12; 3.0691 0.68; 3.0591 0.45; 3.0495 0.65; 3.0402 0.39; 2.5007 2.64; 2.496 5.24; 2.4914 7.23; 2.4867 5.1; 2.482 2.51; 2.2622 |

| Ex. | NMR data |
|---|---|
| | 2.54; 2.2607 2.47; 2.238 16; 2.2367 15.37; 2.2118 0.42; 2.2029 1.09; 1.9749 6.63; 1.966 0.97; 1.9378 1.14; 1.9118 0.45; 1.9042 5.89; 1.8117 0.32; 1.1959 1.69; 1.1781 3.32; 1.1604 1.65; −0.0001 0.52 |
| I-137 | [DMSO-$d_6$] 7.7489 2.82; 7.7304 3.88; 7.7275 3.72; 7.7091 3.42; 7.5856 1.42; 7.5817 1.52; 7.567 2.82; 7.5627 2.99; 7.5473 1.65; 7.5434 1.61; 7.4682 0.72; 7.4637 0.75; 7.4544 0.97; 7.4497 1.83; 7.4348 1.69; 7.4292 2.03; 7.4247 1.21; 7.4153 1.17; 7.411 1.02; 7.3665 5.81; 7.3484 5.39; 7.3083 2.49; 7.2851 2.49; 7.2715 2.83; 7.2618 3.1; 7.2585 3.42; 7.2549 4.97; 7.237 3.22; 7.175 5.63; 7.1613 4.04; 7.1574 5.25; 7.1358 4.58; 7.0418 2.77; 7.0257 6; 6.9116 5.63; 6.8899 3.07; 5.7465 3.95; 5.4185 13.64; 5.4016 14.9; 5.308 0.32; 4.0576 0.48; 4.0399 1.41; 4.0221 1.43; 4.0043 0.47; 3.6975 3.69; 3.6837 4.09; 3.6481 4.16; 3.6357 3.94; 3.5821 15; 3.3131 284.929993; 3.2901 6.77; 3.0382 0.63; 2.8516 0.53; 2.6704 0.35; 2.5403 0.98; 2.5099 21.950001; 2.5058 37.91; 2.5014 46.73; 2.4972 32.07; 2.328 0.32; 1.9874 5.99; 1.3976 1.03; 1.2366 0.39; 1.1932 1.67; 1.1754 3.24; 1.1576 1.62; 0.0078 0.55; −0.0001 8.14; −0.0085 0.35 |
| I-138 | [DMSO-$d_6$] 7.7304 1.77; 7.7119 2.34; 7.7091 2.28; 7.6907 2.08; 7.5662 0.45; 7.5494 0.98; 7.5451 0.94; 7.5283 1.81; 7.5115 0.96; 7.5073 1.09; 7.4906 0.48; 7.3141 3.72; 7.3057 1.81; 7.2959 3.43; 7.2105 0.55; 7.2013 2.85; 7.1813 4.62; 7.1724 4.19; 7.1609 4.17; 7.1447 3.08; 7.1231 2.78; 7.0392 1.71; 7.0247 3.68; 6.9109 3.47; 6.8888 1.84; 5.7457 2.25; 5.4129 15; 4.0582 0.3; 4.0403 0.9; 4.0225 0.91; 4.0047 0.31; 3.6804 2.18; 3.6671 2.64; 3.638 2.69; 3.6248 2.35; 3.5672 10.91; 3.3246 233.389999; 2.5418 0.5; 2.5114 11.3; 2.5072 20.24; 2.5029 25.620001; 2.4986 17.93; 1.9879 3.86; 1.1937 1.06; 1.1759 2.08; 1.1581 1.04; −0.0001 3 |
| I-139 | [DMSO-$d_6$] 7.8288 3.1; 7.8103 4.24; 7.8075 4.16; 7.789 3.93; 7.5543 6.82; 7.5361 6.12; 7.3115 2.78; 7.2404 5.38; 7.2188 5.13; 7.1956 2.47; 7.1776 9.93; 7.1617 3.84; 7.1568 4.09; 7.0449 7.54; 7.0258 10.35; 7.0053 4.7; 6.9858 3.84; 6.9113 6.56; 6.8899 3.52; 5.4244 14.9; 4.0392 0.44; 4.0215 0.45; 3.7389 4.32; 3.7309 4.3; 3.6582 5.2; 3.646 4.94; 3.6252 6.54; 3.6087 6.26; 3.5312 0.33; 3.5226 0.33; 3.5148 0.31; 3.4305 0.52; 3.3034 1135.209961; 3.1479 0.39; 3.1283 0.34; 3.0371 0.32; 2.8503 0.3; 2.7744 5.44; 2.6733 1.44; 2.669 1.91; 2.6645 1.45; 2.6329 0.44; 2.6294 0.45; 2.5388 8.36; 2.5218 13.16; 2.5085 108.489998; 2.5044 192.050003; 2.5 242.100006; 2.4957 169.029999; 2.3312 1.36; 2.3267 1.74; 2.3221 1.27; 2.0845 4.99; 2.069 1.38; 1.9866 1.77; 1.7166 12.6; 1.3984 15; 1.2365 0.68; 1.1927 0.55; 1.1748 0.97; 1.1571 0.52; −0.0001 31.129999; −0.008 1.48 |
| I-140 | [DMSO-$d_6$] 7.7416 2.28; 7.7228 3.26; 7.7019 2.73; 7.3436 4.97; 7.3254 4.65; 7.3102 2.16; 7.1769 4.63; 7.1626 2.34; 7.1319 4.14; 7.1103 3.94; 7.0437 2.3; 7.0266 4.86; 6.9117 4.9; 6.8908 2.49; 5.4225 11.58; 4.937 1.03; 4.925 1.34; 4.9157 1.94; 4.9066 1.33; 4.8941 1.04; 4.8858 0.5; 3.6884 3.74; 3.6538 3.72; 3.6417 3.56; 3.5841 15; 3.3052 1212.689941; 3.3045 1226.640015; 3.0378 0.32; 2.6735 1.47; 2.6694 1.9; 2.6649 1.48; 2.6454 0.38; 2.5391 4.87; 2.5046 205.119995; 2.5005 257.420013; 2.4964 185.020004; 2.327 1.8; 2.0844 0.44; 2.0691 1.21; 1.8665 2.07; 1.8567 2.11; 1.849 2.01; 1.7332 1.91; 1.7177 2.17; 1.7106 2.11; 1.5784 1.05; 1.5561 2.53; 1.5324 3.39; 1.51 2.14; 1.5016 2.07; 1.4518 1.13; 1.429 2.35; 1.3987 12.57; 1.3709 1.84; 1.3377 1.14; 1.3151 0.87; 1.2367 0.78; 0.0006 29.299999; −0.0001 30.09 |
| I-141 | [DMSO-$d_6$] 8.3834 0.31; 8.0644 0.94; 8.0555 3.24; 8.0495 2.7; 8.0423 2; 8.0321 3.43; 7.9289 4.85; 7.9084 7.34; 7.8952 3.34; 7.8902 5.87; 7.8719 4.72; 7.8689 4.02; 7.8505 3.96; 7.7283 0.31; 7.6749 7.17; 7.657 6.15; 7.628 1.96; 7.6212 4.66; 7.616 5.14; 7.6109 7.43; 7.6018 13.29; 7.592 6.34; 7.5867 3.95; 7.5819 4.55; 7.5744 1.17; 7.492 5.61; 7.4733 4.18; 7.3341 0.32; 7.3132 3.3; 7.3032 5.51; 7.2816 5.06; 7.18 6.34; 7.1614 3.03; 7.0468 3.2; 7.0253 6.85; 6.9108 6.5; 6.8894 3.42; 5.4594 0.41; 5.429 15; 5.3057 0.37; 4.3025 0.37; 4.2841 0.32; 4.0567 0.99; 4.0391 2.67; 4.0214 2.74; 4.0034 1.02; 3.902 0.32; 3.8615 0.35; 3.7858 4.7; 3.6807 8.7; 3.6312 5.22; 3.5732 0.69; 3.559 0.71; 3.5312 0.71; 3.5274 0.73; 3.5137 0.83; 3.4853 0.93; 3.3061 2356.01001; 3.1754 0.43; 3.1679 0.37; 3.1599 0.32; 3.1472 0.36; 3.037 0.86; 2.8496 0.75; 2.6738 2.4; 2.6692 3.06; 2.6647 2.25; 2.6497 0.44; 2.6144 0.63; 2.5392 8.1; 2.5085 189.410004; 2.5045 330.869995; 2.5002 411.950012; 2.4959 284.890015; 2.3315 2.39; 2.3268 2.96; 2.3225 2.15; 2.0691 2.92; 2.0491 0.4; 1.9867 11.14; 1.9078 1.33; 1.4114 0.47; 1.3984 5.95; 1.3756 0.33; 1.2532 0.37; 1.2365 1.22; 1.2182 0.31; 1.1927 3.12; 1.1749 6.08; 1.1571 3.09; 0.0078 3.17; −0.0001 60.380001; −0.0082 3.35 |
| I-142 | [DMSO-$d_6$] 7.7382 2.31; 7.7197 3.21; 7.7168 3.06; 7.6985 2.78; 7.3376 4.73; 7.3196 4.58; 7.3095 2.15; 7.2888 0.44; 7.1761 4.61; 7.1622 2.32; 7.148 0.32; 7.1329 3.98; 7.1114 3.73; 7.0431 2.3; 7.026 4.91; 6.9509 0.41; 6.9114 4.76; 6.8902 2.45; 6.0223 1.51; 6.0056 1.2; 5.9967 1.92; 5.9896 1.06; 5.804 1.67; 5.7954 1.7; 5.7783 1.3; 5.7744 1.23; 5.7699 1.28; 5.4203 11.05; 5.3846 1.89; 5.3767 1.85; 5.2495 0.98; 3.6833 3.71; 3.6539 3.8; 3.5807 15; 3.4644 0.56; 3.307 1035.680054; 3.1925 0.53; 3.1679 0.4; 3.1428 0.34; 2.8896 0.36; 2.7315 0.39; 2.6736 1.18; 2.6692 1.49; 2.6649 1.15; 2.5721 0.82; 2.5393 9.38; 2.5085 93.220001; 2.5045 161.199997; 2.5002 199.649994; 2.496 138.639999; 2.4342 0.77; 2.4253 0.62; 2.4161 0.6; 2.4064 0.45; 2.3798 0.35; 2.3662 0.35; 2.3491 0.34; 2.3312 1.18; 2.3268 1.47; 2.3223 1.1; 2.1415 0.43; 2.1313 0.63; 2.1226 0.62; 2.0691 3.21; 2.0493 1.31; 2.0321 1.37; 2.028 1.36; 2.0195 1.17; 1.9965 0.58; 1.9864 0.67; 1.9547 0.73; 1.9383 0.79; 1.929 1.23; 1.9167 1.27; 1.9069 1.13; 1.8956 1.09; 1.8843 0.77; 1.8192 0.67; 1.8097 0.92; 1.7973 1.58; 1.7905 1.47; 1.7845 1.44; 1.7773 1.82; 1.7635 1.9; 1.7497 1.59; 1.7423 1.48; 1.7265 1; 1.6979 0.63; 1.6826 0.99; 1.6743 1.22; 1.6619 1.2; 1.6412 0.85; 1.6285 0.66; 1.5959 0.32; 1.5799 0.32; 1.2924 0.35; 1.2368 0.35; 0.89 0.33; −0.0001 5.26 |
| I-143 | [DMSO-$d_6$] 7.9082 0.3; 7.7288 0.66; 7.7239 0.51; 7.7104 0.85; 7.7073 0.88; 7.7032 0.58; 7.695 1.51; 7.6891 0.89; 7.6766 1.84; 7.6737 1.83; 7.6553 1.62; 7.3543 0.56; 7.3363 0.53; 7.3136 0.4; 7.3085 0.61; 7.294 1.28; 7.2818 0.31; 7.2595 1.22; 7.2408 2.18; 7.2131 1.49; 7.2065 1.08; 7.1952 2.37; 7.1751 3.5; 7.1696 2.77; 7.1606 4.46; 7.1537 4.6; 7.1379 2.02; 7.1272 1.13; 7.1203 1.3; 7.1043 2.31; 7.0868 1.4; 7.0557 0.37; 7.0476 0.62; 7.0422 0.91; 7.0275 2.31; 7.0242 1.96; 7.0178 3.09; 6.9783 1.04; 6.9566 1.14; 6.9445 2.6; 6.923 3.18; 6.9159 4.33; 6.9079 4.7; 6.8984 4.07; 6.888 1.3; 6.882 1.7; 5.807 0.37; 5.7961 0.34; 5.782 0.34; 5.7467 9.2; 5.421 2.79; 5.3834 6.12; 5.0404 0.73; 5.0238 0.8; 5.015 0.91; 4.9994 0.72; 4.0572 0.41; 4.0394 1.13; 4.0216 1.14; 4.004 0.41; 3.7204 0.49; 3.7094 0.53; 3.6619 2.22; 3.6038 3; 3.5749 4.25; 3.5134 3.22; 3.4887 2.51; 3.3033 152.5; 3.1916 0.31; 3.1465 0.86; 2.9507 0.42; 2.8902 1.23; 2.811 |

-continued

| Ex. | NMR data |
|---|---|
| | 0.66; 2.7685 1.39; 2.7592 1.19; 2.7319 1.84; 2.6909 0.63; 2.6688 1.78; 2.6642 1.89; 2.6459 15; 2.6258 1.39; 2.6027 6.45; 2.5392 3.9; 2.5086 33.369999; 2.5046 57.439999; 2.5003 71.279999; 2.4961 49.580002; 2.4604 0.45; 2.3314 0.32; 2.327 0.45; 2.3223 0.33; 2.0692 0.45; 2.0497 0.72; 2.0141 1.32; 1.9868 5.69; 1.9568 1.15; 1.9272 1.6; 1.9081 1.96; 1.9005 1.18; 1.894 1.07; 1.865 0.59; 1.8379 0.46; 1.8218 0.37; 1.8082 0.33; 1.5695 0.44; 1.5587 0.56; 1.5508 0.48; 1.5279 0.5; 1.398 0.74; 1.2365 0.54; 1.1928 1.29; 1.175 2.48; 1.1573 1.23; −0.0001 4.4 |
| I-144 | [DMSO-$d_6$] 19.3265 0.36; 16.4666 0.36; 16.4389 0.37; 16.0506 0.36; 11.5296 0.36; 11.1847 0.5; 10.5635 0.36; 9.1659 1.85; 9.1496 3.47; 9.1331 1.73; 8.8326 0.39; 7.793 0.35; 7.7628 3.39; 7.7445 4.72; 7.7415 4.37; 7.7232 4.13; 7.6439 0.55; 7.6248 7.53; 7.6195 7.65; 7.4773 0.44; 7.4657 0.38; 7.4268 4.27; 7.4216 4.08; 7.4062 5.13; 7.4009 4.86; 7.3729 0.71; 7.3539 7.13; 7.336 6.31; 7.3124 3.41; 7.2925 6.88; 7.2716 5.18; 7.2406 0.71; 7.213 0.38; 7.179 6.74; 7.1622 3.32; 7.1099 5.58; 7.0886 5.15; 7.0461 3.25; 7.026 7.26; 6.9138 7.08; 6.8902 3.87; 5.9352 0.35; 5.7466 1.25; 5.4351 15; 5.3047 0.52; 5.0854 1.33; 4.6341 0.37; 4.5491 7.71; 4.5331 7.38; 4.5088 0.48; 4.5029 0.41; 4.3632 0.84; 4.3501 0.77; 4.2599 0.38; 4.057 0.88; 4.039 2.72; 4.0212 2.72; 4.0034 1.03; 3.9441 0.41; 3.9264 0.42; 3.9022 0.47; 3.8802 0.4; 3.8612 0.45; 3.7599 4.77; 3.7067 1.44; 3.6664 5.32; 3.6554 5.72; 3.5995 5.04; 3.5466 0.79; 3.5353 0.82; 3.5029 0.85; 3.4905 1.02; 3.4853 1.07; 3.4323 1.62; 3.3049 2472.110107; 3.1905 0.89; 3.1462 0.71; 3.1286 0.53; 3.1233 0.53; 3.071 0.36; 3.0369 1.35; 2.944 0.65; 2.8896 0.45; 2.8497 1.05; 2.8159 0.37; 2.7854 0.51; 2.7514 0.46; 2.7306 0.59; 2.7206 0.43; 2.7136 0.39; 2.6931 0.86; 2.6735 2.82; 2.6689 3.72; 2.6642 2.81; 2.6483 0.72; 2.6347 0.68; 2.591 1.3; 2.5391 22.059999; 2.5086 214.75; 2.5044 385.980011; 2.5 491.359985; 2.4957 341.299988; 2.4197 1.16; 2.4028 0.85; 2.3634 0.58; 2.3586 0.63; 2.331 2.75; 2.3265 3.43; 2.3223 2.62; 2.2918 0.42; 2.2767 0.37; 2.2558 0.38; 2.2162 0.39; 2.1878 0.37; 2.1752 0.35; 2.0692 1.74; 2.0493 1.91; 2.0096 0.42; 1.9971 0.6; 1.9866 11.35; 1.9561 0.66; 1.9076 0.83; 1.3984 6.77; 1.2922 2.42; 1.2792 0.54; 1.2382 1.64; 1.2058 0.63; 1.1927 3.35; 1.1749 6.41; 1.1572 3.71; 1.1084 0.42; 1.0906 0.46; 1.0699 0.87; 0.8904 1.45; 0.8551 0.7; 0.8388 0.5; 0.8136 0.37; 0.018 0.56; 0.008 2.55; −0.0001 50.349998; −0.0085 2.57; −0.0212 0.45; −1.2287 0.36; −3.2941 0.36; −3.5272 0.41 |
| I-145 | [DMSO-$d_6$] 7.7926 1.35; 7.7741 1.86; 7.7716 1.79; 7.753 1.57; 7.3515 1.43; 7.3356 1.67; 7.3309 1.42; 7.243 2.89; 7.2249 3.02; 7.2179 2.61; 7.1963 2.77; 7.1901 2.45; 7.1868 2.78; 7.1817 2.75; 7.1747 3.11; 7.1708 2.4; 7.1647 1.74; 7.1576 1.44; 7.1477 1.31; 7.1405 0.82; 7.131 0.49; 7.1242 0.31; 6.4938 3.55; 5.7472 5.82; 5.2796 6.94; 4.1924 9.01; 4.0394 0.47; 4.022 0.49; 3.687 2.16; 3.6568 2.23; 3.587 8.98; 3.2998 129.899994; 2.6691 0.35; 2.539 1.69; 2.5044 40.240002; 2.5001 49.77; 2.4961 35.189999; 2.3255 15; 2.2035 13.54; 1.987 1.96; 1.3982 1.83; 1.193 0.59; 1.1751 1.1; 1.1576 0.59; −0.0001 7.12 |
| I-146 | [DMSO-$d_6$] 9.1367 1.79; 9.1209 3.4; 9.1044 1.66; 7.7785 0.32; 7.7661 3.32; 7.7477 4.39; 7.7265 3.78; 7.626 0.42; 7.5737 0.32; 7.5661 0.4; 7.5589 0.33; 7.5487 0.35; 7.4716 2.41; 7.4674 3.85; 7.4531 2.9; 7.4485 4.53; 7.4315 0.36; 7.3625 6.85; 7.3444 6.53; 7.3363 1.53; 7.3224 3.3; 7.3124 5.86; 7.3057 7.82; 7.301 9.84; 7.2869 9.45; 7.2732 2.92; 7.2656 2.01; 7.1938 0.37; 7.179 6.27; 7.162 3.01; 7.1109 5.52; 7.0895 5.09; 7.0458 3.16; 7.0258 6.6; 6.9132 6.58; 6.8899 3.34; 5.7469 3.54; 5.4349 15; 5.3071 0.34; 4.5854 7.86; 4.5692 7.73; 4.057 0.7; 4.0394 1.87; 4.0215 1.97; 4.0041 0.67; 3.8098 0.35; 3.7641 4.57; 3.6796 4.87; 3.6661 5.35; 3.6576 5.58; 3.646 5.15; 3.6064 4.82; 3.5493 0.39; 3.5275 0.37; 3.4927 0.41; 3.485 0.42; 3.4627 0.47; 3.4362 0.62; 3.4222 0.65; 3.3065 772.119995; 3.2834 15.87; 3.0368 0.79; 2.8496 0.64; 2.6695 1.2; 2.6648 0.93; 2.6167 0.3; 2.5813 0.55; 2.5391 3.12; 2.5046 130.369995; 2.5004 164.139999; 2.4962 116.32; 2.3275 1.18; 2.0695 0.69; 1.9869 7.74; 1.9083 1.1; 1.2367 0.81; 1.1928 2.16; 1.1751 4.05; 1.1572 2.01; −0.0001 16.549999 |
| I-147 | [DMSO-$d_6$] 7.7269 0.44; 7.7081 0.64; 7.7055 0.65; 7.6928 1.19; 7.6869 0.64; 7.6746 1.43; 7.6716 1.33; 7.6532 1.19; 7.2592 0.91; 7.2403 1.53; 7.2237 0.37; 7.2121 0.99; 7.1943 1.55; 7.1743 1.51; 7.1694 1.33; 7.1524 2.02; 7.1382 1.15; 7.1207 0.46; 7.1053 1.44; 7.0874 0.8; 6.9763 0.68; 6.9548 0.8; 6.9425 1.72; 6.9217 2.19; 6.913 2.21; 6.905 0.95; 6.8949 1.94; 6.4939 2.8; 5.7468 0.64; 5.3025 2.08; 5.2659 5.03; 5.0442 0.54; 5.0275 0.61; 5.0184 0.65; 5.0036 0.51; 4.0569 1.14; 4.0391 3.32; 4.0213 3.32; 4.0035 1.16; 3.663 1.69; 3.6031 2.18; 3.5771 2.71; 3.5177 2.38; 3.5059 2.09; 3.4977 2.08; 3.4695 0.58; 3.4527 0.38; 3.4399 0.31; 3.3002 344.73999; 2.8158 0.36; 2.7699 0.87; 2.7382 0.51; 2.7276 0.53; 2.6687 1.5; 2.6642 1.43; 2.6595 1.32; 2.6451 11.39; 2.6027 4.84; 2.5388 3.95; 2.5083 46.98; 2.5041 82.290001; 2.4997 102.830002; 2.4954 70.989998; 2.4289 0.33; 2.3352 0.38; 2.3309 0.61; 2.3267 0.74; 2.3218 0.56; 2.2151 4.29; 2.2024 10.03; 2.069 0.32; 2.0493 0.71; 2.0146 0.93; 1.9866 15; 1.9557 0.8; 1.9263 1.1; 1.9076 0.97; 1.8995 0.82; 1.8654 0.36; 1.8349 0.3; 1.5751 0.35; 1.563 0.43; 1.53 0.39; 1.2373 0.3; 1.1926 3.95; 1.1749 7.88; 1.1571 3.98; −0.0001 14.01 |
| I-148 | [DMSO-$d_6$] 7.7303 0.83; 7.7118 1.18; 7.6904 1.06; 7.6718 1.43; 7.653 1.88; 7.6319 1.66; 7.5134 1.21; 7.4939 1.38; 7.4514 1.67; 7.4318 2.6; 7.4239 2.02; 7.4056 2.49; 7.3845 3.84; 7.3685 3.38; 7.3541 2.71; 7.3357 2.08; 7.3083 1.12; 7.2896 1.31; 7.1748 1.75; 7.1562 3.98; 7.0413 0.95; 7.0233 3.72; 7.02 3.72; 6.9985 1.53; 6.977 1.49; 6.9532 2.8; 6.935 2.89; 6.9105 6.6; 6.8887 3.4; 5.4188 4.06; 5.3454 6.27; 4.7453 4.59; 4.6897 6.02; 4.6611 0.65; 4.0572 0.31; 4.0395 0.85; 4.0217 0.85; 4.0038 0.31; 3.6641 3.1; 3.5839 3.98; 3.4022 3.47; 3.3251 1403.030029; 3.1427 2.45; 3.0373 0.68; 2.9933 15; 2.9694 10.12; 2.9443 0.66; 2.8908 2.22; 2.8501 0.44; 2.7321 1.72; 2.675 0.79; 2.6707 1.04; 2.6579 0.71; 2.5406 4.38; 2.5102 55.810001; 2.506 100.169998; 2.5016 127.290001; 2.4973 88.690002; 2.3329 0.71; 2.3282 0.94; 2.1962 0.36; 2.0686 0.9; 2.0494 0.35; 1.9869 3.61; 1.9086 1.4; 1.3981 0.8; 1.2925 0.47; 1.2363 0.75; 1.193 1.01; 1.1752 1.98; 1.1575 1.04; −0.0001 3.35 |
| I-149 | [DMSO-$d_6$] 7.7989 1.61; 7.7805 2.08; 7.7776 2.07; 7.7592 1.84; 7.4416 0.38; 7.4248 0.84; 7.4207 0.8; 7.4038 1.58; 7.387 0.85; 7.3828 0.97; 7.3661 0.43; 7.2491 3.32; 7.2313 5.65; 7.2098 2.53; 7.1526 0.5; 7.1432 2.54; 7.1233 3.87; 7.1031 2.07; 7.0933 0.38; 6.4966 4; 5.7469 6.8; 5.2869 7.85; 4.2412 7.31; 4.0398 0.68; 4.0221 0.68; 3.687 2.64; 3.6645 2.69; 3.5901 9.75; 3.3094 232.960007; 2.6704 0.32; 2.5404 2.09; 2.5098 19.540001; 2.5057 34.619999; 2.5013 |

| Ex. | NMR data |
|---|---|
| | 43.700001; 2.4971 30.610001; 2.3276 0.32; 2.2079 15; 2.1925 0.62; 1.9874 2.84; 1.1933 0.82; 1.1756 1.6; 1.1578 0.78; −0.0001 1.12 |

A detailed description of the presentation of NMR data in the form of peak lists can be found in the publication "Citation of NMR Peaklist Data within patent applications":

http://www.rdelectronic.co.uk/rd/free/RD564025.pdf

The chemical NMR shifts in ppm were measured at 400 MHz, unless stated otherwise in the solvent DMSO-$d_6$ with tetramethylsilane as internal standard.

The following abbreviations describe the signal splitting:
b=broad, s=singlet, d=doublet, t=triplet, q=quadruplet, m=multiplet Use Examples Example A

*Phytophthora* Test (Tomato)/Protective
Solvent: 49 parts by weight of N,N-dimethylformamide
Emulsifier: 1 part by weight of alkylaryl polyglycol ether To prepare an appropriate active ingredient preparation, 1 part by weight of active ingredient is mixed with the stated amounts of solvent and emulsifier, and the concentrate is diluted with water to the desired concentration.

To test for protective efficacy, young tomato plants are sprayed with the active ingredient preparation at the stated application rate. 1 day after the treatment, the plants are inoculated with a spore suspension of *Phytophthora infestans*, and then stand at 100% rel. humidity and 22° C. for 24 h. Subsequently, the plants are placed in a climate chamber at approx. 96% relative air humidity and a temperature of approx. 20° C.

Evaluation follows 7 days after the inoculation. 0% means an efficacy which corresponds to that of the control, whereas an efficacy of 100% means that no infection is observed.

In this test, the following inventive compounds, at an active ingredient concentration of 500 ppm, exhibit an efficacy of 70% or more. Specifically, the following compounds from Table I exhibited an efficacy of 70% and more, with the precise efficacy for selected examples reported in round brackets:

I-1, I-3 (88%), I-7, I-8, I-9, I-12, I-23, I-24, I-32, I-33, I-34, I-35, I-38, I-39, I-40, I-43, I-45, I-46, I-47, I-48, I-49, I-50, I-51, I-52, I-57, I-60, I-63, I-68 (94%), I-69 (71%), I-70 (97%), I-71 (76%), I-73 (71%), I-75 (71%), I-79, I-89, I-97, I-98, I-99, I-100, I-101, I-102, I-103, I-104, I-105, I-106, I-107, I-108, I-109, I-110, I-111, I-115, I-116, I-117 (93%), I-118 (93%), I-120 (93%), I-123 (93%), I-137 (93%), I-138 (93%), I-140 (93%), I-141 (71%), I-142 (83%), I-143 (71%).

*Plasmopara* Test (Grapevine)/Protective
Solvent: 24.5 parts by weight of acetone
24.5 parts by weight of dimethylacetamide
Emulsifier: 1 part by weight of alkylaryl polyglycol ether To prepare an appropriate active ingredient preparation, 1 part by weight of active ingredient is mixed with the stated amounts of solvent and emulsifier, and the concentrate is diluted with water to the desired concentration.

To test for protective efficacy, young plants are sprayed with the active ingredient preparation at the stated application rate. After the spray coating has dried on, the plants are inoculated with an aqueous spore suspension of *Plasmopara viticola* and then remain in an incubation cabin at approx. 20° C. and 100% relative atmospheric humidity for 1 day. Subsequently, the plants are placed in a greenhouse at approx. 21° C. and approx. 90% air humidity for 4 days. The plants are then moistened and placed into an incubation cabin for 1 day.

Evaluation follows 6 days after the inoculation. 0% means an efficacy which corresponds to that of the control, whereas an efficacy of 100% means that no infection is observed.

In this test, the inventive compounds, at an active ingredient concentration of 100 ppm, exhibit an efficacy of 70% or more. Specifically, the following compounds from Table I exhibited an efficacy of 70% and more, with the precise efficacy for selected examples reported in round brackets:

I-7, I-9, I-33, I-34, I-35, I-43, I-45, I-47, I-48, I-52, I-97, I-98, I-99, I-100, I-102, I-105, I-106, I-107, I-108, I-111, I-115, I-117 (93%), I-140 (71%).

The invention claimed is:
1. A compound of formula (I), a salt, or an N-oxide thereof,

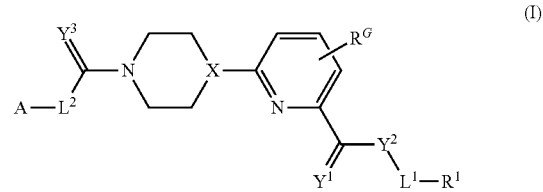

in which
A is
pyrazol-1-yl, pyrazol-3-yl, or pyrazol-4-yl, which optionally, contain up to two substituents, where the substituents are the same or different and are each independently
substituents on carbon:
fluorine, chlorine, bromine, iodine, cyano, nitro, methyl, ethyl, propyl, 1-methylethyl, 1,1-dimethylethyl, chlorofluoromethyl, dichloromethyl, dichlorofluoromethyl, difluoromethyl, trichloromethyl, trifluoromethyl, cyclopropyl, ethoxy, 1-methylethoxy, propoxy, methoxy, trifluoromethoxy, difluoromethoxy, 1-methylethylthio, methylthio, ethylthio, propylthio, difluoromethylthio, trifluoromethylthio or phenyl,
substituents on nitrogen:
methyl, ethyl, propyl, 1-methylethyl, 2,2-trifluoroethyl, 2,2-difluoroethyl, 2,2-dichloro-2-fluoroethyl, 2-chloro-2-difluoroethyl or 2-chloro-2-fluoroethyl,
$L^1$ is $(C(R^{L1})_2)_p$,
p is 0, 1, 2 or 3,
$R^{L1}$ are the same or different and are each independently hydrogen, halogen, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl, $C_1$-$C_4$-haloalkyl or phenyl,
with the proviso that $L^1$ optionally contains not more than two $R^{L1}$ other than hydrogen,
$L^2$ is $NR^{L21}$ or $C(R^{L22})_2$,
$R^{L21}$ is hydrogen, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$- haloalkynyl, $C_2$-$C_4$-alkoxyalkyl, $C_2$-$C_4$-alkylthioalkyl, $C_2$-$C_4$-alkylsulphinylalkyl, $C_2$-$C_4$-alkylsulphonylalkyl, $C_2$-$C_4$-alkylcarbonyl, $C_2$-$C_4$-haloalkylcarbonyl, $C_2$-$C_5$-alkoxycarbonyl, $C_3$-$C_5$-alkoxycarbonylalkyl, $C_2$-$C_5$-alkylaminocarbonyl, $C_3$-$C_5$-dialkylaminocarbonyl, $C_1$-$C_4$-alkylsulphonyl or $C_1$-$C_4$-haloalkylsulphonyl, $R^{L22}$ are the same or different and are each independently hydrogen, $C_1$-$C_4$-alkyl, $C_1$-$C_4$-haloalkyl, cyclopropyl, or halogen, or the two $R^{L22}$ radicals, together with the carbon atom to which they are bonded, form a cyclopropyl ring, $Y^1$ and $Y^3$ are the same or different and are each independently sulphur or oxygen, $Y^2$ is sulphur or oxygen, X is nitrogen, $R^G$ is hydrogen, halogen or $C_1$-$C_3$-alkyl, and $R^1$ is hydrogen, 1,1-dimethylethyl, 3,3-dimethylbutyl, 2,2-dimethylpropyl, 1,2,2-trimethylpropyl, pentyl, 1-ethylpropyl, butyl, 2-methylpropyl, 1-methylethyl, ethyl, propyl, 4-methylpentyl, hexyl, trifluoromethyl, methoxymethyl, ethoxymethyl, ethenyl, prop-2-en-1-yl or but-3-en-1-yl, or $R^1$ is cyclopentyl, cyclohexyl, cycloheptyl or cyclooctyl, each of which optionally contains up to two substituents, where the substituents are each independently cyano, chlorine, fluorine, bromine, iodine, methyl, ethyl, propyl, 1-methylethyl, 1,1-dimethylethyl, ethenyl, 2-propenyl, 2-propynyloxy, phenyl, methoxy, ethoxy, propyloxy, trifluoromethoxy, ethynyl, methylthio, ethylthio or trifluoromethylthio, or $R^1$ is cyclopentenyl, cyclohexenyl or cycloheptenyl, each of which optionally contains up to two substituents, where the substituents are each independently methyl, ethyl, methoxy, ethoxy, trifluoromethoxy, ethynyl, 2-propynyloxy, methylthio, ethylthio or trifluoromethylthio, or $R^1$ is phenyl which optionally contains up to three substituents, where the substituents are each independently fluorine, chlorine, bromine, iodine, cyano, nitro, methyl, ethyl, propyl, 1-methylethyl, butyl, 1,1-dimethylethyl, 1,2-dimethylethyl, ethenyl, ethynyl, trifluoromethyl, difluoromethyl, trichloromethyl, dichloromethyl, cyclopropyl, methoxy, ethoxy, propoxy, 1-methylethoxy, 1,1-dimethylethoxy, methylcarbonyl, ethylcarbonyl, trifluoromethylcarbonyl, methoxycarbonyl, ethoxycarbonyl, propoxycarbonyl, 1-methylethoxycarbonyl, 1,1-dimethylethoxycarbonyl, 2-propynyloxy, methylthio, ethylthio, methylsulphinyl or methylsulphonyl or -$L^3$Q, or $R^1$ is naphthalen-1-yl naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, dihydro-1H-inden-1-yl, 1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl, which optionally contain up to three substituents, where the substituents are each independently methyl, methoxy, cyano, fluorine, chlorine, bromine, or iodine, or $R^1$ is furan-2-yl, furan-3-yl, thiophen-2-yl, thiophen-3-yl, isoxazol-3-yl, isoxazol-4-yl, isoxazol 5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl or pyrazin-2-yl, each of which optionally contains up to two substituents, where the substituents are each independently substituents on carbon:

chlorine, fluorine, bromine, iodine, cyano, nitro, methyl, ethyl, propyl, 1-methylethy, butyl, 1,1-dimethylethyl, ethenyl, ethynyl, trifluoromethyl, difluoromethyl, cyclopropyl, cyclopentyl, cyclohexyl, methylcarbonyl, ethylcarbonyl, methoxycarbonyl, ethoxycarbonyl, methoxy, ethoxy, propoxy, 1-methylethoxy, 2-propynyloxy, trifluoromethoxy, methylcarbonyloxy, methylcarbonylthio, methylthio, ethylthio, trifluoromethylthio, methylsulphinyl, ethylsulphinyl, trifluoromethylsulphinyl, methylsulphonyl, ethylsulphonyl or trifluoromethylsulphonyl, substituents on nitrogen: methyl, ethyl, propyl, cyclopropyl, cyclohexyl, phenyl or 2-propynyl, or $R^1$ is indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, quinolin-2-yl, quinolin-3-yl, quinolin-4-yl, quinolin-5-yl, quinolin-6-yl, quinolin-7-yl, Quinolin-8-yl, isoquinolin-1-yl, isoquinolin-3-yl; isoquinolin-4-yl, isoquinolin-5-yl, isoquinolin-6-yl, isoquinolin-7-yl or isoquinolin-8-yl, each of which optionally contains up to two substituents, where the substituents are each independently substituents on carbon: fluorine, chlorine, bromine, iodine, methyl, methoxy, 2-propynyloxy, or 2-propenyloxy, substituents on nitrogen: methyl, ethyl, propyl, cyclopropyl, cyclohexyl, phenyl or 2-propynyl, or $R^1$ is piperidin-1-yl, piperidin-2-yl, piperidin-3-yl, piperidin-4-yl, piperazin-1-yl, piperazin-2-yl, piperazin-3-yl, morpholin-1-yl, morpholin-2-yl, morpholin-3-yl, tetrahydropyran-2-yl, tetrahydropyran-3-yl, tetrahydropyran-4-yl, 1,2,3,4-tetrahydroquinolin-1-yl, 1,2,3,4-tetrahydroisoquinolin-2-yl, 1,2,3,4-tetrahydroquinoxalin-1-yl, indolin-1-yl, isoindolin-2-yl, decahydroquinolin-1-yl or decahydroisoquinolin-2-yl, each of which optionally contains up to two substituents, where the substituents are each independently substituents on carbon: fluorine, chlorine, bromine, iodine, methyl, methoxy, 2-propynyloxy, or 2-propenyloxy, substituents on nitrogen: methyl, ethyl, propyl, cyclopropyl, cyclohexyl, phenyl or 2-propynyl, L³ is a direct bond, —O, —C(=O), —S(O)$_m$, —CHR$^{L31}$ or —NR$^{L32}$, m is 0, 1 or 2, R$^{L31}$ is hydrogen, C$_1$-C$_4$-alkyl or C$_1$-C$_4$-haloalkyl, R$^{L32}$ is hydrogen, C$_1$-C$_6$-alkyl, C$_1$-C$_6$-haloalkyl, C$_3$-C$_8$-cycloalkyl, C$_2$-C$_6$-alkylcarbonyl, C$_2$-C$_6$-haloalkylcarbonyl, C$_2$-C$_6$-alkoxycarbonyl or C$_2$-C$_6$-haloalkoxycarbonyl, Q is a phenyl.

2. The compound of the formula (I) according to claim 1, in which

L² is CH$_2$

Y¹ is oxygen, and

R$^G$ is hydrogen.

3. A method for controlling phytopathogenic harmful fungi, comprising applying at least one compound of formula (I), a salt, or an N-oxide thereof, according to claim 1 or 2, to the phytopathogenic harmful fungi, their habitat, or a combination thereof.

4. A composition, comprising at least one compound of formula (I), a salt, or an N-oxide thereof, according to claim 1 or 2, and an extender, a surfactant, or a combination thereof.

5. A method of controlling phytopathogenic harmful fungi, comprising applying the composition according to claim 4, to the phytopathogenic harmful fungi, their habitat, or a combination thereof.

6. A process for making a composition, comprising mixing at least one compound of formula (I), a salt, or an N-oxide thereof, according to claim 1 or 2, with an extender, a surfactant, or a combination thereof.

7. A method of treating a seed for controlling phytopathogenic harmful fungi, comprising applying at least one compound of formula (I), a salt, or an N-oxide thereof, according to claim 1 or 2, to the seed.

8. A method of treating a transgenic plant for controlling phytopathogenic harmful fungi, comprising applying at least one compound of formula (I), a salt, or an N-oxide thereof, according to claim 1 or 2, to the transgenic plant.

9. A method of treating a transgenic seed for controlling phytopathogenic harmful fungi, comprising applying at least one compound of formula (I), a salt, or an N-oxide thereof, according to claim 1 or 2, to the transgenic seed.

10. The compound of the formula (I) according to claim 1, in which A is 3,5-bis-(difluoromethyl)-1H-pyrazol-1-yl.

11. The compound of the formula (I) according to claim 1, in which Y² is oxygen.

12. The compound of the formula (I) according to claim 1, in which Y² is sulphur.

13. The compound of the formula (I) according to claim 1, in which

R¹ is hydrogen, 1,1-dimethylethyl, 3,3-dimethylbutyl, 2,2-dimethylpropyl, 1,2,2-trimethylpropyl, pentyl, 1-ethylpropyl, butyl, 2-methylpropyl, 1-methylethyl, ethyl, propyl, 4-methylpentyl, hexyl, trifluoromethyl, methoxymethyl, ethoxymethyl, ethenyl, prop-2-en-1-yl or but-3-en-1-yl, or R¹ is cyclopentyl, cyclohexyl, cycloheptyl or cyclooctyl, each of which optionally contains up to two substituents, where the substituents are each independently cyano, chlorine, fluorine, bromine, iodine, methyl, ethyl, propyl, 1-methylethyl, 1,1-dimethylethyl, ethenyl, 2-propenyl, 2-propynyloxy, phenyl, methoxy, ethoxy, propyloxy, trifluoromethoxy, ethynyl, methylthio, ethylthio or trifluoromethylthio, or R¹ is cyclopentenyl, cyclohexenyl or cycloheptenyl, each of which optionally contains up to two substituents, where the substituents are each independently methyl, ethyl, methoxy, ethoxy, trifluoromethoxy, ethynyl, 2-propynyloxy, methylthio, ethylthio or trifluoromethylthio, or R¹ is phenyl which optionally contains up to three substituents, where the substituents are each independently fluorine, chlorine, bromine, iodine, cyano, nitro, methyl, ethyl, propyl, 1-methylethyl, butyl, 1,1-dimethylethyl, 1,2-dimethylethyl, ethenyl, ethynyl, trifluoromethyl, difluoromethyl, trichloromethyl, dichloromethyl, cyclopropyl, methoxy, ethoxy, propoxy, 1-methylethoxy, 1,1-dimethylethoxy, methylcarbonyl, ethylcarbonyl, trifluoromethylcarbonyl, methoxycarbonyl, ethoxycarbonyl, propoxycarbonyl, 1-methylethoxycarbonyl, 1,1-dimethylethoxycarbonyl, 2-propynyloxy, methylthio, ethylthio, methylsulphinyl or methylsulphonyl or -L³Q, or R¹ is naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, dihydro-1H-inden-1-yl, 1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl, which optionally contain up to three substituents, where the substituents are each independently methyl, methoxy, cyano, fluorine, chlorine, bromine, or iodine, L³ is a direct bond, —O, —C(=O), —S(O)$_m$, —CHR$^{L31}$ or —NR$^{L32}$, m is 0, 1 or 2, R$^{L31}$ is hydrogen, C$_1$-C$_4$-alkyl or C$_1$-C$_4$-haloalkyl, R$^{L32}$ is hydrogen, C$_1$-C$_6$-alkyl, C$_1$-C$_6$-haloalkyl, C$_3$-C$_8$-cycloalkyl, C$_2$-C$_6$-alkylcarbonyl, C$_2$-C$_6$-haloalkylcarbonyl, C$_2$-C$_6$-alkoxycarbonyl or C$_2$-C$_6$-haloalkoxycarbonyl, and Q is a phenyl.

* * * * *